(12) United States Patent
Davies et al.

(10) Patent No.: US 12,162,934 B2
(45) Date of Patent: Dec. 10, 2024

(54) GREMLIN-1 ANTAGONIST FOR THE PREVENTION AND TREATMENT OF CANCER

(71) Applicants: UCB BIOPHARMA SRL, Brussels (BE); OXFORD UNIVERSITY INNOVATION LIMITED, Oxford (GB); THE UNIVERSITY OF ADELAIDE, Adelaide (AU)

(72) Inventors: Gareth Charles Glyndwr Davies, Slough (GB); Simon Leedham, Oxford (GB); Andrew Zannettino, Highbury (AU); Kimberley Clark, Ascot Park (AU); Duncan Hewett, Mile End (AU); Vasilios Panagopoulos, Plympton (AU)

(73) Assignees: UCB BIOPHARMA SRL, Brussels (BE); OXFORD UNIVERSITY INNOVATION LIMITED, Oxford (GB); THE UNIVERSITY OF ADELAIDE, Adelaide (AU)

( * ) Notice: Subject to any disclaimer, the term of this patent is extended or adjusted under 35 U.S.C. 154(b) by 945 days.

(21) Appl. No.: 17/253,660

(22) PCT Filed: Jun. 18, 2019

(86) PCT No.: PCT/GB2019/051699
§ 371 (c)(1),
(2) Date: Dec. 18, 2020

(87) PCT Pub. No.: WO2019/243801
PCT Pub. Date: Dec. 26, 2019

(65) Prior Publication Data
US 2021/0253688 A1 Aug. 19, 2021

(30) Foreign Application Priority Data
Jun. 18, 2018 (GB) .................................... 1809946
Sep. 26, 2018 (GB) .................................... 1815694

(51) Int. Cl.
*A61K 39/395* (2006.01)
*A61K 45/06* (2006.01)
*A61P 35/00* (2006.01)
*C07K 16/24* (2006.01)
*C07K 16/28* (2006.01)
*G01N 33/574* (2006.01)
*A61K 39/00* (2006.01)

(52) U.S. Cl.
CPC .............. *C07K 16/24* (2013.01); *A61K 45/06* (2013.01); *A61P 35/00* (2018.01); *C07K 16/2803* (2013.01); *C07K 16/2896* (2013.01); *G01N 33/5748* (2013.01); *A61K 2039/505* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,667,425 A | 9/1997 | Pineau et al. |
| 5,698,426 A | 12/1997 | Huse |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,821,047 A | 10/1998 | Garrard et al. |
| 5,969,108 A | 10/1999 | McCafferty et al. |
| 6,632,927 B2 | 10/2003 | Adair et al. |
| 7,786,080 B2 | 8/2010 | Muller et al. |
| 9,631,011 B2 | 4/2017 | Kim et al. |
| 10,377,817 B2 | 8/2019 | Economides et al. |
| 10,947,304 B2 | 3/2021 | Dedi et al. |
| 11,524,997 B2 | 12/2022 | Davies et al. |
| 11,807,680 B2 | 11/2023 | Dedi et al. |

(Continued)

FOREIGN PATENT DOCUMENTS

| | | |
|---|---|---|
| EP | 0 392 745 | 10/1990 |
| EP | 0 438 474 | 7/1991 |

(Continued)

OTHER PUBLICATIONS

O'reilly, S et al. "Interleukin-6 (IL-6) Trans Signaling Drives a STAT3-dependent Pathway That Leads to Hyperactive Transforming Growth Factor-β (TGF-β) Signaling Promoting SMAD3 Activation and Fibrosis via Gremlin Protein" *The Journal of Biological Chemistry*, Apr. 4, 2014, pp. 9952-9960, vol. 289, No. 14.

(Continued)

*Primary Examiner* — Christine J Saoud
*Assistant Examiner* — Jon M Lockard
(74) *Attorney, Agent, or Firm* — SALIWANCHIK, LLOYD & EISENSCHENK

(57) ABSTRACT

The invention relates to an anti-GREM1 antagonist for use in a method for the treatment or prevention of a cancer.

29 Claims, 43 Drawing Sheets
Specification includes a Sequence Listing.

(56) References Cited

U.S. PATENT DOCUMENTS

| | | |
|---|---|---|
| 2007/0293425 A1 | 12/2007 | Muller et al. |
| 2009/0041757 A1 | 2/2009 | Zhen et al. |
| 2015/0158938 A1 | 6/2015 | Kim et al. |
| 2015/0183853 A1 | 7/2015 | Sharma et al. |
| 2016/0024195 A1 | 1/2016 | Economides et al. |
| 2019/0330323 A1 | 10/2019 | Dedi et al. |
| 2021/0107973 A1 | 4/2021 | Davies et al. |
| 2021/0163586 A1 | 6/2021 | Dedi et al. |
| 2023/0174635 A1 | 6/2023 | Davies et al. |
| 2024/0076365 A1 | 3/2024 | Dedi et al. |

FOREIGN PATENT DOCUMENTS

| | | |
|---|---|---|
| EP | 0 463 151 | 1/1992 |
| EP | 0 546 073 | 6/1993 |
| EP | 1 571 159 | 9/2005 |
| EP | 2 826 790 | 1/2015 |
| WO | WO 86/01533 | 3/1986 |
| WO | WO 89/00195 | 1/1989 |
| WO | WO 89/01476 | 2/1989 |
| WO | WO 90/02809 | 3/1990 |
| WO | WO 91/09967 | 7/1991 |
| WO | WO 91/10737 | 7/1991 |
| WO | WO 92/01047 | 1/1992 |
| WO | WO 92/02551 | 2/1992 |
| WO | WO 92/18619 | 10/1992 |
| WO | WO 92/22583 | 12/1992 |
| WO | WO 92/22853 | 12/1992 |
| WO | WO 93/06231 | 4/1993 |
| WO | WO 93/11236 | 6/1993 |
| WO | WO 95/15982 | 6/1995 |
| WO | WO 95/20401 | 8/1995 |
| WO | WO 98/25971 | 6/1998 |
| WO | WO 02/054940 | 7/2002 |
| WO | WO 03/031581 | 4/2003 |
| WO | WO 2004/051268 | 6/2004 |
| WO | WO 2004/106377 | 12/2004 |
| WO | WO 2005/003169 | 1/2005 |
| WO | WO 2005/003170 | 1/2005 |
| WO | WO 2005/003171 | 1/2005 |
| WO | WO 2005/113605 | 12/2005 |
| WO | WO 2005/117984 | 12/2005 |
| WO | WO 2007/124486 | 11/2007 |
| WO | WO 2008/038024 | 4/2008 |
| WO | WO 2009/040562 | 4/2009 |
| WO | WO 2013/137686 | 9/2013 |
| WO | WO 2014/159010 | 10/2014 |
| WO | WO 2018/115017 | 6/2018 |
| WO | WO 2019/158658 | 8/2019 |
| WO | WO 2019/243801 | 12/2019 |

OTHER PUBLICATIONS

Sato, M. et al. "Clinical significance of Gremlin 1 in cervical cancer and its effects on cancer stem cell maintenance" *Oncology Reports*, 2016, pp. 391-397, vol. 35.
Uchiyama, H. et al. "Adhesion of Human Myeloma-Derived Cell Lines to Bone Marrow Stromal Cells Stimulates Interleukin-6 Secretion" *Blood*, Dec. 15, 1993, pp. 3712-3720, vol. 82, No. 12.
Van Vlodrop, I. J. H. et al. "Prognostic Significance of Gremlin1 (GREM1) Promoter CpG Island Hypermethylation in Clear Cell Renal Cell Carcinoma" *The American Journal of Pathology*, Feb. 2010, pp. 575-584, vol. 176, No. 2.
Yu, Y. et al. "Overexpression of Gremlin 1 by sonic hedgehog signaling promotes pancreatic cancer progression" *International Journal of Oncology*, 2018, pp. 2445-2457, vol. 53.
Clark, K. C. et al. "Targeted Disruption of Bone Marrow Stromal Cell-Derived Gremlin1 Limits Multiple Myeloma Disease Progression In Vivo" *Cancers*, Aug. 3, 2020, pp. 1-20, vol. 12, No. 2149.
Knappik, A et al. "Fully Synthetic Human Combinatorial Antibody Libraries (HuCAL) Based on Modular Consensus Frameworks and CDRs Randomized with Trinucleotides" *J. Mol. Biol.*, 2000, pp. 57-86, vol. 296, No. 1.
Park, S.-A. et al. "Gremlin-1 augments the oestrogen-related receptor α signalling through EGFR activation: implications for the progression of breast cancer" *British Journal of Cancer*, published online Jun. 23, 2020, pp. 988-999, vol. 123, No. 6.
Cao, A. et al. "Beta-thalassemia" *Genetics In Medicine*, Feb. 2010, pp. 61-76, vol. 12, No. 2.
Dabrowski, M. et al. "Diffuse Idiopathic Skeletal Hyperostosis of Cervical Spine with Dysphagia-Molecular and Clinical Aspects" *International Journal of Molecular Sciences*, 2021, pp. 1-12, vol. 22, No. 4255.
Yin, M. et al. "Gremlin-1 is a key regulator of the invasive cell phenotype in mesothelioma" *Oncology*, 2017, pp. 98280-98297, vol. 8, No. 58.
Honma, R. et al. "Clinicopathological and Prognostic Significance of Epithelial Gremlin1 Expression in Gastric Cancer" *Anticancer Research*, 2018, pp. 1419-1425, vol. 38.
Hsu, D. R et al. "The Xenopus Dorsalizing Factor Gremlin Identifies a Novel Family of Secreted Proteins that Antagonize BMP Activities" *Molecular Cell*, Apr. 1998, pp. 673-683, vol. 1, No. 5.
Written Opinion in International Application No. PCT/EP2017/083650, Jan. 4, 2019, pp. 1-8.
Nolan, K. et al. "Structure of Protein Related to DAN and Cerberus: Insights into the Mechanism of Bone Morphogenetic Protein Antagonism" *Structure*, Aug. 6, 2013, pp. 1417-1429, vol. 21.
United Kingdom Search Report Application No. GB1519083.8, Jul. 29, 2016, pp. 1-5.
Adair, J. R. et al. "Therapeutic Antibodies" *Drug Design Reviews*, 2005, pp. 1-11.
Altschul, S. F. et al. "Basic Local Alignment Search Tool" *J Mol Biol.*, 1990, pp. 403-410, vol. 215.
Altschul, S.F. "A Protein Alignment Scoring System Sensitive at All Evolutionary Distances" *J Mol Evol.*, 1993, pp. 290-300, vol. 36.
Ames, R. S. et al. "Conversion of murine Fabs isolated from a combinatorial phage display library to full length immunoglobulins" *Journal of Immunological Methods*, 1995, pp. 177-186, vol. 184.
Angal, S. et al. "A Single Amino Acid Substitution Abolishes the Heterogeneity of Chimeric Mouse/Human (lgG4) Antibody" *Molecular Immunology*, 1993, pp. 105-108, vol. 30, No. 1.
Attar-Schneider, O. et al. "Multiple Myeloma and Bone Marrow Mesenchymal Stem Cells' Crosstalk: Effect on Translation Initiation" *Molecular Carcinogenesis*, 2016, pp. 1343-1354, vol. 55.
Azab, A. K. et al. "Hypoxia promotes dissemination of multiple myeloma through acquisition of epithelial to mesenchymal transition-like features" *Blood*, Jun. 14, 2012, pp. 5782-5794, vol. 119, No. 24.
Babcook, J. et al. "A novel strategy for generating monoclonal antibodies from single, isolated lymphocytes producing antibodies of defined specificities" *Proc. Natl. Acad. Sci. USA*, Jul. 1996, pp. 7843-7848, vol. 93, No. 15.
Badesch, D. B. et al. "Diagnosis and Assessment of Pulmonary Arterial Hypertension" *J Am Coll Cardiol.*, Jun. 30, 2009, pp. S55-S66, vol. 54, No. 1, Suppl. S.
Bostrom, M. P. G. et al. "The Clinical Use of Allografts, Demineralized Bone Matrices, Synthetic Bone Graft Substitutes and Osteoinductive Growth Factors: A Survey Study" *HSS Journal: The Musculoskeletal Journal of Hospital for Special Surgery*, 2005, pp. 9-18, vol. 1.
Brinkmann, U. et al. "Phage display of disulfide-stabilized Fv fragments" *Journal of Immunological Methods*, 1995, pp. 41-50, vol. 182.
Budd, D. C. et al. "Targeting TGFβ superfamily ligand accessory proteins as novel therapeutics for chronic lung disorders" *Pharmacology & Therapeutics*, 2012, pp. 279-291, vol. 135.
Burton, D. R. et al. "Human Antibodies from Combinatorial Libraries" *Advances in Immunology*, 1994, pp. 191-280, vol. 57.
Buza, J. A. et al. "Bone healing in 2016" *Clinical Cases in Mineral and Bone Metabolism*, 2016, pp. 101-105, vol. 13, No. 2.
Cahill, E. et al. "Gremlin Plays a Key Role in the Pathogenesis of Pulmonary Hypertension" *Circulation*, Feb. 21, 2012, pp. 920-930, vol. 125, No. 7.
Calon, A. et al. "Stromal gene expression defines poor-prognosis subtypes in colorectal cancer" *Nat Genet.*, Apr. 2015, pp. 320-329, vol. 47, No. 4, Online Methods, pp. 1-3.

(56) References Cited

OTHER PUBLICATIONS

Canalis, E. et al. "Gremlin1 is Required for Skeletal Development and Postnatal Skeletal Homeostasis" *J. Cell Physiol.*, 2012, pp. 269-277, vol. 227.
Chen, V. B. et al. "MolProbity: all-atom structure validation for macromolecular crystallography" *Acta Crystallographica Section D*, 2010, pp. 12-21, D66.
Chen, M.-H et al. "Expression of gremlin 1 correlates with increased angiogenesis and progression-free survival in patients with pancreatic neuroendocrine tumors" *J Gastroenterol*, 2013, pp. 101-108, vol. 48.
Chen, J. et al. "BAFF is involved in macrophage-induced bortezomib resistance in myeloma" *Cell Death Dis*, 2017, pp. 1-12, vol. 8, No. 11, e3161.
Cheong, C. M. et al. "Tetraspanin 7 (TSPAN7) expression is upregulated in multiple myeloma patients and inhibits myeloma tumour development in vivo" *Exp Cell Res*, 2015, pp. 24-38, vol. 332.
Chesi, M. et al. "Drug response in a genetically engineered mouse model of multiple myeloma is predictive of clinical efficacy" *Blood*, Jul. 12, 2012, pp. 376-385, vol. 120, No. 2.
Cho, T.-J et al. "Differential Temporal Expression of Members of the Transforming Growth Factor β Superfamily During Murine Fracture Healing" *Journal of Bone and Mineral Research*, Nov. 3, 2002, pp. 513-520, vol. 17, No. 3.
Ciuclan, L. et al. "Imatinib Attenuates Hypoxia-induced Pulmonary Arterial Hypertension Pathology via Reduction in 5-Hydroxytryptamine through Inhibition of Tryptophan Hydroxylase 1 Expression" *Am J Respir Crit Care Med.*, 2013, pp. 78-89, vol. 187, Issue 1.
Ciuclan, L, et al. "Treatment with Anti-Gremlin 1 Antibody Ameliorates Chronic Hypoxia/SU5416-Induced Pulmonary Arterial Hypertension in Mice" *Am J Pathol.*, Nov. 2013, pp. 1461-1473, vol. 183, No. 5.
Curran, S. P. et al. "Deletion of Gremlin1 increases cell proliferation and migration responses in mouse embryonic fibroblasts" *Cellular Signalling*, 2012, pp. 889-898, vol. 24, No. 4.
Dallas, S. L. et al. "Ibandronate Reduces Osteolytic Lesions but not Tumor Burden in a Murine Model of Myeloma Bone Disease" *Blood*, Mar. 1, 1999, pp. 1697-1706, vol. 93, No. 5.
Das, D. S. et al. "A novel hypoxia-selective epigenetic agent RRx-001 triggers apoptosis and overcomes drug resistance in multiple myeloma cells" *Leukemia*, 2016, pp. 2187-2197, vol. 30, No. 11.
Davis, H. et al. "Aberrant epithelial GREM1 expression initiates colonic tumorigenesis from cells outside the stem cell niche" *Nat Med.*, Jan. 2015, pp. 62-70, vol. 21, No. 1, Online Methods, pp. 1-3.
Dean, D. B. et al. "Distinct functionalities of bone morphogenetic protein antagonists during fracture healing in mice" *Journal of Anatomy*, 2010, pp. 625-630, vol. 216, No. 5.
Devereux, J. et al. "A comprehensive set of sequence analysis programs for the VAX" *Nucleic Acids Research*, 1984, pp. 387-395, vol. 12, No. 1.
Diamond, P. et al. "Targeted Disruption of the CXCL12/CXCR4 Axis Inhibits Osteolysis in a Murine Model of Myeloma-Associated Bone Loss" *J Bone Miner Res*, 2009, pp. 1150-1161, vol. 24, No. 7.
Dubowchik, G. M. et al. "Receptor-mediated and enzyme-dependent targeting of cytotoxic anticancer drugs" *Pharmacology and Therapeutics*, 1999, pp. 67-123, vol. 83.
Einhorn, T. A. et al. "Fracture healing: mechanisms and interventions" *Nat. Rev. Rheumatol.*, Jan. 2015, pp. 45-54, vol. 11.
Emsley, P. et al. "Features and development of Coot" *Acta Crystallographica Section D: Biological Crystallography*, 2010, pp. 486-501, D66, No. 4.
Fajardo, M. et al. "Levels of Expression for BMP-7 and Several BMP Antagonists May Play an Integral Role in a Fracture Nonunion: A Pilot Study" *Clinical Orthopaedics and Related Research*, Jul. 14, 2009, pp. 3071-3078, vol. 467, No. 12.
Farber, H. W. et al. "Pulmonary Arterial Hypertension" *The New England Journal of Medicine*, 2004, pp. 1655-1665, vol. 351.
Ferguson, C. et al. "Does adult fracture repair recapitulate embryonic skeletal formation?" *Mechanisms of Development*, 1999, pp. 57-66, vol. 87.
Fowler, J. A. et al. "Bone Marrow Stromal Cells Create a Permissive Microenvironment for Myeloma Development: A New Stromal Role for Wnt Inhibitor Dkk1" *Cancer Research*, 2012, pp. 2183-2189, vol. 72, No. 9.
Gasteiger, E. et al. "Protein Identification and Analysis Tools on the ExPASy Server" *The Proteomics Protocols Handbook*, Humana Press, ed. J. M. Walker, 2005, pp. 571-607.
Gazzerro, E. et al. "Skeletal Overexpression of Gremlin Impairs Bone Formation and Causes Osteopenia" *Endocrinology*, Feb. 1, 2005, pp. 655-665, vol. 146, No. 2.
Gazzerro, E. et al. "Conditional Deletion of Gremlin Causes a Transient Increase in Bone Formation and Bone Mass" *J. Biol. Chem.*, Oct. 26, 2007, pp. 31549-31557, vol. 282, No. 43.
Ghobrial, I. M. "Myeloma as a model for the process of metastasis: implications for therapy" *Blood*, Jul. 5, 2012, pp. 20-30, vol. 120, No. 1.
Gilbane, A. J. et al. "Impaired Bone Morphogenetic Protein Receptor II Signaling in a Transforming Growth Factor-β-Dependent Mouse Model of Pulmonary Hypertension and in Systemic Sclerosis" *Am J Respir Crit Care Med.*, Mar. 15, 2015, pp. 665-677, vol. 191, Issue 6.
Goulet, J. A. et al. "Autogenous Iliac Crest Bone Graft. Complications and Functional Assessment" *Clinical Orthopaedics and Related Research*, Jun. 1997, pp. 76-81, No. 339.
Guan, Y. et al. "Gremlin1 promotes carcinogenesis of glioma in vitro" *Clin Exp Pharmacol Physiol*, 2017, pp. 244-256, vol. 44, No. 2.
Harris, R. J. "Processing of C-terminal lysine and arginine residues of proteins isolated from mammalian cell culture" *Journal of Chromatography A*, 1995, pp. 129-134, vol. 705.
Hellstrom, K. E. et al. "Antibodies for Drug Delivery" *Controlled Drug Delivery*, 2nd Ed., Robinson et al., eds., 1987, pp. 623-653.
Henikoff, S. et al. "Amino acid substitution matrices from protein blocks" *Proc. Natl. Acad. Sci. USA*, Nov. 1992, pp. 10915-10919, vol. 89.
Hewett, D. R. et al. "DNA Barcoding Reveals Habitual Clonal Dominance of Myeloma Plasma Cells in the Bone Marrow Microenvironment" *Neoplasia*, Dec. 2017, pp. 972-981, vol. 19, No. 4.
Hideshima, T. et al. "Understanding multiple myeloma pathogenesis in the bone marrow to identify new therapeutic targets" *Nature Reviews Cancer*, Aug. 2007, pp. 585-598, vol. 7, No. 8.
Hjertner, O. et al. "Bone morphogenetic protein-4 inhibits proliferation and induces apoptosis of multiple myeloma cells" *Blood*, Jan. 15, 2001, pp. 516-522, vol. 97, No. 2.
Hochleitner, E. O. et al. "Characterization of a discontinuous epitope of the human immunodeficiency virus (HIV) core protein p24 by epitope excision and differential chemical modification followed by mass spectrometric peptide mapping analysis" *Protein Science*, 2000, pp. 487-496, vol. 9.
Holien, T. et al. "Bone morphogenetic proteins induce apoptosis in multiple myeloma cells by Smad-dependent repression of MYC" *Leukemia*, 2012, pp. 1073-1080, vol. 26, No. 5.
Holliger, P. et al. "Engineered antibody fragments and the rise of single domains" *Nature Biotech.*, Sep. 2005, pp. 1126-1136, vol. 23, No. 9.
Howe, J. R. et al. "Mutations in the SMAD4/DPC4 Gene in Juvenile Polyposis" *Science*, May 15, 1998, pp. 1086-1088, vol. 280, No. 5366.
Howe, J. R. et al. "Germline mutations of the gene encoding bone morphogenic protein receptor 1A in juvenile polyposis" *Nat Genet.*, Jun. 2001, pp. 184-187, vol. 28, No. 2.
Hu, K. et al. "Gremlin-1 suppression increases BMP-2-induced osteogenesis of human mesenchymal stem cells" *Molecular Medicine Reports*, 2017, pp. 2186-2194, vol. 15.
International Search Report and Written Opinion in International Application No. PCT/EP2019/053726, May 17, 2019, pp. 1-19.
International Search Report and Written Opinion in International Application No. PCT/GB2019/051699, Aug. 16, 2019, pp. 1-11.

(56) References Cited

OTHER PUBLICATIONS

Irshad, S. et al. "Bone morphogenetic protein and Notch signalling crosstalk in poor-prognosis, mesenchymal-subtype colorectal cancer" *J Pathol.*, 2017, pp. 178-192, vol. 242.
Isella, C. et al. "Stromal contribution to the colorectal cancer transcriptome" *Nat Genet.*, Apr. 2015, pp. 312-319, vol. 47, No. 4, Online Methods, pp. 1-4.
Jaeger, E. et al. "Hereditary mixed polyposis syndrome is caused by a 40-kb upstream duplication that leads to increased and ectopic expression of the BMP antagonist GREM1" *Nat Genet.*, Jun. 2012, pp. 699-703, vol. 44, No. 6, Online Methods, pp. 1-2.
Junghans, R. P. et al. "Anti-Tac-H, a Humanized Antibody to the Interleukin 2 Receptor with New Features for Immunotherapy in Malignant and Immune Disorders" *Cancer Res.*, Mar. 1, 1990, pp. 1495-1502, vol. 50.
Kabsch, W. "XDS" *Acta Crystallographica Section D, Biological Crystallography*, 2010, pp. 125-132, vol. D66.
Karagiannis, G. S. et al. "Enrichment map profiling of the cancer invasion front suggests regulation of colorectal cancer progression by the bone morphogenetic protein antagonist, gremlin-1" *Mol Oncol.*, 2013, pp. 826-839, vol. 7, No. 4.
Karagiannis, G. S. et al. "Bone morphogenetic protein antagonist gremlin-1 regulates colon cancer progression" *Biol Chem.*, 2015, pp. 163-183, vol. 396, No. 2.
Karlin, S. et al. "Applications and statistics for multiple high-scoring segments in molecular sequences" *Proc. Natl. Acad. Sci. USA*, Jun. 1993, pp. 5873-5877, vol. 90.
Kashmiri, S. V. S. et al. "SDR grafting—a new approach to antibody humanization" *Methods*, 2005, pp. 25-34, vol. 36.
Kettleborough, C. A. et al. "Isolation of tumor cell-specific single-chain Fv from immunized mice using phage-antibody libraries and the re-construction of whole antibodies from these antibody fragments" *Eur. J. Immunol.*, 1994, pp. 952-958, vol. 24.
Kim, M. et al. "Gremlin-1 Induces BMP-Independent Tumor Cell Proliferation, Migration, and Invasion" *PloS ONE*, Apr. 2012, pp. 1-8, vol. 7, Issue 4, e35100.
Kim, H. S. et al. "GREM1 is expressed in the cancer-associated myofibroblasts of basal cell carcinomas" *PloS ONE*, 2017, pp. 1-13, vol. 12, No. 3, e0174565.
Kohler, G. et al. "Continuous cultures of fused cells secreting antibody of predefined specificity" *Nature*, Aug. 7, 1975, pp. 495-497, vol. 256.
Koketsu, K. et al. "Gremlin, a Bone Morphogenetic Protein Antagonist, Is a Crucial Angiogenic Factor in Pituitary Adenoma" *Int J Endocrinol.*, 2015, pp. 1-7, Article ID 834137.
Kozbor, D. et al. "The production of monoclonal antibodies from human lymphocytes" *Immunology Today*, 1983, pp. 72-79, vol. 4, No. 3.
Krinner, E.-M. et al. "A human monoclonal IgG1 potently neutralizing the pro-inflammatory cytokine GM-CSF" *Mol. Immunol.*, Feb. 2007, pp. 916-925, vol. 44, No. 5.
Kyle, R. A. et al. "Multiple Myeloma" *N Engl J Med*, 2004, pp. 1860-1873, vol. 351, No. 18.
Laurila, R. et al. "The expression patterns of gremlin 1 and noggin in normal adult and tumor tissues" *Int J Clin Exp Pathol.*, 2013, pp. 1400-1408, vol. 6, No. 7.
Lavoz, C. et al. "Gremlin regulates renal inflammation via the vascular endothelial growth factor receptor 2 pathway" *J Pathol.*, 2015, pp. 407-420, vol. 236.
Lawson, M. A. et al. "Osteoclasts control reactivation of dormant myeloma cells by remodelling the endosteal niche" *Nat Commun.*, 2015, pp. 1-15, vol. 6, No. 8983.
Lewis, A. et al. "A Polymorphic Enhancer Near GREM1 Influences Bowel Cancer Risk through Differential CDX2 and TCF7L2 Binding" *Cell Rep.*, Aug. 21, 2014, pp. 983-990, vol. 8, No. 4.
Mccoy, A. J. et al. "Phaser crystallographic software" *J Appl Cryst .*, 2007, pp. 658-674, vol. 40.
Mitola, S. et al. "Gremlin is a novel agonist of the major proangiogenic receptor VEGFR2" *Blood*, Nov. 4, 2010, pp. 3677-3680, vol. 116, No. 18.
Mulvihill, M. S. et al. "Gremlin is Overexpressed in Lung Adenocarcinoma and Increases Cell Growth and Proliferation in Normal Lung Cells" *PloS ONE*, 2012, pp. 1-8, vol. 7, No. 8, e42264.
Murshudov, G. N. et al. "REFMAC5 for the refinement of macromolecular crystal structures" *Acta Crystallographica Section D: Biological Crystallography*, 2011, pp. 355-367, vol. D67.
Namkoong, H. et al. "The bone morphogenetic protein antagonist gremlin 1 is overexpressed in human cancers and interacts with YWHAH protein" *BMC Cancer*, 2006, pp. 1-13, vol. 6, No. 74.
Neufert, C. et al. "An inducible mouse model of colon carcinogenesis for the analysis of sporadic and inflammation-driven tumor progression" *Nat Protoc.*, 2007, pp. 1998-2004, vol. 2, No. 8.
Nolan, K. et al. "Structure of Neuroblastoma Suppressor of Tumorigenicity 1 (NBL1)" *J. Biol. Chem.*, Feb. 20, 2015, pp. 4759-4771, vol. 290, No. 8.
Noll, J. E. et al. "Myeloma plasma cells alter the bone marrow microenvironment by stimulating the proliferation of mesenchymal stromal cells" *Haematologica*, 2014, pp. 163-171, vol. 99, No. 1.
Noll, J. E. et al. "SAMSN1 Is a Tumor Suppressor Gene in Multiple Myeloma" *Neoplasia*, Jul. 2014, pp. 572-585, vol. 16, No. 7.
Noll, J. E. et al. "PTTG1 expression is associated with hyperproliferative disease and poor prognosis in multiple myeloma" *J Hematol Oncol.*, 2015, pp. 1-16, vol. 8, No. 106.
Persic, L. et al. "An integrated vector system for the eukaryotic expression of antibodies or their fragments after selection from phage display libraries" *Gene*, 1997, pp. 9-18, vol. 187.
Plaks, V. et al. "The Cancer Stem Cell Niche: How Essential Is The Niche in Regulating Sternness of Tumor Cells?" *Cell Stem Cell*, Mar. 5, 2015, pp. 225-238, vol. 16, No. 3.
Ponomarev, V. et al. "A novel triple-modality reporter gene for whole-body fluorescent, bioluminescent, and nuclear noninvasive imaging" *Eur J Nucl Med Mol Imaging*, 2004, pp. 740-751, vol. 31, No. 5.
Reineke, U. "Antibody Epitope Mapping Using Arrays of Synthetic Peptides" *Methods Mol Biol*, 2004, pp. 443-463, vol. 248.
Retter, I. et al. "VBASE2, an integrative V gene database" *Nucl. Acids Res.*, 2005, pp. D671-D674, vol. 33.
Riechmann, L. et al. "Reshaping human antibodies for therapy" *Nature*, Mar. 24, 1988, pp. 323-327, vol. 332.
Sato, T. et al. "Single Lgr5 stem cells build crypt-villus structures in vitro without a mesenchymal niche" *Nature*, May 14, 2009, pp. 262-265, vol. 459, No. 7244, Methods, p. 1.
Sato, K. et al. "Establishment of Reproducible, Critical-Sized, Femoral Segmental Bone Defects in Rats" *Tissue Eng Part C.*, 2014, pp. 1037-1041, vol. 20, No. 12.
Schmid, G. J. et al. "Fibroblast Growth Factor Expression During Skeletal Fracture Healing in Mice" *Developmental Dynamics*, 2009, pp. 766-774, vol. 238.
Scoville, D. H. et al. "Current View: Intestinal Stem Cells and Signaling" *Gastroenterology*, 2008, pp. 849-864, vol. 134, No. 3.
Search Report for GB1802486.9, Oct. 17, 2018, pp. 1-5.
Sebald, H.-J. et al. "Inhibition of endogenous antagonists with an engineered BMP-2 variant increases 2 efficacy in rat femoral defect healing" *Acta Biomaterialia*, Oct. 10, 2012, pp. 3816-3820, vol. 8, No. 10.
Sethi, A. et al. "Gremlin utilizes canonical and non-canonical TGFβ signaling to induce lysyl oxidase (LOX) genes in human trabecular meshwork cells" *Exp Eye Res.*, 2013, pp. 117-127, vol. 113.
Shoshkes-Carmel, M. et al. "Subepithelial telocytes are an important source of Wnts that supports intestinal crypts" *Nature*, May 10, 2018, pp. 242-246, vol. 557, Supplemental pp. 1-9.
Simonneau, G. et al. "Updated Clinical Classification of Pulmonary Hypertension" *J Am Coll Cardiol.*, Jun. 30, 2009, pp. S43-S54, vol. 54, No. 1, Suppl S.
Sneddon, J. B. et al. "Bone morphogenetic protein antagonist gremlin 1 is widely expressed by cancer-associated stromal cells and can promote tumor cell proliferation" *Proc Natl Acad Sci USA*, Oct. 3, 2006, pp. 14842-14847, vol. 103, No. 40.
Tamminen, J.A. et al. "Gremlin-1 associates with fibrillin microfibrils in vivo and regulates mesothelioma cell survival through transcription factor slug" *Oncogenesis*, 2013, pp. 1-13, vol. 2, e66.
Thomas, M. et al. "Activin-like kinase 5 (ALK5) Mediates Abnormal Proliferation of Vascular Smooth Muscle Cells from Patients

(56) References Cited

OTHER PUBLICATIONS with Familial Pulmonary Arterial Hypertension and Is Involved in the Progression of Experimental Pulmonary Arterial Hypertension Induced by Monocrotaline" *Am J Pathol.*, Feb. 2009, pp. 380-389, vol. 174, No. 2.

Thorpe, P.E. et al. "The Preparation and Cytotoxic Properties of Antibody-Toxin Conjugates" *Immunol. Rev.*, 1982, pp. 119-158, vol. 62.

Tomlinson, I. P. M. et al. "Multiple Common Susceptibility Variants near BMP Pathway Loci GREM1, BMP4, and BMP2 Explain Part of the Missing Heritability of Colorectal Cancer" *PLoS Genet.*, Jun. 2011, pp. 1-11, vol. 7, No. 6, e1002105.

Topol, L. Z. et al. "Identification of drm, a Novel Gene Whose Expression Is Suppressed in Transformed Cells and Which Can Inhibit Growth of Normal but Not Transformed Cells in Culture" *Mol Cell Biol*, Aug. 1997, pp. 4801-4810, vol. 17, No. 8.

Vande Broek, I. et al. "Extravasation and homing mechanisms in multiple myeloma" *Clin Exp Metastasis*, 2008, pp. 325-334, vol. 25, No. 4.

Vaughan, T. J. et al. "Human antibodies by design" *Nature Biotechnology*, Jun. 1998, pp. 535-539, vol. 16.

Verheyden, J. M. et al. "An Fgf/Gremlin inhibitory feedback loop triggers termination of limb bud outgrowth" *Nature*, Jul. 31, 2008, pp. 1-12, vol. 454, No. 7204.

Verma, R. et al. "Antibody engineering: Comparison of bacterial, yeast, insect and mammalian expression systems" *Journal of Immunological Methods*, 1998, pp. 165-181, vol. 216.

Wang, D.-J. et al. "The bone morphogenetic protein antagonist Gremlin is overexpressed in human malignant mesothelioma" *Oncology Reports*, 2012, pp. 58-64, vol. 27, No. 1.

Worthley, D. L. et al. "Gremlin 1 Identifies a Skeletal Stem Cell with Bone, Cartilage, and Reticular Stromal Potential" *Cell*, Jan. 15, 2015, pp. 269-284, vol. 160, Nos. 1-2.

Yin, Y. et al. "Overexpression of Gremlin promotes non-small cell lung cancer progression" *Tumour Biol*, 2016, pp. 2597-2602, vol. 37.

Yu, Y. Y. et al. "Immunolocalization of BMPs, BMP antagonists, receptors, and effectors during fracture repair" *Bone*, 2010, pp. 841-851, vol. 46.

Rudikoff, S. et al. "Single amino acid substitution altering antigen-binding specificity" *Proceedings of the National Academy of Sciences of the United States of America*, Mar. 1982, pp. 1979-1983, vol. 79, No. 6.

Janeway, Jr., C. A. et al. Immunology: the immune system in health and disease, 3rd ed., 1997, Garland Publications, Inc., Chapter 3, "Structure of the Antibody Molecule and Immunoglobulin Genes" pp. 3:1-3: 11.

Lederman, S. et al. "A Single Amino Acid Substitution in a Common African Allele of the CD4 Molecule Ablates Binding of the Monoclonal Antibody, OKT4" *Molecular Immunology*, 1991, pp. 1171-1181, vol. 28, No. 11.

Li, J. et al. "Temporal associations between interleukin 22 and the extracellular domains of IL-22R and IL-IOR2" *International Immunology*, 2004, pp. 693-711, vol. 4.

Panka, D. J. et al. "Variable region framework differences result in decreased or increased affinity of variant anti-digoxin antibodies" *Proceedings of the National Academy of Sciences of the United States of America*, May 1, 1988, pp. 3080-3084, vol. 85, No. 9.

Amit, A. G. et al. "Three-Dimensional Structure of an Antigen-Antibody Complex at 2.8 Å Resolution" *Science*, Aug. 15, 1986, pp. 747-753, vol. 233, No. 4765.

Harlow, E. et al. "Antibodies, A Laboratory Manual" *Cold Spring Harbor Laboratory*, 1988, Chapter 5, pp. 1-2.

Walsh, D.W. et al. "Extracellular BMP-antagonist regulation in development and disease: tied up in knots" *Trends in Cell Biology*, Feb. 24, 2010, pp. 244-256, vol. 20, No. 5.

Torre, L.A. et al. "Global Cancer in Women: Burden and Trends" *Cancer Epidemiol Biomarkers Prev*, Feb. 21, 2017, pp. 444-457, vol. 26, No. 4.

"Breast Cancer Facts & Figures 2015-2016" *American Cancer Society*, 2015, 2 cover pages and pp. 1-40.

Mittal, S. et al. "The breast tumour microenvironment—role in cancer development, progression and response to therapy" *Expert Review of Molecular Diagnostics*, 2018, pp. 1-34, vol. 18, No. 3.

Merino, R. et al. "The BMP antagonist Gremlin regulates outgrowth, chondrogenesis and programmed cell death in the developing limb" *Development*, 1999, pp. 5515-5522, vol. 126.

Schuetz, C. S. et al. "Progression-Specific Genes Identified by Expression Profiling of Matched Ductal Carcinomas In situ and Invasive Breast Tumors, Combining Laser Capture Microdissection and Oligonucleotide Microarray Analysis" *Cancer Research*, May 15, 2006, pp. 5278-5286, vol. 66, No. 10.

Kuchimaru, T. et al. "A reliable murine model of bone metastasis by injecting cancer cells through caudal arteries" *Nature Communications*, 2018, pp. 1-7, vol. 9, No. 2981.

Kager, L. et al. "Novel insights and therapeutic interventions for pediatric osteosarcoma" *Future Oncol.*, Sep. 21, 2016, pp. 357-368, vol. 13, No. 4.

Kresse, S. H. et al. "Integrative Analysis Reveals Relationships of Genetic and Epigenetic Alterations in Osteosarcoma" *PLoS ONE*, Nov. 7, 2012, pp. 1-20, vol. 7, Issue 11, e48262.

Groeneveld, E. H. J. et al. "Bone morphogenetic proteins in human bone regeneration" *European Journal of Endocrinology*, 2000, pp. 9-21, vol. 142.

Zysk, A. et al. "Zoledronate Enhances the Cytotoxicity of Gamma Delta T Cell Immunotherapy in an Orthotopic Mouse Model of Osteolytic Osteosarcoma" *J Cancer Sci Ther*, 2018, pp. 262-266, vol. 10, No. 9.

Tian, H. et al. "Bone morphogenetic protein-2 and tumor growth: Diverse effects and possibilities for therapy" *Cytokine & Growth Factor Reviews*, 2017, pp. 73-91, vol. 34.

Tian, H. et al. "Bone Morphogenetic Protein-2 Promotes Osteosarcoma Growth by Promoting Epithelial-Mesenchymal Transition (EMT) Through the Wnt/β-Catenin Signaling Pathway" *Journal of Orthopaedic Research*, Jul. 2019, pp. 1638-1648.

Nguyen, A. et al. "Roles of bone morphogenetic protein signaling in osteosarcoma" *International Orthopaedics (SICOT)*, 2014, pp. 2313-2322, vol. 38.

Rycaj, K. et al. "Cellular determinants and microenvironmental regulation of prostate cancer metastasis" *Semin Cancer Biol.*, Jun. 2017, pp. 1-35, vol. 44.

Grillo, E. et al. "Monomeric gremlin is a novel vascular endothelial growth factor receptor-2 antagonist" *Oncotarget*, May 11, 2016, pp. 35353-35368, vol. 7, No. 23.

Gandaglia, G. et al. "Impact of the Site of Metastases on Survival in Patients with Metastatic Prostate Cancer" *European Urology*, 2015, pp. 325-334, vol. 68.

Armstrong, A. J. et al. "A Contemporary Prognostic Nomogram for Men with Hormone-Refractory Metastatic Prostate Cancer: A TAX327 Study Analysis" *Clin Cancer Res*, Nov. 1, 2007, pp. 6396-6403, vol. 13, No. 21.

Muñoz, J. et al. "The Lgr5 intestinal stem cell signature: robust expression of proposed quiescent '+4' cell markers" *The EMBO Journal*, 2012, pp. 3079-3091, vol. 31, No. 14.

Moser, A. R. et al. "The Min (Multiple Intestinal Neoplasia) Mutation: Its Effect on Gut Epithelial Cell Differentiation and Interaction with a Modifier System" *The Journal of Cell Biology*, Mar. 1992, pp. 1517-1526, vol. 116, No. 6.

Shibata, H. et al. "Rapid Colorectal Adenoma Formation Initiated by Conditional Targeting of the Apc Gene" *Science*, Oct. 3, 1997, pp. 120-123, vol. 278.

El Marjou, F. et al. "Tissue-Specific and Inducible Cre-Mediated Recombination in the Gut Epithelium" *genesis*, 2004, pp. 186-193, vol. 39.

Rudling, R. et al. "A simple device to rapidly prepare whole mounts of murine intestine" *Cell Prolif.*, 2006, pp. 415-420, vol. 39.

Sato, T. et al. "Long-Term Expansion of Epithelial Organoids From Human Colon, Adenoma, Adenocarcinoma, and Barrett's Epithelium" *Gastroenterology*, Nov. 2011, pp. 1762-1772, vol. 141, No. 5.

Van Cutsem, E. et al. "Metastatic colorectal cancer: ESMO Clinical Practice Guidelines for diagnosis, treatment and follow-up" *Annals of Oncology*, Sep. 2014, pp. ii1-ii9, vol. 25 (Supplement 3).

(56) References Cited

OTHER PUBLICATIONS

United Kingdom Search Report Application No. GB1809946.5, Jan. 24, 2019, pp. 1-4.
Phillips, S. et al. "The Association of Rheumatoid Arthritis and Non-Union of Traumatic Fractures" *Orthopaedic Proceedings*, 2009, pp. 1-2, vol. 91-B, Supp. 1.
Rabia, L. A. et al. "Understanding and overcoming trade-offs between antibody affinity, specificity, stability and solubility" *Biochemical Engineering Journal*, Sep. 15, 2018, pp. 1-23, vol. 137.

FIG. 12A Non-contact
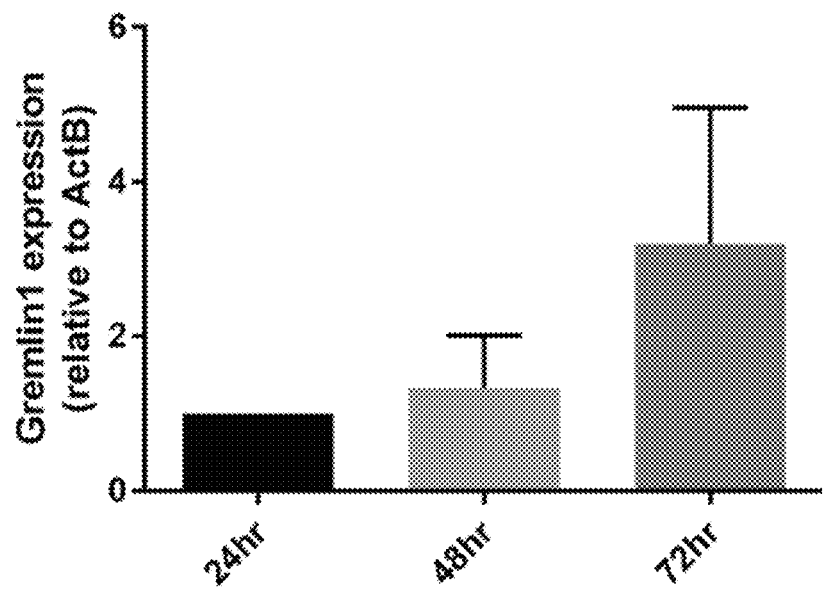
FIG. 12B Contact
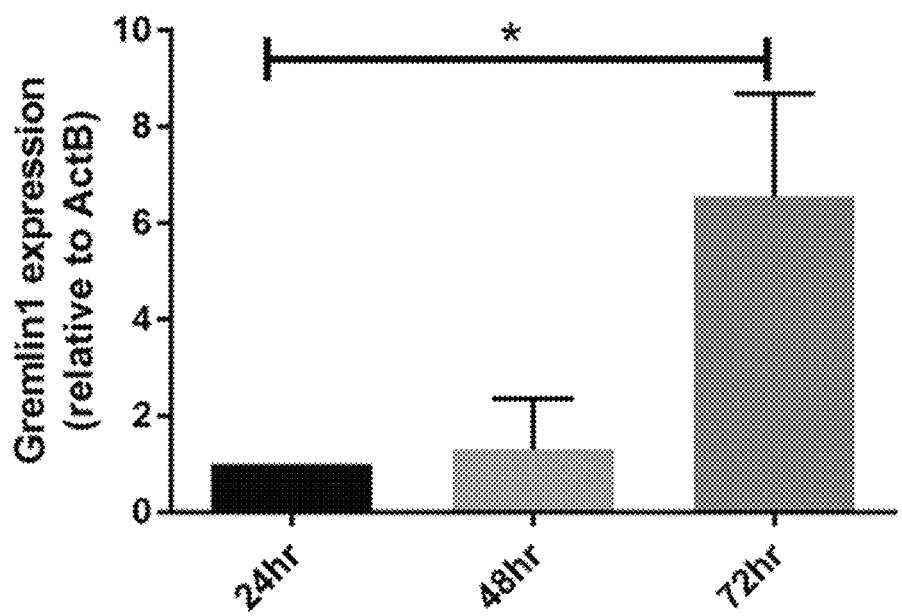

Pancreatic Ductal Adenocarcinoma – Yeh dataset (132 tumours) GEO gse21501, PMID 20644708

Red line – Grem1 low
Blue line – Grem1 high

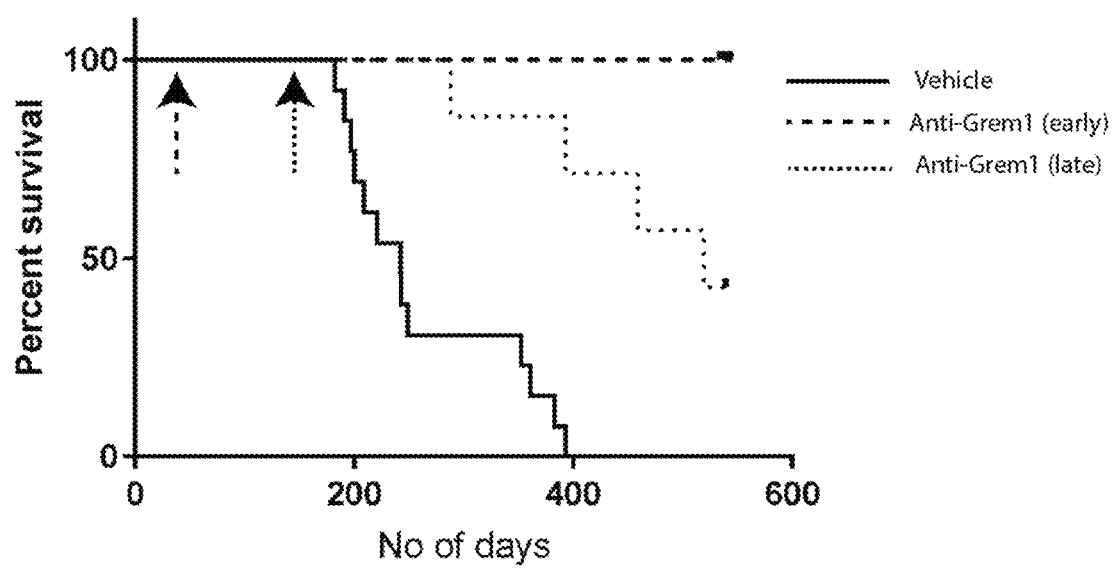
FIG. 40A *Vil1-Grem1* model
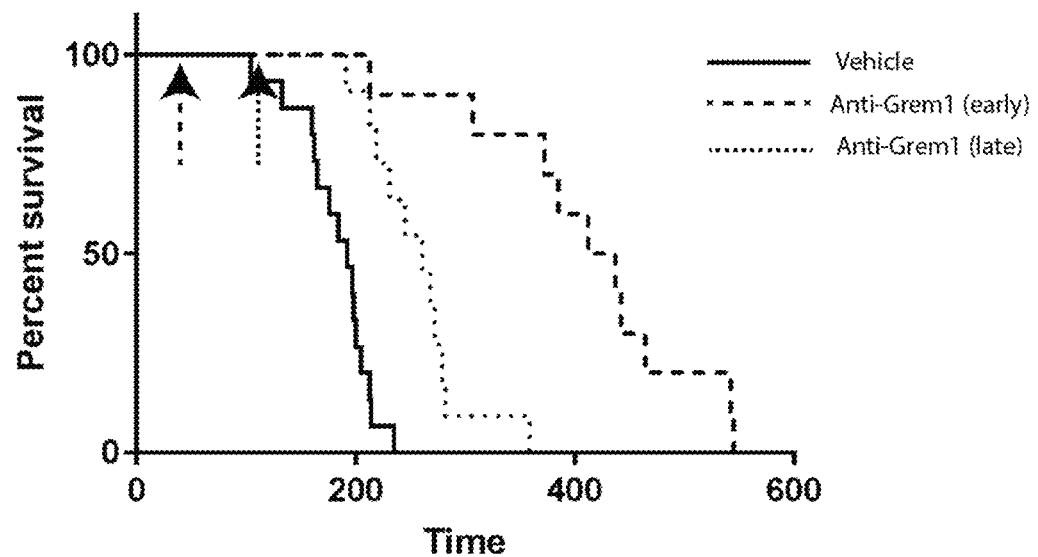
FIG. 40B *ApcMin* model

Ab101.4

Ab73263

GREMLIN-1 ANTAGONIST FOR THE PREVENTION AND TREATMENT OF CANCER

CROSS-REFERENCE TO RELATED APPLICATION

This application is the U.S. national stage application of International Patent Application No. PCT/GB2019/051699, filed Jun. 18, 2019.

STATEMENT REGARDING SEQUENCE LISTING

The Sequence Listing for this application is labeled "Seq-List.txt" which was created on Nov. 25, 2020 and is 85,748 bytes. The entire content of the sequence listing is incorporated herein by reference in its entirety.

FIELD OF THE INVENTION

The present invention relates to an anti-GREM1 antagonist for use in a method of treatment of cancer. The cancer is typically a solid cancer having a stroma, typically having stromal GREM1 overexpression. The cancer may have epithelial GREM1 overexpression. The present invention further relates to combination therapy with a GREM1 antagonist and an additional anti-cancer (such as chemotherapeutic) agent, and related compositions. The present invention also relates to detection, prognosis and selections of treatment for cancer based on stromal GREM1 overexpression.

BACKGROUND TO THE INVENTION

Gremlin-1 (also known as Drm and CKTSF1B1 and GREM1) is a 184 amino acid glycoprotein which forms part of the DAN family of cystine-knot secreted proteins (along with Cerberus and Dan amongst others). GREM1 binds and inhibits the ability of BMP-2, 4, and 7 to signal along with a documented pro-angiogenic role possibly through agonism of VEGFR2. The main role of GREM1 is during development, in which it is vital during kidney formation and during limb bud formation. These vital roles make GREM1 homozygous knock-outs embryonic lethal in mice.

In adulthood, increased levels of GREM1 have been associated with idiopathic pulmonary fibrosis and pulmonary arterial hypertension in which BMP2, 4 and 7 signalling is reduced with an associated rise in TGFβ levels. In both diabetic and chronic allograft nephropathy, GREM1 expression has been correlated with fibrosis score.

Increased levels of GREM1 have also been associated inter alia with scleroderma, diabetic nephropathy, glioma, head and neck cancer, prostate cancer and colorectal cancer (Sneddon et al; Guan et al). GREM1 has been shown to activate cancer cell invasion and proliferation in vitro and is thought to play a role in uterine, cervix, lung, ovary, kidney, breast, colon, pancreatic and sarcoma carcinomas.

There is a need to identify effective therapies for use in treatment and prevention of cancer.

SUMMARY OF THE INVENTION

The inventors have surprisingly shown that GREM1 antagonists are effective therapeutic and preventative agents against neoplasia with stromal and/or epithelial GREM1 overexpression, including colorectal cancer and multiple myeloma. It is envisaged by the inventors based on these results that GREM1 antagonists will be of general utility in treatment and prevention of cancer, including other cancers having stromal GREM1 overexpression. The in vivo results provided herein illustrate long-term prevention of induction of neoplasia in various mouse tumour models by administration of a GREM1 antagonist, and significant therapeutic impact on existing tumours by administration of a GREM1 antagonist. The inventors' findings thus provide for a new approach to prevention and treatment of cancer, including in cancers resistant to standard chemotherapeutic agents.

Thus, in a first aspect of the present invention there is provided an anti-GREM1 antagonist for use in a method for the treatment or prevention of a cancer.

In a further aspect of the invention, there is provided an anti-cancer agent for use in a method for the treatment of a cancer wherein the method comprises separate, sequential or simultaneous administration of an anti-GREM1 antagonist.

In another aspect of the invention, there is provided a method of treating a cancer comprising administering a therapeutically effective amount of an anti-GREM1 antagonist to a subject in need thereof.

In yet another aspect of the invention, there is provided a composition or kit comprising an anti-GREM1 antagonist and an additional anti-cancer agent.

In a further aspect of the invention, there is provided a method for detecting cancer in a patient, the method comprising measuring stromal expression of GREM1 in the patient, wherein stromal overexpression of GREM1 indicates that the patient comprises a cancer.

In yet a further aspect of the invention, there is provided a method for prognosing a cancer in a patient, the method comprising determining whether or not the cancer comprises stromal overexpression of GREM1, wherein stromal overexpression of GREM1 in the cancer indicates that the patient has a worse prognosis than in the situation of normal stromal expression of GREM1.

In another aspect of the invention, there is provided a method for determining whether or not a patient having or suspected of having or being at risk of developing cancer is likely to respond to treatment with a chemotherapeutic agent, which method comprises measuring stromal expression of GREM1 in the patient, and thereby predicting whether or not the patient is likely to respond to treatment with the chemotherapeutic agent.

In yet another aspect of the invention, there if provided a method for determining whether or not a patient having or suspected of having or being at risk of developing cancer is likely to respond to treatment with a GREM1 antagonist, the method comprising measuring stromal expression of GREM1 in the patient, and thereby predicting whether or not the patient is likely to respond to treatment with the GREM1 antagonist.

BRIEF DESCRIPTION OF THE FIGURES

FIG. 9A. Grem1 ISH on wildtype and Villin-CreERT2; Apc fl/fl mice showing profound upregulation of stromal Grem1 in response to acute epithelial Apc loss. FIG. 9B. Transgenic deletion of stromal Grem1 in ApcMin mice reduces mutant Apc tumour burden at 285 days. FIG. 9C. Prolonged treatment with anti-Grem1 antibody (30 mg/kg/week) reduces ApcMin tumour burden and prolongs animal lifespan.

(FIG. 11B) Grem1 expression in the BM stroma isolated from the hind limbs of tumour-bearing mice was correlated with the tumour burden in the respective limbs, as detected by BLI (Pearson Correlation; p<0.05, R2=0.414).

FIGS. 12A-12B. Grem1 expression was analysed in the murine, bone-marrow derived stromal OP9 cell lines following 24, 48 and 72 hr co-culture with (FIG. 12A) 5TGM1.Bmx1 cells, co-cultured in the upper 3 μm transwell (FIG. 12B) 5TGM1.parental cells, plated directly onto the adherent stromal cells. For contact culture, OP9.GFP+ cells were sorted by FACS from the 5TGM1.parental MM PCs for analysis of Grem1 expression via real-time PCR. A significant increase in Grem1 expression was observed in the OP9 stromal cells following 72 hrs of co-culture. Data presented as mRNA expression relative to ActB and normalised to media only control. (mean±SEM of 3 replicate experiments, *P<0.05, t-test).

(FIG. 15A) C57Bl6/KaLwRij mice injected with 5TGM1.Bmx1 MM PCs and subsequently treated with a Grem1-neutralising antibody displayed a significant reduction in overall tumour burden compared to mice treated with an IgG control after 4 weeks as shown by BLI. Mean±SEM, n=13 mice per group **P<0.0001, one-way ANOVA. (FIG. 15B) SPEP was performed on mice bled at week 4 post-tumour cell injection. M-spike intensity relative to serum albumin was used a measure of disease burden. Mice treated with the anti-Grem1 antibody had significantly lower M-spike intensity compared to mice receiving the IgG control treatment. Mean±SD, P<0.01, t-test. (C) Representative BLI ventral scan images for IgG control and Grem1-neutralising antibody treated mice.

(FIG. 18A) C57Bl6/KaLwRij mice that received treatment of Grem1-neutralising antibody (Ab7326) prior to inoculation with 5TGM1.Bmx1 MM PCs displayed a significant reduction in overall tumour burden at 4 weeks post-cell inoculation, compared to mice treated with that received an IgG control (Ab101.4), as shown by BLI. Mean±SEM, n=7-8 mice per group **P<0.0001, one-way ANOVA. (FIG. 18B) SPEP was performed on mice bled at week 4 post-tumour cell injection. M-spike intensity relative to serum albumin was used a measure of disease burden. Mice treated with the anti-Grem1 antibody had significantly lower M-spike intensity compared to mice receiving the IgG control treatment. Mean±SD, P<0.0001, t-test. (FIG. 18C) Representative BLI ventral scan images for IgG control and Grem1-neutralising antibody treated mice 4-weeks post-tumour cell inoculation.

(FIG. 31A) Vil1-Grem1 mice. (FIG. 31B) Vil1-Grem1;Apc$^{Min}$ mice.

(FIG. 32A) Kaplan-Meier plot showing that prolonged treatment with anti-Grem1 antibody (30 mg/kg/week) reduces Apc$^{Min}$ tumour burden and prolongs animal lifespan. (FIG. 32B) In situ hybridization for Apc$^{Min}$ and Grem1.

(FIG. 35A) Kaplan-Meier curve denoting survival of mice. (FIG. 35B) Plot showing colonic polyp burden. (FIG. 35C). Plot showing colonic polyp size.

(FIG. 38A) Wnt 5A; (FIG. 38B) Wnt 2B; and (FIG. 38C) Foxl1 telocyte marker expression using ISH in wild-type and Vil1-Grem1 mice and quantified post antibody treatment.

FIGS. 40A-40B. Kaplan Meier survival curves for preventative therapy and treatment of established polyposis. Arrows indicate treatment initiation time point in treated groups. (FIG. 40A) Vil1-Grem1 mice. Vehicle (solid line): median survival 242 days (n=13); anti-Grem1 therapy late-stage treatment (dotted line): 519 days, n=7; anti-Grem1 early stage treatment (dashed line): 540 days, (n=11) log rank p<0.01 for both groups. (FIG. 40B) Apc$^{Min}$ mice. Vehicle (solid line): median survival: 192 days (n=15); anti-Grem1 late-stage treatment (dotted line): 261 days (n=11); anti-Grem1 early stage treatment (dashed line): 424.5 days, (n=10), log rank p<0.01 for both groups.

(FIG. 41A) IVIS BLI imaging of mice at the conclusion of the study (at day 13) showed significantly lower tumour burden in Ab7326-treated mice compared with Ab101.4-treated mice. Mean±SEM, Student's t-test, Ab101.4; n=12, Ab7326; n=13, *p<0.05. (FIG. 41B) Representative BLI images at day 13.

(FIG. 42A) Plot showing results of ex vivo BLI imaging for tumour burden in the lungs of AB7326 treated mice compared to Ab101.4 treated mice. (FIG. 42B) Plot showing results of BLI imaging for liver tumour burden in Ab7326 and Ab101.4 treatment groups. Mean±SEM, Student's t-test, Ab101.4; n=6, Ab7326; n=7, *p<0.05.

(FIG. 46B) ex vivo liver BLI; (FIG. 46C) ex vivo hindlimb; and (FIG. 46D) ex vivo lung. Mean±SEM, Student's t-test, n=5-7, *p<0.05, p<0.01, *p<0.001.

DETAILED DESCRIPTION OF THE INVENTION

Figure 1:
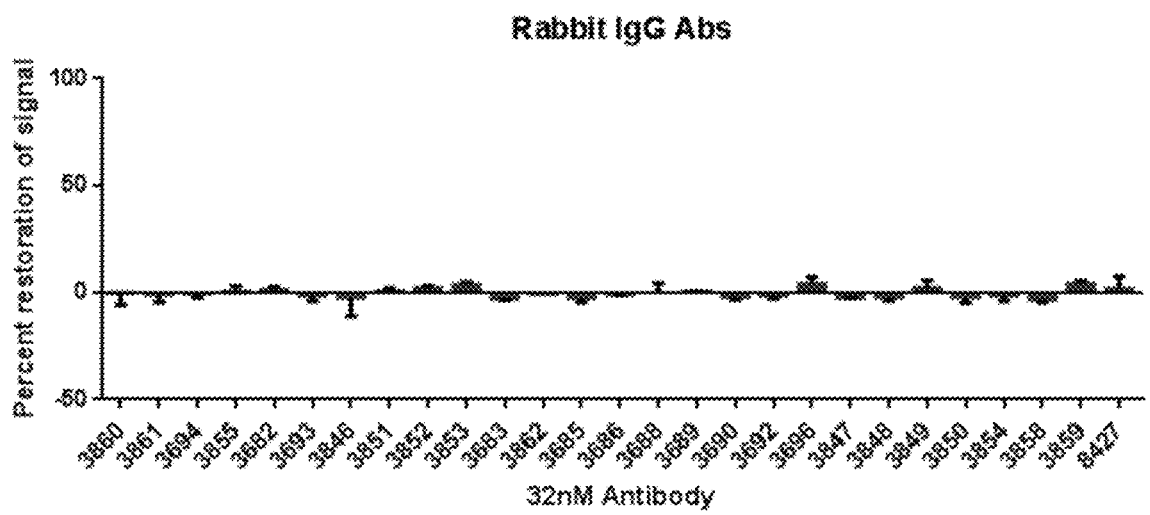
FIG. 1. Percentage restoration of signal for the immunisation derived antibodies in the HEK-ID1 reporter gene assay.

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "an inhibitor" includes two or more such inhibitors, or reference to "an oligonucleotide" includes two or more such oligonucleotide and the like.

All publications, patents and patent applications cited herein, whether supra or infra, are hereby incorporated by reference in their entirety.

Treatment and Prevention of Cancer

The present invention provides an anti-GREM1 antagonist for use in a method of prevention or treatment of cancer. The cancer typically has a stroma (such as a desmoplastic stroma), typically having stromal GREM1 overexpression. The cancer may additionally or alternatively have epithelial GREM1 overexpression or be GREM1-initiated.

Cancer

The cancer may be any cancer or tumour having a stroma, typically a desmoplastic stroma. The cancer may be any cancer or tumour which is GREM1-initiated. The cancer may be any cancer where stromal and/or epithelial GREM1 overexpression is observed. The cancer or tumour may have stromal GREM1 overexpression and no epithelial GREM1 overexpression. The cancer or tumour may have epithelial GREM1 overexpression and no stromal GREM1 overexpression. In preferred embodiments, the cancer or tumour has an overexpression of GREM1 in the desmoplastic stroma.

The cancer or tumour may be a solid tumour. The solid tumour may have a desmoplastic stroma.

Particularly preferred cancers that may be treated include colorectal cancer, multiple myeloma, pancreatic cancer, bladder cancer, breast cancer, lung cancer, stomach cancer, duodenal cancer, oesophageal cancer, prostate cancer, head and neck cancer, endometrial cancer, liver cancer, spleen cancer, bone-resident cancer, and osteosarcoma. The cancer that may be treated may be intestinal cancer, colon cancer, or rectal cancer. The cancer to be treated may be a disseminated cancer, for example a metastatic cancer. A disseminated cancer should be understood as one that has spread from its initial site of origin within the body. For example, a disseminated cancer could be one that originated in the bone marrow, colon, prostate, or breast tissue of a patient but has spread to e.g. the patient's liver or lung.

The GREM1 antagonist may also be used to prevent the dissemination of a cancer.

The GREM1 antagonist may be used to prevent polyposis associated with a cancer.

Grading systems are used in cancer biology and medicine to categorize cancer cells with respect to their lack of cellular differentiation. This reflects the extent to which the cancer cells differ in morphology from healthy cells found in the tissue from which the cancer cell originated. The grading system can be used to provide an indication of how quickly a particular cancer might be expected to grow. Typically used grades of cancer are Grades (G) X and 1 to 4. GX indicates that the cancer grade cannot be assessed. G1 (low grade) cancer cells have a similar morphology to normal, healthy, cells (i.e. they are well differentiated) and would be expected to grow slowly, and are less likely to spread. G2 (intermediate grade) cancer cells are moderately differentiated, i.e. they appear more abnormal and would be expected to grow slightly faster than G1 cells. G3 (high grade) cancer cells have a very different morphology compared to normal cells (i.e. they are poorly differentiated) and would be expected to grow faster than G1 and G2 cells. G4 (high grade) cancer cells are undifferentiated (also referred to as anaplastic) and would be expected to have the highest capacity for proliferation.

Cancer grading is different to cancer staging, which gives an indication of how a cancer might spread. A common cancer staging system has five stages, namely Stage 0: cancer cells in situ (i.e. located in their normal tissue); Stage I: cancers are localized to one part of the body; Stage II: cancers are locally advanced; Stage III: cancers are also locally advanced (whether a cancer is designated as Stage II or Stage III can depend on the specific type of cancer); and Stage IV: cancers have often metastasized, or spread to other organs or throughout the body.

A person skilled in the art knows how to determine the grade and/or stage of a cancer. In one embodiment, the invention relates to use of an anti-GREM1 antagonist for the treatment and/or prevention of an established cancer. In one embodiment, the cancer is an established cancer. An established cancer may be a high grade cancer, for example a G3 or a G4 cancer. An established cancer may be a cancer that is Stage II or above. An established cancer may be a Stage III or a stage IV cancer. In one embodiment, the established cancer is a Stage IV cancer that has metastasized.

Colorectal Cancer

The invention relates in one preferred aspect to prevention or treatment of colorectal cancer. By way of background, the intestinal mucosa is a complex ecosystem and the epithelium has an inter-dependent relationship with its microenvironment, particularly the underlying stroma. Mesenchymal-epithelial crosstalk is intimately involved in regulating homeostasis and is dynamically altered in intestinal regeneration and cancer. Cell-signalling networks are the effector pathways of inter-compartmental crosstalk and control epithelial cell fate determination, but can be co-opted and corrupted by the tumour microenvironment in colorectal cancer.

The current chemotherapeutic management of colorectal cancer has not substantially changed for the last 20 years and is predominantly based around the use of combination cytotoxic agents (such as FOLFOX and FOLFIRI regimens, see Worldwide Website: cancerresearchuk.org/about-cancer/cancer-in-general/treatment/cancer-drugs/drugs) against the proliferating tumour epithelium, and resistance to these epithelial targeted agents may arise. It is now more important than ever to identify new therapies for use in colorectal cancer.

A particularly preferred cancer or tumour for treatment is thus colorectal cancer or a colorectal tumour. An especially preferred form of colorectal cancer for treatment is colorectal cancer that is characterised by having overexpression of GREM1 in stromal cells, i.e. stromal GREM1 overexpression. The stromal cells may be cancer associated fibroblasts. A colorectal cancer with stromal GREM1 overexpression may display no epithelial GREM1 overexpression. A colorectal cancer with stromal GREM1 overexpression may comprise stromal Foxl1 overexpression. A particularly suitable form of colorectal cancer for treatment is colorectal cancer that is a mesenchymal subtype colorectal cancer, also described as CMS4 (Guinney et al, Nat Med 2015). Any other subtypes of colorectal cancer may also be treated including any of CMS1, CMS2 and CMS3 as described in Guinney et al supra. A colorectal cancer as described herein may be a proximal colorectal cancer (or a proximal colorectal tumour). The proximal colon is the region of the large bowel upstream of the splenic flexure, meaning the caecum, the ascending colon and the transverse colon. Cancers or tumours in this region are also referred to as right-sided cancers or tumours. The invention may concern treating right-sided colorectal cancer or a right-sided colorectal tumour.

The colorectal cancer may be distal colorectal cancer (or a distal colorectal tumour). The distal colon is the region of the large bowel downstream of the splenic flexure, meaning the descending colon, the sigmoid colon and the rectum. Cancers or tumours in this region are also referred to as left-sided cancers or tumours. The invention may concern treating left-sided colorectal cancer or a left-sided colorectal tumour. A cancer having stromal overexpression of GREM1 may preferably be a sporadic cancer. The sporadic cancer may be caused by a somatic mutation. The sporadic cancer may be caused by a carcinogenic agent. A sporadic cancer is not due to an inherited genetic mutation. The sporadic cancer may cause the stromal overexpression of GREM1. Proliferation of the sporadic cancer may be dependent on the stromal overexpression of GREM1 in the cancer.

At least three single nucleotide polymorphisms (SNPs) close to GREM1 are independently associated with risk of colorectal cancer (CRC) in white northern Europeans, and probably in other ethnic groups (Tomlinson et al, PLos Genet, 2011). There is a direct link with GREM1 expression and it is likely that the other SNPs have similar effects. In addition, two common SNPs near BMP2, two near BMP4 and one near BMP7 influence the expression of BMP ligands and affect CRC risk. Thus, the cancer may comprise one or more of the above SNPs.

A further type of cancer or tumour for treatment according to the invention is one that exhibits overexpression of GREM1 in epithelial cells. The overexpression of GREM1 in epithelial cells may cause the cancer. Proliferation of the cancer may be dependent on the epithelial overexpression of GREM1. Thus, the cancer may be of epithelial origin. The cancer is typically colorectal cancer or duodenal cancer. Preferably, the cancer is colorectal cancer. The cancer may be GREM1-initiated. By GREM1-initiated it is meant that a mutagenic event enhancing activity or expression of GREM1 is causative of the cancer. Such a cancer may be due to an inherited genetic mutation. The cancer may thus be a familial cancer (see below).

A preferred type of colorectal cancer for treatment may be resistant to one or more known anti-cancer agents (such as chemotherapeutic agents), as described further below.

The colorectal cancer may be a disseminated colorectal cancer. The colorectal cancer may be a metastatic colorectal cancer. The colorectal cancer may be metastatic colorectal cancer of the lung. The colorectal cancer may be metastatic colorectal cancer of the liver. The colorectal cancer may be metastatic colorectal cancer of the bone.

The colorectal cancer may be characterised by stromal overexpression of the Foxl1. The colorectal cancer may be characterised by stromal overexpression of one or more Wnt ligand. For example, the colorectal cancer may be characterised by stromal overexpression of Wnt5A and/or Wnt2B. A colorectal cancer may be particularly suitable for prevention or treatment using a GREM1 antagonist if said colorectal cancer has stromal overexpression of Foxl1 and/or a Wnt ligand e.g. Wnt5A or Wnt2B.

Familial Cancer

Familial cancers include cancers resulting from a mutation or mutations in the GREM1 encoding gene, or any other mutation affecting expression of the GREM1 gene. The autosomal dominant condition Hereditary Mixed Polyposis Syndrome (HMPS) is caused by a 40 kb duplication upstream of GREM1 that results in a pathological compartment expression switch from a restricted mesenchymal gradient to ectopic GREM1 gene expression throughout the epithelium.

The subject to be treated with anti-GREM1 antagonist may have been previously determined as being at risk of developing a familial cancer. For example, the subject may have been determined as being at risk on the basis of their family history and/or because the subject carries a mutation in a gene known to give rise to, or increase the risk of developing, the familial cancer.

The familial cancer may be Lynch syndrome, which is also referred to as hereditary nonpolyposis colorectal cancer (HNPCC). The familial cancer may be familial adenomatous polyposis (FAP).

The present inventors have demonstrated that use of an anti-GREM1 antibody substantially increases the survival of Apc$^{Min}$ model mice (see e.g. Examples 11, 19, and 23 below). Apc$^{Min}$ mice are a well established model for familial adenomatous polyposis (FAP). Thus, patients or subjects suffering with FAP may be particularly suitable for treatment with the anti-GREM1 antagonist. The familial cancer to be treated or prevented with the anti-GREM1 antagonist (e.g. an anti-GREM1 antibody) may be FAP. A subject who has previously suffered from FAP may be preventatively administered with an anti-GREM1 antagonist, e.g. to prevent relapse. A subject who has not previously suffered from FAP but has been previously determined to be at risk of developing FAP may be preventatively administered with an anti-GREM1 antagonist. A subject may have been determined as being at risk of developing FAP because it has been found that the subject carries a deleterious mutation in their Apc gene.

Multiple Myeloma

The invention relates in another preferred aspect to treatment or prevention of multiple myeloma. Multiple Myeloma (MM) is a haematological malignancy characterised by the clonal proliferation of plasma cells (PCs) within the bone marrow (BM). It is well known that the BM supports tumour growth in MM, with bi-directional signalling between the tumour cells and the BM critical for the continued growth, spread and survival of the MM PCs. Cellular and non-cellular BM components exert different effects upon the growth and spread of MM PC. While recent studies have identified components of the BM that play a role in disease progression, and therapies targeting these have been developed, the standard-of-care treatments in MM still rely primarily on targeting the tumour cells themselves. While such therapies are effective in prolonging patient survival, due to the large role the BM plays in the growth, spread, survival and drug resistance of MM cells, more effective therapies that target this important aspect of disease are needed. Indeed, MM is a largely incurable disease, with disease relapse a key issue faced in effectively treating this disease.

The invention accordingly is also preferably directed to treatment or prevention of multiple myeloma. Multiple myeloma typically comprises the presence of more than one mass of plasma cells within the bone marrow. Multiple myeloma is thus typically associated with aberrant proliferation of plasma cells in the bone marrow. An especially preferred form of multiple myeloma for treatment is characterised by having overexpression of GREM1 in the bone marrow. The multiple myeloma may therefore comprise stromal GREM1 overexpression. The stromal GREM1 overexpression may be present in the compact bone compartment of the bone. The stromal GREM1 overexpression may reflect an increased number of stromal cells, or an increase in the expression levels of GREM1 within existing GREM1-expressing stromal cells. The bone marrow may comprise osteochrondroreticular (OCR) stem cells. The stromal cells overexpressing GREM1 may comprise OCR stem cells. A preferred type of multiple myeloma for treatment may be resistant to one or more known anti-cancer agents (such as chemotherapeutic agents), as described further below.

Breast Cancer

The invention relates in another preferred aspect to treatment or prevention of breast cancer. As described in more detail in the Examples, the inventors have observed that GREM1 induces breast cancer cell proliferation and further that co-culture of breast cancer cells with Grem-1 expressing stromal cells also induces such proliferation. Additionally, a GREM1 antagonist is able to neutralise activatory effects of GREM1 on breast cancer cells.

Accordingly, the results obtained in breast cancer support a role for GREM1 in breast cancer cell proliferation, including by GREM1 expression in stromal cells.

The inventors have also demonstrated the in vivo efficacy of a GREM1 antagonist in the prevention and treatment of breast cancer in a pre-clinical mouse models (see Example 24 below). In particular, it was observed that breast cancer tumour-bearing mice treated with the GREM1 antagonist showed a reduction in: overall tumour burden, tumour burden in the lung, and tumour burden in the liver.

The invention therefore provides for treatment and prevention of breast cancer by administering an anti-GREM1 antagonist. The breast cancer may comprise stromal GREM1 overexpression. The stromal breast cells overexpressing GREM1 may comprise stromal fibroblasts, also described herein as cancer-associated fibroblasts. A preferred type of breast cancer for treatment may be resistant to one or more known anti-cancer agents (such as chemotherapeutic agents), as described further below. The breast cancer may be a disseminated breast cancer. The breast cancer may be a metastatic breast cancer. The breast cancer may be metastatic breast cancer of the lung. The breast cancer may be metastatic breast cancer of the liver. The breast cancer may be metastatic breast cancer of the bone.

Prostate Cancer

In a further aspect, the present invention relates to the treatment or prevention of prostate cancer.

As described in more detail in Example 25, the inventors have demonstrated the efficacy of a GREM1 antagonist in the prevention and treatment of prostate cancer in a pre-clinical mouse model. In particular, it was observed that prostate cancer tumour-bearing mice treated with the GREM1 antagonist showed a reduction in: overall tumour burden, tumour burden in liver, skeletal tumour burden, and tumour burden in the lung.

The present invention therefore further provides for treatment and prevention of prostate cancer by administering an anti-GREM1 antagonist. The prostate cancer may be a disseminated prostate cancer. The prostate cancer may be a metastatic prostate cancer. The prostate cancer may be metastatic prostate cancer of the lung. The prostate cancer may be metastatic prostate cancer of the liver. The prostate cancer may be metastatic prostate cancer of the bone.

Other Cancers

In addition to specifically exemplified applications in treatment and prevention of colorectal cancer, multiple myeloma, breast cancer, and prostate cancer, the inventors envisage that the therapeutic efficacy of GREM1 antagonists as illustrated in these cancers will also be applicable to treatment of other cancers having corresponding features. In particular, it is envisaged that GREM1 antagonists will be useful in preventing or treating cancers in which there is stromal and/or epithelial GREM1 overexpression, and this overexpression contributes to malignant cell growth. Such cancers include pancreatic cancer, bladder cancer, lung cancer, stomach cancer, duodenal cancer, oesophageal cancer, head and neck cancer, glioma, endometrial cancer, liver cancer, spleen cancer, bone-resident cancer, and osteosarcoma. The relationship between Grem1 expression and survival implications in various solid tumours as determined using publically available data (from R2 server, hgserver1.amc.nl/cgi-bin/r2/main.cgi) is shown in FIGS. 24 to 29.

Stroma and Epithelium

The cancers described for prevention or treatment herein may comprise stromal and/or epithelial GREM1 overexpression.

The terms "stromal cell(s)" or "stroma" as used herein refers to structural and/or connective portions of a tissue or organ.

Stromal tissue is primarily made of extracellular matrix containing connective tissue cells. Extracellular matrix is primarily composed of ground substance—a porous, hydrated gel, made mainly from proteoglycan aggregates—and connective tissue fibers. There are three types of fibers commonly found within the stroma: collagen type I, elastic, and reticular (collagen type III) fibres. Fibroblasts and pericytes are among the most common types of stromal cells.

In the context of a cancer or tumour (e.g. initiating in the epithelium of a tissue or organ), the stroma of the tissue or organ may assist cancer growth and progression. The stroma associated with the cancer or tumour may be a desmoplastic stroma caused by growth of fibrous or connective tissue around the cancer or tumour.

The overexpression of GREM1 may be observed in any part of the stroma/any stromal cells. The stromal cells may be fibroblasts or fibroblast-like support cell. The stromal cells may be fibroblasts or fibroblast-like support cell isolated from a desmoplastic stroma of any cancer or tumour described above, such as from the colon or rectum in a colorectal cancer, or the bone marrow in multiple myeloma. The stromal cells may be cancer-associated fibroblasts.

The term "epithelial" as used herein refers to a cell derived from the outer lining of a tissue or organ. In relation to the colon, the intestinal epithelium is the layer of cells that form the luminal surface or lining of both the small and large intestine of the gastrointestinal tract. It is composed of simple columnar epithelium. The "upper barrier" is the intestinal epithelial single layer of columnar cells consisting of four intestinal epithelial cell types: the absorbent enterocytes, the goblet cells, the Paneth cells and the enteroendocrine cells. Upper barrier features are similar in small and large bowel. The main difference is constituted by the presence of elevations and projections (circular folds, villi and microvilli) in duodenum, jejunum and ileum that allows the increase of the absorption surface. This is not observed in the colon, which instead shows a flat surface. Amongst the mucous membrane protrusions termed villi, there are inflections called crypts of Lieberkühn, which are distinct glandular invaginations. The cell in which epithelial GREM1 overexpression is observed may be any epithelial cell, such as any intestinal epithelial cell.

While not being bound by theory, the present inventors postulate that overexpression of GREM1 in the epithelium and/or stroma may promote a stem/progenitor cell phenotype (increasing the number of stem/progenitor cells), promoting epithelial stem cell behaviour and driving cancer progression and/or resistance to chemotherapeutic agents. Thus, a GREM1 antagonist used according to the invention may prevent induction of an aberrant cancer stem/progenitor cell phenotype, reduce epithelial stem cell behaviour and/or decrease the number of stem/progenitor cells, in the epithelium of a tissue or organ of a subject in which cancer is to be prevented or treated, such as in the intestinal epithelium. The ability of a GREM1 antagonist to affect stem cell behaviour may be assayed clinically by the assessment of known epithelial and cancer stem cell markers.

GREM1

The terms GREM1 or Gremlin-1 as used in the present invention in the context of a protein refer to a protein that typically has the amino acid sequence as set out in the UniProt entry O60565 (SEQ ID NO: 1), human GREM1. The terms GREM1 and Gremlin-1 may also refer to a Gremlin-1 polypeptide which:
  (a) comprises or consists of the amino acid sequence of SEQ ID NO: 1 with or without the N-terminal signal peptide, i.e. may comprise or consist of the mature peptide sequence as shown in SEQ ID NO: 21; or
  (b) is a derivative having one or more amino acid substitutions, modifications, deletions or insertions relative to the amino acid sequence of SEQ ID NO: 1 with or without the N-terminal signal peptide (as shown in SEQ ID NO: 21), which retains the activity of Gremlin-1, such as the amino acid sequence of SEQ ID NO: 20.
  (c) a variant thereof, such variants typically retain at least about 60%, 70%, 80%, 90%, 91%, 92%, 93%, 94% or 95% identity to SEQ ID NO: 1 (or SEQ ID NO: 20 or 21) (or even about 96%, 97%, 98% or 99% identity). In other words, such variants may retain about 60%-about 99% identity to SEQ ID NO: 1, suitably about 80%-about 99% identity to SEQ ID NO: 1, more suitably about 90%-about 99% identity to SEQ ID NO: 1 and most suitably about 95%-about 99% identity to SEQ ID NO: 1. Variants are described further below.

As discussed further below, residue numbers are typically quoted based on the sequence of SEQ ID NO: 1. However, residue numbering could readily be extrapolated by the skilled person to a derivative or variant sequence as discussed above. Where residue numbers are quoted, the invention also encompasses these residues on a variant or derivative sequence.

A GREM1 or Gremlin-1 nucleic acid sequence may comprise or consist of the sequence of SEQ ID NO: 36 or SEQ ID NO: 37 or a variant thereof. Variant nucleic acid sequences are described further below. A GREM1 or Gremlin-1 nucleic sequence may comprise or consist of any GREM1 transcript variant. Examples of GREM1 transcripts variants are Transcript 1 (NCBI: NM_013372.6; ENSEMBL: ENST00000560677.5); Transcript 2: NCBI: NM_001191323.1; ENSEMBL: ENST00000560830.1); Transcript 3: NCBI: NM_001191322.1; ENSEMBL: ENST00000622074.1. The sequences available at the above accession numbers as of 18 Jun. 2018 are incorporated by reference herein.

Overexpression

The overexpression of GREM1 in the stroma and/or epithelium may be determined by any means. The overexpression of GREM1 is typically determined by comparison to the level of the marker in normal cells of the same tissue type, i.e. basal expression level. The expression is typically normalized against the expression level of other genes, preferably comprising one or more housekeeping genes. GREM1 may also be classified as showing an overexpression or underexpression in a threshold percentage of a population of cancer patients. The overexpression in each patient in the population may be higher than 2 from the geometric mean. At least 10%, more preferably at least 15% or more of the patients in the population may display such an overexpression.

GREM1 stromal overexpression refers to stromal GREM1 levels being higher than that of a matched normal tissue. For example, stromal GREM1 levels may be at least two fold higher than that of matched normal tissue.

Where GREM1 is overexpressed, its amount may be increased by any amount relative to basal. For example, GREM1-initiated cancers such as MIPS may comprise a several thousand-fold upregulation of epithelial GREM1, whereas no GREM1 expression is observed in normal epithelium. Sporadic cancers comprising stromal GREM overexpression may comprise any level of stromal overexpression over the physiological GREM1 expression level in normal stroma of the organ. The skilled person is able to evaluate the existence of an overexpression in stroma or epithelium compared with the level of GREM1 in normal cells of the same type.

The amount determined may be the amount of mRNA. The cancer may thus comprise an overexpression of GREM1 mRNA. The cancer may comprise an increased amount of GREM1 mRNA compared with normal cells of the same tissue type. The mRNA may be increased by any amount. The amount of mRNA can be measured using a quantitative reverse transcription polymerase chain reaction (qRT-PCR), such as real time qRT-PCR, quantigene assay (Affymetrix/Thermo Fisher), by northern blotting or using microarrays, RNA sequencing. mRNA expression is preferably determined by comparing the gene expression of a sample to the distribution of expression levels of the specific gene across a reference sample composed of tumours that are diploid for that gene. A z-score may be derived using RNAseq by expectation maximisation (RSEM) algorithm (cBioportal for Cancer Genomics, see Worldwide Website: cbioportal.org; Gao et al, 2013 and Serami eta al 2012). A z-score of 2 SD higher or lower than the mean of the reference set is preferably considered as overexpression or underexpression respectively.

The amount determined may be the amount of protein. The cancer may comprise an overexpression of GREM1 protein, such as compared with normal cells of the same tissue type. The protein may be increased by any amount. The amount of protein can be measured using immunohistochemistry, western blotting, mass spectrometry or fluorescence-activated cell sorting (FACS), including by use of an anti-GREM1 antibody of the invention. The thresholds for determining expression may vary between techniques used, and may be validated against immunohistochemistry scores.

The uses of GREM1 antagonists for treating or preventing cancer in a patient as described herein may thus comprise (a) measuring the amount of GREM1 in the cancer and (b) if the cancer comprises an overexpression of GREM1, administering to the patient the GREM1 antagonist and thereby treating or preventing the cancer. The amount of GREM1 may be the mRNA or protein amount, and the overexpression any overexpression discussed above.

Sample

The above measurements may be carried out in any suitable sample from the patient. The measurements may be carried out in a cancer or tumour biopsy obtained from the patient. The stroma and/or epithelium (stromal and/or epithelial cells) may be isolated from the biopsy. The biopsy tissue may be formalin fixed paraffin embedded (FFPE) tissue or fresh tissue. The tissue may be pancreatic tissue, bladder tissue, lung tissue, endometrial tissue, breast tissue, stomach tissue, duodenal tissue, oesophageal tissue, bone marrow or colorectal tissue. Any of the methods discussed above may be carried out on the cancer biopsy. Such methods may also be carried out on cancer cells circulating in the blood of the patient. The RNA methods may be carried out on urinary or blood exosomes.

Antagonist

An anti-GREM1 antagonist is any molecule that reduces the function or activity of GREM1. The anti-GREM1 antagonist may reduce function or activity of GREM1 by any amount. The anti-GREM1 antagonist may reduce GREM1 function or activity by at least 10%, at least 20%, at least 30% at least 40%, at least 50%, at least 60%, at least 70%, at least 80%, at least 90% or at least 95%, or may prevent any GREM1 function or activity. The extent to which an anti-GREM1 antagonist reduces GREM1 function or activity may be determined by measuring GREM1 function or activity in cells in the presence and absence of the anti-GREM1 antagonist. The cells may be normal cells or cancer cells. The cells may be cancer cells as described above. They may be colorectal cancer cells. The colorectal cancer cells may be present in Vil1-Grem1 and/or APC(Min) mouse models as described in the Examples. Thus, an in vivo assay for activity of a GREM1 antagonist in colorectal cancer may be performed in a mouse model of GREM1-initiated cancer or of a sporadic cancer resulting in stromal GREM1 overexpression. Alternatively, the cancer cells may be multiple myeloma cancer cells, such as plasma cells isolated from a myeloma present in the bone marrow. More generally, a GREM1 antagonist shown to reduce function or activity of GREM1 by any means may then be assayed in vitro or in vivo for its ability to prevent or reduce proliferation of cancer cells, such as colorectal cancer cells or multiple myeloma cancer cells or breast cancer cells, or to prevent, reduce or eliminate a cancer or tumour.

The antagonist may decrease GREM1 function by any means. It may increase or decrease the activity or amount of any molecule affecting GREM1 function directly or indirectly. It may decrease the amount of GREM1 at the mRNA or protein level. It may increase degradation of GREM1. It may decrease the function of GREM1 by inhibitory modification. It may decrease the transcription of a molecule enhancing GREM1 function. It may disrupt DNA encoding GREM1 or a molecule enhancing GREM1 function, using an agent such as a zinc finger nuclease.

The antagonist may be an agent interacting with Gremlin-1. An agent that interacts with Gremlin-1 is typically an agent which binds Gremlin-1. Agents that interact with Gremlin-1 may modulate Gremlin-1. An inhibitory modulating agent may have an effect on any of the functions of Gremlin-1, but typically reduces binding of Gremlin-1 to BMP (BMP 2/4/7). The antagonist may be a BMP-7 mimetic molecule Gremlin-1 is a negative regulator of BMP, so reduced binding increases signalling through BMP. An activating modulating agent may increase binding of Gremlin-1 to BMP.

BMP binding and signalling may be detected by any method known in the art. For example, the Examples of the present application describe a SMAD phosphorylation assay. SMAD1, 5 and 8 are phosphorylated upon BMP signalling. An increase in SMAD phosphorylation may therefore be used to determine increased BMP signalling, which may reflect a reduction in binding to Gremlin-1. The Examples also describe an Id1 reporter gene assay, where the Id1 gene is a target gene of BMP signalling. An increase in recovery of the signal in this assay may therefore also be used to determine if an agent inhibits Gremlin-1 binding to BMP.

The antagonist may act by binding the active site of GREM1 or act allosterically by binding at a different site. The antagonist may act by binding a regulator or ligand for GREM1, to thereby reduce activation of GREM1. The antagonist may be reversible or irreversible.

A GREM1 antagonist may be a small molecule inhibitor, a peptide, a protein, an antibody, a polynucleotide, an oligonucleotide, an antisense RNA, small interfering RNA (siRNA) or small hairpin RNA (shRNA).

An antagonist of GREM1 may be an oligonucleotide which specifically hybridises to an mRNA encoding GREM1 or an mRNA encoding a molecule which enhances GREM1 activity. An antagonist of GREM1 may be a polynucleotide encoding any molecule that decreases GREM1 function. For example, the GREM1 antagonist may be a polynucleotide encoding an anti-GREM1 antibody described herein.

An antagonist of GREM1 may be an antibody which specifically binds to any target molecule (typically a protein) so as to decrease GREM1 function directly or indirectly. The antagonist may be an antibody specifically binding GREM1. In this aspect, the antibody may decrease GREM1 function by allosteric inactivation or by blocking interaction between its target and a ligand required for activity.

Interaction of an antagonist agent with protein residues may be determined by any appropriate method known in the art, such as distances between the residue and agent as determined by x-ray crystallography (typically less than 6 Å, or less than 4 Å). As discussed in the Examples below, the region of Gremlin-1 which may be targeted by a therapeutic may include amino acids Asp92-Leu99, Arg116-His130, Ser137-Ser142, Cys176-Cys178. These are within 6 Å of those mutated on the surface of Gremlin-1.

Antibody Antagonists

The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as HCVR or $V_H$) and a heavy chain constant region. Each light chain is comprised of a light chain variable region (abbreviated herein as LCVR or $V_L$) and a light chain constant region. The variable regions of the heavy and light chains contain a binding domain that interacts with an antigen. The $V_H$ and $V_L$ regions can be further subdivided into regions of hypervariability, termed complementarity determining regions (CDR), interspersed with regions that are more conserved, termed framework regions (FR).

The constant regions of the antibodies may mediate the binding of the immunoglobulin to host tissues or factors, including various cells of the immune system (e.g., effector cells) and the first component (C1q) of the classical complement system.

An antibody used according to the invention may be a monoclonal antibody or a polyclonal antibody, and will typically be a monoclonal antibody. An antibody used according to the invention may be a chimeric antibody, a CDR-grafted antibody, a nanobody, a human or humanised antibody or an antigen-binding portion of any thereof. For the production of both monoclonal and polyclonal antibodies, the experimental animal is typically a non-human mammal such as a goat, rabbit, rat or mouse but the antibody may also be raised in other species.

Polyclonal antibodies may be produced by routine methods such as immunisation of a suitable animal, with the antigen of interest. Blood may be subsequently removed from the animal and the IgG fraction purified.

Antibodies against Gremlin-1 may be obtained, where immunisation of an animal is necessary, by administering the polypeptides to an animal, e.g. a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies used according to the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and WO2004/106377.

The antibodies can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, but not necessarily from the same antibody. Examples of fully human antibodies may include antibodies produced, for example by the phage display methods described above and antibodies produced by mice in which the murine immunoglobulin variable and optionally the constant region genes have been replaced by their human counterparts e.g. as described in general terms in EP 0546073, U.S. Pat. Nos. 5,545,806, 5,569,825, 5,625,126, 5,633,425, 5,661,016, 5,770,429, EP 0438474 and EP 0463151.

Alternatively, an antibody used according to the invention may be produced by a method comprising immunising a non-human mammal with a Gremlin-1 immunogen; obtaining an antibody preparation from said mammal; deriving therefrom monoclonal antibodies that recognise Gremlin-1.

The antibody molecules used according the present invention may comprise a complete antibody molecule having full length heavy and light chains or a fragment or antigen-binding portion thereof. The term "antigen-binding portion" of an antibody refers to one or more fragments of an antibody that retain the ability to selectively bind to an antigen. It has been shown that the antigen-binding function of an antibody can be performed by fragments of a full-length antibody. The antibodies and fragments and antigen binding portions thereof may be, but are not limited to Fab, modified Fab, Fab', modified Fab', $F(ab')_2$, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO 2005/003169, WO 2005/003170 and WO 2005/003171 and Fab-dAb fragments described in International patent application WO2009/040562. Multi-valent antibodies may comprise multiple specificities or may be monospecific (see for example WO 92/22853 and WO 05/113605). These antibody fragments may be obtained using conventional techniques known to those of skill in the art, and the fragments may be screened for utility in the same manner as intact antibodies.

The constant region domains of the antibody molecule, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

An antibody used according to the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

An antibody used according to the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma that includes a B cell obtained from a transgenic nonhuman animal, e.g., a transgenic mouse, having a genome comprising a human heavy chain transgene and a light chain transgene fused to an immortalized cell.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanized antibody" is intended to refer to CDR-grafted antibody molecules in which CDR sequences derived from the germline of another mammalian species, such as a mouse, have been grafted onto human framework sequences. Additional framework region modifications may be made within the human framework sequences.

As used herein, the term 'CDR-grafted antibody molecule' refers to an antibody molecule wherein the heavy and/or light chain contains one or more CDRs (including, if desired, one or more modified CDRs) from a donor antibody (e.g. a murine or rat monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the CDR-grafted antibody according to the present invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available for example at: Worldwide Website: vbase2.org/ (see Retter et al, Nucl. Acids Res. (2005) 33 (supplement 1), D671-D674).

In a CDR-grafted antibody described herein, the acceptor heavy and light chains do not necessarily need to be derived from the same antibody and may, if desired, comprise composite chains having framework regions derived from different chains.

Also, in a CDR-grafted antibody described herein, the framework regions need not have exactly the same sequence as those of the acceptor antibody. For instance, unusual residues may be changed to more frequently occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995).

In one embodiment the antibody heavy chain comprises a CH1 domain and the antibody light chain comprises a CL domain, either kappa or lambda.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or surface carries no net electrical charge. In one embodiment the antibody or fragment according to the present disclosure has an isoelectric point (pI) of at least 7. In one embodiment the antibody or fragment has an isoelectric point of at least 8, such as 8.5, 8.6, 8.7, 8.8 or 9. In one embodiment the pI of the antibody is 8. Programs such as ** ExPASY, Worldwide Website expasy.ch/tools/pi_tool.html (see Walker, The Proteomics Protocols Handbook, Humana Press (2005), 571-607) may be used to predict the isoelectric point of the antibody or fragment.

In order to characterise preferred Gremlin-1 epitopes, the inventors have crystallised human Gremlin-1 alone, and in complex with an antibody termed Ab 7326 (Fab fragments). Crystallisation of Gremlin-1 has allowed putative residues in the BMP binding site to be determined. Furthermore, crystallisation with Ab 7326, which is an allosteric inhibitory antibody, has allowed residues in the antibody epitope to be determined. Antibodies binding this epitope have particular potential as therapeutic agents in the treatment of diseases associated with Gremlin-1.

The preferred Ab 7326 antibody described herein has been identified to bind the following residues of Gremlin-1: Ile110 (131), Lys126 (147), Lys127 (148), Phe128 (149), Thr129 (150), Thr130 (151), Arg148 (169), Lys153 (174) and Gln154 (175), where Lys126 (147), Lys127 (148), Phe128 (149), Thr129 (150), Thr130 (151), Arg148 (169), Lys153 (174) and Gln154 (175) are present on one Gremlin-1 monomer and Ile110 (131) is present on the second Gremlin-1 monomer. Numbering not in brackets is based on the structural file and (which matches the numbering of mouse Gremlin-2 based on structural alignment). The numbers in brackets represent the residues based on the UniProt entry O60565 of SEQ ID NO: 1. As discussed in the Examples section, these epitope residues were identified using NCONT analysis at 4 Å from the Gremlin-1-Ab 7326 Fab complex.

Antibodies described herein may therefore bind to an epitope which comprises at least one residue selected from Ile131, Lys147, Lys148, Phe149, Thr150, Thr151, Arg169, Lys174 and Gln175 (with residue numbering based on SEQ ID NO: 1). Antibodies described herein may bind an epitope which comprises 2, 3, 4, 5, 6, 7, 8 or all 9 of these residues (preferably at least 5 residues).

Antibodies described herein may also recognise an epitope where Ile131 is present on a different Gremlin-1 monomer to the other residues.

Although these residues are provided for a particular sequence of human Gremlin-1, the skilled person could readily extrapolate the positions of these residues to other corresponding Gremlin sequences (e.g. mouse) using routine techniques. Antibodies binding to epitopes comprising the corresponding residues within these other Gremlin sequences are therefore also provided by the invention.

To screen for antibodies that bind to a particular epitope, a routine cross-blocking assay such as that described in Antibodies, Harlow and Lane (Cold Spring Harbor Press, Cold Spring Harb., NY) can be performed. Other methods include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science 9: 487-496). Such methods are well known in the art.

Antibody epitopes may also be determined by x-ray crystallography analysis. Antibodies of the present disclosure may therefore be assessed through x-ray crystallography analysis of the antibody bound to Gremlin-1. Epitopes may, in particular, be identified in this way by determining residues on Gremlin-1 within 4 Å of an antibody paratope residue.

An antibody as described herein may thus bind to an epitope on Gremlin-1 comprising at least one residue selected from Trp93, Phe117, Tyr119, Phe125, Tyr126 and Phe138, wherein the residue numbering is according to SEQ ID NO: 1. Further described herein is an antibody which binds an epitope comprising all of Trp93, Phe117, Tyr119, Phe125, Tyr126 and Phe138. Additionally described is an antibody which binds an epitope which comprises the following residues: Ile131, Lys147, Lys148, Phe149, Thr150, Thr151, Arg169, Lys174 and Gln175. Preferably, Lys147, Lys148, Phe149, Thr150, Thr151, Arg169, Lys174 and Gln175 are located on one monomer of Gremlin-1 and Ile131 is located on the other monomer of Gremlin-1 (Gremlin-1 dimers bind to BMP dimers).

An antibody may bind an above Gremlin-1 residue if the antibody paratope is within 4 Å of the Gremlin-1 residue as determined by x-ray crystallography.

Antibodies which bind to an epitope disclosed herein may comprise at least one, at least two or all three heavy chain CDR sequences of SEQ ID NOS: 4 to 6 (HCDR1/HCDR2/HCDR3 respectively). These are the HCDR1/HCDR2/HCDR3 sequences of the Ab 7326 antibody of the Examples as determined using Kabat methodology.

The Kabat and Chothia methods for determining CDR sequences are well known in the art (as well as other techniques). CDR sequences may be determined using any appropriate method and in the present invention, whilst Kabat is typically employed, other techniques could be used as well. In the present instance, SEQ ID NO: 3 presents the Ab 7326 HCDR1 sequence as determined using a combined Chothia & Kabat definition.

Antibodies used according to the invention may comprise at least one, at least two or all three light chain CDR sequences of SEQ ID NOS: 7 to 9 (LCDR1/LCDR2/LCDR3 respectively). These are the LCDR1/LCDR2/LCDR3 sequences of Ab 7326 using Kabat methodology.

The antibody preferably comprises at least a HCDR3 sequence of SEQ ID NO: 6.

Typically, the antibody comprises at least one heavy chain CDR sequence selected from SEQ ID NOS: 4 to 6 and at least one light chain CDR sequence selected from SEQ ID NOS 7 to 9. The antibody may comprise at least two heavy chain CDR sequences selected from SEQ ID NOS: 4 to 6 and at least two light chain CDR sequences selected from SEQ ID NOS: 7 to 9. The antibody typically comprises all three heavy chain CDR sequences of SEQ ID NOS: 4 to 6 (HCDR1/HCDR2/HCDR3 respectively) and all three light chain CDR sequences SEQ ID NOS: 7 to 9 (LCDR1/LCDR2/LCDR3 respectively). The antibodies may be chimeric, human or humanised antibodies.

The antibody may comprise a heavy chain variable region (HCVR) sequence of SEQ ID NO: 10 or 12 (the HCVR of Ab 7326 variants 1 and 2). The antibody may comprise a light chain variable region (LCVR) sequence of SEQ ID NO: 11 or 13 (the LCVR of Ab 7326 variants 1 and 2). The antibody preferably comprises the heavy chain variable region sequence of SEQ ID NO: 10 or 12 and the light chain variable region sequence of SEQ ID NO: 11 or 13 (especially HCVR/LVCR pairs of SEQ ID NOs: 10/11 or 12/13).

The antibody may comprise a heavy chain (H-chain) sequence of
SEQ ID NO: 14 mouse full length IgG1 heavy chain variant 1, or SEQ ID NO: 28 mouse full length IgG1 heavy chain variant 2, or
SEQ ID NO: 30 human full length IgG1 heavy chain variant 1, or
SEQ ID NO: 16 human full length IgG1 heavy chain variant 2, or
SEQ ID NO: 22 human full length IgG4P heavy chain variant 1, or
SEQ ID NO: 34 human full-length IgG4P heavy chain variant 2, or
SEQ ID NO: 18 Fab heavy chain variant 1, or
SEQ ID NO: 32 Fab heavy chain variant 2.

The antibody may comprise a light chain (L-chain) sequence of
SEQ ID NO: 15 mouse full length IgG1 light chain variant 1, or
SEQ ID NO: 29 mouse full length IgG1 light chain variant 2, or
SEQ ID NO: 31 human full length IgG1 light chain variant 1, or
SEQ ID NO: 17 human full length IgG1 light chain variant 2, or
SEQ ID NO: 23 human full length IgG4P light chain variant 1, or
SEQ ID NO: 35 human full-length IgG4P light chain variant 2, or
SEQ ID NO: 19 Fab light chain variant 1, or
SEQ ID NO: 33 Fab light chain variant 2.

In one example, the antibody comprises a heavy chain/light chain sequence pair of
SEQ ID NOs: 14/15 mouse full length IgG1 variant 1, or
SEQ ID NOs: 28/29 mouse full length IgG1 variant 2, or
SEQ ID NOs: 30/31 human full length IgG1 variant 1, or
SEQ ID NOs: 16/17 human full length IgG1 variant 2, or
SEQ ID NOs: 22/23 human full length IgG4P variant 1, or
SEQ ID NOs: 34/35 human full-length IgG4P variant 2, or
SEQ ID NOs: 18/19 Fab light chain variant 1, or
SEQ ID NOs: 32/33 Fab light chain variant 2.

The variant forms of corresponding sequences may be interchanged. For example, the antibody may comprise a heavy chain/light chain sequence pair of
SEQ ID NOs: 14/29 mouse full length IgG1 heavy chain variant 1/light chain variant 2, or
SEQ ID NOs: 28/15 mouse full length IgG1 heavy chain variant 2/light chain variant 1, or
SEQ ID NOs: 30/17 human full length IgG1 heavy chain variant 1/light chain variant 2, or
SEQ ID NOs: 16/31 human full length IgG1 heavy chain variant 2/light chain variant 1, or
SEQ ID NOs: 22/35 human full length IgG4P heavy chain variant 1/light chain variant 2, or
SEQ ID NOs: 34/23 human full-length IgG4P heavy chain variant 2/light chain variant 1, or
SEQ ID NOs: 18/33 Fab heavy chain variant 1/light chain variant 2, or
SEQ ID NOs: 32/19 Fab heavy chain variant 2/light chain variant 1.

The antibodies may be chimeric, human or humanised antibodies.

The antibody may alternatively be or may comprise a variant of one of the specific sequences recited above. The following description of antibody variants is also applicable to selection of GREM1 polypeptide variants as described above.

For example, a variant may be a substitution, deletion or addition variant of any of the above amino acid sequences.

A variant antibody may comprise 1, 2, 3, 4, 5, up to 10, up to 20 or more (typically up to a maximum of 50) amino acid substitutions and/or deletions from the specific sequences discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants typically involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | | | | |
|---|---|---|---|---|
| Ala | aliphatic, hydrophobic, neutral | | Met | hydrophobic, neutral |
| Cys | polar, hydrophobic, neutral | | Asn | polar, hydrophilic, neutral |
| Asp | polar, hydrophilic, charged (−) | | Pro | hydrophobic, neutral |
| Glu | polar, hydrophilic, charged (−) | | Gln | polar, hydrophilic, neutral |
| Phe | aromatic, hydrophobic, neutral | | Arg | polar, hydrophilic, charged (+) |
| Gly | aliphatic, neutral | | Ser | polar, hydrophilic, neutral |
| His | aromatic, polar, hydrophilic, charged (+) | | Thr | polar, hydrophilic, neutral |
| Ile | aliphatic, hydrophobic, neutral | | Val | aliphatic, hydrophobic, neutral |
| Lys | polar, hydrophilic, charged (+) | | Trp | aromatic, hydrophobic, neutral |
| Leu | aliphatic, hydrophobic, neutral | | Tyr | aromatic, polar, hydrophobic |

"Derivatives" or "variants" generally include those in which instead of the naturally occurring amino acid the amino acid which appears in the sequence is a structural analog thereof. Amino acids used in the sequences may also be derivatized or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Variant antibodies may have an amino acid sequence which has more than about 60%, or more than about 70%, e.g. 75 or 80%, typically more than about 85%, e.g. more than about 90 or 95% amino acid identity to the amino acid sequences disclosed herein (particularly the HCVR/LCVR sequences and the H- and L-chain sequences). Furthermore, the antibody may be a variant which has more than about 60%, or more than about 70%, e.g. 75 or 80%, typically more than about 85%, e.g. more than about 90 or 95% amino acid identity to the HCVR/LCVR sequences and the H- and L-chain sequences disclosed herein, whilst retaining the exact CDRs disclosed for these sequences. Variants may retain at least about 90%, 91%, 92%, 93%, 94%, 95%, 96%, 97%, 98% or 99% identity to the HCVR/LCVR sequences and to the H- and L-chain sequences disclosed herein (in some circumstances whilst retaining the exact CDRs).

Variants typically retain about 60%-about 99% identity, about 80%-about 99% identity, about 90%-about 99% identity or about 95%-about 99% identity. This level of amino acid identity may be seen across the full length of the relevant SEQ ID NO sequence or over a part of the sequence, such as across about 20, 30, 50, 75, 100, 150, 200 or more amino acids, depending on the size of the full length polypeptide.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

Antibodies having specific sequences and variants which maintain the function or activity of these chains are therefore provided.

Antibodies may compete for binding to Gremlin-1 with, or bind to the same epitope as, those defined above in terms of H-chain/L-chain, HCVR/LCVR or CDR sequences. In particular, an antibody may compete for binding to Gremlin-1 with, or bind to the same epitope as, an antibody which comprises a HCDR1/HCDR2/HCDR3/LCDR1/LCDR2/LCDR3 sequence combination of SEQ ID NOs: 4/5/6/7/8/9. An antibody may compete for binding to Gremlin-1 with, or bind to the same epitope as, an antibody which comprises a HCVR and LCVR sequence pair of SEQ ID NOs: 10/11 or 12/13 or full length chains of SEQ ID NOs: 14/15 or 16/17.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

One can easily determine whether an antibody binds to the same epitope as, or competes for binding with, a reference antibody by using routine methods known in the art. For example, to determine if a test antibody binds to the same epitope as a reference antibody of the invention, the reference antibody is allowed to bind to a protein or peptide under saturating conditions. Next, the ability of a test antibody to bind to the protein or peptide is assessed. If the test antibody is able to bind to the protein or peptide following saturation binding with the reference antibody, it can be concluded that the test antibody binds to a different epitope than the reference antibody. On the other hand, if the test antibody is not able to bind to protein or peptide following saturation binding with the reference antibody, then the test antibody may bind to the same epitope as the epitope bound by the reference antibody of the invention.

To determine if an antibody competes for binding with a reference antibody, the above-described binding methodology is performed in two orientations. In a first orientation, the reference antibody is allowed to bind to a protein/peptide under saturating conditions followed by assessment of binding of the test antibody to the protein/peptide molecule. In a second orientation, the test antibody is allowed to bind to the protein/peptide under saturating conditions followed by assessment of binding of the reference antibody to the protein/peptide. If, in both orientations, only the first (saturating) antibody is capable of binding to the protein/peptide, then it is concluded that the test antibody and the reference antibody compete for binding to the protein/peptide. As will be appreciated by the skilled person, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50%, 75%, 90% or even 99% as measured in a competitive binding assay (see, e.g., Junghans et al., Cancer Res, 1990: 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Antibodies can be tested for binding to Gremlin-1 by, for example, standard ELISA or Western blotting. An ELISA assay can also be used to screen for hybridomas that show positive reactivity with the target protein. The binding selectivity of an antibody may also be determined by monitoring binding of the antibody to cells expressing the target protein, for example by flow cytometry. Thus, a screening method may comprise the step of identifying an antibody that is capable of binding Gremlin-1 by carrying out an ELISA or Western blot or by flow cytometry.

Antibodies may selectively (or specifically) recognise Gremlin-1. An antibody, or other compound, "selectively binds" or "selectively recognises" a protein when it binds with preferential or high affinity to the protein for which it is selective but does not substantially bind, or binds with low affinity, to other proteins. The selectivity of an antibody may be further studied by determining whether or not the antibody binds to other related proteins as discussed above or whether it discriminates between them. Antibodies used according to the invention typically recognise human Gremlin-1.

Antibodies may also have cross-reactivity for related proteins, or for human Gremlin-1 and for Gremlin-1 from other species.

By specific (or selective), it will be understood that the antibody binds to the protein of interest with no significant cross-reactivity to any other molecule. Cross-reactivity may be assessed by any suitable method described herein. Cross-reactivity of an antibody may be considered significant if the antibody binds to the other molecule at least about 5%, 10%, 15%, 20%, 25%, 30%, 35%, 40%, 45%, 50%, 55%, 60%, 65%, 70%, 75%, 80%, 85%, 90% or 100% as strongly as it binds to the protein of interest. An antibody that is specific (or selective) may bind to another molecule at less than about 90%, 85%, 80%, 75%, 70%, 65%, 60%, 55%, 50%, 45%, 40%, 35%, 30%, 25% or 20% the strength that it binds to the protein of interest. The antibody may bind to the other molecule at less than about 20%, less than about 15%, less than about 10% or less than about 5%, less than about 2% or less than about 1% the strength that it binds to the protein of interest.

Anti-gremlin antibodies have been previously described, for example WO2014/159010A1 (Regeneron) describes anti-gremlin antibodies that inhibit Gremlin-1 activity, with binding affinity $K_D$ values ranging from 625 pM to 270 nM at 25° C. Ciuclan et al (2013) describe an anti-Gremlin-1 monoclonal antibody with a binding affinity $K_D$ $5.6 \times 10^{-10}$ M.

The anti-Gremlin-1 antibodies newly described herein (and also in PCT/GB2017/083650 filed 19 Dec. 2017, incorporated herein by reference in its entirety) are allosteric inhibitors of Gremlin-1 activity, and bind to a novel epitope as described above, distal from the BMP binding site. The antibodies bind to Gremlin-1 with exceptionally high affinity with Kd values<100 pM. The antibodies therefore represent a significant improvement over currently available antibodies and are expected to be particularly useful for the treatment of Gremlin-1 mediated diseases.

Thus, antibodies suitable for use with the present invention may have a high affinity binding for (human) Gremlin-1. The antibody may have a dissociation constant ($K_D$) of less than <1 nM, and preferably <500 pM. In one example, the antibody has a dissociation constant ($K_D$) of less than 200 pM. In one example, the antibody has a dissociation constant ($K_D$) of less than 100 pM. A variety of methods can be used to determine the binding affinity of an antibody for its target antigen such as surface plasmon resonance assays, saturation assays, or immunoassays such as ELISA or RIA, as are well known to persons of skill in the art. An exemplary method for determining binding affinity is by surface plasmon resonance analysis on a BIAcore™ 2000 instrument (Biacore AB, Freiburg, Germany) using CM5 sensor chips, as described by Krinner et al., (2007) Mol. Immunol. February; 44 (5):916-25. (Epub 2006 May 11)).

Antibodies used according to the invention are typically inhibitory antibodies. Gremlin-1 negatively regulates BMP-2, 4 and 7, so inhibition of Gremlin-1 results in increased signalling through BMP.

As mentioned above, the Examples of the present application describe two functional assays for screening whether an antibody is capable of inhibiting Gremlin 1, namely the SMAD phosphorylation assay and the Hek Id1 reporter gene assay. Typically, an inhibitory antibody restores SMAD phosphorylation and/or restores signalling of BMP in the Hek Id1 reporter gene assay. SMAD phosphorylation may be restored to at least 80%, 90% or 100% when compared with a BMP control. In the Hek Id1 reporter gene assay, an inhibitory antibody may have an $IC_{50}$ of less than 10 nM, preferably less than 5 nM.

Once a suitable antibody has been identified and selected, the amino acid sequence of the antibody may be identified by methods known in the art. The genes encoding the antibody can be cloned using degenerate primers. The antibody may be recombinantly produced by routine methods.

The present disclosure also provides an isolated DNA sequence encoding the heavy and/or light chain variable regions(s) (or the full length H- and L-chains) of an antibody molecule newly described herein.

A variant polynucleotide may comprise 1, 2, 3, 4, 5, up to 10, up to 20, up to 30, up to 40, up to 50, up to 75 or more nucleic acid substitutions and/or deletions from any of the nucleic acid sequences (including GREM1 and anti-GREM1 antibody nucleic acid sequences) given in the sequence listing. Generally, a variant has 1-20, 1-50, 1-75 or 1-100 substitutions and/or deletions.

Suitable variants may be at least about 70% homologous to a polynucleotide of any one of nucleic acid sequences disclosed herein, typically at least about 80 or 90% and more suitably at least about 95%, 97% or 99% homologous thereto. Variants may retain at least about 90%, 91%, 92%, 93%, 94%, 95%, 96%, 97%, 98% or 99% identity. Variants typically retain about 60%-about 99% identity, about 80%-about 99% identity, about 90%-about 99% identity or about 95%-about 99% identity. Homology and identity at these levels is generally present at least with respect to the coding regions of the polynucleotides. Methods of measuring homology are well known in the art and it will be understood by those of skill in the art that in the present context, homology is calculated on the basis of nucleic acid identity. Such homology may exist over a region of at least about 15, at least about 30, for instance at least about 40, 60, 100, 200 or more contiguous nucleotides (depending on the length). Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached.

The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, typically less than about 0.1, suitably less than about 0.01, and most suitably less than about 0.001. For example, the smallest sum probability may be in the range of about 1-about 0.001, often about 0.01-about 0.001.

The homologue may differ from a sequence in the relevant polynucleotide by less than about 3, 5, 10, 15, 20 or more mutations (each of which may be a substitution, deletion or insertion). For example, the homologue may differ by 3-50 mutations, often 3-20 mutations. These mutations may be measured over a region of at least 30, for instance at least about 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

The DNA sequence may comprise synthetic DNA, for instance produced by chemical processing, cDNA, genomic DNA or any combination thereof.

DNA sequences which encode an antibody molecule described herein can be obtained by methods well known to those skilled in the art. For example, DNA sequences coding for part or all of the antibody heavy and light chains may be synthesised as desired from the determined DNA sequences or on the basis of the corresponding amino acid sequences.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Nucleic Acid Antagonists

A polynucleotide, such as a nucleic acid, is a polymer comprising two or more nucleotides. The nucleotides can be naturally occurring or artificial. A nucleotide typically contains a nucleobase, a sugar and at least one linking group, such as a phosphate, 2'O-methyl, 2' methoxy-ethyl, phosphoramidate, methylphosphonate or phosphorothioate group. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP.

The nucleotides may contain additional modifications. In particular, suitable modified nucleotides include, but are not limited to, 2'amino pyrimidines (such as 2'-amino cytidine and 2'-amino uridine), 2'-hydroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

The nucleotides in the polynucleotide may be attached to each other in any manner. The nucleotides may be linked by phosphate, 2'O-methyl, 2' methoxy-ethyl, phosphoramidate, methylphosphonate or phosphorothioate linkages. The nucleotides are typically attached by their sugar and phosphate groups as in nucleic acids. The nucleotides may be connected via their nucleobases as in pyrimidine dimers.

The GREM1 antagonist may be a polynucleotide encoding an anti-GREM1 antibody described herein.

The polynucleotide can be a nucleic acid, such as deoxyribonucleic acid (DNA) or a ribonucleic acid (RNA). The polynucleotide may be any synthetic nucleic acid known in the art, such as peptide nucleic acid (PNA), glycerol nucleic acid (GNA), threose nucleic acid (TNA), locked nucleic acid (LNA), morpholino nucleic acid or other synthetic polymers with nucleotide side chains. The polynucleotide may be single stranded or double stranded.

The polynucleotide sequence may be cloned into any suitable expression vector. In an expression vector, the polynucleotide sequence encoding a construct is typically operably linked to a control sequence which is capable of providing for the expression of the coding sequence by the host cell. Such expression vectors can be used to express a construct.

In one embodiment, the anti-GREM1 antagonist is a polynucleotide encoding an anti-GREM1 antibody described herein. The polynucleotide may be provided for use in gene therapy. The polynucleotide may be provided in any suitable vector capable of providing for expression of the anti-GREM1 antibody in vivo.

The polynucleotide encoding the anti-GREM1 antibody may be a DNA sequence. The DNA sequence may be provided in any suitable vector, e.g. an expression vector, for administration to a subject in need thereof. For example, the DNA sequence may be administered to the subject in an expression vector capable of providing for expression of the anti-GREM1 antibody in vivo. The expression vector may be a viral expression vector, such as an adeno-associated virus (AAV) vector. In one embodiment, the anti-GREM1 antagonist is a DNA sequence which encodes an anti-GREM1 antibody described herein. In one embodiment, the anti-GREM1 antagonist is a DNA sequence for use in gene therapy, wherein the DNA sequence encodes an anti-GREM1 antibody described herein. In one embodiment, the anti-GREM1 antagonist is an AAV comprising a DNA sequence which encodes an anti-GREM1 antibody described herein. In one embodiment, the anti-GREM1 antagonist is an AAV for use in gene therapy, wherein the AAV comprises a DNA sequence which encodes an anti-GREM1 antibody described herein.

The polynucleotide encoding the anti-GREM1 antibody may be an RNA sequence. The RNA sequence may be administered to a subject in need thereof in any suitable vector. The RNA sequence may be a messenger RNA (mRNA) sequence. The mRNA sequence may be administered to a subject in need thereof in a stabilised form. For example the mRNA sequence may be provided in a lipid nanoparticle (LNP) composition. The LNP composition may comprise any suitable LNPs capable of encapsulating the mRNA sequence to provide for increased stability of said mRNA sequence. Thus, in one embodiment, the anti-GREM1 antagonist is a stabilised mRNA sequence encoding an anti-GREM1 antibody described herein. In one embodiment, the anti-GREM1 antagonist is a stabilised mRNA sequence for use in gene therapy, wherein the mRNA sequence encodes an anti-GREM1 antibody described herein. In one embodiment, the anti-GREM1 antagonist is a LNP composition which comprises an mRNA encoding an anti-GREM1 antibody described herein. In one embodiment, the anti-GREM1 antagonist is an LNP composition for use in gene therapy, wherein the LNP composition comprises an mRNA encoding an anti-GREM1 antibody described herein.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence.

A GREM1 antagonist which is nucleic acid-based may reduce expression of GREM1. Antisense and RNA interference (RNAi) technology for knocking down protein expression are well known in the art and standard methods can be employed to knock down expression of a molecule of interest. Both antisense and siRNA technology interfere with mRNA. Antisense oligonucleotides interfere with mRNA by binding to (hybridising with) a section of the mRNA. The antisense oligonucleotide is therefore designed to be complementary to the mRNA (although the oligonucleotide does not have to be 100% complementary as discussed below). In other words, the antisense oligonucleotide may be a section of the cDNA. Again, the oligonucleotide sequence may not be 100% identical to the cDNA sequence. This is also discussed below. RNAi involves the use of double-stranded RNA, such small interfering RNA (siRNA) or small hairpin RNA (shRNA), which can bind to the mRNA and inhibit protein expression.

Accordingly, the antagonist may be a oligonucleotide which specifically hybridises to an mRNA encoding GREM1, such as the encoding sequence of SEQ ID NO: 36 or SEQ ID NO: 37 or a variant thereof. An oligonucleotide "specifically hybridises" to a target sequence when it hybridises with preferential or high affinity to the target sequence but does not substantially hybridise, does not hybridise or hybridises with only low affinity to other sequences. More preferably, the oligonucleotide hybridises to the target sequence with a $T_m$ that is at least 5° C., at least at least 10° C., at least 20° C., at least 30° C. or at least 40° C., greater than its $T_m$ for other nucleic acids. Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). The hybridisation conditions may be stringent conditions as described in the art.

Oligonucleotides are short nucleotide polymers which typically have 50 or fewer nucleotides, such 40 or fewer, 30 or fewer, 22 or fewer, 21 or fewer, 20 or fewer, 10 or fewer or 5 or fewer nucleotides. The oligonucleotide used may be 20 to 25 nucleotides in length, more preferably 21 or 22 nucleotides in length. The nucleotides can be naturally occurring or artificial. The nucleotides can be any of those described above.

The GREM1 antagonist may be an antibody that binds to GREM1, typically specifically binding GREM1. An antibody "specifically binds" to a protein when it binds with preferential or high affinity to that protein but does not substantially bind, does not bind or binds with only low affinity to other proteins. For instance, an antibody "specifically binds" a target molecule when it binds with preferential or high affinity to that target but does not substantially bind, does not bind or binds with only low affinity to other human proteins.

An antibody binds with preferential or high affinity if it binds with a Kd of 1×10-7 M or less, more preferably 5×10-8 M or less, more preferably 1×10-8 M or less or more preferably 5×10-9 M or less. An antibody binds with low affinity if it binds with a Kd of 1×10-6 M or more, more preferably 1×10-5 M or more, more preferably 1×10-4 M or more, more preferably 1×10-3 M or more, even more preferably 1×10-2 M or more. The antibody may be, for example, a monoclonal antibody, a polyclonal antibody, a single chain antibody, a chimeric antibody, a bispecific antibody, a CDR-grafted antibody or a humanized antibody. The antibody may be an intact immunoglobulin molecule or a fragment thereof such as a Fab, F(ab')$_2$ or Fv fragment.

Patient

Any patient may be treated in accordance with the invention. The patient is typically human. However, the patient may be another mammalian animal, such as a commercially farmed animal, such as a horse, a cow, a sheep, a fish, a chicken or a pig, a laboratory animal, such as a mouse or a rat, or a pet, such as a guinea pig, a hamster, a rabbit, a cat or a dog.

Pharmaceutical Compositions, Dosages and Dosage Regimes

A GREM1 antagonist of the invention may be provided in a pharmaceutical composition. The pharmaceutical composition will normally be sterile and will typically include a pharmaceutically acceptable carrier and/or adjuvant. A pharmaceutical composition of the present invention may additionally comprise a pharmaceutically acceptable adjuvant and/or carrier.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intravenous, intramuscular, intradermal, intraocular, intraperitoneal, subcutaneous, spinal or other parenteral routes of administration, for example by injection or infusion. Alternatively, the carrier may be suitable for non-parenteral administration, such as a topical, epidermal or mucosal route of administration. The carrier may be suitable for oral administration. Depending on the route of administration, the modulator may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be desirable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients.

Also within the scope of the present disclosure are kits comprising antagonists described herein and instructions for use. The kit may further contain one or more additional reagents, such as an additional therapeutic or prophylactic agent as discussed herein.

The antagonists described herein or formulations or compositions thereof may be administered for prophylactic and/or therapeutic treatments.

In therapeutic applications, compounds are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is typical.

An antagonist or pharmaceutical composition of the invention may be administered via one or more routes of administration using one or more of a variety of methods known in the art. As will be appreciated by the skilled artisan, the route and/or mode of administration will vary depending upon the desired results. Examples of routes of administration for compounds or pharmaceutical compositions of the invention include intravenous, intramuscular, intradermal, intraocular, intraperitoneal, subcutaneous, spinal or other parenteral routes of administration, for example by injection or infusion. The phrase "parenteral administration" as used herein means modes of administration other than enteral and topical administration, usually by injection. Alternatively, antibody/modulatory agent or pharmaceutical composition of the invention can be administered via a non-parenteral route, such as a topical, epidermal or mucosal route of administration. The antibody/modulatory agent or pharmaceutical composition of the invention may be for oral administration.

A suitable dosage of an antibody/modulatory agent or pharmaceutical composition of the invention may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 µg/kg to about 1000 mg/kg body weight, typically from about 0.1 µg/kg to about 100 mg/kg body weight, of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the antagonist in the patient and the duration of treatment desired.

As mentioned above, modulators/antibodies or pharmaceutical compositions of the invention may be co-administered with one or other more other therapeutic agents.

Combined administration of two or more agents may be achieved in a number of different ways. Both may be administered together in a single composition, or they may be administered in separate compositions as part of a combined therapy. For example, the one may be administered before or separately, after or sequential, or concurrently or simultaneously with the other.

Pharmaceutical Compositions and Modes of Administration

The antagonists for use in the methods of treatment described herein may be formulated in pharmaceutical compositions. These compositions may comprise, in addition to the therapeutically active ingredient(s), a pharmaceutically acceptable excipient, carrier, diluent, buffer, stabiliser or other materials well known to those skilled in the art. Such materials should be non-toxic and should not interfere with the efficacy of the active ingredient. The pharmaceutical carrier or diluent may be, for example, an isotonic solution.

The precise nature of the carrier or other material may depend on the route of administration, e.g. oral, intravenous, cutaneous or subcutaneous, nasal, intramuscular and intraperitoneal routes. For example, solid oral forms may contain, together with the active substance, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to an individual may be provided with an enteric coating comprising, for example, Eudragit "S", Eudragit "L", cellulose acetate, cellulose acetate phthalate or hydroxypropylmethyl cellulose.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active substance, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

For suppositories, traditional binders and carriers may include, for example, polyalkylene glycols or triglycerides; such suppositories may be formed from mixtures containing the active ingredient in the range of 0.5% to 10%, preferably 1% to 2%.

Polynucleotide or oligonucleotide inhibitors maybe naked nucleotide sequences or be in combination with cationic lipids, polymers or targeting systems. They may be delivered by any available technique. For example, the polynucleotide or oligonucleotide may be introduced by needle injection, preferably intradermally, subcutaneously or intramuscularly. Alternatively, the polynucleotide or oligonucleotide may be delivered directly across the skin using a delivery device such as particle-mediated gene delivery. The polynucleotide or oligonucleotide may be administered topically to the skin, or to mucosal surfaces for example by intranasal, oral, or intrarectal administration.

Uptake of polynucleotide or oligonucleotide constructs may be enhanced by several known transfection techniques, for example those including the use of transfection agents. Examples of these agents include cationic agents, for example, calcium phosphate and DEAE-Dextran and lipofectants, for example, lipofectam and transfectam. The dosage of the polynucleotide or oligonucleotide to be administered can be altered.

Administration is typically in a "prophylactically effective amount" or a "therapeutically effective amount" (as the case may be, although prophylaxis may be considered therapy), this being sufficient to show benefit to the individual, e.g. an effective amount to prevent or delay onset of the disease or condition, to ameliorate one or more symptoms, to induce or prolong remission, or to delay relapse or recurrence.

The dose may be determined according to various parameters, especially according to the substance used; the age, weight and condition of the individual to be treated; the route of administration; and the required regimen. A physician will be able to determine the required route of administration and dosage for any particular individual. A typical daily dose is from about 0.1 to 50 mg per kg of body weight dependent on the conditions mentioned above. The dose may be provided as a single dose or may be provided as multiple doses, for example taken at regular intervals, for example 2, 3 or 4 doses administered hourly. Typically polynucleotide or oligonucleotide inhibitors are administered in the range of 1 pg to 1 mg, preferably to 1 pg to 10 µg nucleic acid for particle mediated delivery and 10 µg to 1 mg for other routes.

Examples of the techniques and protocols mentioned above can be found in Remington's Pharmaceutical Sciences, 20th Edition, 2000, pub. Lippincott, Williams & Wilkins.

Therapeutic Combinations

A composition of the invention as described above may be used/administered alone or in combination with other therapeutic compositions or treatments, for example as adjunct therapy. The other therapeutic compositions or treatments may for example be one or more of those discussed herein, and may be administered either simultaneously or sequentially with the composition of the invention.

As discussed above, GREM1 antagonists have particular utility in combination treatments, since they may be used to sensitise a cancer or tumour to another anti-cancer agent, such as a chemotherapeutic agent, or to another cancer therapy, such as radiotherapy or surgery. The cancer may be resistant to the other anti-cancer agent or cancer therapy in the absence of the GREM1 antagonist.

Thus, an anti-GREM1 antagonist may be used in combination with any other cancer therapy or any other therapeutic agent for a cancer, such as a chemotherapeutic agent. The other cancer therapy may be selected from any known therapy for the relevant cancer, such as any known therapy for colorectal cancer. The other cancer therapy may be a radiotherapy. Suitable radiotherapy treatments are described for example in Van Cutsem (and others) Annals of Oncology, 2014. Vol 25, Issue 3. The radiotherapy may be carried out before surgery on a cancer or after surgery on a cancer. The radiotherapy may be adjuvant radiotherapy. The radiotherapy may be carried out in combination with a chemotherapy, for example administration of a chemotherapeutic agent as described below.

The other therapeutic agent for a cancer, such as a chemotherapeutic agent may be selected from any known therapeutic agent for the relevant cancer, including any known chemotherapeutic agent or combination of chemotherapeutic agents for the relevant cancer. For example, a GREM1 antagonist may be used in combination with one or more of 5-fluoruracil, oxaliplatin, irinotecan, and folinic acid, particularly in treatments of colorectal cancer. Further examples of combination treatments combining GREM1 antagonists with other anti-cancer agents for treatment of colorectal cancer and multiple myeloma are described below in the context of compositions and kits for treatment. The cancer may be resistant to one or more chemotherapeutic agents (such as one of the above chemotherapeutic agents) when not administered in combination with a GREM1 antagonist. A GREM1 antagonist may be used in combination with cetuximab, nivolumab or bevacizumab. A bispecific antibody combining an anti-GREM1 specificity and a nivolumab or bevacizumab specificity may be administered.

As part of the above aspects, the invention provides an anti-GREM1 antagonist for use in a method of treatment and/or prevention of cancer according to the invention, wherein the method comprises separate, sequential or simultaneous administration of a chemotherapeutic agent. The invention also provides an anti-GREM1 antagonist for use in a method of treatment and/or prevention of cancer according to the invention, wherein the method comprises separate, sequential or simultaneous radiotherapy. The invention further provides a chemotherapeutic agent for use in a method for the treatment of a cancer having stromal GREM1 overexpression wherein the method comprises separate, sequential or simultaneous administration of an anti-GREM1 antagonist. The invention also provides a chemotherapeutic agent for use in a method for the prevention or treatment of a cancer having epithelial GREM1 overexpression wherein the method comprises separate, sequential or simultaneous administration of an anti-GREM1 antagonist.

Additionally provided is a composition or kit comprising an anti-GREM1 antagonist and an additional anti-cancer agent. The additional anti-cancer agent may be a targeted therapeutic or a chemotherapeutic agent. The additional anti-cancer agent may be any anti-cancer agent described above. More than one such additional anti-cancer agents may be incorporated in the composition or kit. The composition or kit may comprise an anti-GREM1 antagonist and one or more anti-cancer agents selected from: 5-fluoruracil, oxaliplatin, irinotecan, and folinic acid, cetuximab, nivolumab and bevacizumab, particularly as part of a composition or kit for treatment of colorectal cancer. A composition or kit for treatment of multiple myeloma may comprise an anti-GREM1 antagonist and one or more of an anti-CD38 antibody (such as daratumumab), an anti-SLAMF7 antibody (such as elotuzumab) and/or an anti-IL-6 antibody (such as siltuximab). A bispecific antibody combining an anti-GREM1 specificity and one of the other above specificities may be provided in a composition or kit. A preferred combination comprises an anti-GREM1 antagonist and an anti IL-6 antibody (preferably siltuximab). A composition or kit for treatment of multiple myeloma may comprise an anti-GREM1 antagonist and bortezumib and/or iMID (lenalidomide/pomalenomide) or an analogue of either thereof. The anti-GREM1 antagonist in any of the above compositions and kits may preferably be an anti-GREM1 antibody.

Therapeutic Indications

Antagonists of the present invention are used in treating or preventing cancer.

Prevention of cancer may include preventing the subject from ever being diagnosed with cancer or deferring the onset of cancer. Prevention of cancer may also include prevention of relapse or recurrence of cancer in a subject who has been previously diagnosed with cancer. Prevention of cancer may additionally include increasing the survival of a subject who has not been diagnosed with cancer or who has been previously diagnosed with cancer.

Treatment of cancer may ameliorate one or more symptoms of, induce or prolong remission from, or delay relapse or recurrence of the cancer. Treatment may cure, alleviate or partially arrest the cancer. It may result in a decrease in severity of disease symptoms, or an increase in frequency or duration of symptom-free periods. Treatment of cancer may also include preventing a cancer (e.g. an established cancer) from spreading from its initial site within a patient's body to one or more secondary sites within the patient's body. Thus, treatment of cancer may include prevention of the dissemination or the metastasis of an existing cancer. Treatment of colorectal cancer may result in a reduction in polyp burden (number of polyps) as assayed for example by endoscopy. Treatment of multiple myeloma may result in a reduction in bone marrow tumour burden, for example as assayed by MRI/CT scan, and/or a reduction in plasma cell burden, which may be determined following bone marrow biopsy, and/or reduction of one or more serum markers such as monoclonal antibody production (paraprotein) and serum free light chain (FLC) ratio, and/or reduction in associated lytic lesions of the skeleton, which may be detectable by radiography.

Detection and Diagnosis

Based on the correlation between stromal GREM1 and cancer, the present invention also provides for additional means of detection and diagnosis of cancer, and for prognosis of cancer and prediction of responsiveness of a cancer to a treatment.

The invention thus provides a method for detecting cancer in a patient, the method comprising measuring stromal expression of GREM1 in the patient, wherein stromal overexpression of GREM1 indicates that the patient comprises a cancer. The invention also provides a method for prognosing a cancer in a patient, the method comprising determining whether or not the cancer comprises stromal overexpression of GREM1, wherein stromal overexpression of GREM1 in the cancer indicates that the patient has a worse prognosis than in the situation of normal stromal expression of GREM1. The cancer may be any cancer described herein. The cancer is preferably colorectal cancer, typically comprising a desmoplastic stroma, multiple myeloma or breast cancer.

Diagnosis includes determining whether or not an individual has a cancer or tumour and/or determining the severity of the cancer or tumour.

Prognosis includes predicting whether or not an individual will develop a cancer or tumour, whether or not they will need treatment, the type of treatment the individual will need, whether or not they will respond to a treatment, whether or not and/or when they will suffer a cancer episode, recurrence or relapse, and the severity or duration of a symptom or a cancer episode, recurrence or relapse. The method of prognosis may predict whether or not an individual in remission from cancer will have a recurrence. Predicting whether or not the individual will have a recurrence includes determining the likelihood that the individual will have a recurrence, and/or predicting when they will have a recurrence. The invention further provides a method for determining whether or not a patient having or suspected of having or being at risk of developing cancer is likely to respond to treatment with a chemotherapeutic agent, which method comprises measuring stromal expression of GREM1 in the patient, and thereby predicting whether or not the patient is likely to respond to treatment with the chemotherapeutic agent.

The invention additionally provides a method for determining whether or not a patient having or suspected of having or being at risk of developing cancer is likely to respond to treatment with a GREM1 antagonist, the method comprising measuring stromal expression of GREM1 in the patient, and thereby predicting whether or not the patient is likely to respond to treatment with the GREM1 antagonist. The above methods may further predict responsiveness to combined treatment with a GREM1 antagonist and a chemotherapeutic agent, or combined treatment comprising administration of a GREM1 antagonist and radiotherapy.

Predicted responsiveness in an individual to a given therapy means that the individual is expected to derive benefit, or a sufficient extent of benefit, from receiving the therapy. Predicted non-responsiveness in an individual to a therapy means that the individual is not expected to derive benefit, or a sufficient extent of benefit, from receiving the therapy. The method for predicting the response may be carried out before administration of the GREM1 antagonist or chemotherapeutic agent. The prediction may then be taken into account when selecting or recommending a suitable treatment for the individual. Alternatively, the method may be carried out after treatment with the therapy and used to monitor and predict the individual's response to treatment. Typically the method is for predicting whether or not the individual will have a primary response to treatment with the therapy, i.e. whether or not the individual will respond when first receiving the treatment. In some cases the method is for predicting secondary non-responsiveness, i.e. whether or not an individual who initially responds to treatment will later stop responding to treatment or will respond less well to the treatment.

According to the present invention, increased stromal and/or epithelial level of GREM1 in an individual, as compared with a reference sample or reference level, indicates a positive diagnosis relating to the presence of cancer, for example that the individual has a cancer or a particular form of cancer or has more severe cancer. An increased stromal and/or epithelial level of GREM1 also indicates a negative prognosis, that is a poor predicted outcome for the individual, for example that the individual will not respond to a particular therapy, that an individual in remission from cancer will have a recurrence or that the individual is at increased risk of developing the cancer.

Conversely, a decreased or normal level of GREM1 indicates a negative diagnosis, for example that the individual does not have the cancer or has less severe cancer. A decreased level of GREM1 may indicate a positive prognosis, that is a good outcome for the patient, for example that the individual will respond to a particular therapy or that an individual in remission from the cancer will not have a recurrence or is not at increased risk of developing the disease or condition. For diagnosing whether or not an individual has the cancer, the reference sample or level typically represents a baseline level of GREM1 in an individual who does not have the relevant cancer, or who is suspected of having a cancer, but is subsequently confirmed to not have the cancer.

The method of diagnosis or prognosis may include selecting or recommending a suitable treatment for the individual, i.e. based on the diagnosis or prognosis. The selected or recommended treatment may then be administered to the individual. Thus, the above methods of detection, diagnosis, prognosis and prediction of responsiveness may further comprise a step of administering one or more prophylactic or therapeutic anti-cancer agents to the individual, or administering a cancer therapy, such as radiotherapy. The one or more agents typically comprise a GREM1 antagonist, any may further comprise an additional anti-cancer agent as described above.

In some cases, an overexpression of GREM1, as compared with a reference sample or reference level, indicates that the individual will respond to therapy with a GREM1 antagonist. A therapy including use of a GREM1 antagonist may then be selected or recommended, and may then further be administered to the individual. Similarly, a therapy comprising use of a GREM1 antagonist and an additional anti-cancer agent may be selected based on the overexpression of GREM1.

In other cases, a decreased or normal level of GREM1, as compared with a reference sample or reference level, indicates that the individual will not respond to therapy with a GREM1 antagonist. A GREM1 antagonist is then not administered to the individual. Further, a therapeutic treatment other than GREM1 antagonist may be selected or recommended for treatment of the individual, and may then further be administered to the individual.

In all aspects of the invention, an individual having cancer (e.g. colorectal cancer or multiple myeloma or breast cancer) or an individual suspected of having the disease or condition and/or an individual at risk of developing the disease or condition may be selected for treatment or identified. For example, the individual may not have been formally diagnosed but may be suspected of having the disease or condition because of the presence of one or more symptoms. The individual may be considered at risk of developing cancer if they have one or more risk factors associated with cancer and/or one or more predispositions which increase their susceptibility to cancer. Risk factors in relation to colorectal cancer include SNPs as described above and for example in Tomlinson et al, PLos Genet, 2011, discussed supra, and inherited genetic mutations such as mutation or mutations in the GREM1 encoding gene, or any other mutation affecting expression of the GREM1 gene, including the mutation causative of HMPS.

The following Examples illustrate the invention.

EXAMPLES

Example 1—Protein Expression, Purification, Refolding and Structure Determination Protein Expression and Inclusion Body Preparation A truncated human Gremlin-1 coding sequence (SEQ ID NO: 20), optimised for expression in *E. coli*, was cloned into a modified pET32a vector (Merck Millipore) using BamHI/XhoI, generating a vector encoding the Gremlin sequence with an N-terminal 6His-TEV tag (pET-hGremlin1).
Expressed Sequence:

SEQ ID NO: 2
*MGSSHHHHHHSSGENLYFQGS*AMPGEEVLESSQEALHVTERKYLKRDWC

KTQPLKQTIHEEGCNSRTIINRFCYGQCNSFYIPRHIRKEEGSFQSCSF

CKPKKFTTMMVTLNCPELQPPTKKKRVTRVKQCRCISIDLD;

(with non-Gremlin residues of the 6His-TEV tag shown in italics). Sequence numbering based on UniProt O60565 & SEQ ID NO: 1.

The pET-hGremlin1 plasmid DNA was used to transform BL21(DE3) cells. A single ampicillin resistant colony was picked from a LB/Amp agar plate and used to inoculate a 100 ml starter culture of LB/Amp. After shaking (200 rpm) for 16 hr at 37° C., 25 ml of the starter culture was used to inoculate 500 mL of 2×TY/Amp media. The culture was shaken (250 rpm) at 37° C. until an $OD_{600}$ of 3 was achieved. Subsequently, the culture was supplemented with 20 mL of a MOPS+glycerol feed mix (1M MOPS pH 7.4, 40% glycerol, 0.5% $MgSO_4$, 0.42% $MgCl_2$), induced with 300 μM IPTG and further incubated at 17° C., 180 rpm for 16 hours. Cells were harvested in a centrifuge (4,000 g for 20 minutes at 4° C.).

Cell pellets were resuspended in Lysis Buffer (PBS pH 7.4, 0.35 mg/ml lysozyme, g/ml DNase and 3 mM $MgCl_2$) at 4° C. and the insoluble fraction was harvested by centrifugation at 3,500 g for 30 minutes at 4° C. Pelleted inclusion bodies were washed three times by resuspending in wash buffer (50 mM Tris, 500 mM NaCl, 0.5% Triton X-100, pH 8.0), followed by centrifugation at 21,000 g for 15 minutes. An additional two washes were performed using wash buffer without Triton X-100.

Solubilisation

Inclusion bodies were resuspended in denaturing buffer (8 M Urea, 100 mM Tris, 1 mM EDTA, 10 mM $Na_2S_4O_6$ and 100 mM $Na_2SO_3$, pH 8.5), stirred for 16 hrs at room-temperature and clarified by centrifugation at 21,000 g for 15 minutes.

Pre-Refolding Purification

The solubilized inclusion bodies were loaded onto a Sephacryl S-200 26/60 column (120 mL) equilibrated in 8 M Urea, 50 mM MES, 200 mM NaCl, 1 mM EDTA, pH 6.0. Fractions containing Gremlin-1 protein were diluted with 6 M Urea, 20 mM MES, pH 6.0 and loaded onto HiTrap SP HP cation exchange columns and eluted with a 1 M NaCl gradient over 10 column volumes (10 CVs). Fractions containing purified, denatured hGremlin-1 protein were pooled.

Refolding

Denatured purified Gremlin-1 protein was added dropwise to re-folding buffer (50 mM Tris, pH 8.5, 150 mM NaCl, 5 mM GSH and 5 mM GSSG, 0.5 mM Cysteine, 5 mM EDTA, 0.5 M Arginine) to a final concentration of 0.1 mg/ml and incubated at 4° C. with constant stirring for 5 days. After 5 days the Gremlin-1 protein was dialysed against 20 mM HEPES, 100 mM NaCl, pH 7.5.

Following dialysis protein was applied to heparin HiTrap column and eluted using a gradient of 0-100% heparin elution buffer (20 mM HEPES, 1 M NaCl, pH 7.5) over 20 CV. Correctly folded protein eluted at 1 M NaCl whereas any misfolded protein eluted at lower salt concentrations.

Protein eluting at 1 M NaCl was concentrated and purified further on a S75 26/60 column equilibrated with 20 mM Hepes, pH 7.5, 1 M NaCl.

Protein was characterised by SDS PAGE (shift in gel), demonstrated to have the expected molecular weight and correct arrangement of disulphide bonds using liquid chromatography mass spectrometry (LC-MS) and to be active in a cell assay (ID1 reporter assay).

Gremlin 1 Structure Determination

Gremlin 1 protein crystals were grown using the hanging-drop method by mixing a solution of Gremlin 1 at 6.6 mg/ml and 0.1 M citric acid at pH 4, 1 M lithium chloride and 27% polyethylene glycol (PEG) 6000 in a 1:1 ratio. Before data collection, crystals were cryo-protected by adding 20% glycerol to the crystallization buffer. Diffraction data were collected at the Diamond Light Source and were processed using XDS (Kabsch, Wolfgang (2010) Acta Crystallographica Section D 66, 125-132). Diffraction data statistics are summarized in the table below:

TABLE 2

Diffraction data statistics

| Diffraction Statistics | |
|---|---|
| Wavelength (Å) | 0.97949 |
| Space group | C2 |
| Cell dimensions | a = 84.55 Å, |

TABLE 2-continued

Diffraction data statistics

|  |  |
|---|---|
|  | b = 107.22 Å, |
|  | c = 77.09 Å; |
|  | α = 90.00°, |
|  | β = 120.43°, |
|  | γ = 90.00° |
| Resolution range* (Å) | 26.19-2.72 (2.79-2.72) |
| Completeness (%) | 98.5 (99.0) |
| Multiplicity | 3.4 (3.4) |
| I/sigma | 9.6 (2.0) |
| Rmerge | 0.095 (0.622) |
| Refinement Statistics |  |
| Resolution Range (Å) | 26.19-2.72 |
| $R_{cryst}$ | 0.24 |
| $R_{free}$ | 0.29 |
| R.m.s.d. bonds (Å)** | 0.013 |
| R.m.s.d. angles (°) | 1.782 |

*values in parenthesis correspond to the highest resolution shell
**r.m.s.d root mean square deviation Gremlin-1 structure was solved by molecular replacement using Phaser (McCoy et al, J Appl Cryst (2007), 40, 658-674) and a Gremlin-1 model available from proprietary Gremlin-1/Fab complex coordinates. The resultant model of Gremlin-1 contained four copies of Gremlin 1 monomer organised as two dimers. Model corrections were made with Coot (Emsley et al Acta Crystallographica Section D: Biological Crystallography 66 (4), 486-501) and coordinates were refined using Refmac (Murshudov et al REFMAC5 for the refinement of macromolecular crystal structures. Acta Crystallographica Section D: Biological Crystallography. 2011; 67(Pt 4):355-367). Final coordinates were validated with Molprobity (Chen et al. (2010) MolProbity: all-atom structure validation for macromolecular crystallography. Acta Crystallographica D66:12-21). A summary of model refinement statistics is shown in Table 2 above. Full structural data for Gremlin-1 crystallography is provided in Table 1 (FIG. 1) of PCT/EP2017/083650 filed 19 Dec. 2017, incorporated herein by reference.

Example 2—BMP Binding Residues on Gremlin-1

As discussed above, Gremlin-1 belongs to the bone morphogenic protein (BMP) antagonist protein family within a sub-group known as the DAN family. Within the DAN family, Gremlin-1 shares greatest homology with Gremlin-2 (PRDC).

The 2.7 Å human Gremlin-1 structure resolved in Example 1 shares many features in common with the published mouse Gremlin-2 structure (Nolan et al (2013), Structure, 21, 1417-1429). The overall fold is very similar, with two copies of Gremlin-1 forming an antiparallel, non-covalent dimer, arranged in an arch. Each monomer adopts the characteristic finger-wrist-finger arrangement with a cystine-knot motif towards the wrist end, opposite the fingers. Sequence identity between the proteins is 52% rising to 67% within the sequence visible in the two structures. The most highly conserved region lies in the extensive dimer interface where all the key contact residues are 100% conserved.

Residues involved in BMP's 2, 4 & 7 binding to mouse Gremlin-2 (PRDC) and DAN (NBL1) have been identified using mutagenesis (Nolan et al (2013), Structure, 21, 1417-1429 and Nolan et al (2014) J. Biol. Chem. 290, 4759-4771). The predicted BMP binding epitope encompasses a hydrophobic patch spanning across both monomers on the convex surface of the dimer. Six residues were identified by mutagenesis; Trp72, Phe96, Tyr98, Phe104, Tyr105 & Phe117 and are 100% conserved in human Gremlin-1 (numbering based on the mouse Gremlin-2 sequence). The degree of homology extends to the positioning of the side chains which adopt an identical conformation in both proteins.

The amino acid numbering used in the Gremlin PDB file matches the numbering in the published mouse Gremlin-2 structure based on a structural alignment. This enables like for like comparison of amino acids when describing the structures. However, for clarity the key residues identified as playing a role in BMP binding are shown below with numbering based on the PDB file and UniProt file of SEQ ID NO: 1 in brackets:

Trp72(93), Phe96(117), Tyr98(119), Phe104(125), Tyr105(126) & Phe117(138).

In both mouse Gremlin-2 and human Gremlin-1 the hydrophobic BMP binding epitope is partially buried by an alpha helix formed by the N-terminal residues of each protein. A model of BMP binding has been proposed whereby the N-terminus can flex, exposing the full BMP binding interface (Nolan et al (2013), Structure, 21, 1417-1429). In the present analysis, the N-terminal residues were removed from the human Gremlin-1 and mouse Gremlin-2 structures before rendering a surface to reveal the similarity of the BMP binding faces on each protein.

The literature only describes mutagenesis of six resides that have an effect on BMP binding. It is possible that the actual BMP epitope covers a larger surface area, encompassing neighbouring amino acids. By highlighting all residues, within 6 Å of those mutated, on the surface of Gremlin-1, a larger region of Gremlin-1 is revealed that could potentially be targeted by a therapeutic. This more extensive region encompasses the following amino acids of human Gremlin-1:

Asp92-Leu99
Arg116-His130
Ser137-Ser142
Cys176-Cys178
(Numbering based on SEQ ID NO: 1).

By combining published information with the crystal structure information of human Gremlin-1, regions of human Gremlin-1 that offer themselves as a potential route for therapeutic intervention blocking its interaction with BMP's have been identified.

Example 3—Hek Id1 Reporter Gene Assay

Background

The Hek Id1 reporter gene assay uses Clone 12 Hek293-Id1 reporter cells. This cell line was stably transfected with Id1 transcription factor. Id1 is a transcription factor in the BMP signalling pathway. Gremlin is known to bind BMPs prevent binding to their receptors reducing the luciferase signal from the reporter gene. Therefore, using this reporter assay, it is possible to screen anti-Gremlin antibodies and see if there are any that block the interaction of Gremlin with BMPs. A restoration of the luciferase signal is seen in these cells if there is a blocking of this interaction.

Method

Clone 12 cells were cultured in DMEM containing 10% FCS, 1× L-Glutamine & 1× NEAA. Cells are also grown in the presence of Hygromycin B (200 µg/ml) to ensure cells do not lose Id1 gene expression. Cells were assayed in DMEM containing 0.5% FCS, 1× L-Glutamine & 1× NEAA. Hygromycin B is not needed for the short time that the cells are in the assay.

The cells were washed in PBS, lifted off using cell dissociation buffer, spun and counted before being seeded at 5×104/well in 70 μl (Density of 7.14×10$^5$/ml). Plates used were white, opaque Poly-D-Lysine coated 96-well sterile. Cells go in incubator for about 3-4 hours to settle down. BMP heterodimers were reconstituted to 200 μg/ml in 4 mM HCL. BMP was diluted to 10 μg/ml in assay media using a glass vial to give a new working stock.

In a polypropylene plate, Gremlin-1 was diluted 1:2 for an 8 point dose response curve with a top final dose of 1 μg/ml.

An additional volume of 20 μl media was added per well and plates were incubated at 37° C. for 45 mins.

BMP prepared at 100× was added to all wells except wells containing cells only. All wells are made up to 60 μl with assay medium and incubated for a further 45 mins at 37° C.

Post incubation, 30 μl of sample was transferred per well of assay plate and incubated for 20-24 hours before measuring luminescence signal.

Cell Steady Glo was thawed in advance at room temperature. Assay plates were cooled to room temperature for about 10-15 mins before adding the reagent. Luciferase signal was detected by addition of cell steady glo reagent (100 μl) for 20 minutes on shaker at room temperature and measuring luminescence using cell titre glo protocol on Synergy 2.

The maximum signal was generated from wells containing BMP and the minimum signal was generated from the wells containing cells only.

Results

Gremlin-1 full length and truncated forms were tested in the Hek-Id1 reporter gene assay to confirm the blocking activity against BMP4/7.

The percentage of inhibition from dose response assays was calculated based on the maximum and minimum signals in the assay and the data fitted using 4 parameter logistical fit. The IC$_{50}$ was calculated based on the inflexion point of the curve.

TABLE 3

Potency results for full length Gremlin-1 and truncated Gremlin-1 in the Hek-Id1 reporter gene assay.

| Hek-Id1 Reporter gene assay | N | Geometric mean (nM) | 95% CI (or range where N = <4) |
|---|---|---|---|
| Gremlin 1 Full length | 2 | 1.6 | 1.3-1.9 |
| Gremlin 1 truncated | 2 | 1.7 | 1.1-2.5 |

Conclusion
Gremlin 1 was able to inhibit the BMP 4/7 signalling in the Hek-Id1 reporter gene assay.

Example 4—Production of Anti-Gremlin-1 Antibodies

Anti-Gremlin-1 antibodies were derived by immunisation using purified gremlin-1 as described in Example 1, and by library panning. The library was generated in-house as a naïve human library with the V-regions amplified from blood donations.

Immunisation yielded 26 distinct antibodies binding Gremlin-1 from the first round of immunisation. These antibodies were scaled up and purified for testing in screening assays.

25 human and mouse cross-reactive antibodies from the library were panned using recombinant human Gremlin from R&D Systems. 10 antibodies were selected for scale up and purified as scFvs for testing in the screening assays.

Example 5—Screening of Anti-Gremlin-1 Antibodies

Antibodies were screened using the Hek-Id1 reporter gene assay described in Example 3 and by measuring SMAD phosphorylation. SMAD1, 5 and 8 are phosphorylated upon BMP signalling. Inhibitors of Gremlin-1 therefore increase SMAD phosphorylation.

SMAD phosphorylation assays were conducted on A549 cells or on human lung fibroblasts. Phosphorylation levels were determined using MSD.

Results

In the Hek-Id1 reporter gene assay, there were no apparent hits with the immunisation derived antibodies (with a 10 fold excess of antibody tested against a BMP4/7 heterodimer). Results are shown in FIG. 1.

Figure 2:
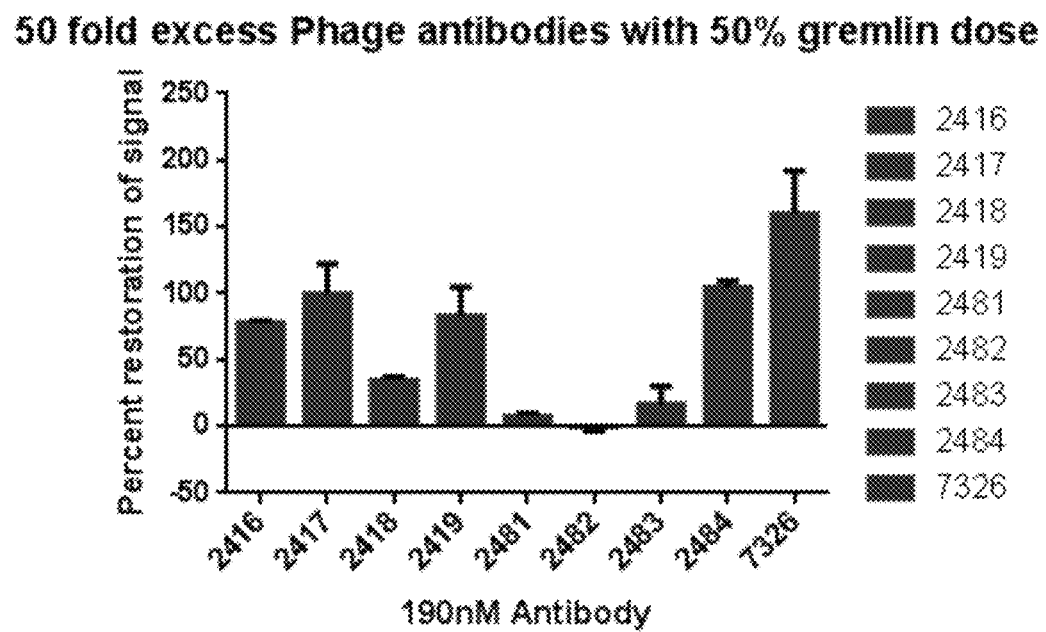
FIG. 2. Percentage restoration of signal for library derived antibodies in the HEK-ID1 reporter gene assay.

In contrast, a number of library derived antibodies were capable of restoring signal in the Hek-Id1 reporter gene assay (50-fold excess of antibodies with a 50% gremlin dose) (FIG. 2). Of these, Ab2416 and Ab2417 contained high levels of endotoxin. Ab7326 maintained blocking ability at a 10-fold excess and 80% inhibition Gremlin-1 concentration.

Figures 3A, 3B:
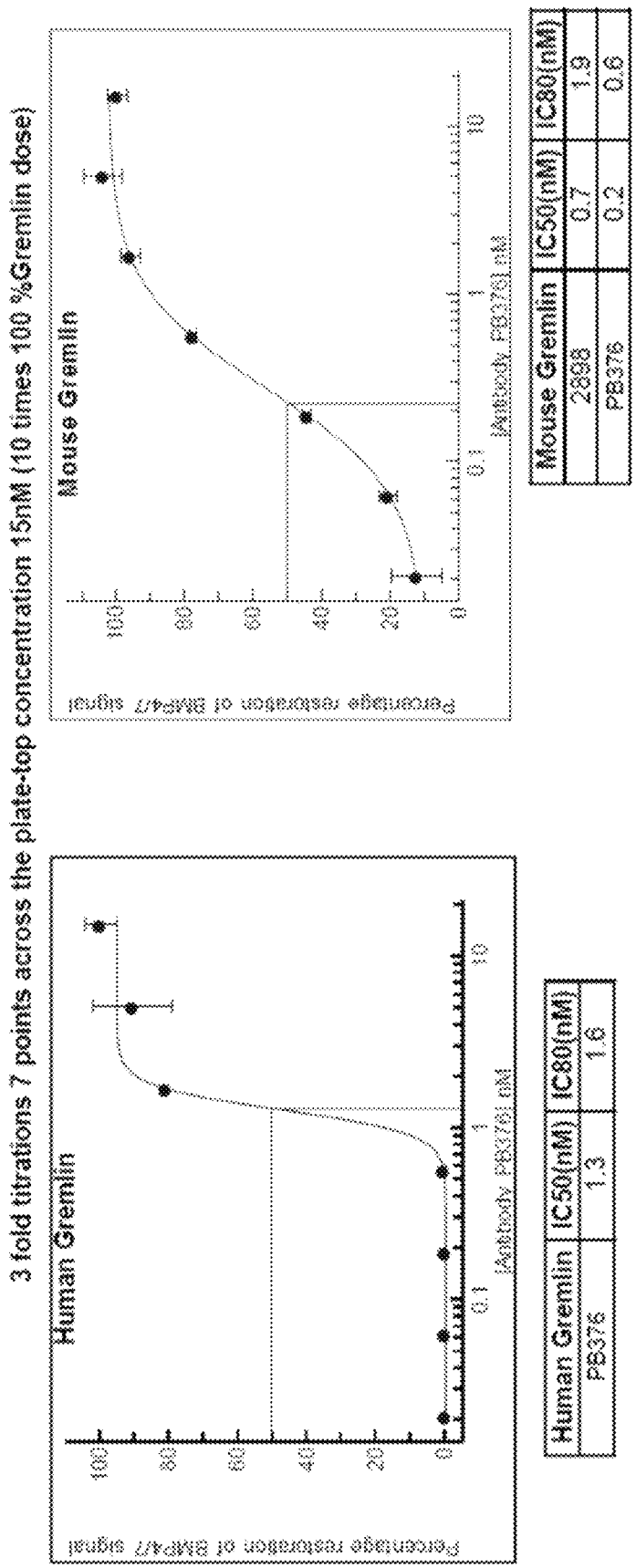
FIGS. 3A-3B. Results for the HEK-ID1 reporter gene assay with titrations of human Gremlin (FIG. 3A) and mouse Gremlin (FIG. 3B) and the effect of antibody 7326 (shown as antibody PB376) in restoring signalling of BMP.

Additional results are presented in FIGS. 3A (human gremlin) and 3B (mouse Gremlin). These figures show titrations of Ab7326 (labelled as PB376) up to 15 nM. Ab7326 was shown to restore signalling of BMP when blocked by either human (IC$_{50}$ of 1.3 nM) or mouse (IC$_{50}$ of 0.2 nM Gremlin). The antibody functions both as a human and mouse IgG1.

Sequences of the mouse and human full length IgG1 are presented below. In order to synthesise the mouse and human full length IgG1 proteins, the Ab7326 variable regions derived from the library were re-cloned into vectors comprising the appropriate antibody constant domains.

Because Ab7326 came from a naïve human library, where Abs are cloned as scFvs, in order to re-clone the 7326 variable regions as full length Abs or Fabs, it was necessary to PCR amplify the VH and VK using pools of primers/degenerate primers. The amplified PCR products were then digested and cloned simultaneously into mouse and human vectors. As the VH and VK were amplified by pools of primers/degenerate primers, two variant forms of the products were obtained, differing by a single amino acid residue derived from subtly different primers annealing during the PCR process.

The two variant forms of heavy chain variable region differed by a single amino acid at position 6, and the two variant forms of the light chain variable region differed by a single amino acid at position 7, as shown below:

Heavy chain variable region variant 1 has glutamic acid (E) at position 6.
Heavy chain variable region variant 2 has glutamine (Q) at position 6.
Light chain variable region variant 1 has serine (S) at position 7.
Light chain variable region variant 2 has threonine (T) at position 7.

Mouse Full Length IgG1—Heavy Chain Variant 1 (SEQ ID NO: 14)

QVQLVESGAE VKKPGATVKI SCKVSGYTFT DYYMHWVQQA

PGKGLEWMGL VDPEDGETIY AEKFQGRVTI TADTSTDTAY

MELSSLRSED TAVYYCATDA RGSGSYYPNH FDYWGQGTLV

```
TVSSAKTTPP SVYPLAPGSA AQTNSMVTLG CLVKGYFPEP

VTVTWNSGSL SSGVHTFPAV LQSDLYTLSS SVTVPSSTWP

SETVTCNVAH PASSTKVDKK IVPRDCGCKP CICTVPEVSS

VFIFPPKPKD VLTITLTPKV TCVVVDISKD DPEVQFSWFV

DDVEVHTAQT QPREEQENST FRSVSELPIM HQDWLNGKEF

KCRVNSAAFP APIEKTISKT KGRPKAPQVY TIPPPKEQMA

KDKVSLTCMI TDFFPEDITV EWQWNGQPAE NYKNTQPIMD

TDGSYFVYSK LNVQKSNWEA GNTFTCSVLH EGLHNHHTEK

SLSHSPGK
```

Mouse Full Length IgG1—Light Chain Variant 1 (SEQ ID NO: 15)

```
DIVMTQSPDS LAVSLGERAT INCKSSQSVL YSSNNKNYLA

WYQQKPGQPP KLLIYWASTR ESGVPDRESG SGSGTDFTLT

INSLQAEDVA VYFCQQYYDT PTFGQGTRLE IKRTDAAPTV

SIFPPSSEQL TSGGASVVCF LNNFYPKDIN VKWKIDGSER

QNGVLNSWTD QDSKDSTYSM SSTLTLTKDE YERHNSYTCE

ATHKTSTSPI VKSENRNEC
```

Mouse Full Length IgG1—Heavy Chain Variant 2 (SEQ ID NO: 28)

```
QVQLVQSGAE VKKPGATVKI SCKVSGYTFT DYYMHWVQQA

PGKGLEWMGL VDPEDGETIY AEKFQGRVTI TADTSTDTAY

MELSSLRSED TAVYYCATDA RGSGSYYPNH FDYWGQGTLV

TVSSAKTTPP SVYPLAPGSA AQTNSMVTLG CLVKGYFPEP

VTVTWNSGSL SSGVHTFPAV LQSDLYTLSS SVTVPSSTWP

SETVTCNVAH PASSTKVDKK IVPRDCGCKP CICTVPEVSS

VFIFPPKPKD VLTITLTPKV TCVVVDISKD DPEVQFSWFV

DDVEVHTAQT QPREEQENST FRSVSELPIM HQDWLNGKEF

KCRVNSAAFP APIEKTISKT KGRPKAPQVY TIPPPKEQMA

KDKVSLTCMI TDFFPEDITV EWQWNGQPAE NYKNTQPIMD

TDGSYFVYSK LNVQKSNWEA GNTFTCSVLH EGLHNHHTEK

SLSHSPGK
```

Mouse Full Length IgG1—Light Chain Variant 2 (SEQ ID NO: 29)

```
DIVMTQTPDS LAVSLGERAT INCKSSQSVL YSSNNKNYLA

WYQQKPGQPP KLLIYWASTR ESGVPDRESG SGSGTDFTLT

INSLQAEDVA VYFCQQYYDT PTFGQGTRLE IKRTDAAPTV

SIFPPSSEQL TSGGASVVCF LNNFYPKDIN VKWKIDGSER

QNGVLNSWTD QDSKDSTYSM SSTLTLTKDE YERHNSYTCE

ATHKTSTSPI VKSENRNEC
```

Human Full Length IgG1—Heavy Chain Variant 1 (SEQ ID NO: 30)

```
QVQLVESGAE VKKPGATVKI SCKVSGYTFT DYYMHWVQQA

PGKGLEWMGL VDPEDGETIY AEKFQGRVTI TADTSTDTAY

MELSSLRSED TAVYYCATDA RGSGSYYPNH FDYWGQGTLV

TVSSASTKGP SVFPLAPSSK STSGGTAALG CLVKDYFPEP

VTVSWNSGAL TSGVHTFPAV LQSSGLYSLS SVVTVPSSSL

GTQTYICNVN HKPSNTKVDK KVEPKSCDKT HTCPPCPAPE

LLGGPSVELF PPKPKDTLMI SRTPEVTCVV VDVSHEDPEV

KENWYVDGVE VHNAKTKPRE EQYNSTYRVV SVLTVLHQDW

LNGKEYKCKV SNKALPAPIE KTISKAKGQP REPQVYTLPP

SRDELTKNQV SLTCLVKGFY PSDIAVEWES NGQPENNYKT

TPPVLDSDGS FFLYSKLTVD KSRWQQGNVF SCSVMHEALH

NHYTQKSLSL SPGK
```

Human Full Length IgG1—Light Chain Variant 1 (SEQ ID NO: 31)

```
DIVMTQSPDS LAVSLGERAT INCKSSQSVL YSSNNKNYLA

WYQQKPGQPP KLLIYWASTR ESGVPDRESG SGSGTDFTLT

INSLQAEDVA VYFCQQYYDT PTFGQGTRLE IKRTVAAPSV

FIFPPSDEQL KSGTASVVCL LNNFYPREAK VQWKVDNALQ

SGNSQESVTE QDSKDSTYSL SSTLTLSKAD YEKHKVYACE

VTHQGLSSPV TKSENRGEC
```

Human Full Length IgG1—Heavy Chain Variant 2 (SEQ ID NO: 16)

```
QVQLVQSGAE VKKPGATVKI SCKVSGYTFT DYYMHWVQQA

PGKGLEWMGL VDPEDGETIY AEKFQGRVTI TADTSTDTAY

MELSSLRSED TAVYYCATDA RGSGSYYPNH FDYWGQGTLV

TVSSASTKGP SVEPLAPSSK STSGGTAALG CLVKDYFPEP

VTVSWNSGAL TSGVHTFPAV LQSSGLYSLS SVVTVPSSSL

GTQTYICNVN HKPSNTKVDK KVEPKSCDKT HTCPPCPAPE

LLGGPSVELE PPKPKDTLMI SRTPEVTCVV VDVSHEDPEV

KENWYVDGVE VHNAKTKPRE EQYNSTYRVV SVLTVLHQDW

LNGKEYKCKV SNKALPAPIE KTISKAKGQP REPQVYTLPP

SRDELTKNQV SLTCLVKGFY PSDIAVEWES NGQPENNYKT

TPPVLDSDGS FFLYSKLTVD KSRWQQGNVF SCSVMHEALH

NHYTQKSLSL SPGK
```

Human Full Length IgG1—Light Chain Variant 2 (SEQ ID NO: 17)

```
DIVMTQTPDS LAVSLGERAT INCKSSQSVL YSSNNKNYLA

WYQQKPGQPP KLLIYWASTR ESGVPDRESG SGSGTDFTLT
```

-continued

```
INSLQAEDVA VYFCQQYYDT PTFGQGTRLE IKRTVAAPSV

FIFPPSDEQL KSGTASVVCL LNNFYPREAK VQWKVDNALQ

SGNSQESVTE QDSKDSTYSL SSTLTLSKAD YEKHKVYACE

VTHQGLSSPV TKSENRGEC
```

Antibody CDRs were determined using the Kabat method (highlighted in bold in the above sequences). Additional HCDR1 residues using the Chothia definition are in italics. Constant region sequences are underlined.

Restoration of p-SMAD signalling with anti-Gremlin 1 antibodies is shown in Table 4 below.

TABLE 4

Restoration of p-SMAD signalling

| | 2417 | 2418 | 2419 | 2481 | 2482 | 2483 | 2484 | 7326 | 8427 |
|---|---|---|---|---|---|---|---|---|---|
| BMP 2 50 ng/ml | 109.1% +/− 2.8% | 58.2% +/− 1.9% | 32.6% +/− 1.4% | 40.4% +/− 0.6% | 35.3% +/− 0.8% | 43.1% +/− 2.1% | 104.0% +/− 2.7% | 107.2% +/− 3.5% | 51.3% +/− 1.4% |
| BMP 4 25 ng/ml | 109.6% +/− 3.0% | 71.3% +/− 3.1% | 31.7% +/− 1.2% | 60.1% +/− 2.2% | 54.4% +/− 1.3% | 72.5% +/− 2.1% | 105.2% +/− 3.3% | 110.0% +/− 3.8% | 78.2% +/− 2.5% |
| BMP 7 200 ng/ml | 111.5% +/− 3.8% | 99.5% +/− 3.2% | 53.8% +/− 3.4% | 64.4% +/− 1.3% | 52.3% +/− 1.1% | 66.2% +/− 1.2% | 105.2% +/− 4.3% | 108.0% +/− 3.2% | 72.6% +/− 2.5% |
| BMP-2/7 50 ng/ml | 119.3% +/− 2.6% | 78.6% +/− 3.6% | 50.8% +/− 2.7% | 53.7% +/− 3.1% | 47.6% +/− 1.5% | 56.1% +/− 2.5% | 120.4% +/− 4.4% | 128.5% +/− 2.9% | 62.8% +/− 2.5% |
| BMP4/7 50 ng/ml | 113.7% +/− 3.1% | 78.0% +/− 4.0% | 61.4% +/− 4.0% | 48.3% +/− 2.1% | 41.7% +/− 1.7% | 50.8% +/− 1.7% | 112.4% +/− 2.5% | 127.0% +/− 3.1% | 63.3% +/− 2.1% |

Results are shown as a percentage of SMAD phosphorylation by BMP alone (control BMP). Experiments were performed using lung fibroblasts from idiopathic pulmonary fibrosis patients. rhGremlin-1 and the anti-Gremlin-1 antibodies were preincubated for 45 minutes at room temperature. rhGremlin-1 and the anti-Gremlin-1 antibodies were then added with BMP to the cells for 30 minutes.

Table 5 then shows further results in the SMAD phosphorylation assay, where displacement of BMP-2 or BMP4/7 from Gremlin 1-BMP complexes by anti-Gremlin-1 antibodies was investigated. Experiments were again performed using lung fibroblasts from idiopathic pulmonary fibrosis patients. rhBMP-2 or rhBMP 4/7 were preincubated with rhGremlin-1 for 1 hour at room temperature. The BMP-2- or BMP4/7-Gremlin-1 complexes were incubated with different concentrations of the anti-Gremlin-1 antibodies overnight at 4° C. Antibody concentrations represent the final concentration on the plate.

TABLE 5

Displacement of BMP-2 or BMP4/7 from Gremlin 1-BMP complexes by anti-Gremlin-1 antibodies

| | | 81.3 µg/ml | 40.6 µg/ml | 20.3 µg/ml | 10.2 µg/ml | 5.1 µg/ml | 2.55 µg/ml | 1.27 µg/ml | 0.63 µg/ml |
|---|---|---|---|---|---|---|---|---|---|
| 2484 | BMP 2 50 ng/ml | 100.3% +/− 3.5% | 98.8% +/− 2.7% | 97.0% +/− 2.9% | 93.5% +/− 2.6% | 86.4% +/− 2.0% | 79.9% +/− 1.9% | 66.5% +/− 2.8% | 54.8% +/− 0.3% |
| 2484 | BMP4/7 50 ng/ml | 136.4% +/− 4.2% | 133.2% +/− 1.0% | 121.4% +/− 1.4% | 108.1% +/− 4.9% | 86.6% +/− 4.4% | 74.7% +/− 2.2% | 65.8% +/− 0.6% | 60.7% +/− 1.5% |
| 7326 | BMP 2 50 ng/ml | 103.7% +/− 1.1% | 101.5% +/− 2.4% | 99.4% +/− 3.8% | 103.8% +/− 2.4% | 100.3% +/− 2.2% | 103.2% +/− 4.3% | 102.8% +/− 2.8% | 97.0% +/− 2.9% |
| 7326 | BMP4/7 50 ng/ml | 133.7% +/− 0.8% | 132.3% +/− 1.8% | 130.3% +/− 4.2% | 125.6% +/− 10.0% | 121.4% +/− 4.2% | 120.9% +/− 3.3% | 111.1% +/− 2.3% | 102.0% +/− 4.5% |

The results shown in Table 5 demonstrate that Ab7326 can displace already complexed BMP-2 or BMP4/7 from Gremlin 1-BMP complexes. Ab7326 can achieve this displacement at much lower concentrations that the comparison antibody 2484. This provides evidence that Ab7326 is an allosteric inhibitor, consistent with our finding that the binding site for Ab7326 is distal from the known BMP binding regions on gremlin-1. Thus Ab7326 is able to access the allosteric binding site even when BMP is complexed to gremlin-1, resulting in significantly improved inhibition of gremlin activity.

Example 6—Obtaining the Crystal Structure of Gremlin-1 in Complex with the 7326 Fab The crystal structure of human Gremlin-1 in complex with Ab7326 Fab was solved at a resolution of 2.1 Å. Fab sequences are shown below:

```
Heavy chain:
                                              SEQ ID NO: 18
QVQLVESGAEVKKPGATVKISCKVSGYTFTDYYMHWVQQAPGKGLEWMG

LVDPEDGETIYAEKFQGRVTITADTSTDTAYMELSSLRSEDTAVYYCAT

DARGSGSYYPNHFDYWGQGTLVTVSSASTKGPSVFPLAPSSKSTSGGTA

ALGCLVKDYFPEPVTVSWNSGALTSGVHTFPAVLQSSGLYSLSSVVTVP

SSSLGTQTYICNVNHKPSNTKVDKKVEPKSC

Light chain:
                                              SEQ ID NO: 19
DIVMTQSPDSLAVSLGERATINCKSSQSVLYSSNNKNYLAWYQQKPGQP

PKLLIYWASTRESGVPDRFSGSGSGTDFTLTINSLQAEDVAVYFCQQYY

DTPTFGQGTRLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSENRGEC
```

The CCP4 software NCONT was then used to identify all contacts at 4 Å between Gremlin-1 and the Fab. The following residues were identified: Ile131, Lys147, Lys148, Phe149, Thr150, Thr151, Arg169, Lys174 and Gln175 (numbering based on the UniProt Sequence of SEQ ID NO: 1 (numbered as Ile110, Lys126, Lys127, Phe128, Thr129, Thr130, Arg148, Lys153 and Gln154 in the structure file which matches the numbering of mouse Gremlin-2).

Figure 4:
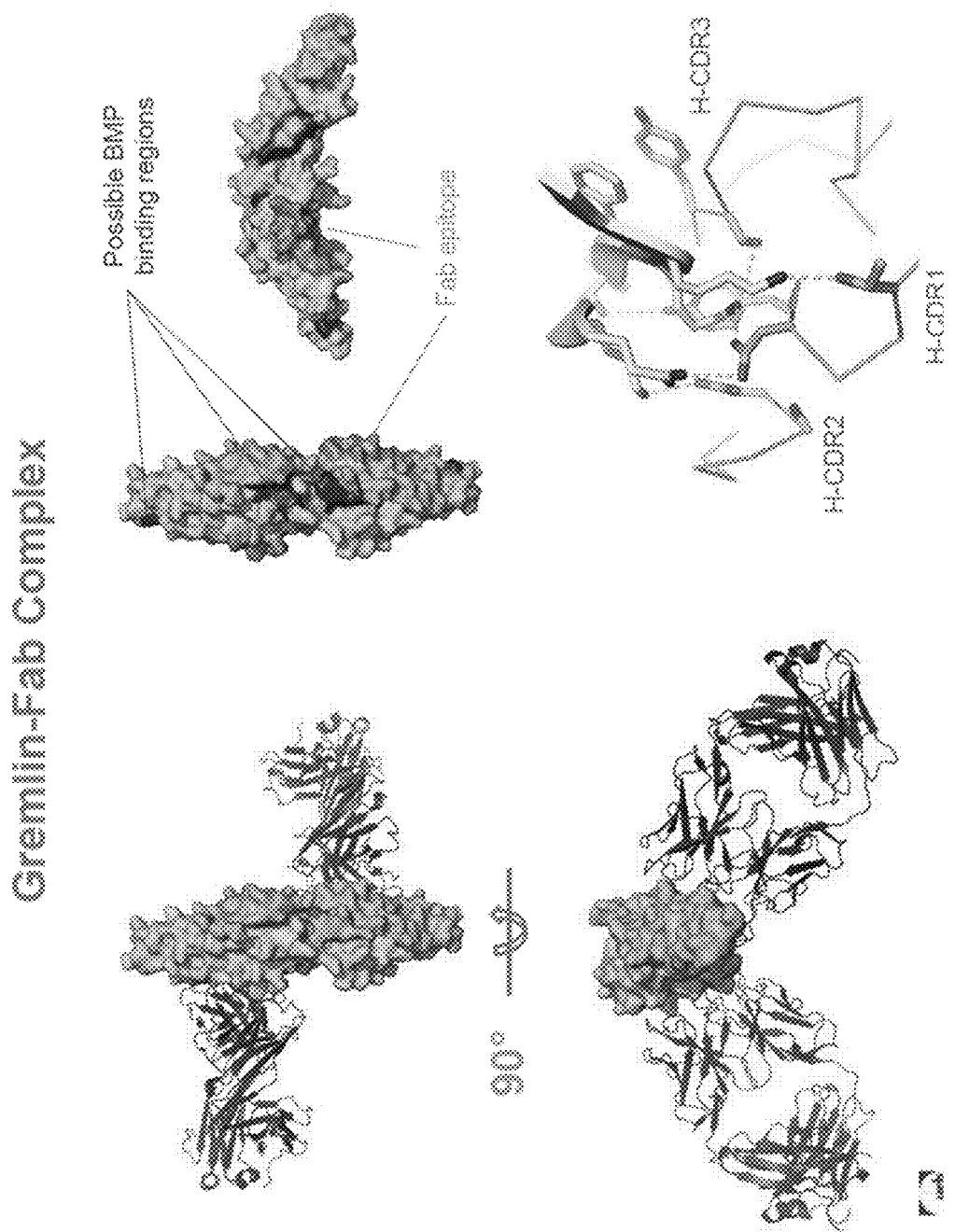
FIG. 4. A structural model of the Gremlin-Fab complex, with the possible BMP binding regions and the Fab epitope highlighted.

FIG. 4 shows structural models of the Gremlin-Fab complex, with the Fab epitope residues shown relative to the BMP binding regions.

Ab7326 is an inhibitory antibody which acts allosterically, i.e. it binds away from the BMP binding regions.

Example 7—Affinity Measurements for Binding of Anti-Gremlin-1 Antibody Ab7326 to Gremlin-1

Method

The affinity of anti-Gremlin mIgG for human Gremlin 1 was determined by biamolecular interaction analysis using surface plasmon resonance (SPR) technology on a Biacore T200 system, GE Healthcare Bio-Sciences AB. Anti-Gremlin mIgG was captured by an immobilised anti-mouse Fc surface and Gremlin 1 was titrated over the captured mIgG.

The capture ligand (affinipure F(ab')$_2$ fragment of goat anti-mouse IgG, Fc fragment specific, 115-006-071, Jackson ImmunoResearch Inc.) was immobilised at 50p g/ml in 10 mM NaAc, pH 5.0 on flow cell 2 of a CM4 Sensor Chip via amine coupling chemistry, using 600 s activation and deactivation injections, to a level of ~1600 response units (RU). HBS-EP+ buffer (0.01 M HEPES pH 7.4, 0.15 M NaCl, 3 mM EDTA, 0.05% Surfactant P20) was used as the running buffer with a flow rate of 10 µl/min. A reference surface was prepared on flow cell 1 by activating and deactivating the surface as for flow cell 2 but omitting the capture ligand.

The assay buffer was HBS-EP+ plus an extra 150 mM NaCl to give a final NaCl concentration of 300 mM plus 1% CMD40. A 60 s injection of anti-Gremlin mIgG (at 5 µg/ml in running buffer) was passed over flow cells 1 and 2 to give a capture level of approximately 100 RU on the immobilised anti-mouse IgG, Fc surface. Recombinant human Gremlin 1 was titrated in running buffer from 5 nM (using 2-fold dilutions) and injected over flow cells 1 and 2 at a flow rate of 30 µl/min for 3 min followed by a 5 min dissociation phase. A buffer only control was also included. The surface was regenerated at a flow rate of 10 µl/min by a 60 s injection of 50 mM HCl, a 30 s injection of 5 mM NaOH and a 30 s injection of 50 mM HCl.

The kinetic data was determined using Biacore T200 evaluation software. The affinity measurements were made at 25° C.

Results

Binding affinity, taken as the average $K_D$ value for 5 determinations, was found to be below 100 pM.

Example 8—Anti-Grem1 Antibody Inhibited Mouse Organoid Culture

Materials and Methods

Mouse procedures. All procedures were carried out in accordance to Home Office UK regulations and the Animals (Scientific Procedures) Act 1986. All mice were housed at the animal unit at Functional Genomics Facility, Wellcome Trust Centre for Human Genetics, Oxford University. All strains used in this study were maintained on C57Bl/6J background for ≥6 generations. Genotyping protocols for the Apc$^{Min}$ (1) and Vil1-Grem1 (2), Apc$^{fl/fl}$ (3) and VillinCre-ERT2 (4) mice have previously been reported. To generate Kaplan-Meier data, mice were sacrificed when reached humane-end points (exhibited anaemia, hunching and inactivity). Anti-Grem1 antibody (UCB Ab7326 mouse IgG1, as also used in all subsequent mouse experiments) or mouse IgG1 control Ab101.4 antibody (UCB) were administered at a dose of 10 mg/kg or 30 mg/kg weekly or bi-weekly subcutaneous injections. For long-term treatment cohorts, a 30 mg/kg dose was delivered weekly in Vil-Grem1 and Apc$^{Min}$ mice from 6-weeks of age and the Vil1-Grem1/Apc$^{Min}$ cohort treatment commenced at 3-weeks of age, twice weekly for 6 weeks, once weekly thereafter.

Tissue preparation and histology. Mice were sacrificed at pre-defined time points or when showing symptoms of intestinal polyps (anaemia, hunching) by cervical dislocation. The intestinal tract was removed immediately and divided into small intestine (proximal/SB1, middle/SB2 and distal/SB3) and large intestine. The intestines were opened longitudinally, using a gut preparation apparatus (5), washed in PBS, fixed overnight in 10% neutral buffered formalin (NBF). For visualization of polyps, gut preparations were stained with 0.2% methylene blue for 10 s and viewed with the aid of a light box. Specimens of 10% formalin-fixed tissue were embedded in paraffin and then sectioned at 4 µm. Fixed specimens were embedded and H&E stained following standard protocols.

Immunohistochemistry. Formalin-fixed, paraffin-embedded tissue sections (4 µm) were de-waxed in xylene and rehydrated through graded alcohols to water. Endogenous peroxidase was blocked using 1.6% $H_2O_2$ for 20 min. For antigen retrieval, sections were pressure cooked in 10 mmol/L citrate buffer (pH 6.0) for 5 min. Sections were blocked with 10% serum for 30 min. Slides were incubated with primary antibody for 2 h. The following antibodies have been used in this study; Cytokeratin 20 (Abcam, ab118574, 1:200), EphB2 (R and D, AF467, 1:125), Ki67 (CST, 122025, 1:500), Lysozyme (DAKO, EC 3.2.1.17, 1:500) and Sox9 (Millipore, ab5535, 1:1000). Appropriate secondary antibodies were applied for 1 h at room temperature. Sections were then incubated in ABC (Vector labs) for 30 min. DAB solution was applied for 2-5 min and development of the colour reaction was monitored microscopically. Slides were counterstained with haematoxylin, dehydrated, cleared and then mounted.

In situ hybridisation (ISH). 4 µm sections were prepared using DEPC (Sigma) treated $H_2O$. In situ hybridisation was carried out using Grem1 (314741) (Advanced Cell Diagnostics) probe and the RNAscope 2.5 HD Detection Kit (Advanced Cell Diagnostics) following manufacturer's instructions.

Culture of mouse intestinal crypts. Mouse intestinal crypts were isolated and cultured as described by Sato et al (6). In brief, crypts were isolated, resuspended in Matrigel (BD Biosciences) and plated out in 24-well plates. The basal culture medium (advanced Dulbecco's modified Eagle medium/F12 supplemented with penicillin/streptomycin, 10 mmol/L HEPES, Glutamax, 1×N2, 1×B27 (all from Invitrogen), and 1 mmol/L N-acetylcysteine (Sigma)) was overlaid containing the following growth factors; Epidermal Growth Factor at 50 ng/ml (Life Technologies), Gremlin1 at 100 ng/ml (R and D), R-spondin1 at 500 ng/ml (R and D) [EGR media]. Anti-Grem1 antibody (UCB) was used at a concentration of 1 mg/ml. The media was changed every two days.

Western blotting. Isolation of colon epithelium cells was carried out by incubating a 2 cm long piece of tissue with 30 mM EDTA for 2 h with agitation at 4° C. Pelleted epithelial cells were lysed RIPA lysis buffer with the addition of protease inhibitors (Complete Mini, Roche) and phosphatase inhibitors (PhosSTOP, Roche). All lysates were quantified using the BCA assay (Thermo Scientific), 35 mg was diluted in an appropriate amount of 4× loading dye (Invitrogen) and denatured at 95° C. for 5 minutes. Western blotting was done with the NuPAGE Gel system, (Invitrogen) according to manufacturer's protocol. Briefly, denatured lysates were loaded onto a 4-12% gel and run at 100 V for at least 2 hours. The gels were transferred onto PVDF membrane (Immobilon P, Millipore) in a semi-dry tank (120 mA for at least 2 hours) and blocked by incubating for 1 hour at room temperature in TBS containing 10% milk (Marvel). The membranes were then incubated overnight in the appropriate primary antibody in TBS with 5% milk, pSmad1/5/8 (Cell Signalling, 9516S, 1:500), Actin (Santa Cruz, sc-47778, 1:2500). After washing, the membranes were incubated with HRP-conjugated secondary antibodies for 1 hour at room temperature. After further washes, the blots were incubated in ECL reagents (GE healthcare) and chemiluminescence was detected by chemiluminescence film (GE Healthcare).

Figure 5:
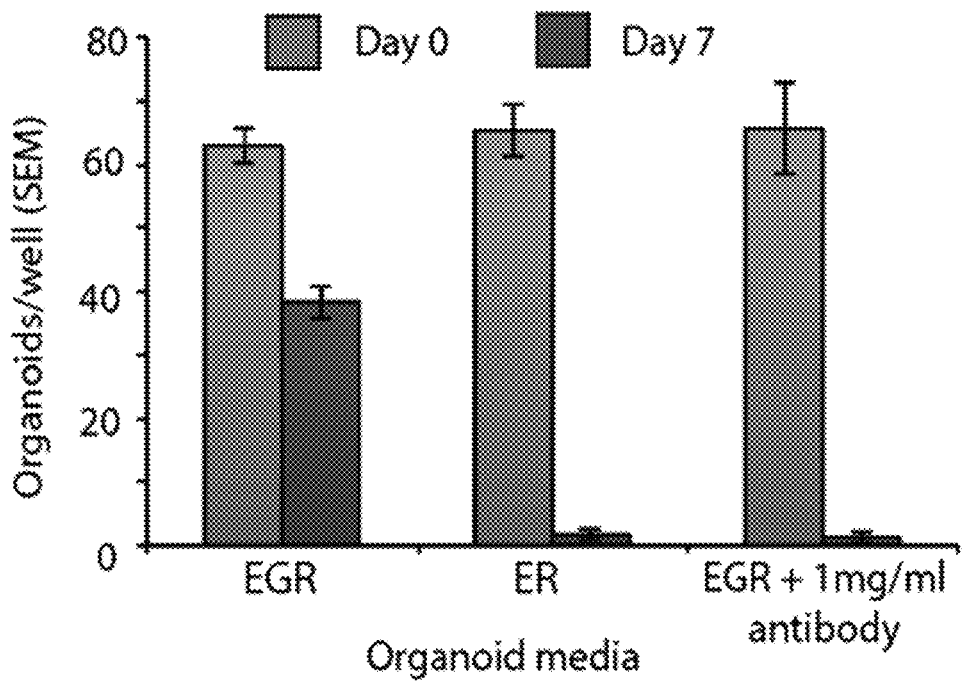
FIG. 5. Organoid culture from mouse intestinal crypts at day 0 and day 7 following seeding. Media contains recombinant protein supplementation and/or test anti-Grem1 antibody. E=Epidermal growth factor, G=Grem1, R=Rspo1.

Description of Results (see also FIG. 5)

A mouse organoid culture was used to assess effects of an anti-GREM1 antibody. Successful intestinal epithelial organoid culture is dependent on media supplementation of exogenous BMP antagonist. Recombinant Noggin and Gremlin1 can be used interchangeably for this purpose, and intestinal crypt culture in the absence of one of these proteins does not proceed past day 4 of culture.

Approximately 60% of crypts formed organoids in media fully supplemented with recombinant epidermal growth factor (E), Grem1 (G) and R-Spondin1, (R) (EGR media). Culture success rate dropped to less than 2% at 7 days in media lacking recombinant Grem1 (ER media).

Addition of 1 mg/ml of anti-Grem1 antibody to otherwise fully supplemented media (EGR+antibody) prevented successful intestinal organoid culture, consistent with an abrogation of the BMP antagonistic effects of Grem1 in fully supplemented media. These results were indistinguishable from Grem1 excluded media (ER).

Figure 6:
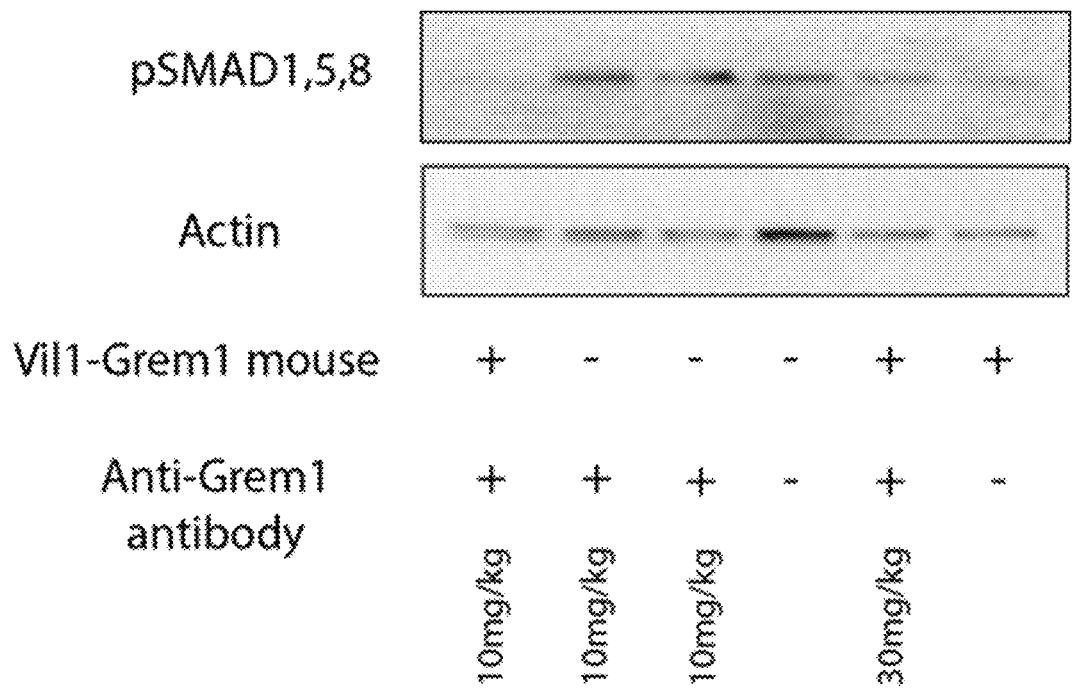
FIG. 6. Western blot on proteins extracted from Vil1-Grem1 mouse epithelium. 6 weeks of antibody administration at 30 mg/kg is able to restore epithelial pSMAD1,5 signalling.

Example 9—Anti-Grem1 Antibody Treatment Partially Restores Intestinal pSMAD1,5 Signalling in Treated Vil1-Grem1 Animals (See Also FIG. 6)

Epithelial BMP activity can be measured by phosphorylation of the SMAD 1,5,8 intracellular signalling transducers.

In Vil1-Grem1 animals, aberrant epithelial expression of Grem1 initiates polyposis through promotion of an aberrant stem/progenitor cell phenotype in cells situated outside of the colonic crypt base. Vil1-Grem1 mice develop a profound pan intestinal polyposis from about 8 weeks of age, characterised by villus ectopic crypt formation, aberrant cell proliferation and initiation of villus dysplasia.

The aberrant epithelial Grem1 expression in Vil1-Grem1 mice suppressed physiological intestinal BMP pathway activity with reduction in detected pSMAD1,5 protein levels detected by Western blot.

Weekly subcutaneous anti-Grem1 antibody administration at a dose of 30 mg/kg but not at the lower dose of 10 mg/kg, was able to restore intestinal epithelial pSMAD1,5 signalling in Vil1-Grem1 intestinal epithelium. Indicating functional antagonism of Grem1.

Figure 7:
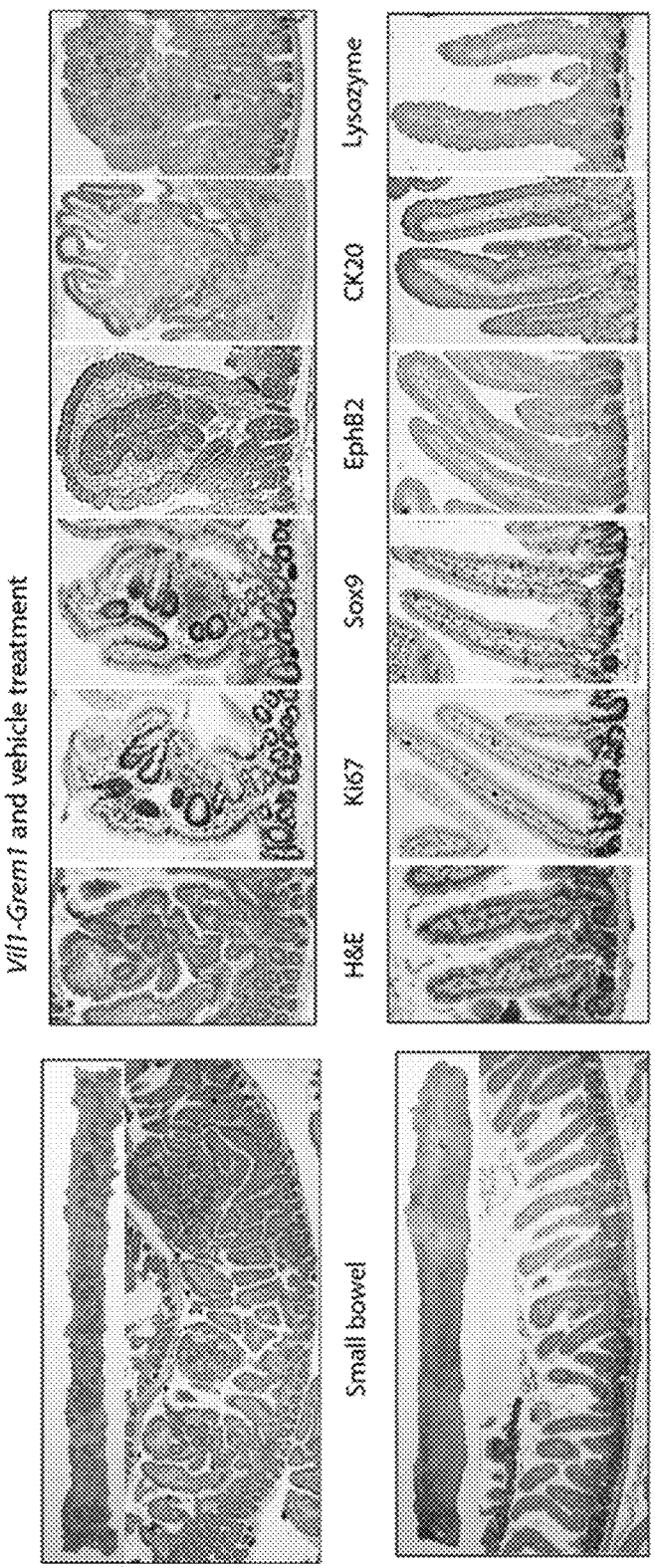
FIG. 7. Antibody treated Vil1-Grem1 animal phenotype after 6 weeks of treatment with anti-Grem1 antibody. Antibody treatment normalises small intestinal phenotype and prevents profound polyposis development. Antibody treatment prevents villus ectopic crypt formation and normalises cell fate determination with appropriate restriction of Ki67, Sox9, EphB2 and lysozyme staining to the base of the intestinal crypt, and resolution of normal CK20 staining in the differentiating cells of the small intestinal villus.
Figure 30:
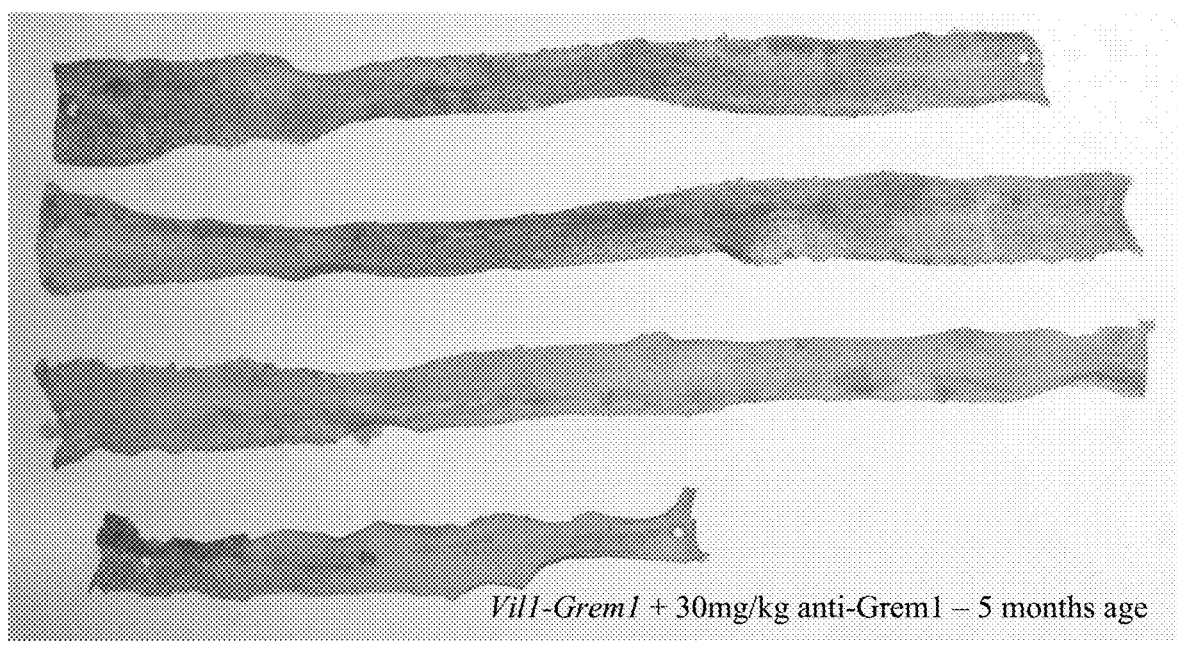
FIG. 30. Antibody treated Vil1-Grem1 bowel phenotype after 6 weeks of treatment with anti-Grem1 antibody.

Example 10—Anti-Grem1 Antibody Treatment Abrogates Vil1-Grem1 Pan-Intestinal Polyposis Phenotype and Restores Normal Cell Fate Determination (See FIGS. 7 and 30)

Twice weekly, subcutaneous administration of anti-Grem1 antibody (30 mg/kg) for a period of 6 weeks to the Vil1-Grem1 mice also resulted in a dose-dependent and highly significant abrogation of this pan-intestinal polyposis phenotype, alongside therapeutic near-normalization of the aberrant intestinal crypt-villus architecture that characterizes this animal model.

Immunohistochemical staining of treated animals showed reversal of villus ectopic crypt formation and deranged cell fate determination that characterised the untreated tissue (FIGS. 7 and 30).

Figure 8:
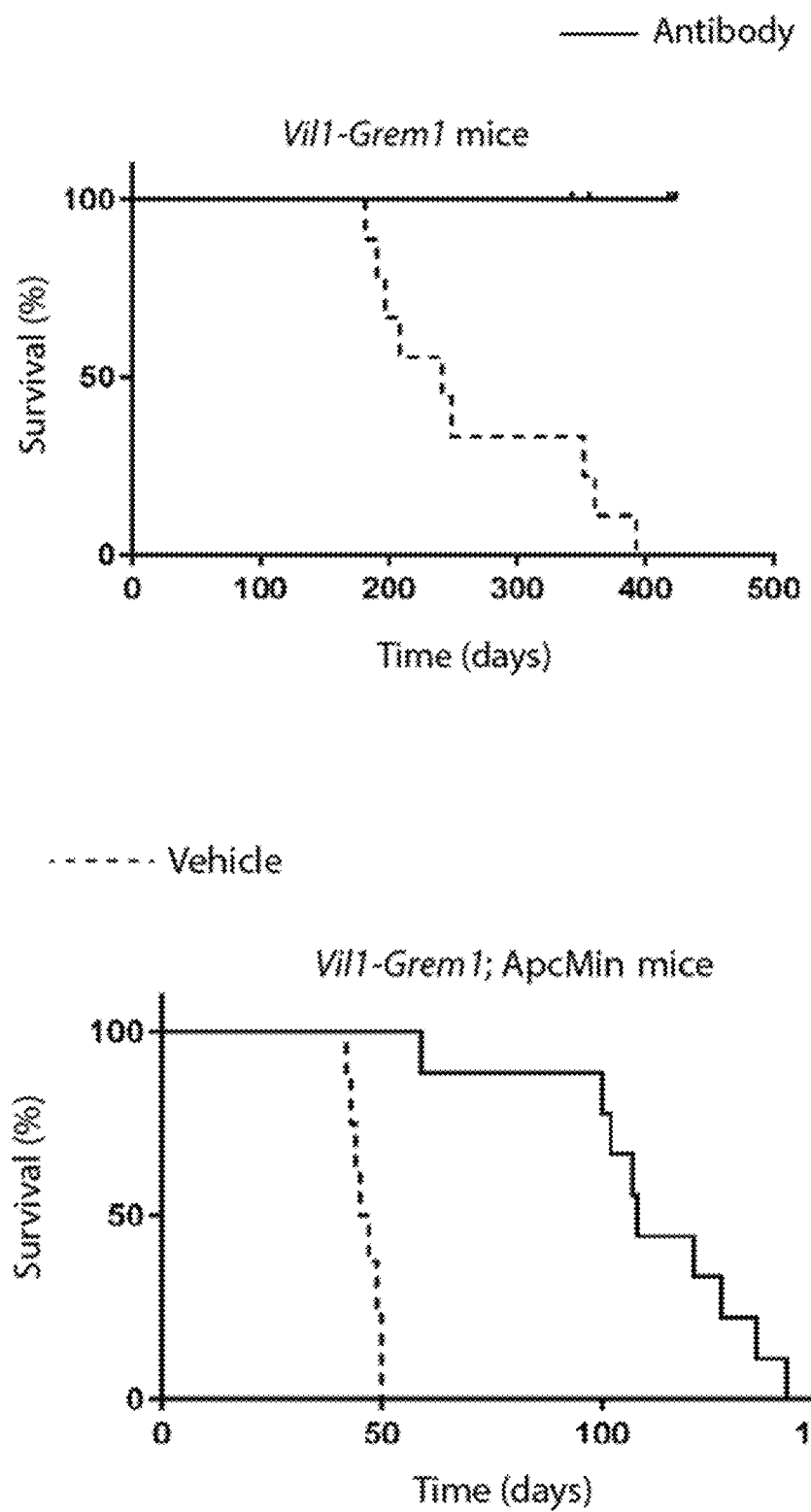
FIG. 8. Kaplan-Meier plots of survival of Grem1 initiated polyposis mouse strains following long term anti-Grem1 antibody treatment.
Figure 31A:
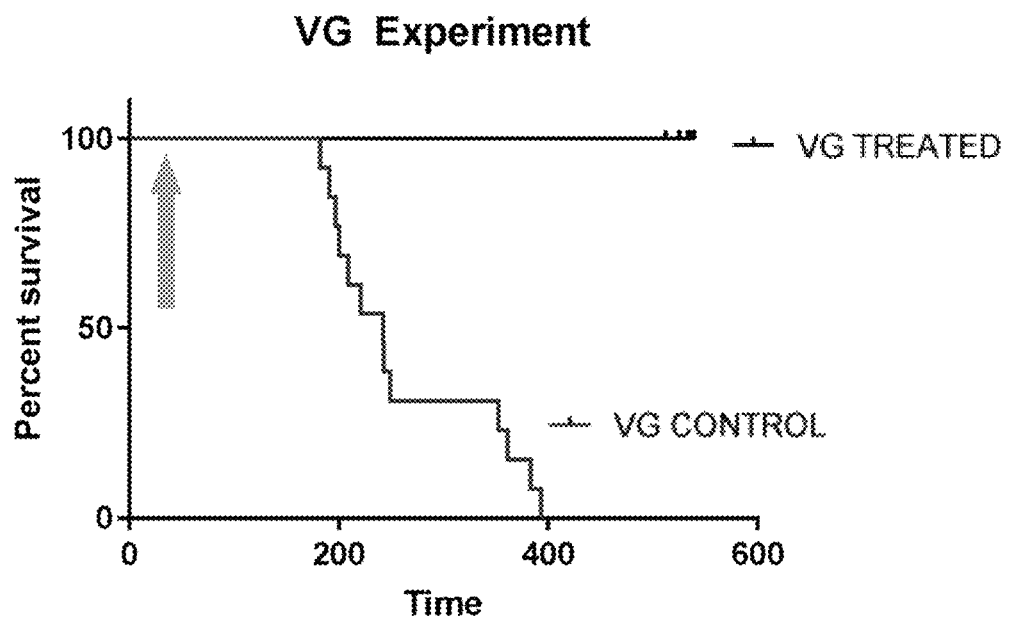
FIGS. 31A-31B. Kaplan-Meier plots of survival of Grem1 initiated polyposis mouse strains following long term anti-Grem1 antibody treatment.
Figure 31B:
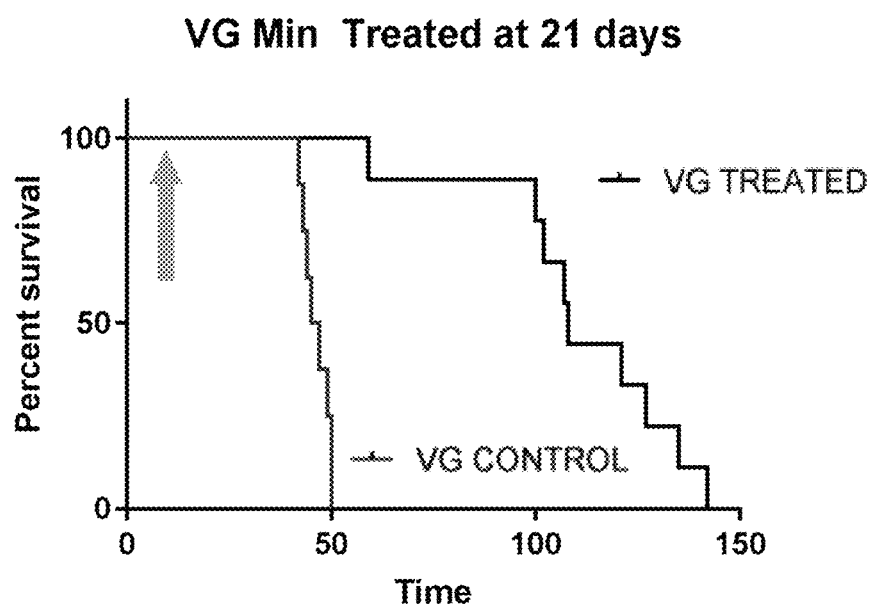

Example 11—Prolonged Treatment with Anti-Grem1 Antibody in Animal Models with Grem1 Initiated Polyposis is Safe and Significantly Prolongs Animal Lifespan (See FIGS. 8 and 31)

Animals were treated with twice weekly (Vil1-Grem1; Apc$^{Min}$) or weekly (Vil1-Grem1) with subcutaneous anti- Grem1 antibody at a dose of 30 mg/kg, initiated at 3 (Vil1-Grem1;Apc$^{Min}$) or 6 weeks of age (Vil1-Grem1).

Prolonged dosing of anti-Grem1 antibody in Grem1 initiated tumourigenesis models slowed polyp formation, reduces tumour burden and significantly prolongs animal lifespan in Vil1-Grem1 animals. This tumour abrogating effect was consistent across lesions initiated by aberrant epithelial Grem1 expression, even in the aggressive Vil1-Grem1; Apc$^{Min}$ strain, where antibody treatment more than doubles animal lifespan (VG-min mean lifespan 46 days versus VG-min treated mean lifespan 108 days, p=2.21×10-6) No consistent adverse events have been observed to date in animals treated for more than 400 days.

Figure 9A:
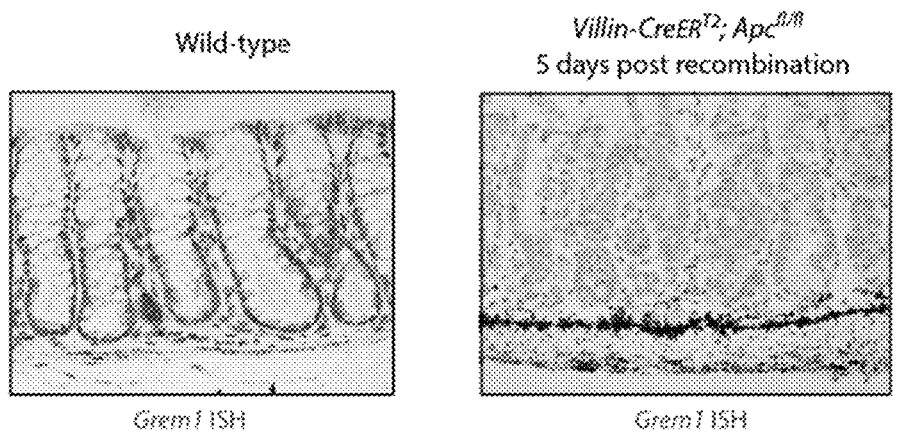
FIGS. 9A-9C. Stromal Grem1 in Apc-driven tumourigenesis.
Figure 9B:
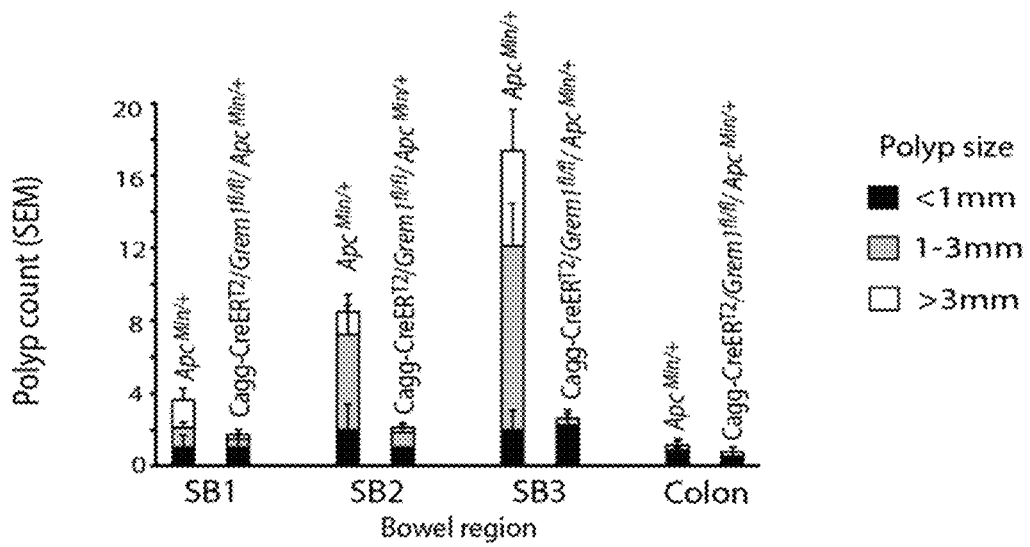
Figure 9C:
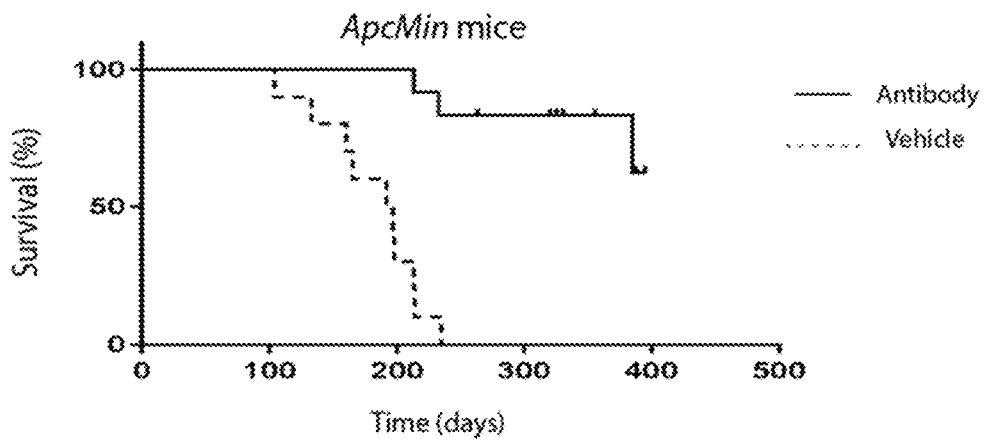
Figure 32A:
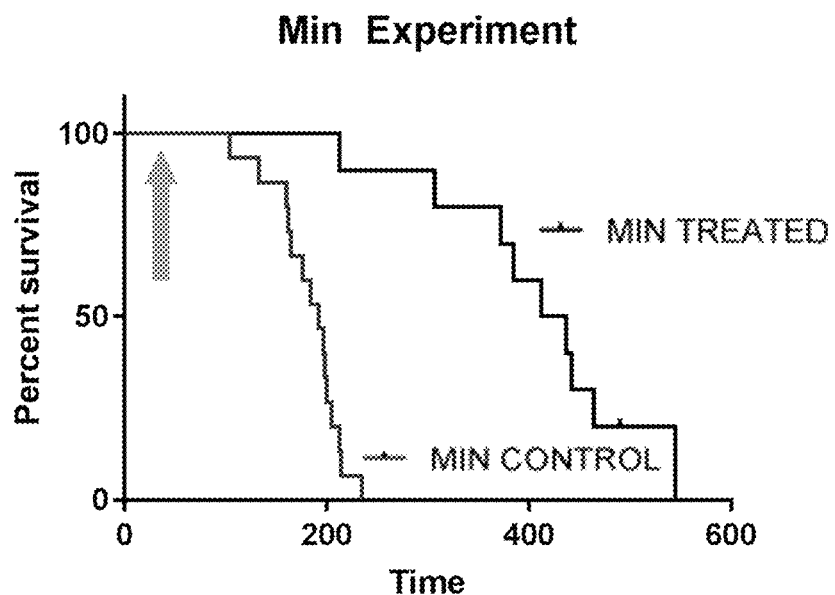
FIGS. 32A-32B.
Figure 32B:
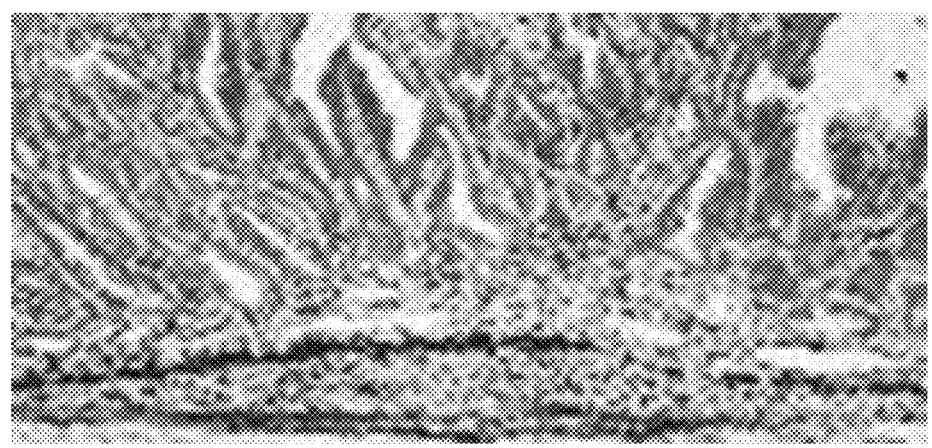
Figure 33A:
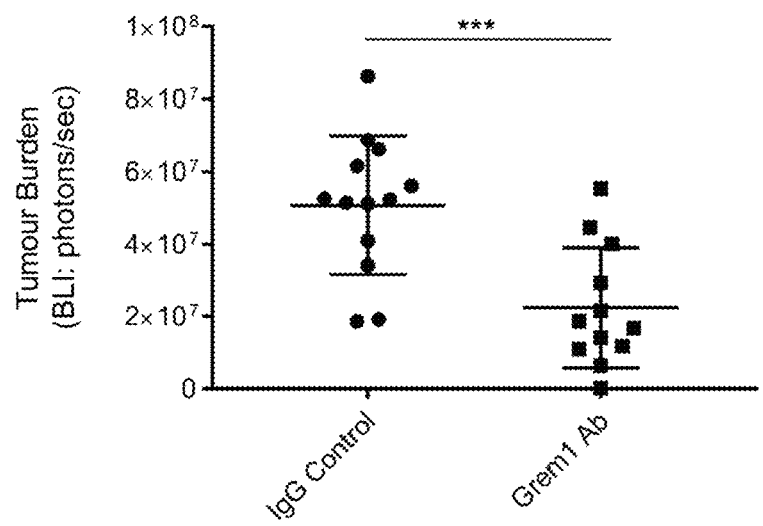
FIGS. 33A-33D. Tumour burden in C57B16/KaLwRij mice is significantly reduced in the hindlimb bones when mice are treated with Grem1-neutralising antibody, Ab7326, (FIG. 33A) post-tumour cell inoculation and (FIG. 33B) pre-tumour cell inoculation, compared to IgG control (as shown by bioluminescent imaging (BLI)). A downwards trend in splenic tumour burden is observed between treatment groups in the (FIG. 33C) post-, or (FIG. 33D) pre-tumour cell inoculation setting. Students t-test,  p<0.01, * p<0.001.
Figure 33B:
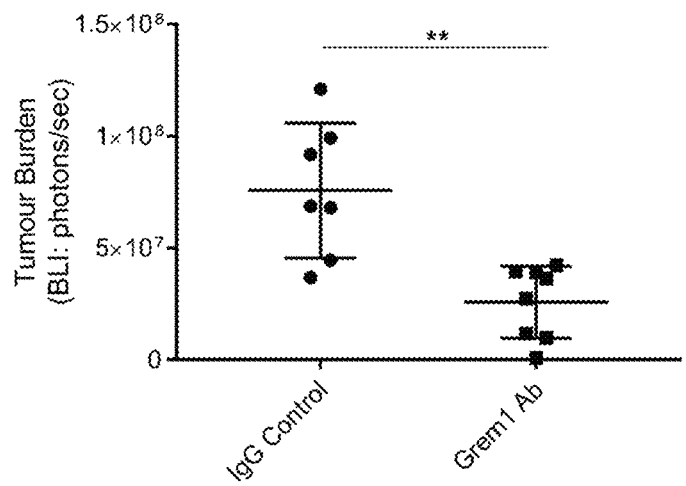
Figure 33C:
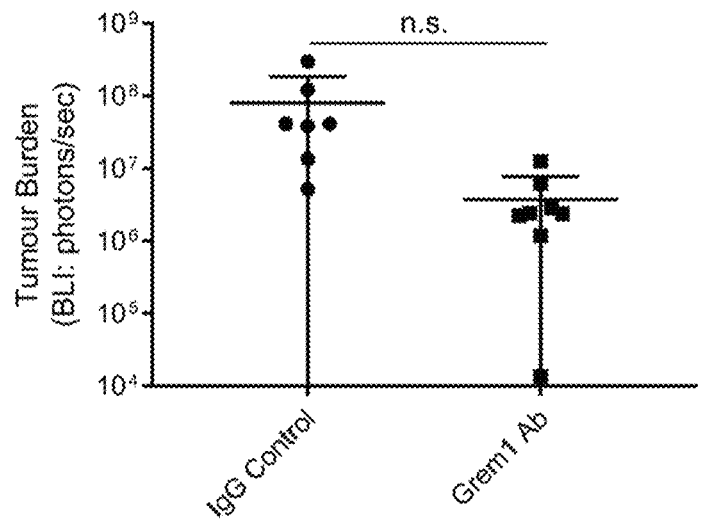
Figure 33D:
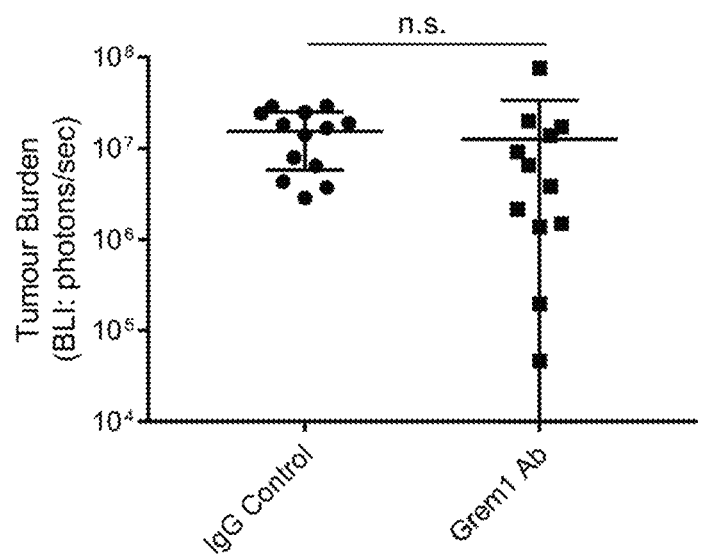

Example 12—Pharmacological Downregulation of Grem1 Attenuates Mutant Apc-Driven Tumourigenesis in Apc$^{Min}$ Mice (See FIGS. 9 and 32)

The effect of GREM1 antagonism was also investigated in a mouse model of sporadic cancer, caused by epithelial Apc inactivation. Epithelial-mesenchymal signalling crosstalk means that stromal cells are responsive to acute epithelial inactivation of Apc, with rapid upregulation of intestinal muscularis and propria Grem1 occurring just 5 days after epithelial cell inactivation of Apc in Villin-CreERT2;Apcfl/fl mice (FIG. 9A).

Long term treatment with anti-Grem1 antibody initiated at 6 weeks of age had a consistent effect on Apc$^{Min}$ mouse polyp development, allowing prolonged survival of animals through reduced tumour burden. This work indicates that stromal upregulation of Grem1 may exacerbate mutant Apc-driven tumourigenesis and that anti-Grem1 therapy may be useful for treatment of non-Grem1 initiated tumourigenesis.

Example 13—Grem1 is Overexpressed in the Myeloma Bone Marrow Microenvironment and can be Targeted to Reduce Myeloma Growth This study demonstrates for the first time that Grem1 plays a role in multiple myeloma (MM) disease progression. Analysis of stromal cells derived from patient bone marrow (BM) trephine biopsies demonstrated a significant increase in Grem1 expression from the BM microenvironment during MM. In addition, the data presented here shows that increased levels of Grem1 promote the proliferation of MM PC, and that Grem1 can be targeted to significantly reduce MM tumour burden in a preclinical mouse model of MM. This represents the first evidence that Grem1 plays a role in MM disease progression, and as such represents a therapeutic target for the treatment of MM.

Methods

Culture of Myeloma Cell Lines: Unless otherwise stated, all tissue culture media contained 10% (v/v) FCS and additives (2 mM L-glutamine, 1 mM sodium pyruvate, 15 mM HEPES, 50 U/mL penicillin and 50 µg/mL streptomycin; all from Sigma-Aldrich, Sydney, Australia). Mouse 5TGM1 MM cells were maintained in Iscove's Modified Eagle's Medium supplemented with 20% (v/v) FCS and additives. We have previously modified the 5TGM1 cells (Dallas et al., 1999) with a trimodality retroviral NES-TGL construct (Diamond et al., 2009; Ponomarev et al (2004) encoding thymidine kinase, green fluorescent protein (GFP), and firefly luciferase (Noll et al., 2014), and a new clonal subline was established that exhibits consistent bone tropism (Noll et al., 2014; (Noll et al., 2015). OP9 bone marrow stromal cells were maintained in Dulbecco's Modified Eagle Medium with 10% (v/v) FCS and additives. Co-culture of 5TGM1 cells and OP9 cells were maintained in Iscove's Modified Eagle's Medium supplemented with 20% (v/v) FCS and additives. Human MM cell lines RPMI-8226, U266, KMS-11 and H929 were all cultured in RPMI-1640 medium (Cheong et al., 2015). All cell lines were maintained in a humidified environment at 37° C. with 5% carbon dioxide.

Isolation of RNA from murine BM stroma: C57BL6/KaLwRij.Hsd mice were injected with 5×10$^5$ 5TGM1.Bmx1 MM PCs, and tumour growth was established over 4 weeks (as previously described) (Noll et al., 2014; Hewett et al., 2017). Briefly, 5TGM1 cells were resuspended at 5×10$^6$ cells per ml in phosphate-buffered saline (PBS), and then 5×10$^5$ cells were injected into the tail vein of 6- to 8-week-old C57BL/KaLwRij mice. Growth of tumours was monitored by whole animal bioluminescent imaging (BLI) using a Xenogen IVIS 100 Imaging System (Caliper Life Sciences, Hopkinton, USA)) after intraperitoneal injection (i.p.) of 150 mg/kg of D-Luciferin (Biosynth, Raad, Switzerland). Tumour burden was quantitated using Living Image software. Mice with tumour burden and age-matched non-tumour controls were humanely culled as per SAHMRI ethics SAM165. Femurs and tibias for each mouse was isolated and flushed of marrow with PBS, 2% FCS, and 2 mM EDTA (PFE). Bones were crushed and digested in 3 ml of 3 mg/ml collagenase I for 2 hours at 37° C. in a shaking incubator. Suspension was diluted to 10 ml with PFE. Spun at 1400 g for 5 min to collect cells. Wash with 1×PFE and repeat spin. The cell pellet and bone chips were resuspended in 1 ml of TRIzol (Thermo Fisher Scientific Inc., Massachusetts, USA)—vortex and incubated on ice for 15 min. The TRIzol was collected and processed for RNA extraction by chloroform/isopropanol precipitation (as previously described).

Assessment of Grem1 expression in human and murine stroma: Iliac crest trephines were collected, with informed consent, from randomly selected patients with symptomatic MM who presented at the Royal Adelaide Hospital (Adelaide, Australia), and from haematologically normal age-matched controls. All MM patients were newly diagnosed and had not had previous therapy. Ethical approval for this study was obtained from the Royal Adelaide Hospital institutional ethics review committee (ethics approval number #030206). Adherent stromal cells were expanded ex vivo from each trephine and cryopreserved after one further passage. Stromal samples were retrieved from storage in liquid nitrogen and cultured for 24 hours prior to collection in TRIzol for downstream RNA extraction as described previously. RNA underwent DNase treatment with RQ1 DNase (Promega, Wisconsin, USA) prior to cDNA manufactured using SuperScriptIII (Thermo Fisher Scientific Inc., Massachusetts, USA) Quantitative PCR analysis of Grem1 expression in both human and murine samples was performed using RT2 SYBR-green master mix (Qiagen, Hilden, Germany) on a BioRad CFX Connect with normalisation to B-actin as the endogenous control using the standard curve method. The following primers were used: mouse Grem1: forward 5'-GCGCAAGTATCTGAAGCGAG-3' (SEQ ID NO: 38); reverse 5'-CGGTTGATGATAGTGCGGCT-3' (SEQ ID NO: 39), human Grem1: forward 5'-AGGCCCAGCACAATGACTCAG-3' (SEQ ID NO: 40); reverse 5'-GTCTCGCTTCAGGTATTTGCG-3' (SEQ ID NO: 41); B-actin: forward 5'-GATCATTGCTCCTCCT-GAGC-3' (SEQ ID NO: 42); reverse 5'-GTCAT-AGTCCGCCTAGAAGCAT-3' (SEQ ID NO: 43).

Generation of a murine stromal Grem1-overexpressing cell line: The murine cDNA for Grem1 was isolated from a pCMV6-K$^R$ vector kindly provided by the Gastrointestinal Cancer Biology Group, SAHMRI. The murine Grem1 sequence was excised by EcoR1 and Not1 restriction enzyme digest and cloned into the pLeGoiT2 vector. Following lentiviral infection of OP9-GFP+ cells, cells positive for GFP and TdTomato were sorted by FACS. Transgene expression was confirmed by quantitative-PCR and Western blot.

Co-culture of MM PC and BM stroma: OP9 stromal cells were seeded in both a 6 cm TC dish and 24-well plate at [cell density], respectively and allowed to adhere for 5 hours. 5TGM1 MM PC were suspended at $1 \times 10^5$ cells/ml and added to the stromal cell cultures. Stromal cells were collected at 24, 48 and 72 hours post co-culture initiation. For contact co-culture the GFP+OP9 cells were isolated by FACS from the GFP negative 5TGM1-parental MM PCs to obtain a pure stromal population for analysis. For non-contact co-culture, 5TGM1.Bmx1 PCs were separated from the OP9 cells using a 4 μm Transwell for the duration of the co-culture. Human MM cell lines RPMI-8226, U266, KMS-11 and H929 were each cultured with 3 primary human BM stromal samples isolated from haematopoietically-healthy individuals for 72 hours. Human MM cell lines were washed thoroughly from the adherent stroma twice with 1×PBS. Stromal cells were lysed in TRIzol and processed by chloroform/isopropanol isolation. RNA underwent DNase treatment with RQ1 DNase prior to cDNA manufactured using SuperScriptIII (Invitrogen). Grem1 expression was assessed by quantitative-PCR using the primers sequences stated previously.

Luciferase Proliferation Assay: Grem1-overexpressing and vector-only OP9 stromal cells were seeded into a 24-well plate at $5 \times 10^4$ cells per well and allowed to adhere overnight. The following day 5TGM1.Bmx1 MM PC were seeded onto both stromal cell populations and cultured for 72 hours. Following incubation, the entire contents of each well was transferred to a corresponding microfuge tube by vigorously pipetting. Cells were collected by spinning at 2000 g for 5 mins at 4° C. Cells were washed once with PBS. The cell pellet for each well was lysed in 1× cell lysis buffer (supplier name). 20 μl of cell lysate was transferred to a 96-well plate. Immediately prior to reading the plate 100 μl of luciferase reaction buffer (5 mM $MgCl_2$, 30 mM HEPES, 150 μM ATP, 250 μM of Coenzyme A and 150 g/mL D-luciferin) was added to the cell lysate. Bioluminescence was measured using a Wallac 1420 Victor Microplate reader (Perkin Elmer, Massachusetts, USA), with light intensity used as a direct correlation of MM PC number.

Targeting Grem1 in an immunocompetent murine model of systemic MM: C57BL/KaLwRij mice (6-8-week-old) were inoculated with $5 \times 10^5$ 5TGM1.Bmx1 cells via tail vein injection. Three days post-inoculation with 5TGM1.Bmx1 MM PCs, KaLwRij mice were administered with 30 mg/kg Grem1-neutralising antibody Ab7326 or IgG control Ab101.4 (UCB-Pharma, UK) by subcutaneous (s.c.) injection. Mice were treated every 3 days for the duration of the 4-week model. Tumour burden was monitored weekly by BLI as previously described. At the end of the experiment, blood was collected by tail bleed, centrifuged at 2100 g for 10 min and serum collected. Serum paraprotein levels were analysed using the Hydragel 30 β1β2 kit (Sebia Electrophoresis, Georgia, USA) following the instructions of the manufacturer. The band corresponding to paraprotein was quantitated relative to serum albumin levels. (SAAMRI Animal Ethics SAM165)

Statistics: Numerical data are presented as mean±standard error of the mean (S.E.M.). Data representing two testing conditions were analysed by Student's T-Test. Data with more than two testing conditions were analysed by one-way analysis of variance (ANOVA) followed by a Tukey multiple comparison post-hoc test to determine the statistical significance of differences. All statistical analyses were performed using GraphPad Prism 7 (GraphPad Software, Inc, San Diego, CA). All experiments were performed in triplicate.

Description of Results

Grem1 Expression is Upregulated in MM Bone Marrow Stroma

Figure 10:
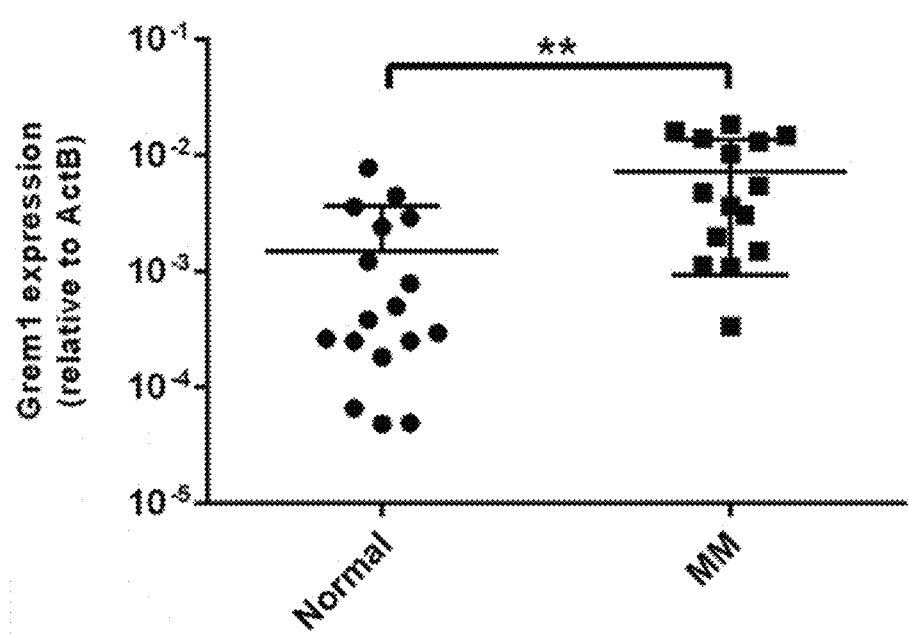
FIG. 10. Grem1 expression is elevated in primary stromal cultures from myeloma patients. RNA was extracted from bone marrow trephine derived stromal cell cultures from age and gender matched healthy donors and myeloma patients and the expression on Grem1 was analysed by real-time PCR. The expression of Grem1 was significantly higher in the myeloma patient cohort comparative to healthy donors. Data presented as mRNA expression normalised to ActB. (mean±SD, **P<0.001, T-test, Normal; n=17 and MM; n=15).
Figure 11A:
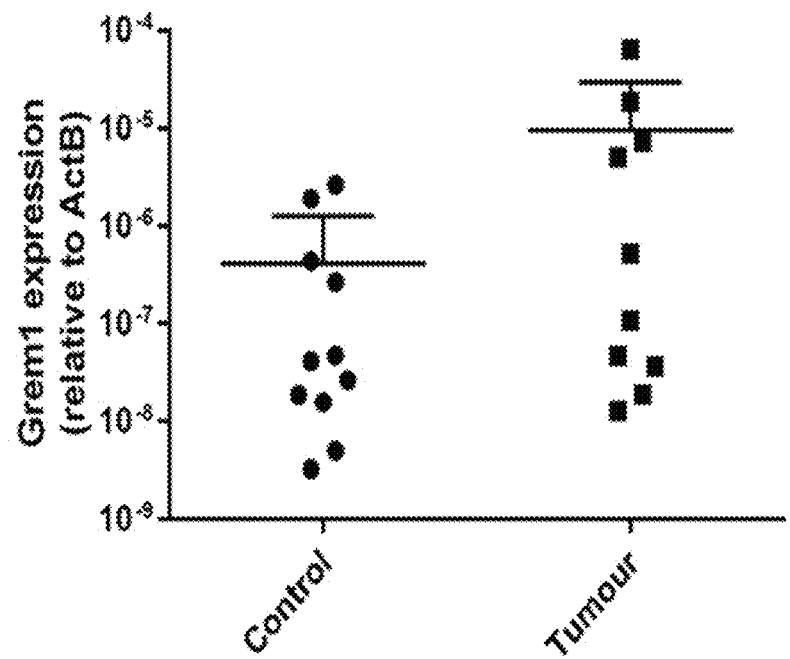
FIGS. 11A-11B. Grem1 expression was (FIG. 11A) analysed in the compact bone of healthy C57Bl6/KaLwRij.Hsd mice and mice injected with 5TGM1.Bmx1 MM PCs with disease detectable via BLI. (mean±SD, P=0.1120, T-test, Normal; n=11 and Tumour-bearing; n=9).
Figure 11B:
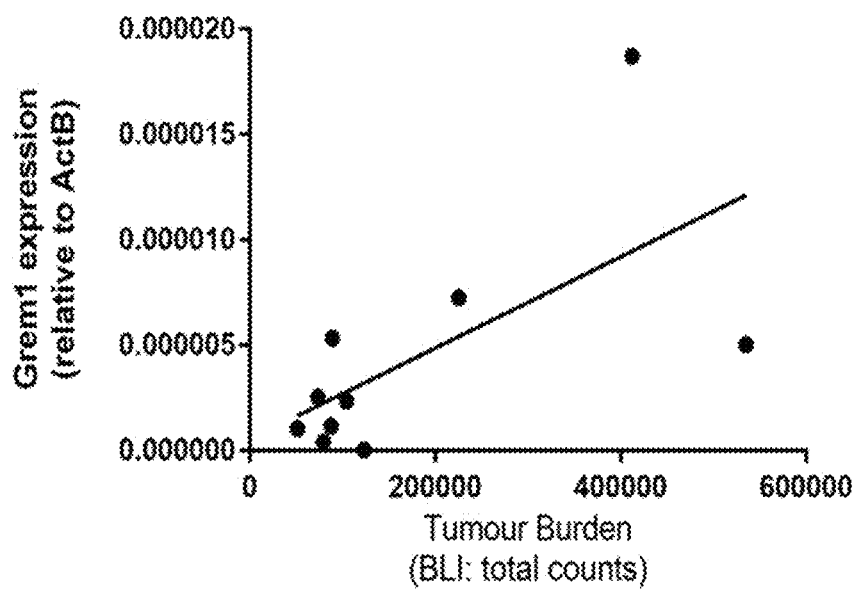

The expression of Grem1 was analysed in mRNA samples obtained from healthy- and MM patient-derived BM stroma. MM patient BM stroma (n=15) had significantly higher expression of Grem1 compared to BM stroma from age-matched haematopoietically normal donors (n=17) ($p<0.001$) (FIG. 10). Grem1 expression was also investigated in the 5TGM1/KaLwRij.Hsd mouse model of myeloma. Compact bone was isolated from healthy- and MM tumour bearing-C57BL/KaLwRij.Hsd mice and analysed for differences in Grem1 expression. BM stroma from tumour-bearing mice demonstrated no significant increase in the expression of Grem1 compared to the healthy controls, however a trend toward increased Grem1 expression was observed (FIG. 11A). Importantly, the mice with the greatest tumour burden, as determined by bioluminescent imaging, displayed the greatest expression of Grem1 (FIG. 11B). This result demonstrates that the increase in Grem1 in response to MM tumour growth supports the finding in the human setting.

MM Cells Promote Increased Grem1 Expression in BM Stroma

Figure 13:
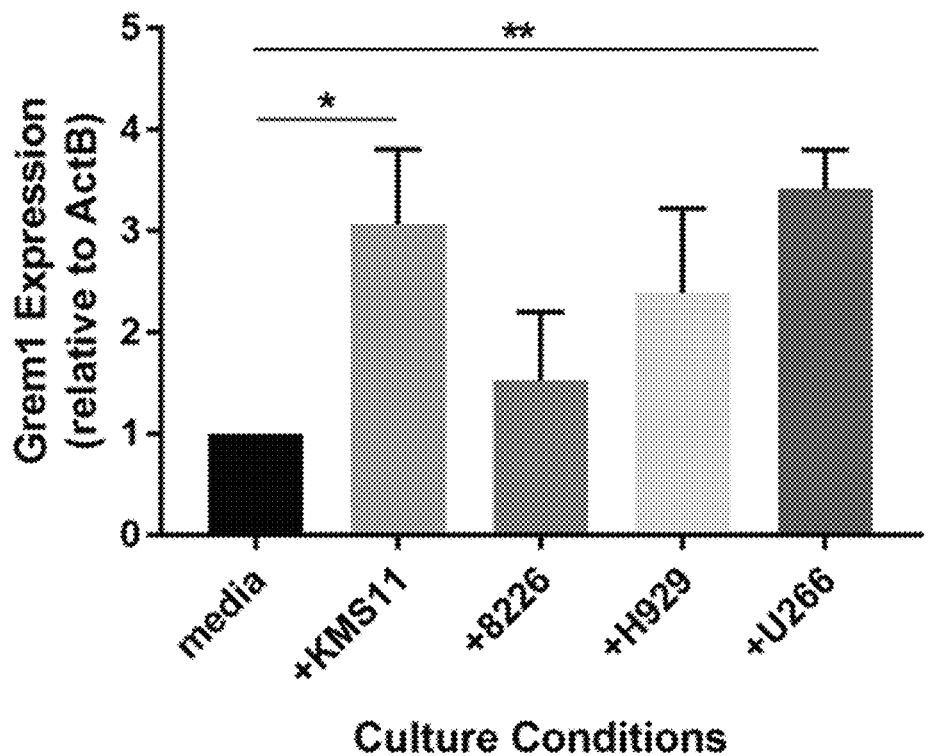
FIG. 13. Gremlin1 expression was analysed in normal human stroma co-cultured with various human MM cell lines for 72 hrs. MM cells were washed from stroma prior to collection for analysis of Grem1 expression. Significant increase in Gremlin1 expression in KMS-11 (p=0.0159) and U266 (p=0.0343) co-culture conditions (ANOVA). Data presented as replicates from co-culture with three separate normal stroma donors, normalised to media only control.
Figure 14A:
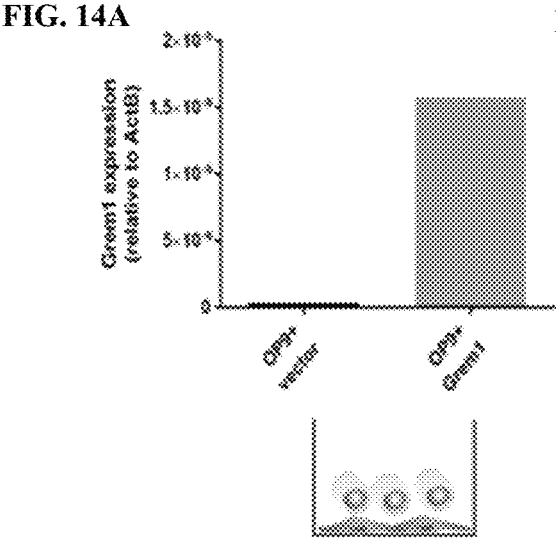
FIGS. 14A-14D. Grem1 transgene expression in OP9-stromal cells was confirmed by (FIG. 14A) RT-PCR and (FIG. 14B) Western blot. 5TGM1 MM PCs in (FIG. 14C) cell contact (FIG. 14D) transwell co-cultures with OP9-stromal cells modified to overexpress Grem1 displayed increased rates of proliferation compared to co-culture with OP9 vector-only controls, as measured by relative luciferase activity. (Mean±SEM of 3 replicate experiments,  P<0.01, *P<0.001, t-test).
Figure 14B:
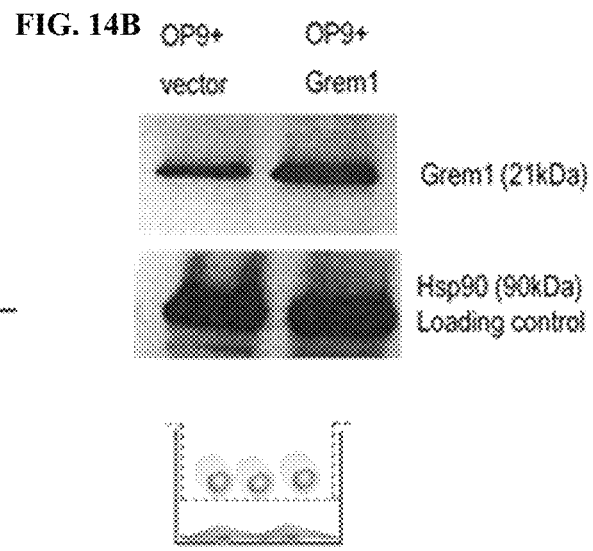
Figure 14C:
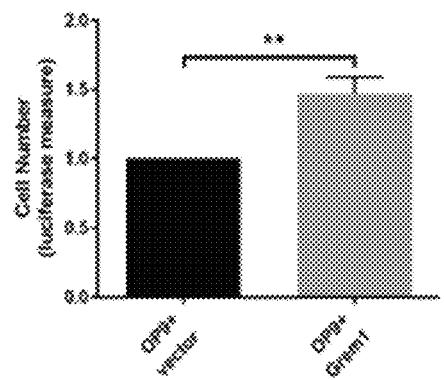
Figure 14D:
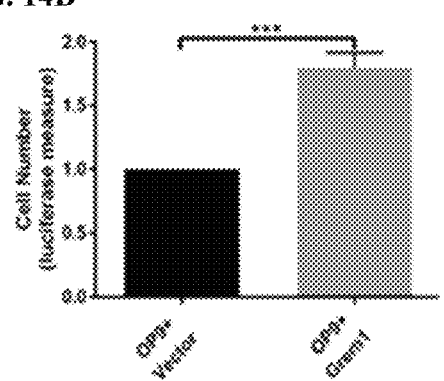

Co-culture experiments utilizing murine MM cell line 5TGM1.Bmx1 with the BM-derived stromal cell line, OP9 were performed to determine the effect of MM PCs on Grem1 expression within the BM microenvironment. Following 72 hours of co-culture, expression of Grem1 was significantly greater in the BM stromal cells cultured in the presence of the MM PC than those that did not have contact with the MM PC line ($p<0.05$) (FIG. 12A). The earlier time points at 24 and 48 hours of co-culture did not demonstrate a significant change in stromal Grem1 expression (FIG. 12A). Co-culture was performed in both Transwell and cell contact conditions, however only the cell contact co-cultures exhibited changes in stromal Grem1 expression (FIG. 12B). Primary human bone marrow stromal cells derived from haematopoietically normal individuals was also cultured with the human MM cell lines KMS-11, RPMI.8226, H929 and U266. The KMS-11 and U266 cell lines demonstrated an ability to induce an increase in Grem1 expression from BM stroma after 72 hours of co-culture, while co-culture with cell lines RPMI.8226 and H929 did not result in changes in Grem1 expression in the stroma (FIG. 13).

Increased Grem1 Expression Promotes MM PC Proliferation

Figure 16:
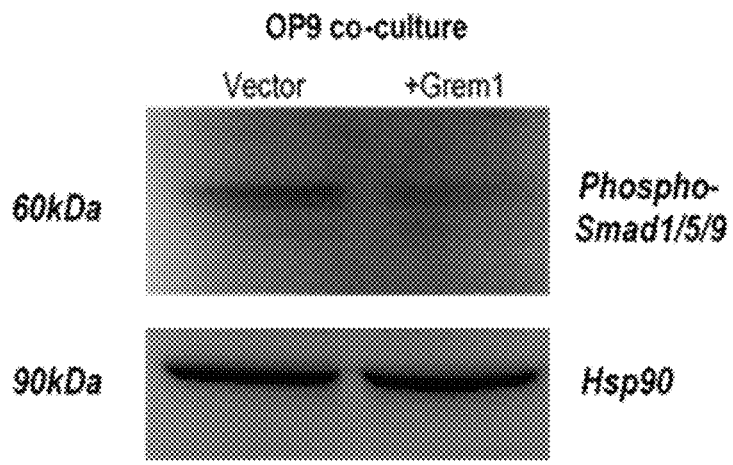
FIG. 16. 5TGM1 MM cells were co-cultured in 3 μm transwells in the presence of OP9-Grem1 overexpressing cells or vector-only controls for 72 hrs. Lysate from the 5TGM1 cells was analysed by Western blot for phosphorylation of Smads 1/5/9. 5TGM1 cells display a reduction in phosphorylation of Smads 1/5/9 when cultured in the presence of Grem1-overexpressing BM stromal cells, compared to vector-only controls. Hsp90 was used as a loading control. Image representative of two replicate experiments.

To further investigate the importance of Grem1 in the setting of MM, stromal cells overexpressing Grem1 were generated and used in co-cultures with 5TGM1 MM PCs. MM PCs demonstrated a significant increase in proliferation when co-cultured with the Gremlin1-overexpressing stromal cells, both in transwell and cell-contact culture settings (FIG. 14) ($p<0.01$ and $p<0.001$, respectively). The MM PC co-cultured with the Grem1-overexpressing BM stroma, subsequently exhibited a reduction in BMP signalling pathway activation, as demonstrated by a reduction in the phosphorylation of Smads-1/5/9 (FIG. 16). The BMP pathway is known to inhibit MM PC proliferation and promote apoptosis and represents a potential mechanism for the reduction in MM PC proliferation observed (Hjertner et al., 2001; Holien et al 2012).

Targeting Grem1 Reduces MM Tumour Burden In Vivo

Figure 15A:
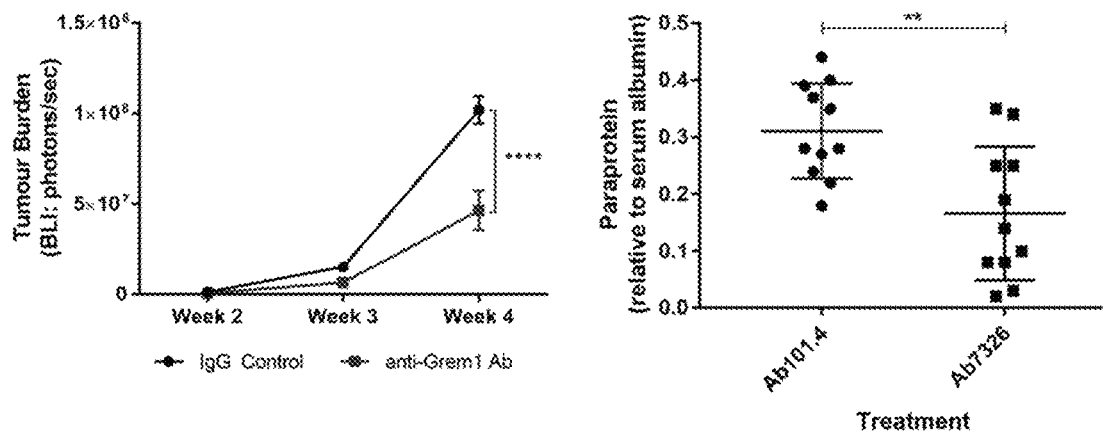
FIGS. 15A-15B.
Figure 15B:
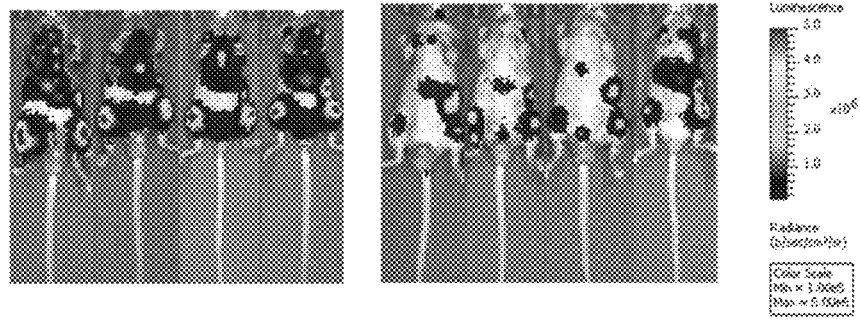

To examine the importance of Gremlin1 in MM tumour establishment and growth in vivo we utilized the 5TGM1/KaLwRij mouse MM model. Following disease initiation, mice were randomly assigned (n=13/treatment group) to receive treatment with Gremlin1 neutralising antibody (Ab7326, UCB-CellTech, UK) or IgG control, and disease burden was monitored weekly over four-weeks via bioluminescent imaging. These studies demonstrated that treatment with an anti-Gremlin1 therapy significantly reduced MM tumour burden in vivo (FIG. 15) (two-way ANOVA, p=0.0056). SPEP analysis of disease burden demonstrated a comparable result, with mice treated with the anti-Grem1 antibody having a significantly lower M-spike intensity relative to serum albumin, compared to the control treated mice.

DISCUSSION

Figure 17:
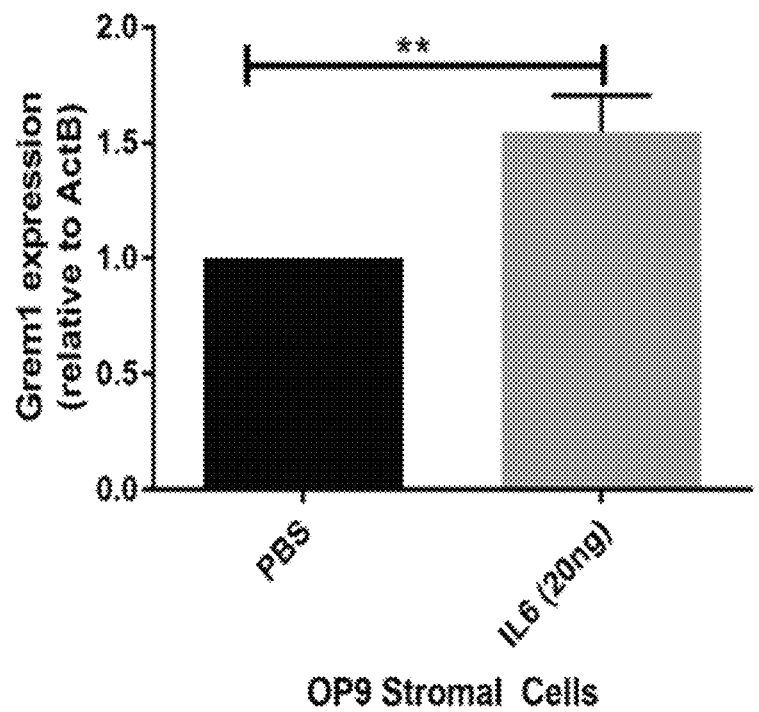
FIG. 17. The BM stromal cell line, OP9 was assessed for expression of Grem1 following treatment with 20 ng/ml of recombinant IL6 for 72 hrs. A significant increase in Grem1 expression was observed in the OP9 cells stimulated with IL6. (Mean±SEM of 3 replicate experiments, ** P<0.01).

The findings of increased Grem1 in the BM stroma of MM patients are consistent with previous studies that have reported increased Gremlin1 produced by microenvironmental cell populations. In addition, a trend toward increased Grem1 expression in the bones of mice with MM-like tumours was observed. When further studies were conducted utilizing the cell line used for the in vivo model, it was shown that culturing the mouse MM PC line directly upon a stromal cell line derived from the BM, that there was a subsequent increase in Grem1 expression from the stroma. This finding was not replicated when the MM PCs where unable to have direct cell-to-cell contact with the stromal cells, however a trend toward increased expression was observed. This indicates that the MM cell-derived factors responsible for the increased Grem1 expression from the stroma rely primarily on cell contact. This was also observed in two of the four human MM cell lines cultured with normal human stroma. The MM cell lines KMS-11 and U266 were able to induce an increase in Grem1 expression, but the RPMI.8226 and H929 cell lines were not. The ability of some human MM cell lines to induce a change in Grem1 expression, but not others may indicate that there are fundamental differences in the expression of key factors responsible for the regulation of Grem1 between these cell lines, with preliminary studies suggesting a role for interleukin-6 (IL-6) in the regulation of Grem1 in MM (FIG. 17). Further study is also required to determine whether the ability of the cell line to induce stromal Grem1 expression, correlates with their proliferative response to Grem1.

To examine the role of Grem1 in MM, BM stromal cells overexpressing Grem1 were generated and co-cultured with MM PCs in order to partially replicate the cross-talk between tumour microenvironment and tumour cells. MM PCs demonstrated a significant increase in proliferation in co-culture with Grem1 overexpressing stromal cells. A decrease in the downstream activation of BMP signalling was observed, as indicated by decreased phosphorylation of Smads 1, 5 and 9 in response to increased Grem1 (FIG. 16).

As Grem1 displays clear mitogenic roles in MM, we investigated whether therapeutically targeting Grem1 represented a treatment option. Use of the Grem1-neutralising antibody Ab7326 in the 5TGM1/KaLwRij mouse model of MM demonstrated almost a 50% reduction in MM tumour burden. As the 5TGM1 MM PC do not express Grem1, this effect can be attributed a purely a result of targeting the microenvironment.

In summary, this study shows that Grem1 represents a therapeutic target in MM.

Example 14—Pre-Treatment of Grem1 in a Mouse Model of MM

Introduction

Application of the Grem1-neutralising antibody 3 days after inoculation of mice with multiple myeloma (MM) tumour resulted in a reduction in tumour burden of approximately 50%. This established a clear role for Grem1 in the progression of MM disease, however it remained to be determined if Grem1 played a role in MM disease initiation. To address this question, Grem1-neutralising antibody was administered to the 5TGM1/KaLwRij mouse model prior to tumour inoculation.

Methods

Targeting Grem1 prior to tumour cell inoculation in an immunocompetent murine model of systemic MM: C57BL/KaLwRij mice (6-8-week-old) were administered two doses of 30 mg/kg Grem1-neutralising antibody Ab7326 or IgG control Ab101.4 (UCB-Pharma, UK) by subcutaneous (s.c.) injection three days and one day prior to tumour inoculation. At Day 0, mice were inoculated with $5\times10^5$ 5TGM1.Bmx1 cells via tail vein injection. Mice continued to receive either 30 mg/kg Grem1-neutralising antibody Ab7326 or IgG control Ab101.4 (UCB-Pharma, UK) by s.c. injection every 3 days for the duration of the 4-week model. Tumour burden was monitored weekly by BLI as previously described. At the end of the experiment, blood was collected by tail bleed, centrifuged at 2100 g for 10 min and serum collected. Serum paraprotein levels were analysed using the Hydragel 30 β1β2 kit (Sebia Electrophoresis, Georgia, USA) according to the manufacturer's instructions. The band corresponding to paraprotein was quantitated relative to serum albumin levels. (SAHMRI Animal Ethics SAM165)

Results/Discussion

Figure 18A:
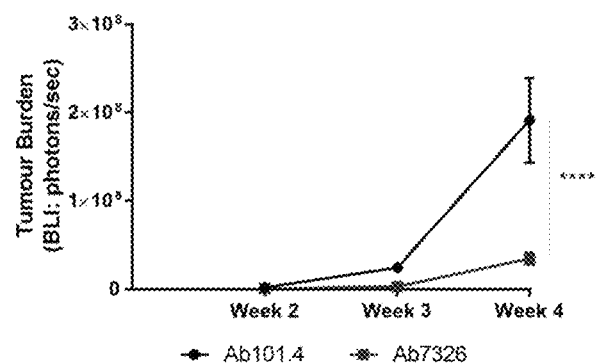
FIGS. 18A-18C.
Figure 18B:
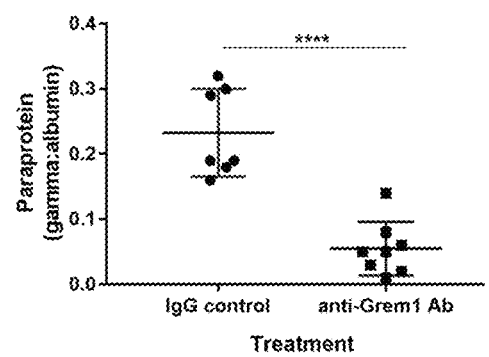
Figure 18C:
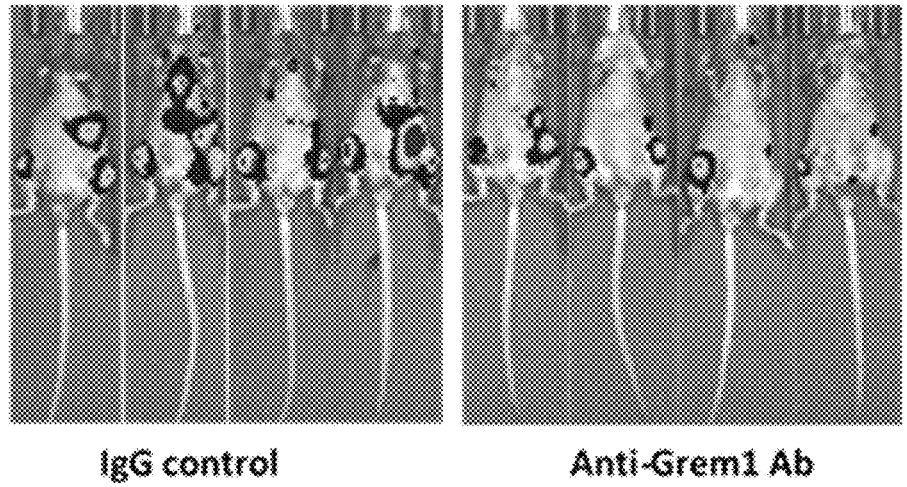

Our previous data demonstrated that Grem1 can be targeted to reduce MM tumour burden in the 5TGM1/KaLwRij mouse model of myeloma. This established that Grem1 is a key microenvironmental factor that contributes to disease progression and can be targeted therapeutically. However, it was still unclear whether Grem1 also plays a role in the initiation of MM disease. To address this question, mice received the Grem1-neutralising antibody treatment, or IgG control, prior to MM tumour cell inoculation. As shown in FIG. 18, a reduction in tumour burden of approximately 75% at 4-weeks post-tumour cell inoculation was observed.

Blocking Grem1 prior to the administration of MM tumour cells, showed an additional 25% reduction in overall tumour burden by the end of the study, when compared with treatment following tumour cell inoculation. The increased efficacy of the Grem1-neutralising antibody when administered prior to the initiation of tumour model, suggests a role for Grem1 in the initiation of MM disease.

Example 15—Grem1-Induced Proliferation of Breast Cancer Cells and Antagonism of Grem1 Effects with an Anti-Grem1 Antibody Materials and Methods Real-Time Polymerase Chain Reaction (RT-PCR)

Human MDA-MB-231-TXSA breast cancer cells and human MF9 mammary fibroblasts were seeded into 6-well plates and cultured in either normoxic or hypoxic conditions for 48 hrs. Normoxic conditions were maintained at 37° C. with 5% $CO_2$, 20% $O_2$, while hypoxic conditions were maintained in a hypoxic in vitro chamber at 5% $O_2$, 10% $CO_2$ (Coy Laboratory Products, Grass Lake, MI, USA). Total RNA was extracted using TRIzol (Life Technologies, Carlsbad, CA, USA). After removing genomic DNA contamination with DNase I (Promega, Madison, WI, USA), superscript IV (Invitrogen, Carlsbad, CA) was used to synthesize cDNA. 1 μg of each RNA sample was reverse transcribed and Grem1 gene expression was quantified by RT-PCR using SYBR Green Fluor qPCR mastermix (Qiagen) on a Biorad CFX Connect. Experiments were performed in triplicate with gene expression standardised to β-actin, applying the $2^{-\Delta CT}$ method. Data is presented as fold change relative to normoxia control.

Primer Pairs:

Human Grem1:
  5'-AGGCCCAGCACAATGACTCAG-3' (forward) (SEQ ID NO: 40),
  5'-GTCTCGCTTCAGGTATTTGCG-3' (reverse) (SEQ ID NO: 41);

β-Actin:
  5'-GATCATTGCTCCTCCTGAGC-3' (forward) (SEQ ID NO: 42),
  5'-GTCATAGTCCGCCTAGAAGCAT-3' (reverse) (SEQ ID NO: 43).

Proliferation Assays in Hypoxia

Luciferase expressing MDA-MB-231-TXSA cells were seeded in 96-well microtiter plates ($1 \times 10^4$ cells/well). Cells were cultured either under normoxic or hypoxic conditions and allowed to adhere overnight. Cells were then serum starved for 6 hrs before treatment with increasing concentrations of rhGrem1 protein (0-1000 ng/ml). At 24 and 48 hr time points, luciferase expression was evaluated and used as a surrogate measure of cell number. Briefly, cells were washed in 1×PBS, and subsequently lysed in cell culture lysis buffer (Promega). Luciferase Assay Reagent (5 mM $MgCl_2$, 30 mM HEPES, 150 μM ATP, 50 mg/mL Coenzyme A and 150 μg/mL D-luciferin (Biosynth AG, Staad, Switzerland)) was added to cell lysates, and luminescence was quantified immediately using a luminometer plate reader (Wallac 3000).

Transwell Co-Culture Proliferation Assays

Luciferase-expressing murine 4T1 breast cancer cells ($1 \times 10^4$ cells) were seeded into 3 μm polycarbonate membrane transwells (Costar, Washington, D.C., USA) in a 24-well plate. Following overnight culture, 4T1 cells were starved in serum free DMEM for 6 hrs to synchronise cell growth. GFP+ murine stromal OP9 cells, previously transduced with a control or Grem1 expressing pLEGOiT2 construct were seeded into lower chambers ($2 \times 10^4$ cells) in 10% FCS DMEM. Cells were co-cultured for 72 hrs, before analysing 4T1 cell proliferation via luciferase expression.

Western Blot Analysis

Murine 4T1 BrCa cells were seeded into 6-well plates and cultured until 80% confluent. Cells were starved in serum-free medium overnight, and then stimulated with indicated treatments for 2 hrs. Cell lysates were prepared and equivalent amounts of protein (50 μg) were separated on 10% sodium dodecyl sulphate-polyacrylamide gel electrophoresis (SDS-PAGE) gels and transferred to nitrocellulose membranes. Immunoblotting was performed with phospho-Smad1/5/9 antibodies (cell signalling technologies, 1:1000 dilution). Equal loading of protein samples was confirmed by blotting membranes with antibodies against β-actin (Sigma Aldrich, 1:2500 dilution). Proteins were visualised using the Odyssey Infrared Imaging System (LI-COR Bioscience, Lincoln, NE, USA).

Figure 19A:
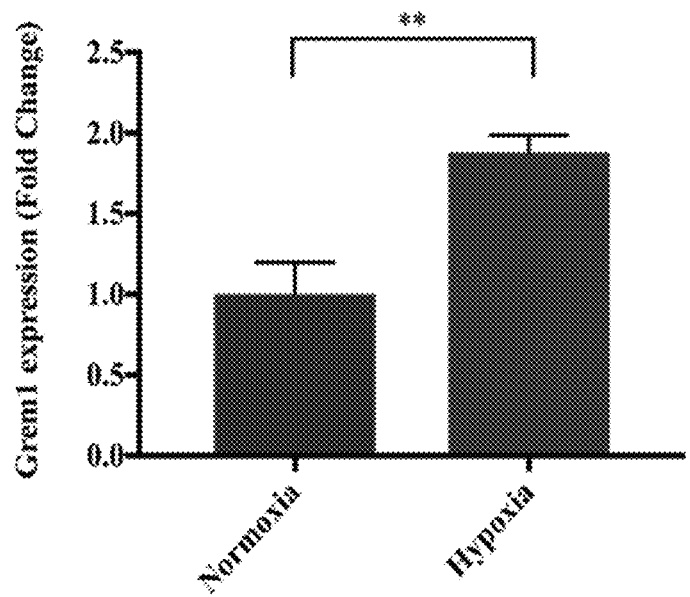
FIGS. 19A-19B. Quantitative RT-PCR analysis of Grem1 mRNA expression. Grem1 gene expression was analysed in (FIG. 19A) human MDA-MB-231-TXSA breast cancer cells and (FIG. 19B) human MF9 mammary fibroblasts following 48 hr culture in normoxic and hypoxic conditions (n=1). Expression levels were measured by RT-PCR and normalised to β-actin. Mean±SD of triplicate wells, *p<0.05, **p<0.005, Student's unpaired t-test.
Figure 19B:
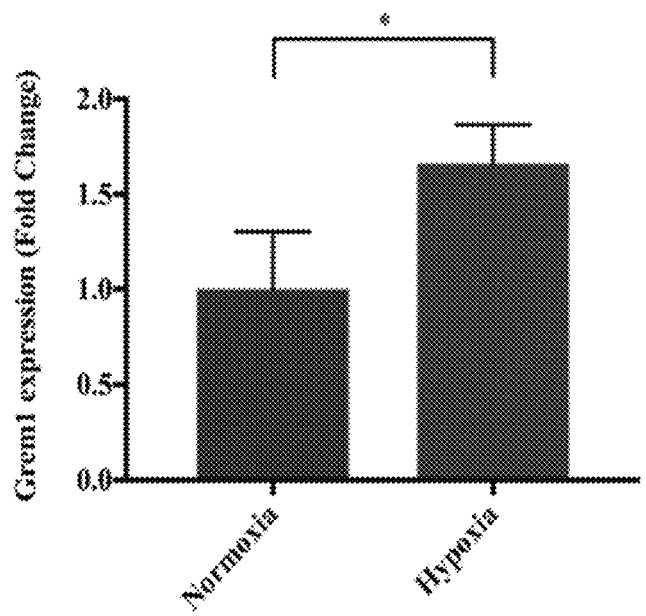

Results and Discussion:

We identified that Grem1 induces proliferation of human breast cancer cells under hypoxic conditions. While the mechanism by which Grem1 promotes breast cancer proliferation remains unknown, BMP expression has been shown to be elevated under hypoxia in several other cell types. Therefore, Grem1 may induce proliferation under hypoxia by inhibiting the anti-proliferative effects of BMPs. Human MDA-MB-231-TXSA breast cancer cells and human MF9 mammary fibroblasts were cultured in either normoxic (20% $O_2$) or hypoxic (5% $O_2$) conditions for 48 hrs. Quantification of Grem1 mRNA by RT-PCR revealed elevated Grem1 expression under hypoxia in both MDA-MB-231-TXSA cells (p=0.0024) and MF9 cells (p=0.034) compared to normoxia controls (FIG. 19).

Figure 20A:
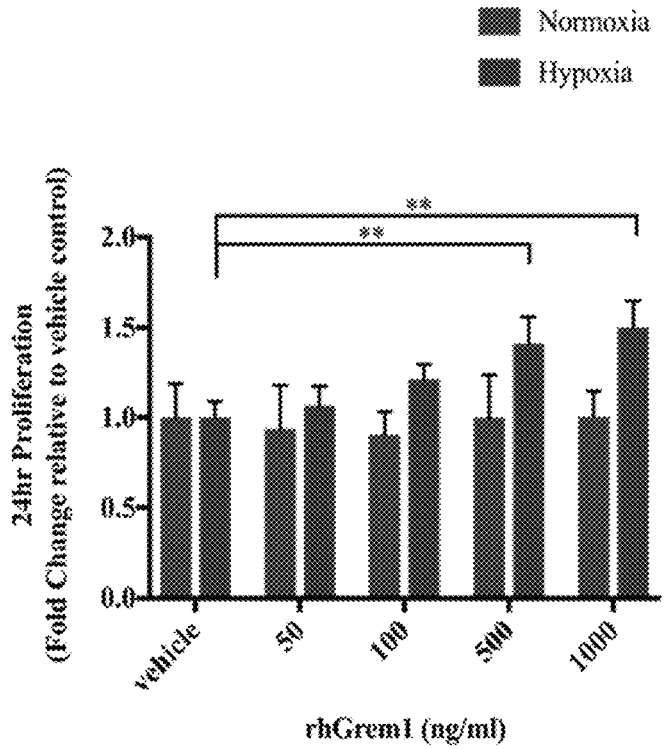
FIGS. 20A-20B. Human breast cancer cell proliferation in response to stimulation with Grem1. MDA-MB-231-TXSA cells were stimulated with various concentrations of rhGrem1 and cultured under normoxic (left-hand bar of each pair) and hypoxic conditions (right-hand bar of each pair) for (FIG. 20A) 24 and (FIG. 20B) 48 hrs. Data is a representative of three independent experiments performed in triplicate. Mean±SD, *p<0.05, p<0.005, *p<0.0005, two-way ANOVA with Tukey's multiple comparisons test.
Figure 20B:
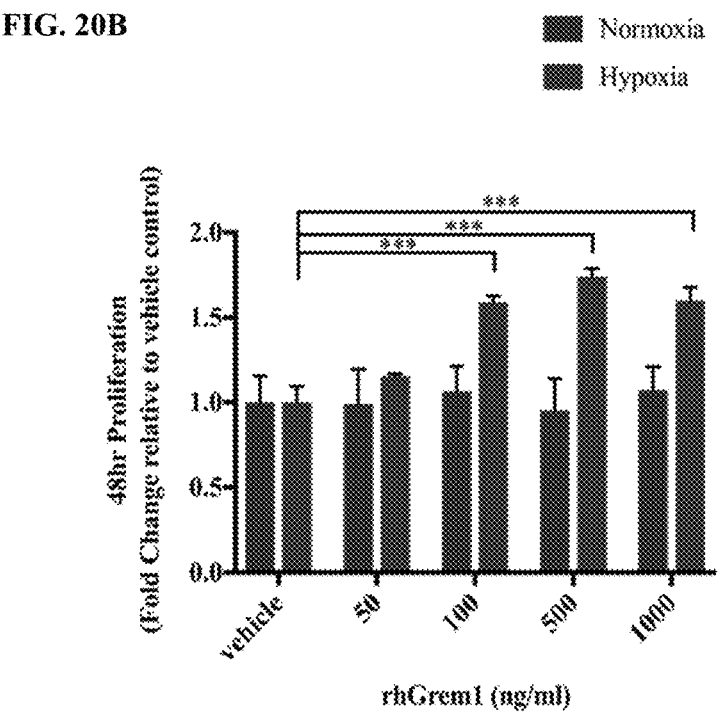

When cultured under hypoxic conditions, rhGrem1 stimulated a dose-dependent increase in MDA-MB-231-TXSA proliferation, with a maximal 1.5-fold (p<0.005) and 1.7-fold (p<0.0005) compared to normoxic conditions, after 24 hr and 48 hr respectively (FIG. 20).

Figure 21:
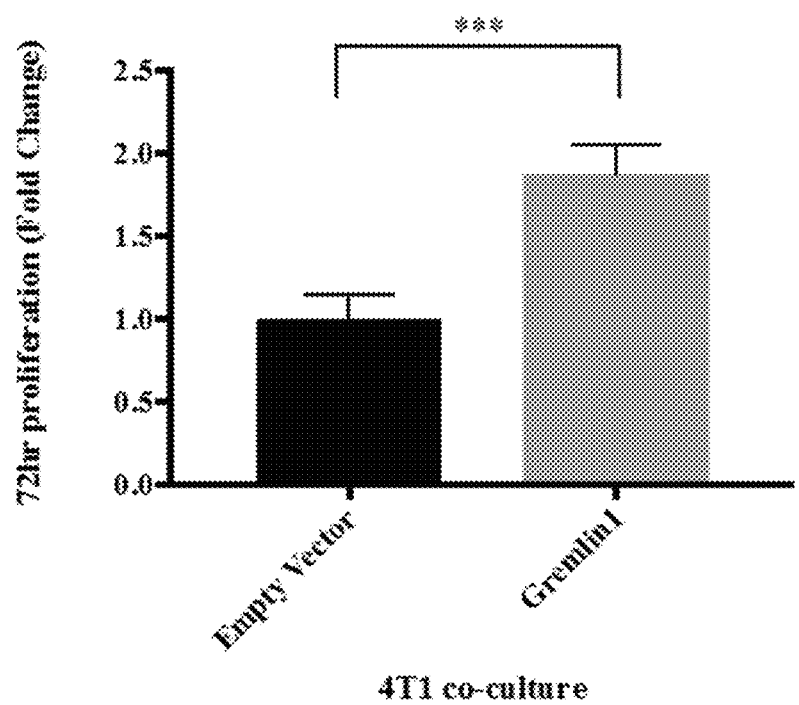
FIG. 21. Murine 4T1 breast cancer cell proliferation in response to stromal-derived Grem1. 4T1 cells were co-cultured with Grem1-expressing or vector control OP9 stromal cells for 72 hrs. Data is a representative of three independent experiments performed in triplicate. Mean±SD, ***p<0.0005, Student's unpaired t-test (two-sided).

To further investigate if Grem1 induced proliferation of breast cancer cells in the context of other stromal factors, murine 4T1 breast cancer cells were co-cultured with stromal OP9 cells expressing either Grem1 or a control vector. Stromal cell-derived Grem1 significantly increased breast cancer cell proliferation by 1.8-fold (p<0.0005) after 72 hr culture (FIG. 21). This further suggests that Grem1 may induce proliferation by antagonising stromal derived BMPs.

Figure 22:
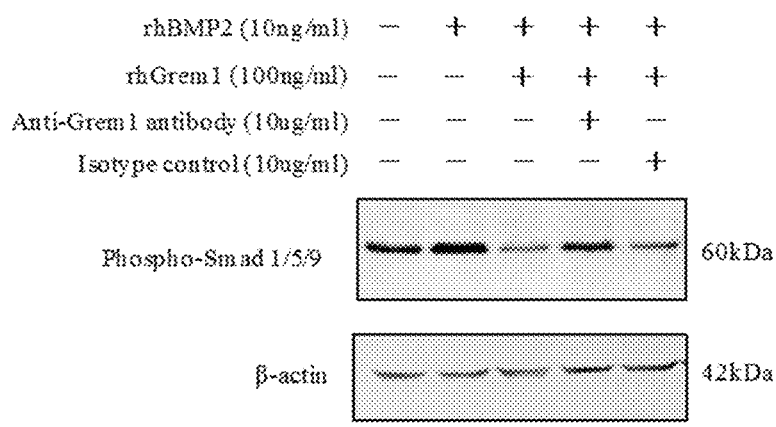
FIG. 22. Novel anti-Grem1 antibody (Ab7326) reverses Grem1-mediated inhibition of Smad1/5/9 phosphorylation in murine 4T-1 breast cancer cells. Murine 4T1 breast cancer cells were stimulated for 2 hrs with combinations of treatments as indicated and subjected to Western blot analysis using an antibody reactive to phospho-Smad1/5/9 (upper panel). β-actin (lower panel) served as a loading control.

As Grem1 is a known BMP-2/4/7 antagonist, we assessed the ability of UCB antibody Ab7326 to inhibit Grem1-induced inhibition of Smad1/5/9 phosphorylation via western blot analysis. Murine 4T1 breast cancer cells exposed to 10 ng/ml BMP2 which led to Smad1/5/9 phosphorylation. Co-incubation with 100 ng/ml rhGrem1 inhibited this BMP2-mediated Smad1/5/9 phosphorylation. Notably, compared to 4T1 cells exposed to rhGrem1 pre-incubated with an isotype control, pre-incubation of rhGrem1 with Ab7326, partially restored Smad1/5/9 phosphorylation in 4T1 cells (FIG. 22). These results provide confirmation that Ab7326 can effectively target and neutralise the effects of Grem1.

Example 16—the Effect of Monotherapy and Combination Therapy in VG/Min Mice

Mice were treated with 30 mg/kg weekly anti-Grem1 antibody and/or two intraperitoneal daily doses of 40 mg/kg 5-fluorouracil (5FU, Sigma) at or from the age of 35 days onwards, which is very late in the Vil1-Grem1 Apc$^{Min}$ disease process. To generate Kaplan-Meier data, mice were sacrificed when humane-end points were reached (mice exhibited anaemia, hunching and inactivity).

Figure 23:
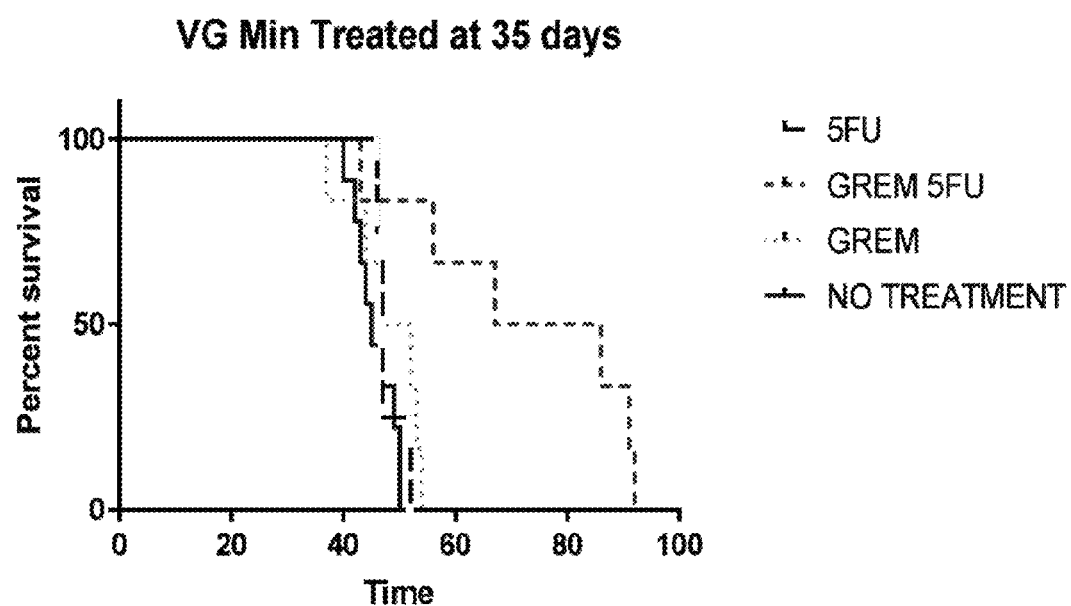
FIG. 23. The effect of monotherapy and combination therapy in VG/Min mice.
Figure 24:
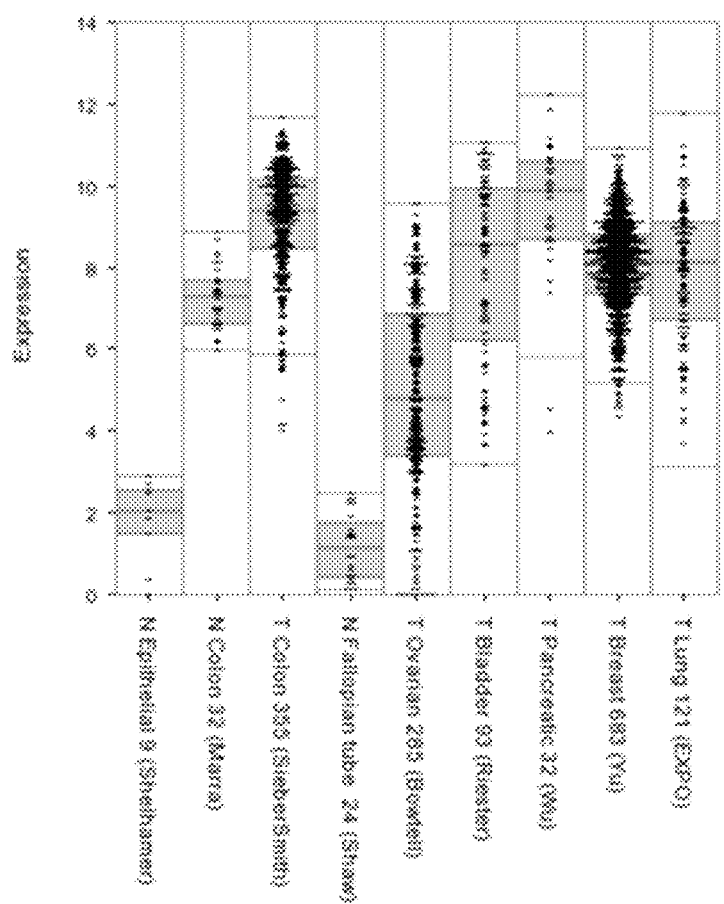
FIG. 24. Grem1 expression in various solid tumours.
Figure 25:
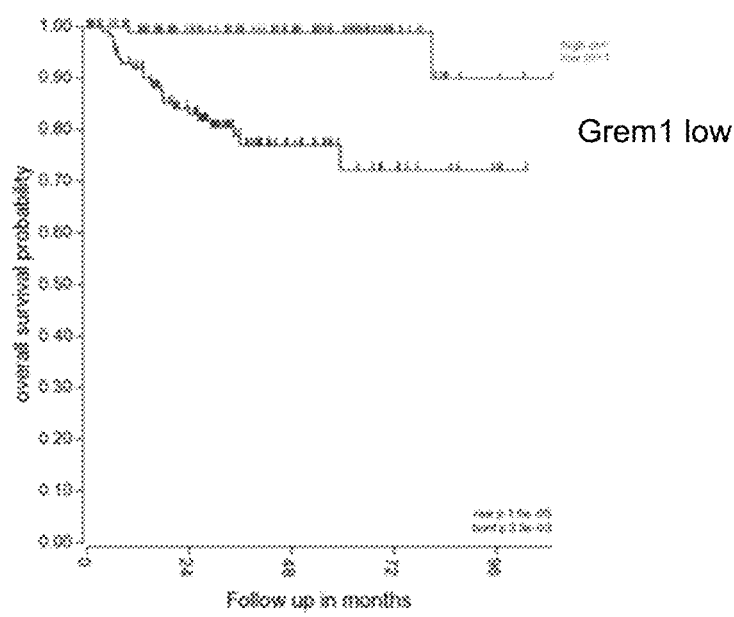
FIG. 25. The relationship between Grem1 expression and survival implications in bladder carcinoma. Top line—Grem1 low; bottom line—Grem1 high.
Figure 26:
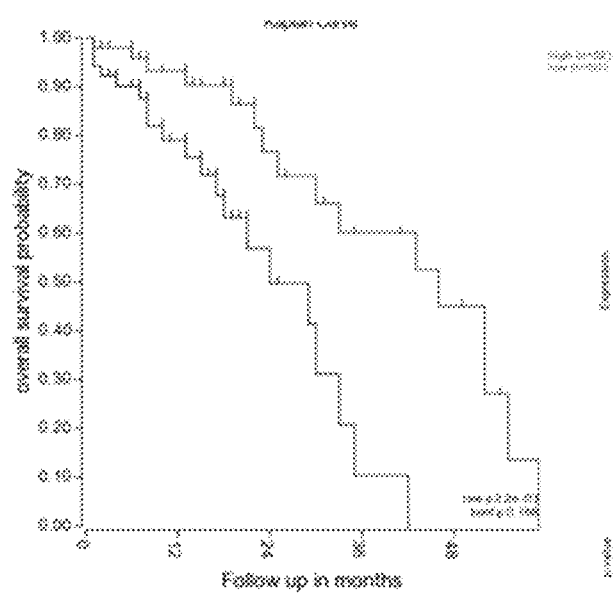
FIG. 26. The relationship between Grem1 expression and survival implications in pancreatic ductal adenocarcinoma. Top line—Grem1 low; bottom line—Grem1 high.
Figure 27:
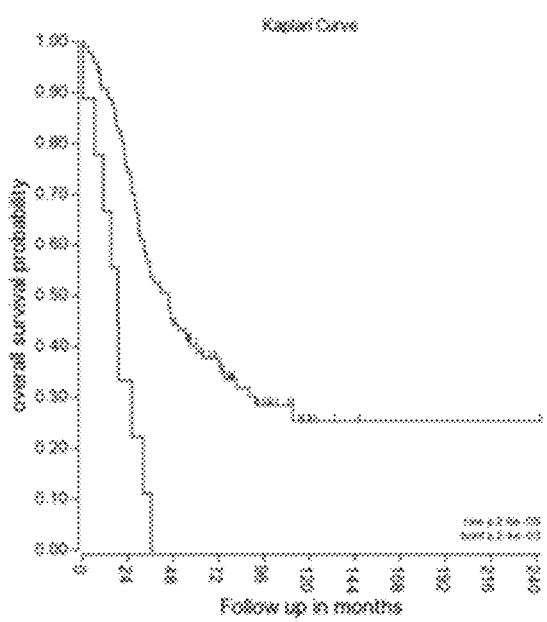
FIG. 27. The relationship between Grem1 expression and survival implications in ovarian adenocarcinoma. Top line—Grem1 low; bottom line—Grem1 high.
Figure 28:
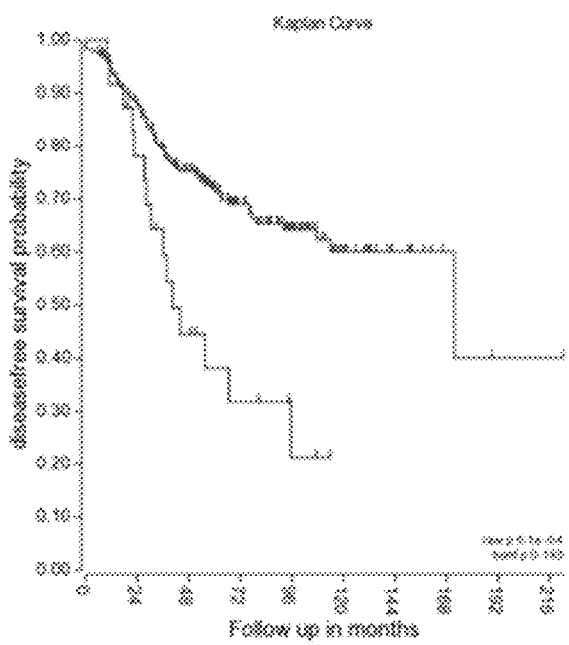
FIG. 28. The relationship between Grem1 expression and survival implications in basal breast carcinoma. Top line—Grem1 low; bottom line—Grem1 high.
Figure 29:
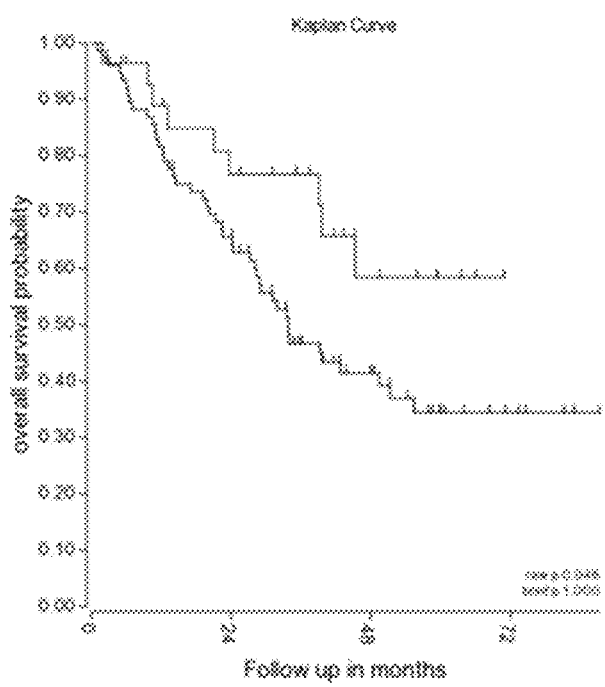
FIG. 29. The relationship between Grem1 expression and survival implications in lung carcinoma. Top line—Grem1 low; bottom line—Grem1 high.

Monotherapy with either 5FU or anti-Grem1 in this late stage of disease had no effect on the lifespan of the mice, but combination therapy significantly prolonged mouse lifespan (median survival: no treatment 45 days (n=9), 5FU alone 47 days (n=4), anti-Grem1 alone 49.5 days (n=6), combination therapy 76.5 days (n=6): log rank p<0.01), see FIG. 23. These data show the efficacy of combination therapy in late stage, established disease, using anti-Grem1 antibody together with standard chemotherapy targeted against the proliferating epithelium.

Example 17—the Effect of Anti-Grem1 Antibody in Human Patient Derived Xenograft (PDX) Models The efficacy of the anti-gremlin-1 Ab7326 as a mouse IgG1 will be tested in eight Patient Derived Xenograft (PDX) models. The human PDX models were selected based on their increased expression of the GREM1 gene product over control tissue. The models selected include xenografts derived from pancreatic, lung, renal, colorectal, gastric, head and neck and liver cancers. Ab7326 will be dosed weekly subcutaneously. Tumour size will be evaluated throughout the model duration and tumours and plasma samples will be collected and analysed at the end of the experiments.

Example 18—the Effect of Anti-Grem1 Antibody on Tumour Burden in C57B16/KaLwRij Mice (FIG. 33)

It was observed that tumour burden in C57B16/KaLwRij mice was significantly reduced in the hindlimb bones when mice are treated with Grem1-neutralising antibody, Ab7326 (see FIG. 33). A significant reduction in tumour burden was seen when the anti-Grem1 antibody was administered after tumour cell inoculation (FIG. 33A), as compared to IgG control (measured by BLI). A significant reduction in tumour burden was also seen when the anti-Grem1 antibody was administered prior to tumour cell inoculation (FIG. 33B), again as compared to IgG control (measured by BLI). A downwards trend in splenic tumour burden was also observed in groups treat-ed with anti-Grem1 antibody, in both the (FIG. 33C) post-, or (FIG. 33D) pre-tumour cell inoculation groups.

C57B16/KaLwRij mice are a model for multiple myeloma (MM) in which MM cells grow within the bone marrow (BM) and the spleen. The data presented in FIG. 33 demonstrate that anti-Grem1 treatment targets BM-associated tumours as well as MM cells in the spleen. Accordingly, anti-Grem1 therapy may be used to treat both bone-resident tumours, such as osteosarcoma, as well as disseminated cancers, such as liver, breast and/or prostate cancer.

Example 19—Late Stage Treatment of Established Vil1-Grem1 and Apc$^{Min}$ Polyposis with Anti-Grem1 Antibody, Slows Disease Progression and Reverts Vil1-Grem1 Mouse Intestinal Phenotype (FIG. 34)

Figure 34A:
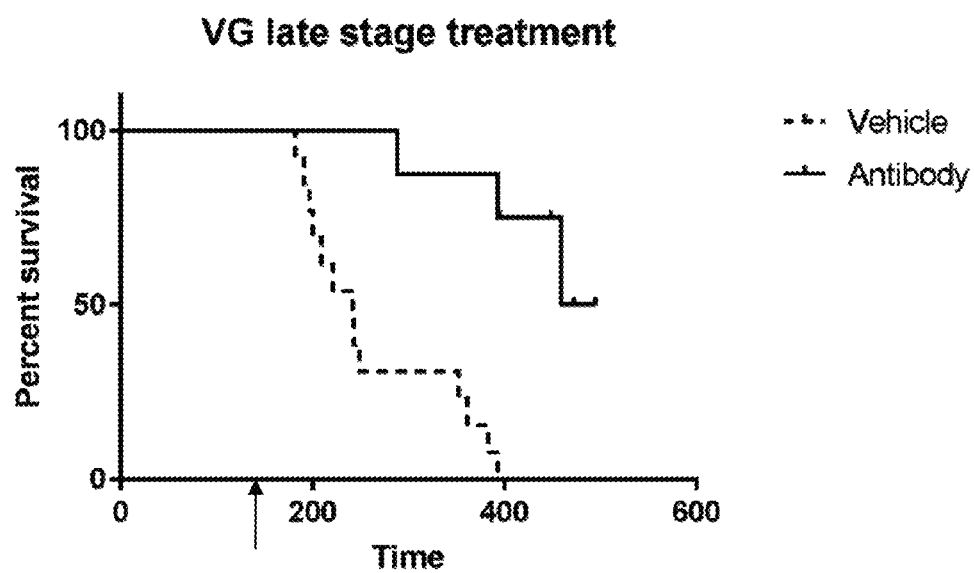
FIGS. 34A-34B. Kaplan Meier survival plots for treatment of established polyposis in (FIG. 34A) Vil1-Grem1 mice and (FIG. 34B) Apc$^{Min}$ mice. Median survival: Apc$^{Min}$ Vehicle: 192 days (n=15); Apc$^{Min}$ anti-Grem1: 264.5 days (n=10); Vil-Grem1 Vehicle: 242 days (n=13); and Vil-Grem1 anti-Grem1: 477 days (n=8), log rank p<0.01 in both cases. Arrows indicate treatment initiation in treated groups.
Figure 34B:
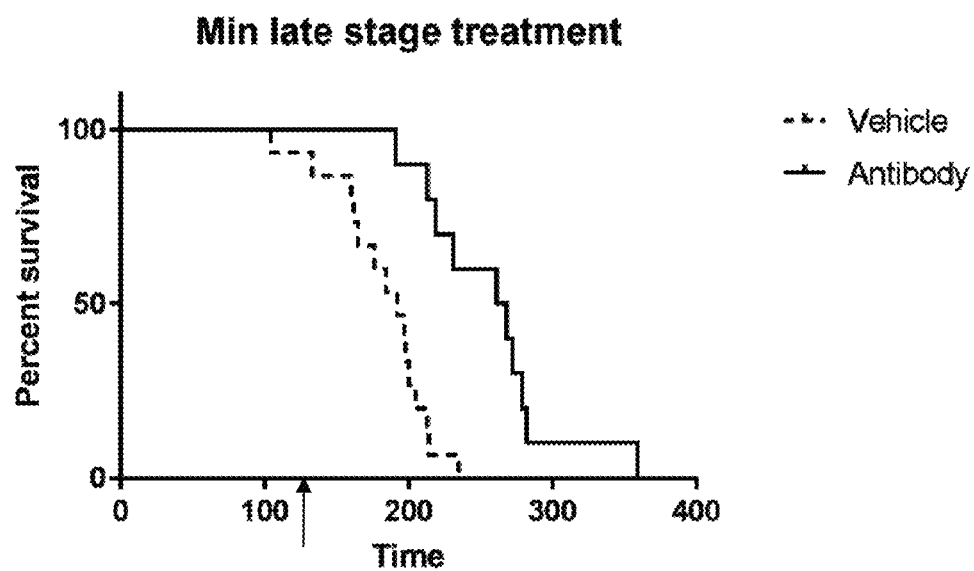

Anti-Grem1 antibody (UCB) or control antibody (UCB) were administered at a dose of 30 mg/kg weekly subcutaneous injections, starting at the age of 4 months for Apc$^{Min}$ (FIG. 34B) and 5 months for Vil1-Grem1 mice (FIG. 34A).

Mice were aged to allow development of an intestinal polyposis prior to commencement of antibody treatment (at the age of 4 months for Apc$^{Min}$ and 5 months for Vil1-Grem1 mice). To generate Kaplan-Meier data, mice were sacrificed when humane-end points were reached (mice exhibited anaemia, hunching and inactivity). In both the Vil1-Grem1 (A) and the Apc$^{Min}$ (B) models, treatment with anti-Grem1 antibody significantly prolonged the lifespan of the mice. Timed sacrifice showed a reversion of the Vil1-Grem1 intestinal phenotype over 4 weeks of treatment.

Figure 35A:
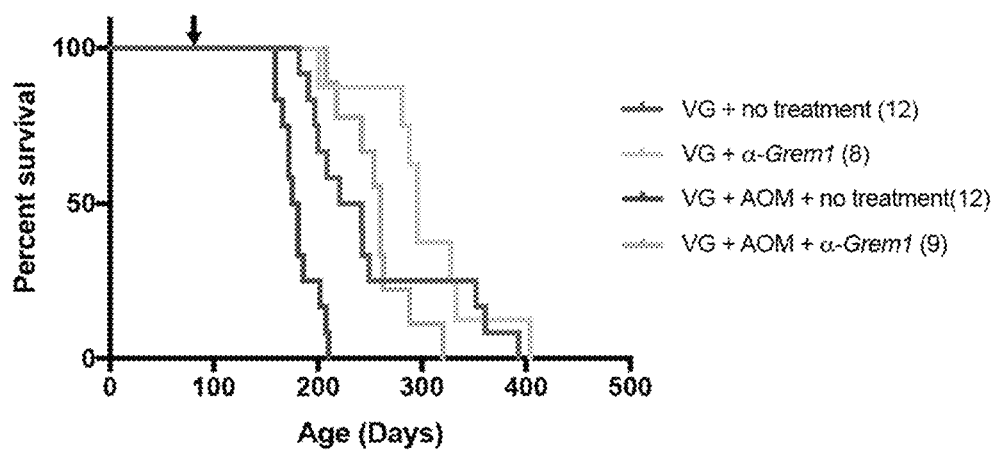
FIGS. 35A-35C. Plots showing survival and colonic polyp burden in four treatment groups, namely: (i) untreated Vil1-Grem1 mice (VG+no treatment); (ii) Vil1-Grem1 mice treated with azoxymethane only (VG+AOM+no treatment); (iii) Vil1-Grem1 mice treated with anti-Grem1 antibody only (VG+α-Grem1); and (iv) Vil1-Grem1 mice treated with both azoxymethane and anti-Grem1 antibody (VG+AOM+α-Grem1).
Figure 35B:
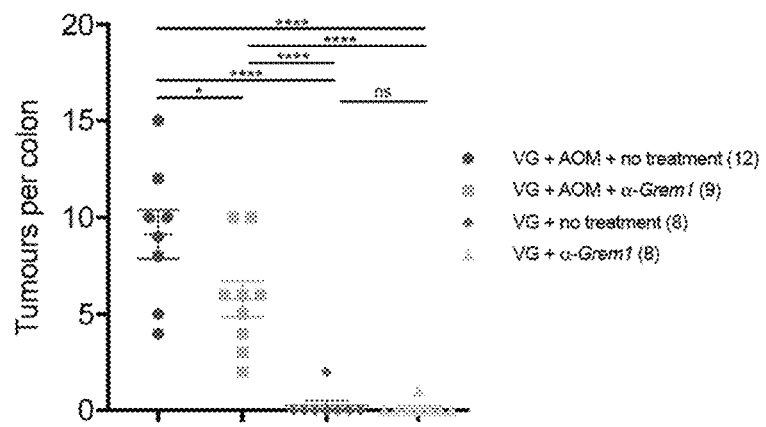
Figure 35C:
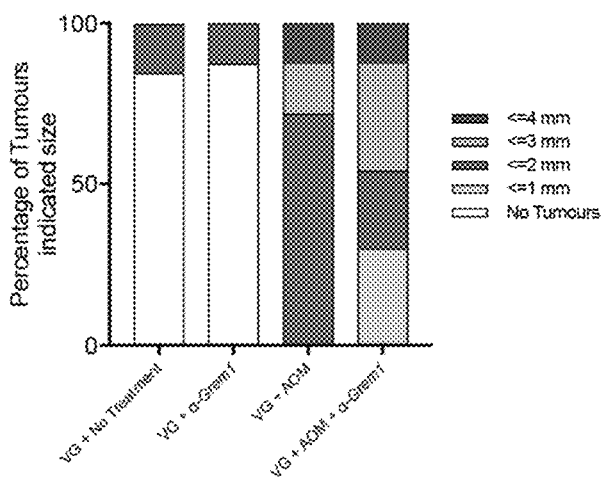

Example 20—Anti-Grem1 Antibody Treatment Protects Vil1-Grem1 Mice from AOM Mutagenesis (FIG. 35)

Aberrant epithelial Grem1 expression in Vil1-Grem1 mice promotes an epithelial stem/progenitor cell phenotype (Davis et al., 2015), and we hypothesised that these cells would be susceptible to somatic mutation. We used azoxymethane (AOM) administration to examine the effect of a mutagenic insult on untreated Vil1-Grem1 and anti-Grem1 treated Vil1Grem1 mice. AOM is a well-documented mutagen widely utilised in murine models to recapitulate spontaneous CRC carcinogenesis (Neufert and Neurath, 2007). To generate Kaplan-Meier data, mice were sacrificed when humane-end points were reached (mice exhibited anaemia, hunching and inactivity).

Mice were treated with three subcutaneous doses of 30 mg/kg weekly anti-Grem1 antibody followed by three intraperitoneal doses of 10 mg/kg weekly azoxymethane (AOM, Sigma) or vehicle (saline) prior to a further three weeks of 30 mg/kg weekly anti-Grem1 antibody. Treatment commenced at or from the age of 90 days onwards, which is late enough in the Vil1-Grem1 disease process to ensure expansion of the progenitor cell population and subsequent formation of ectopic crypt foci.

AOM administration markedly enhanced polyp formation in untreated Vil1-Grem1 mice. Colonic polyp burden was significantly increased in the AOM treated animals (FIG. 35B). This negatively impacted mouse survival (FIG. 35A): compare group VG+no treatment and group VG+AOM+no treatment. The increased tumour burden and reduced survival of the AOM-treated animals was partially abrogated by administration of anti-Grem1 antibody in the period surrounding the mutagenic insult: compare group VG+AOM-+ no treatment with group VG+AOM-+αGrem1. These data suggest that the normalisation of cell fate determination by the anti-Grem1 antibody in Vil1-Grem1 mice prevents epithelial stem/progenitor promotion and protects the epithelium from the AOM mutagenic insult.

Figure 36:
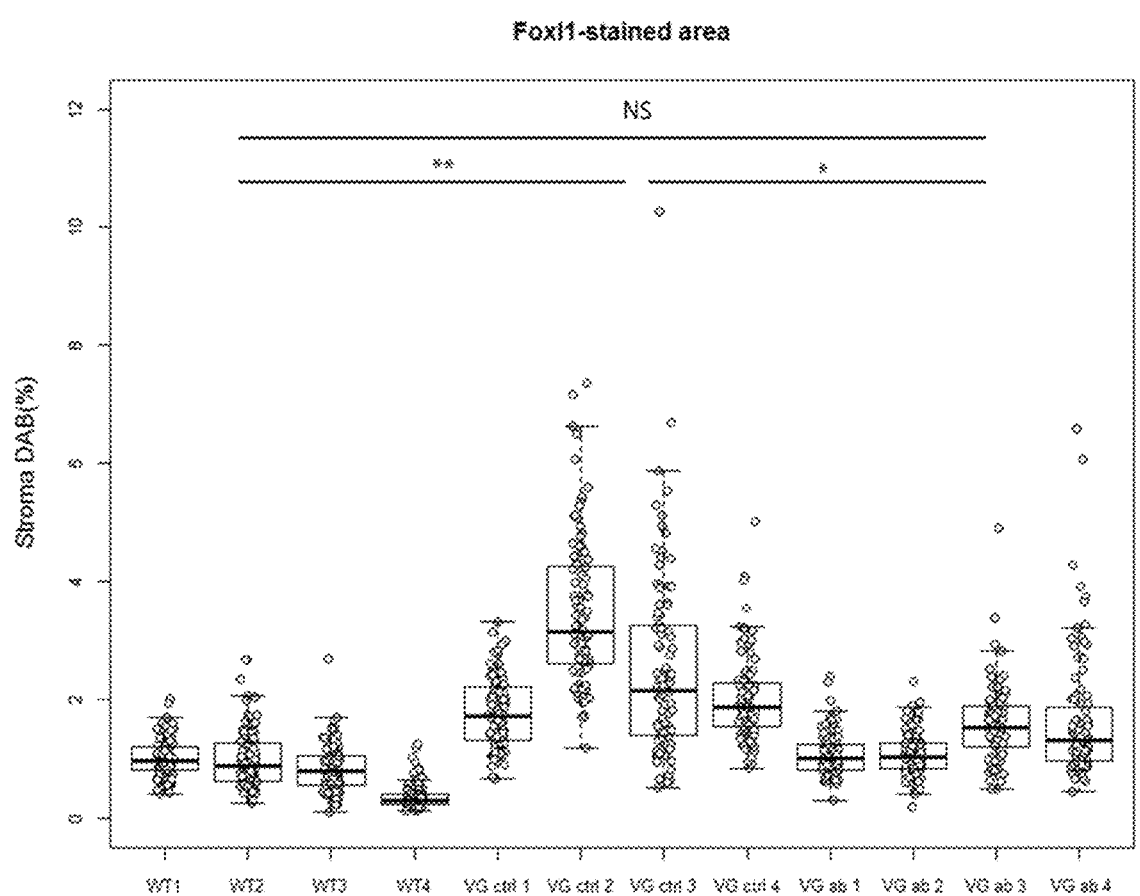
FIG. 36. Stromal levels of Foxl1 expression in villi from WT, untreated Vil1-Grem1 and anti-Grem1 antibody treated Vil1-Grem1 mice (*: p-value<0.05, **: p-value<0.01).
Figure 37:
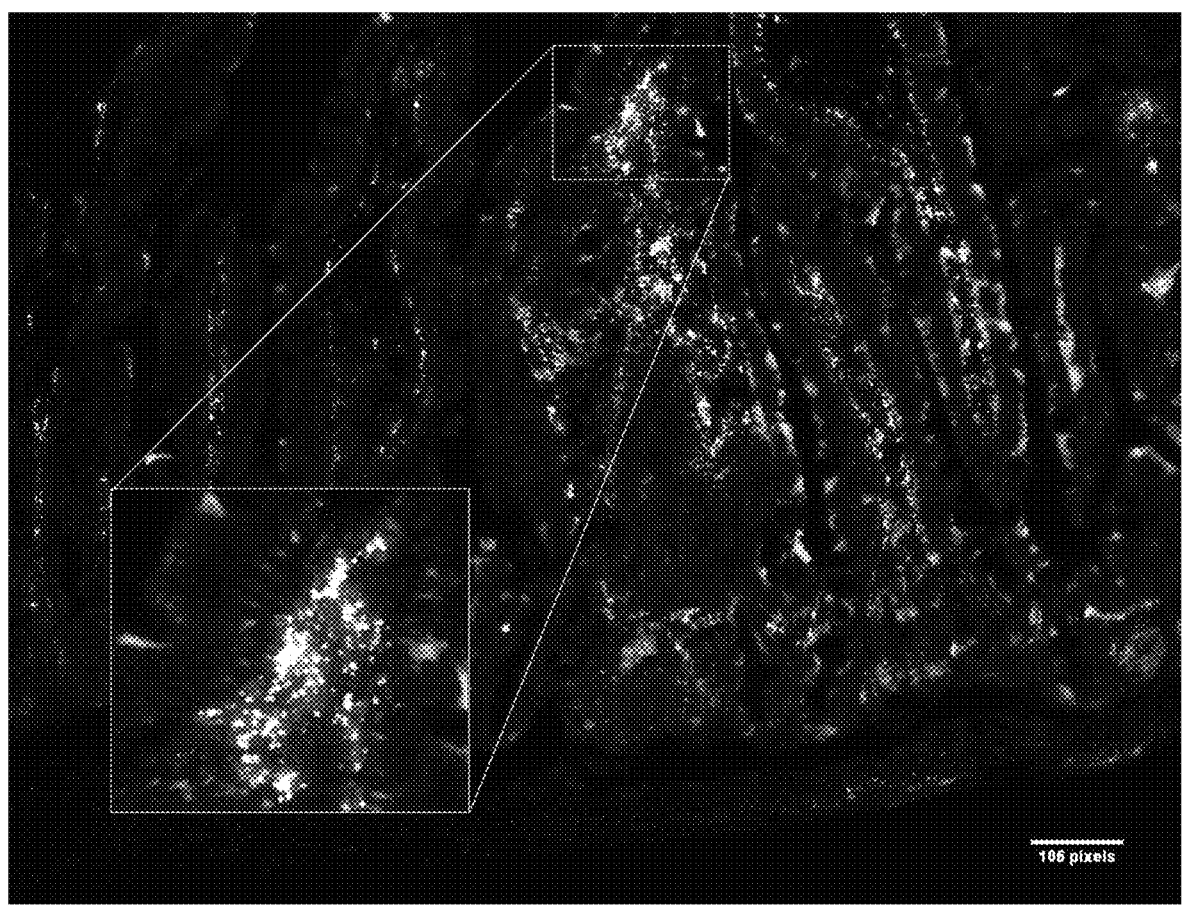
FIG. 37. Multiplex Fluorescent ISH for Foxl1 (green) and Wnt5a (red) in Vil1-Grem1 mouse small bowel. Sections were counter-stained using DAPI. Combined expression of Foxl1 and Wnt5a was observed (in the yellow areas).
Figure 38A:
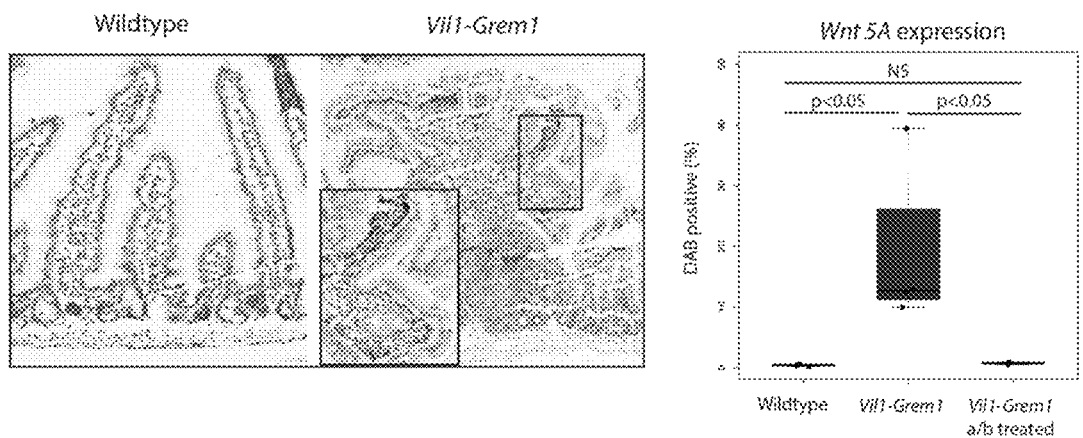
FIGS. 38A-38C. Tissue expression of Wnt ligands and telocyte cell marker in wildtype, Vil1-Grem1 and treatment models.
Figure 38B:
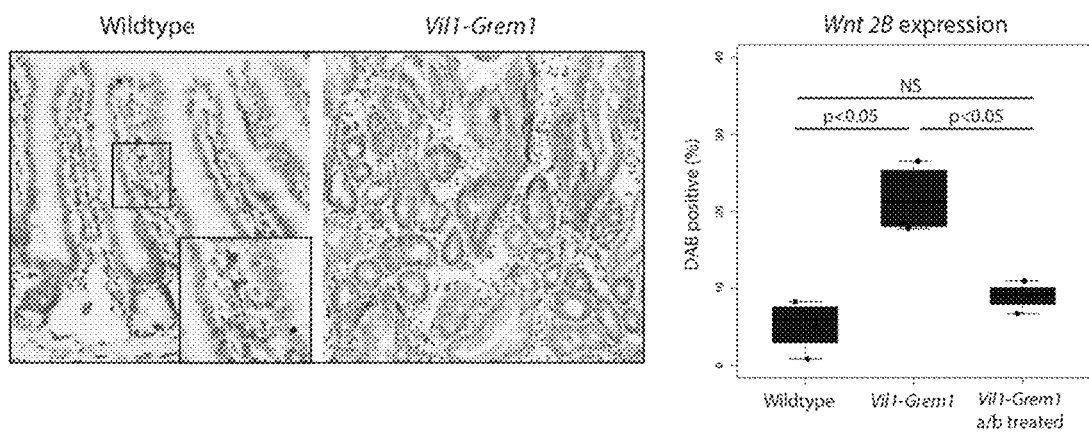

Example 21—Foxl1, Wnt5A, and Wnt 2B Expression is Upregulated in Vil1-Grem1 Stroma and this Phenotype is Abrogated by Anti-Grem1 Antibody Treatment (FIGS. 36-38)

Figure 38C:
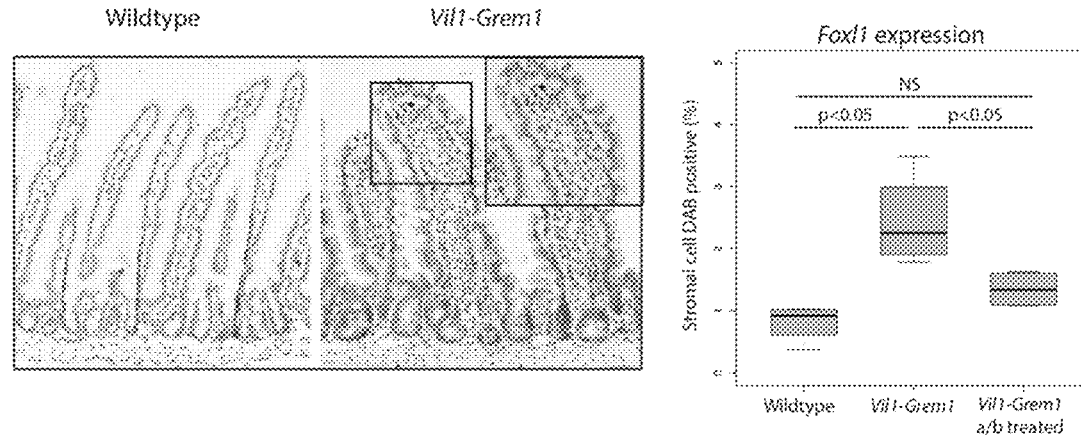

To investigate the source of Wnt ligand expression in the villus ectopic crypts in antibody treated and untreated Vil1-Grem1 mice (n=4) we used Foxl1 in situ hybridization (ISH) to identify sub-epithelial telocyte cells as described by Shoshkes-Carmel et al. (2018). Foxl1 expression levels were quantified using the HALO image analysis software. Villus stromal Foxl1 expression was significantly increased in untreated Vil1-Grem1 mice (p=0.0037) (FIG. 36 and FIG. 38C). Treatment with anti-Grem1 antibody restored Foxl1 expression levels (p-value WT vs antibody-treated Vil1-Grem1 mice (p=0.4864), indicating the stromal remodelling and Foxl1 cell recruitment is epithelial Grem1 dependent.

In order to determine which mediators were being produced by Foxl1+ cells, multiplex ISH was used to demonstrate the combination of Foxl1 and Wnt5A expression in villus subepithelial fibroblasts (see FIG. 37). The staining marked thin structures with long protrusions which resemble the telocytes described by Shoshkes-Carmel et al. (2018).

Epithelial Grem1 expression in the Vil1-Grem1 model causes activation of villus stromal cell populations that subsequently express Wnt ligands 5A and 2B. Treatment with anti-Grem1 antibody prevented stromal cell activation and abrogated Wnt ligand expression (FIGS. 38A and 38B) indicating that stromal remodelling is epithelial Grem1 dependent.

Methods

In Situ Hybridization

Paraffin blocks were sectioned (thickness=0.4 µm) using DEPC (Sigma) treated $H_2O$ and sections were baked for 2 hours at 60° C. Tissue was deparaffinised and treated with RNAscope Hydrogen Peroxide (ACD 322335) for 10 min at room temperature (RT). Antigen retrieval was performed for 15 minutes using RNAscope 1× Target Retrieval Reagents (1:10 ACD 322000) at 100° C. Samples were treated with RNAscope Protease Plus (ACD 322331) for 30 minutes at 40° C. using an HybEZ Hybridization System (ACD). Probes were incubated for 2 h at 40° C. Probes used were as follows: LGR4 (ACD 318321), LGR5 (ACD 312171), FZD5 (ACD 404911), FZD7 (ACD 534101), WNT2B (ACD 405031), WNT5A (ACD 316791), WNT5A-C3 (ACD, 316791-C3) and FOXL1 (ACD 407401). Slides were counter-stained using Haematoxylin (brown) or DAPI (Fluorescent).

ISH Quantification

Slides were scanned at 20× magnification using an Aperio CS2 Digital Pathology Scanner (Leica Biosystems). 100 villi per mouse were annotated using the Aperio ImageScope Pathology Slide Viewing Software (Leica Biosystems). Foxl1 expression levels were quantified using the HALO image analysis platform (PerkinElmer) and expressed as % of DAB staining per area. Two-way ANOVA and multiple comparisons applying Bonferroni correction were used to compare DAB levels between conditions. Differences were considered significant at a p value of <0.05. Analysis were performed using the statistical software R.

Figure 39:
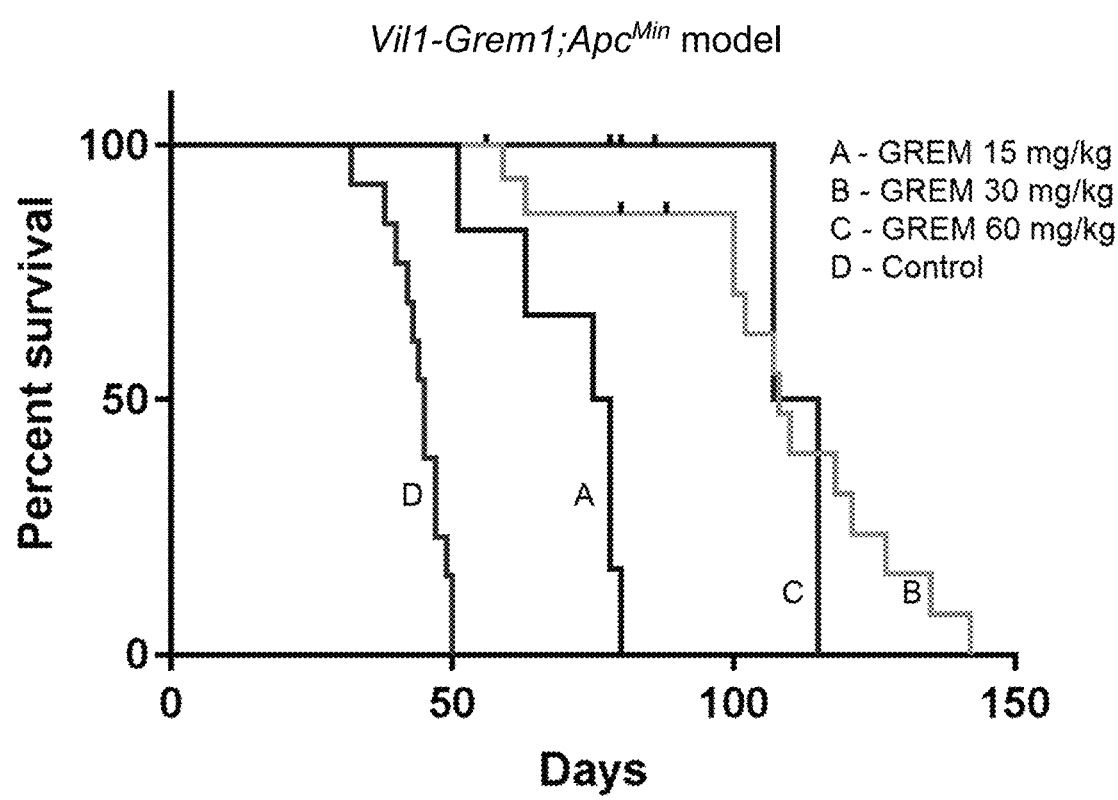
FIG. 39. Kaplan Meier survival curves of Vil1-Grem1; Apc$^{Min}$ mouse models treated with control vehicle (line D, median survival 45 days, n=13) and with anti-Grem1 antibody at 15 mg/kg weekly (line A, median survival 76.5 days, n=6), 30 mg/kg weekly (line B, median survival 108 days, n=15, ongoing experiment: two mice still alive) and 60 mg/kg weekly (line C, median survival 111 days, n=7, ongoing experiment: five mice still alive).

Example 22—Anti-Grem1 Antibody Shows a Dose Response Relationship in Vil1-Grem1;$Apc^{Min}$ Treated Mice (FIG. 39)

Anti-Grem1 antibody (UCB) or control antibody (UCB) were administered at variable doses of 15, 30 and 60 mg/kg weekly subcutaneous injections biweekly for 6-weeks, followed weekly thereafter, starting at the age of 21 days in Vil1-Grem1;$Apc^{Min}$ mice. To generate Kaplan-Meier data (presented in FIG. 39), mice were sacrificed when humane-end points were reached (mice exhibited anaemia, hunching and inactivity). Treatment with anti-Grem1 prolonged mouse lifespan in a dose dependent fashion with no additional survival benefit seen from a dose >30 mg/kg weekly.

Example 23—Comparison of Early and Late Phase Treatment with Anti-Grem1 Antibody in Vil1-Grem1 Mice and $Apc^{Min}$ Mice (FIG. 40)

Anti-Grem1 antibody (UCB) or control antibody (UCB) was administered to Vil1-Grem1 mice (FIG. 40A) and $Apc^{Min}$ mice (FIG. 40B) at a dose of 30 mg/kg weekly subcutaneous injections, starting at the age of 42 days (early stage treatment) or 120 days after development of an intestinal polyposis (late stage treatment).

To generate Kaplan-Meier data, mice were sacrificed when humane-end points were reached (mice exhibited anaemia, hunching and inactivity). Treatment with the anti-Grem1 antibody initiated at both time points significantly prolonged the lifespan of the mice. Specifically, for the Vil1-Grem1 mice (FIG. 40A) the median survival of the vehicle group (242 days (n=13)) was significantly increased by treatment with anti-Grem1 antibody: late-stage treatment: 519 days; early stage treatment: 540 days. In the $Apc^{Min}$ mice (FIG. 40B), the median survival of the vehicle treatment group was significantly extended from 192 days to 261 days (late stage treatment) and 424.5 days (early stage treatment) as a result of treatment with anti-Grem1 antibody.

Example 24—Use of a Grem1-Neutralising Antibody Significantly Reduces Breast Cancer Tumour Growth within the Bone and Lung in Pre-Clinical Models of Breast Cancer (FIGS. 41-45)

Using novel anti-Grem1 neutralising monoclonal antibodies, the in vivo contribution of Grem1 in the establishment and progression of breast cancer was investigated using two clinically relevant pre-clinical mouse models of breast cancer.

Methods

Cell Culture

The PyMT-B01 mouse-derived breast cancer cell was kindly donated by Professor Sheila Stewart (St Louis, MO, USA) and the MDA-MB-231 human breast cancer cell line was kindly provided by Dr Toshiyuki Yoneda (formerly at University of Texas Health Sciences Centre, San Antonio, TX). Both cell lines express luciferase produced by retroviral expression of the SFG-NES-TGL vector (Ponomarev, V., et al. Eur J Nucl Med Mol Imaging, 2004. 31(5): p. 740-51. Cancer cells were cultured in Dulbecco's Modified Eagle's Medium (DMEM, Life Technologies, Australia) supplemented with 10% foetal bovine serum (FBS, Life Technologies, Australia), 100 IU/mL penicillin (Life Technologies, Australia), 100 µg/mL streptomycin (Life Technologies, Australia) and 25 mM HEPES (Life Technologies, Australia) at 37° C. in a 5% CO2 humidified atmosphere.

Animals

Animal studies were performed in accordance with animal protocol procedures approved by the Animal Ethics Committee of the South Australian Health and Medical Research Institute (SAHMRI) under ethics number SAM373, and conform to the guidelines established by the 'Australian Code of Practice for the Care and Use of Animals for Scientific Purposes'.

Grem1 Antibody Treatment in Pre-Clinical Breast Cancer Models

PyMT-B01: 5-week old C57BL6 immunocompetent mice were subcutaneously (s.c) administered two 30 mg/kg doses of anti-Grem1 antibody Ab7326 or IgG control, Ab101.4, the week prior to tumour cell inoculation. $1 \times 10^5$ luciferase expressing PyMT-B01 mouse breast cancer cells were injected systemically via the caudal artery (CA).

MDA-MB-231: 5-week old NOD/SCiD/gamma (NSG) immunocompromised mice were subcutaneously (s.c) administered two 30 mg/kg doses of anti-Grem1 antibody UCB6114 or IgG control, AbA33, the week prior to tumour cell inoculation. $1 \times 10^5$ luciferase expressing MDA-MB-231 human breast cancer cells were injected systemically via the CA.

Treatment continued twice weekly for the duration of the study. At weekly intervals, mice were administered 150 mg/kg luciferin intraperitoneally (i.p) and imaged using the Xenogen IVIS Bioluminescence Imaging System, and tumour burden was quantitated using Living Image software. The study ended on day 13 and day 22 post-tumour cell injection for the PyMT-B01 and MDA-MB-231 models respectively, according to animal ethics requirements. Organs were dissected upon culling animals and BLI imaged ex vivo for analysis of tumour metastasis.

Results

Figure 41A:
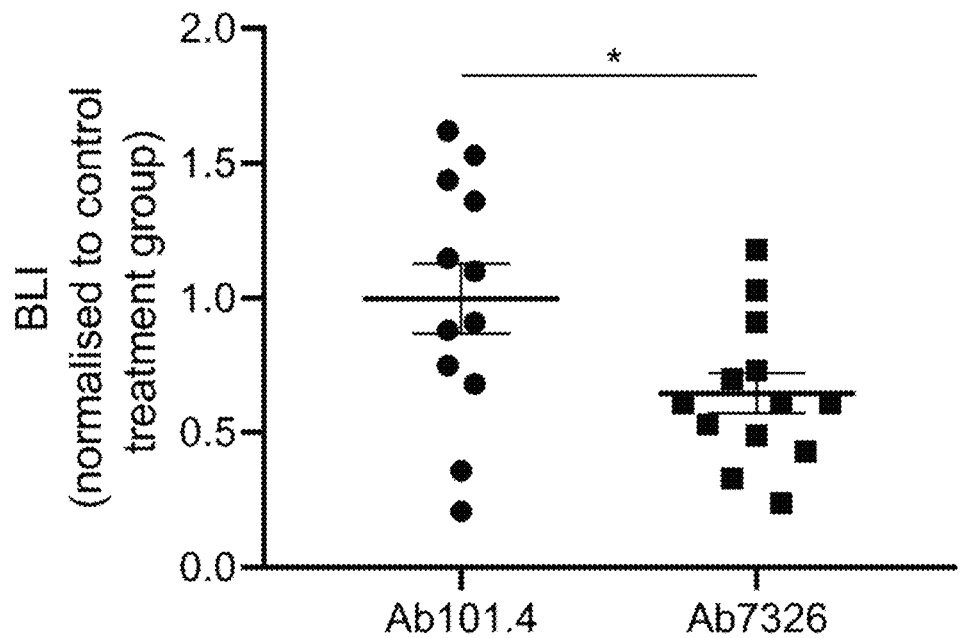
FIGS. 41A-41B. C57BL6 mice inoculated with PyMT-B01 breast cancer cells by systemic CA injection and treated with Grem1-neutralising antibody (Ab7326) had significantly reduced tumour burden compared to mice treated with isotype control antibody (Ab101.4).
Figure 41B:
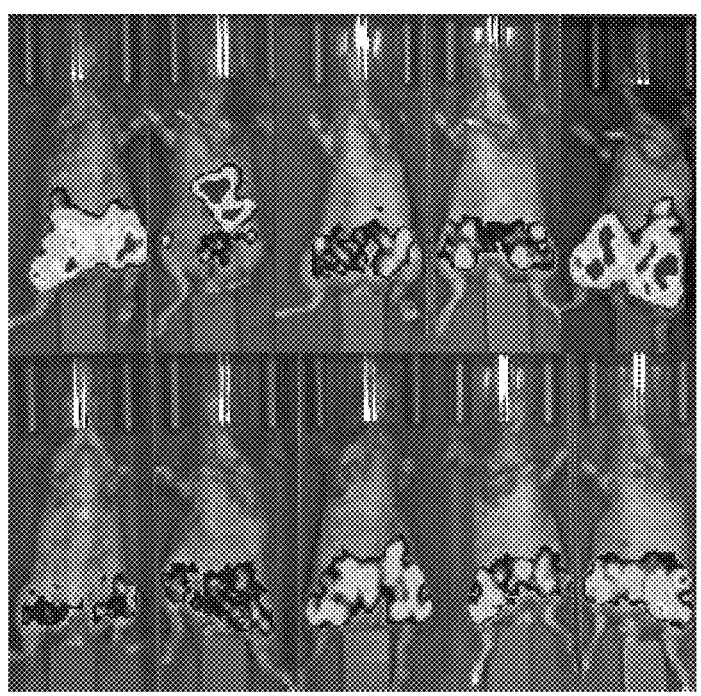
Figure 42A:
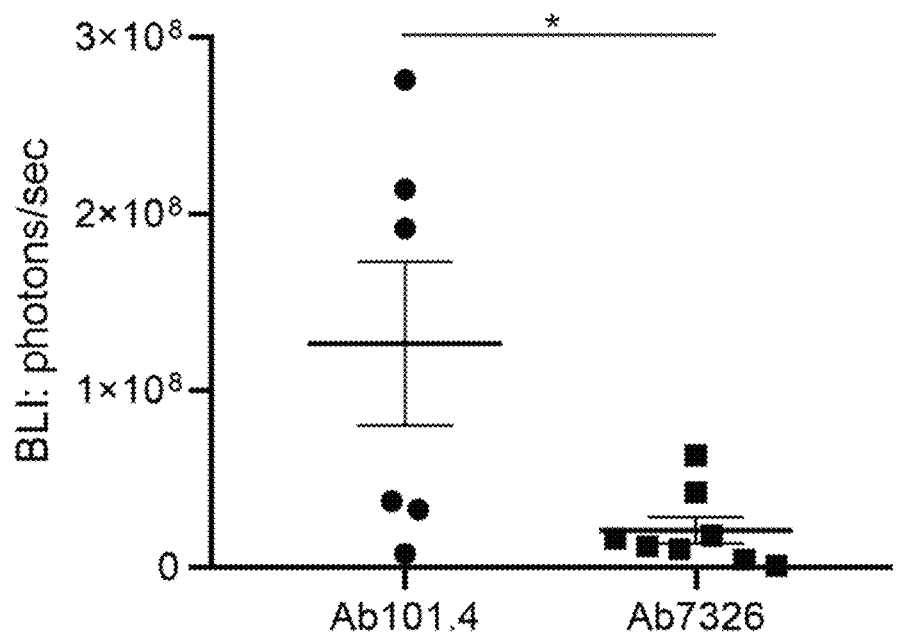
FIGS. 42A-42B. PyMT-B01 tumour bearing C57BL6 mice treated with Grem1-neutralising antibody (Ab7326) had reduced lung and liver metastasis, compared to mice treated with isotype control (Ab101.4).
Figure 42B:
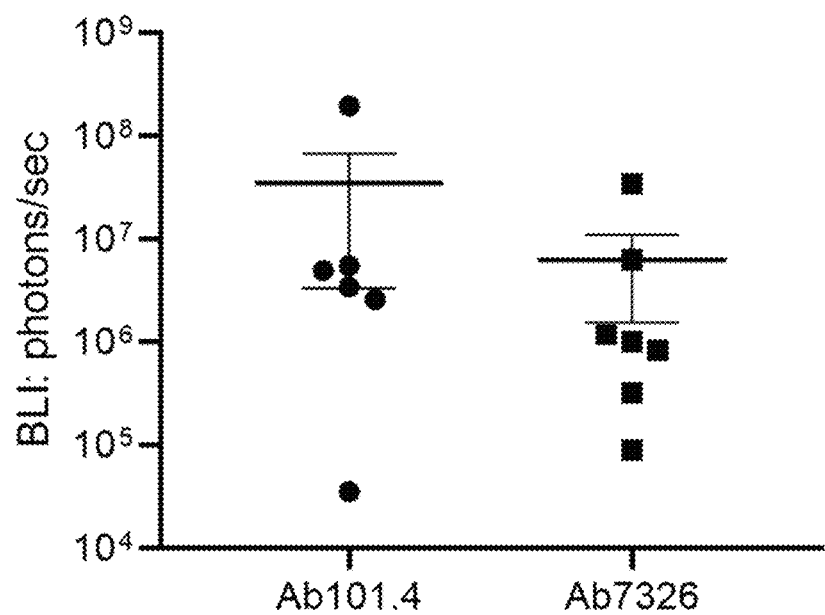

At the conclusion of the study, the PyMT-B01 tumour bearing mice treated with Grem1-neutralising antibody, Ab7326, had a 35% reduction in overall tumour burden, compared to mice treated with isotype control, Ab101.4, when tumour was injected via the CA (FIG. 41). This BLI signal is primarily concentrated in the hindlimbs, indicative of the extensive skeletal tumour involvement associated with this model. A statistically significant reduction in lung metastatic tumour burden was also observed in mice treated with Grem1-neutralising antibody compared to isotype controls (FIG. 42A). A downward trend in liver metastatic tumour burden was also observed in the PyMT-B01 tumour-bearing mice treated with the Grem1-neutralising antibody (FIG. 42B).

Figure 43:
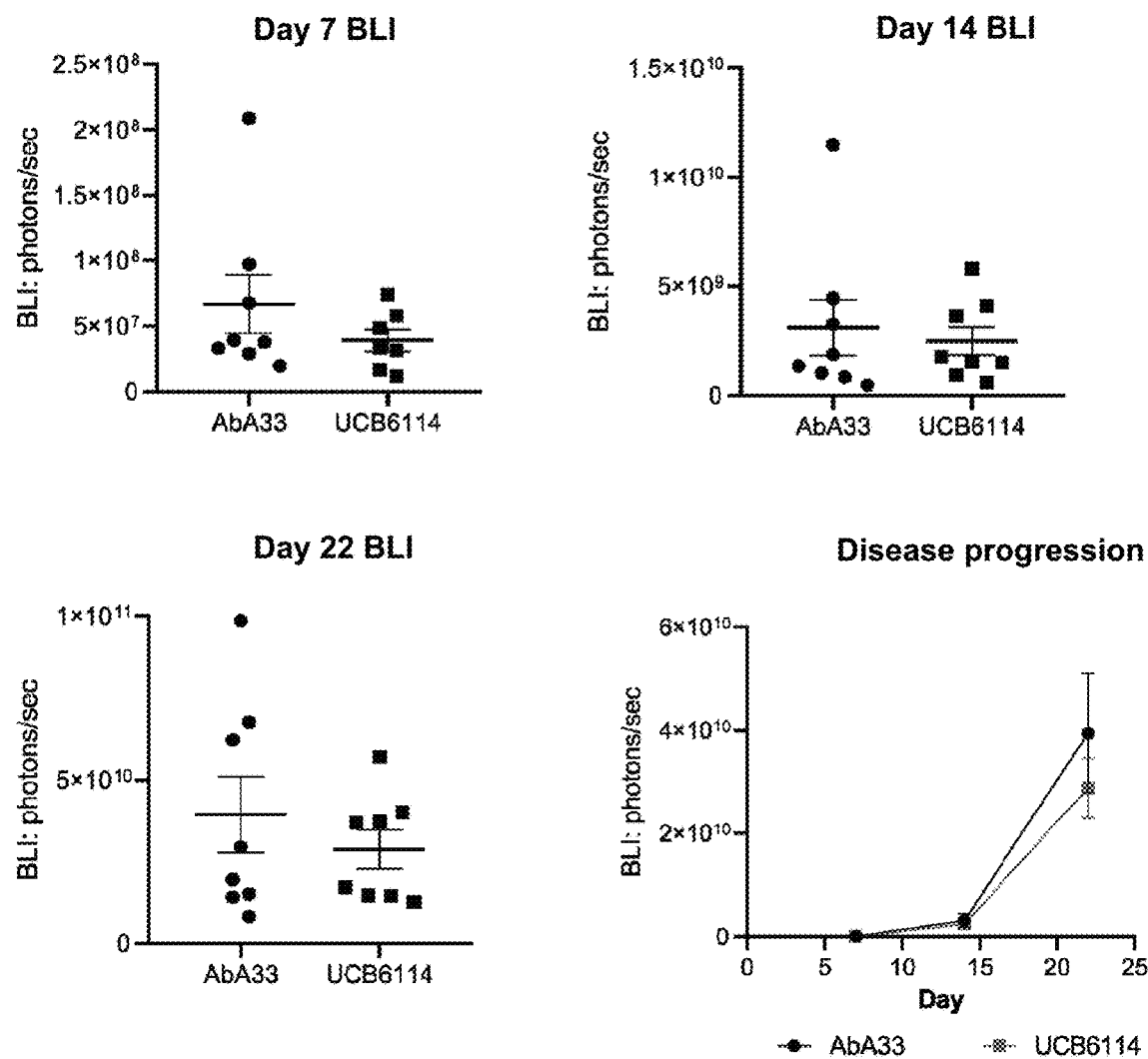
FIG. 43. Plots showing results of IVIS BLI imaging of MDA-MB-231 tumour-bearing NSG mice treated with isotype control antibody (AbA33) and Grem1-neutralising antibody (UCB6114). Mean±SEM, Student's t-test, n=8, p>0.05.
Figure 44:
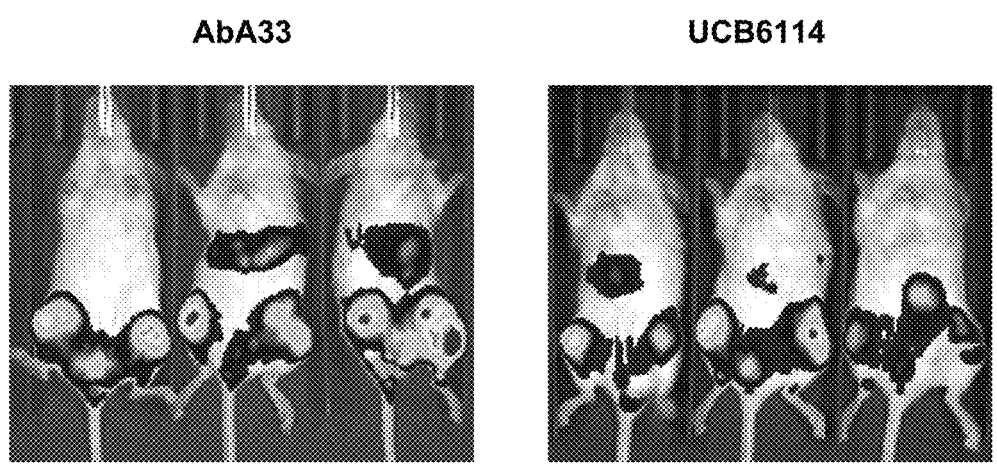
FIG. 44. Representative IVIS BLI images of MDA-MB-231 tumour-bearing mice treated with isotype control (AbA33) or Grem1-neutralising antibody (UCB6114) at day 22 post-tumour cell inoculation.

At the conclusion of the second study (day 22), the mean tumour burden for MDA-MB-231 tumour-bearing NSG mice was lower in the Grem1-neutralising antibody (UCB6114) treatment group compared to the control group treated with AbA33 (FIG. 43).

Figure 45:
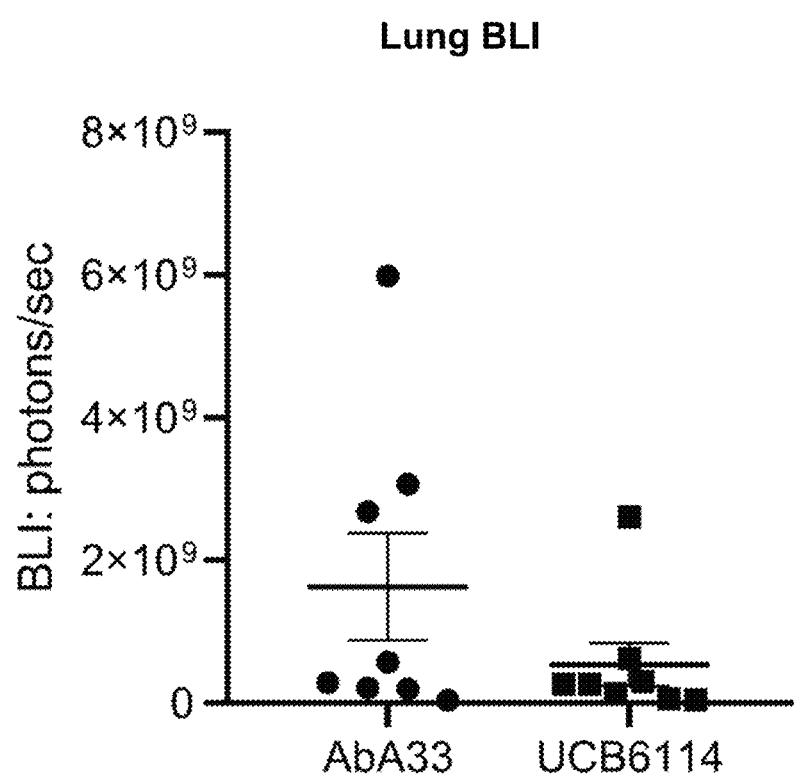
FIG. 45. Plot showing results of ex vivo IVIS BLI imaging of the lungs of MDA-MB-231 tumour-bearing NSG mice treated with isotype control antibody (AbA33) or Grem1-neutralising antibody (UCB6114). Mean±SEM, Student's t-test, n=8, p>0.05.
Figure 46A:
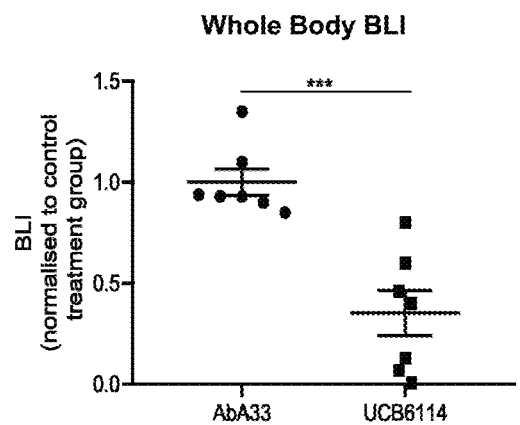
FIGS. 46A-46D. Plots showing results of BLI imaging of NSG mice inoculated with PC-3 prostate cancer cells by systemic CA injection and treated with Grem1-neutralising antibody (UCB6114) or isotype control antibody (AbA33). BLI imaging was carried out on (FIG. 46A) the whole body.
Figure 46B:
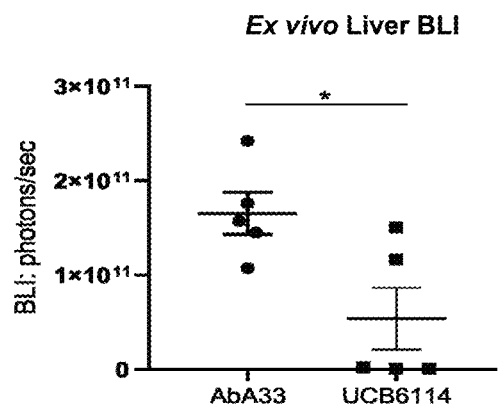
Figure 46C:
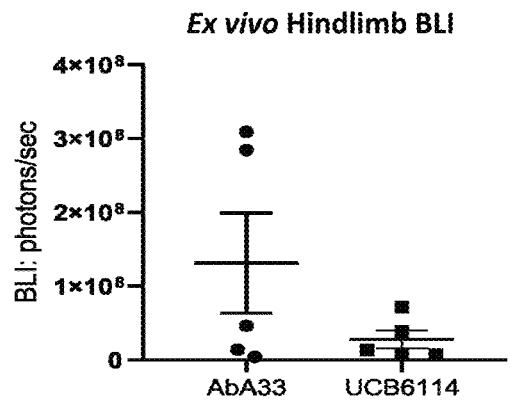
Figure 46D:
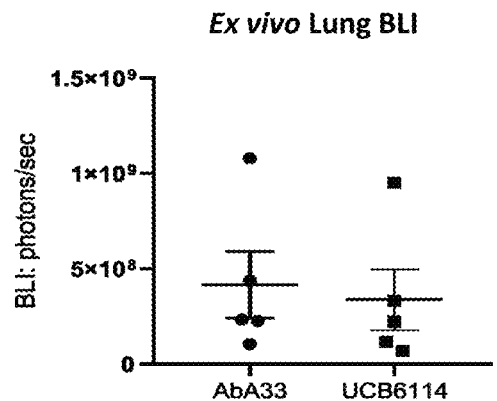

A reduction in mean tumour burden for lung metastasis in mice treated with the anti-Grem1 antibody (UCB6114) was also observed (FIG. 45). These results show that targeting Grem1 with a Grem1-neutralising antibody significantly reduces breast cancer tumour growth within the bone and lung. These studies support the hypothesis that anti-Grem1 therapy may represent a suitable treatment option in metastatic breast cancer. In conclusion, the present inventors provide the first evidence that targeting Grem1 with a Grem1-neutralising antibody in vivo represents an effective therapeutic strategy for reducing breast cancer skeletal and lung metastatic tumour growth.

Figure 47:
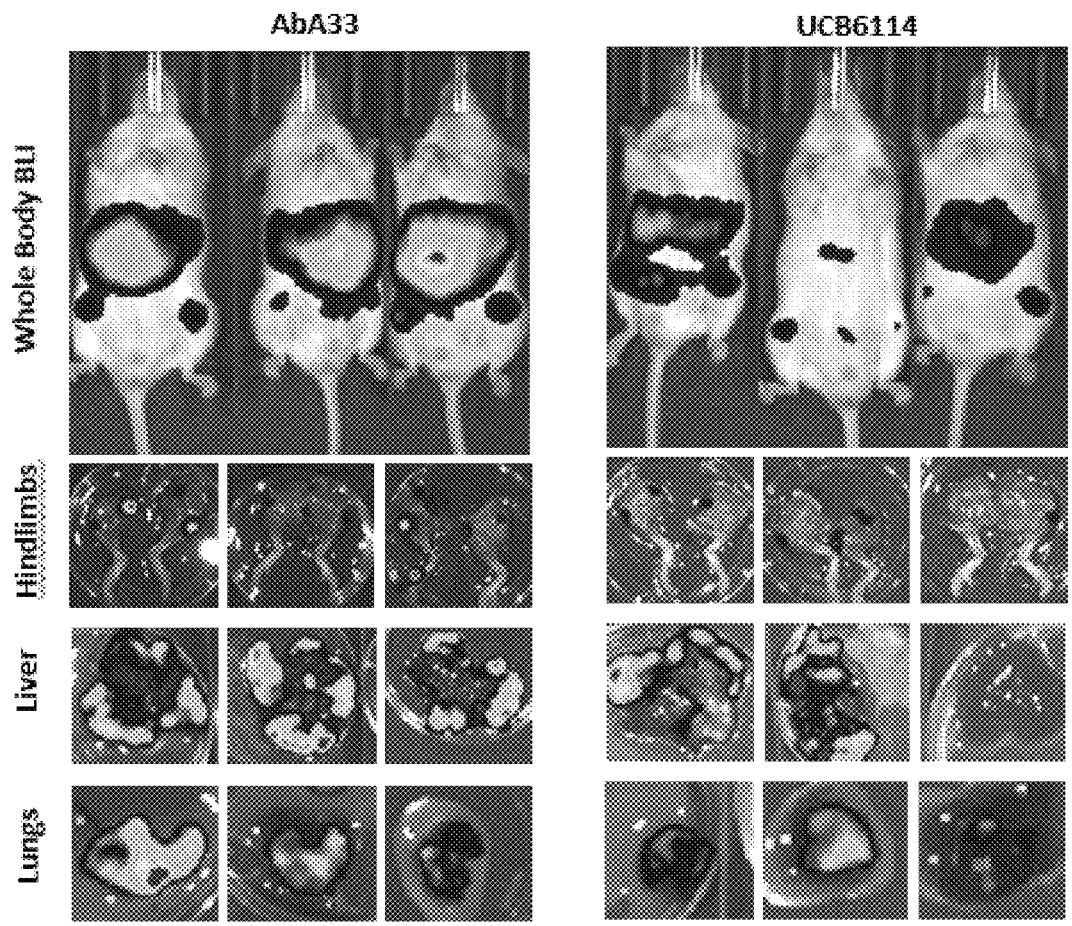
FIG. 47. Representative BLI images of NSG mice with systemic PC-3 tumour burden treated with either isotype control antibody (AbA33) or Grem1-neutralising antibody (UCB6114) at the conclusion of the study (at day 25). Liver, hindlimbs and lungs were dissected and imaged ex vivo immediately after the final whole-body scan.

Example 25—Use of a Grem1-Neutralising Antibody Reduces Prostate Cancer Tumour Growth in a Pre-Clinical Model of Prostate Cancer (FIGS. 46 and 47)

Using the novel anti-Grem1 neutralising monoclonal antibody (UCB6114), the in vivo contribution of Grem1 in the establishment and progression of prostate cancer in a pre-clinical murine models of prostate cancer was investigated.

Methods
Cell Culture

The PC-3 human prostate cancer cell line was obtained from ATCC (Manassas, VA, USA). The cell line expresses luciferase produced by retroviral expression of the SFG-NES-TGL vector (Ponomarev, V., et al. 2004). Cancer cells were cultured in RPMI1640 (Life Technologies, Australia) supplemented with 10% foetal bovine serum (FBS, Life Technologies, Australia), 100 IU/mL penicillin (Life Technologies, Australia), 100 µg/mL streptomycin (Life Technologies, Australia) and 25 mM HEPES (Life Technologies, Australia) at 37° C. in a 5% $CO_2$ humidified atmosphere.

Animals

Animal studies were performed in accordance with animal protocol procedures approved by the Animal Ethics Committee of the South Australian Health and Medical Research Institute (SAHMRI) under ethics number SAM373, and conform to the guidelines established by the 'Australian Code of Practice for the Care and Use of Animals for Scientific Purposes'.

Grem1 Antibody Treatment in Pre-Clinical Prostate Cancer Models 5-week old NOD.Cg-Prkd$^{scid}$ Il2rg$^{tm1Wjl}$/SzJ (NSG) immunocompromised mice were subcutaneously (s.c) administered two 30 mg/kg doses of anti-Grem1 antibody (UCB6114) or IgG control, AbA33, the week prior to tumour cell inoculation. $5 \times 10^5$ luciferase expressing PC-3 mouse prostate cancer cells were injected systemically via the caudal artery (CA).

Antibody treatment continued twice weekly for the duration of the study. A t weekly intervals, mice were administered 150 mg/kg luciferin intraperitoneally (i.p) and imaged using the Xenogen IVIS Bioluminescence Imaging System, and tumour burden was quantitated using Living Image software (PerkinElmer, MA, USA). At the end of each study, organs were dissected upon culling animals and BLI imaged ex vivo for analysis of tumour metastasis.

Results

The PC-3 prostate cancer model showed significant liver tumour burden (another common site of prostate cancer metastasis) from day 7, in addition to evidence of skeletal tumour burden by BLI. A significant reduction in whole animal (FIG. 46A) and liver (FIG. 46B) tumour burden was observed in mice treated with Grem1-neutralising antibody (UCB6114) as compared to mice treated with isotype control antibody (AbA33). A downward trend in hindlimb (FIG. 46C) and lung (FIG. 46D) tumour burden was also observed for the mice treated with Grem1-neutralising antibody.

Sequence Listing (Human Gremlin-1; Uniprot ID: O60565)

SEQ ID NO: 1

MSRTAYTVGALLLLLGTLLPAAEGKKKGSQGAIPPPDKAQHNDSEQTQS

PQQPGSRNRGRGQGRGTAMPGEEVLESSQEALHVTERKYLKRDWCKTQP

LKQTIHEEGCNSRTIINRFCYGQCNSFYIPRHIRKEEGSFQSCSFCKPK

KFTTMMVTLNCPELQPPTKKKRVTRVKQCRCISIDLD (Human truncated Gremlin-1 used in crystallography with N-terminal tag)

SEQ ID NO: 2

MGSSHHHHHHSSGENLYFQGSAMPGEEVLESSQEALHVTERKYLKRDWC

KTQPLKQTIHEEGCNSRTIINRFCYGQCNSFYIPRHIRKEEGSFQSCSF

CKPKKFTTMMVTLNCPELQPPTKKKRVTRVKQCRCISIDLD (Ab7326 HCDR1 combined Kabat & Chothia)

SEQ ID NO: 3

GYTFTDYYMH (Ab7326 HCDR1 Kabat)

SEQ ID NO: 4

DYYMH (Ab7326 HCDR2 Kabat)
SEQ ID NO: 5
LVDPEDGETIYAEKFQG (Ab7326 HCDR3 Kabat)
SEQ ID NO: 6
DARGSGSYYPNHFDY (Ab7326 LCDR1 Kabat)
SEQ ID NO: 7
KSSQSVLYSSNNKNYLA (Ab7326 LCDR2 Kabat)
SEQ ID NO: 8
WASTRES (Ab7326 LCDR3 Kabat)
SEQ ID NO: 9
QQYYDTPT (Ab7326 Heavy chain variable region variant 1)
SEQ ID NO: 10
QVQLVESGAEVKKPGATVKISCKVSGYTFTDYYMHWVQQAPGKGLEWMG
LVDPEDGETIYAEKFQGRVTITADTSTDTAYMELSSLRSEDTAVYYCAT
DARGSGSYYPNHFDYWGQGTLVTVSS (Ab7326 Light chain variable region variant 1)
SEQ ID NO: 11
DIVMTQSPDSLAVSLGERATINCKSSQSVLYSSNNKNYLAWYQQKPGQP
PKLLIYWASTRESGVPDRFSGSGSGTDFTLTINSLQAEDVAVYFCQQYY
DTPTFGQGTRLEIK (Ab7326 Heavy chain variable region variant 2)
SEQ ID NO: 12
QVQLVQSGAEVKKPGATVKISCKVSGYTFTDYYMHWVQQAPGKGLEWMG
LVDPEDGETIYAEKFQGRVTITADTSTDTAYMELSSLRSEDTAVYYCAT
DARGSGSYYPNHFDYWGQGTLVTVSS (Ab7326 Light chain variable region variant 2)
SEQ ID NO: 13
DIVMTQTPDSLAVSLGERATINCKSSQSVLYSSNNKNYLAWYQQKPGQP
PKLLIYWASTRESGVPDRFSGSGSGTDFTLTINSLQAEDVAVYFCQQYY
DTPTFGQGTRLEIK (Mouse full length IgG1 heavy chain variant 1)
SEQ ID NO: 14
QVQLVESGAEVKKPGATVKISCKVSGYTFTDYYMHWVQQAPGKGLEWMG
LVDPEDGETIYAEKFQGRVTITADTSTDTAYMELSSLRSEDTAVYYCAT
DARGSGSYYPNHFDYWGQGTLVTVSSAKTTPPSVYPLAPGSAAQTNSMV
TLGCLVKGYFPEPVTVTWNSGSLSSGVHTFPAVLQSDLYTLSSSVTVPS
STWPSETVTCNVAHPASSTKVDKKIVPRDCGCKPCICTVPEVSSVFIFP
PKPKDVLTITLTPKVTCVVVDISKDDPEVQFSWFVDDVEVHTAQTQPRE
EQFNSTFRSVSELPIMHQDWLNGKEFKCRVNSAAFPAPIEKTISKTKGR
PKAPQVYTIPPPKEQMAKDKVSLTCMITDFFPEDITVEWQWNGQPAENY
KNTQPIMDTDGSYFVYSKLNVQKSNWEAGNTFTCSVLHEGLHNHHTEKS
LSHSPGK (Mouse full length IgG1 light chain variant 1)
SEQ ID NO: 15
DIVMTQSPDSLAVSLGERATINCKSSQSVLYSSNNKNYLAWYQQKPGQP
PKLLIYWASTRESGVPDRFSGSGSGTDFTLTINSLQAEDVAVYFCQQYY
DTPTFGQGTRLEIKRTDAAPTVSIFPPSSEQLTSGGASVVCFLNNFYPK
DINVKWKIDGSERQNGVLNSWTDQDSKDSTYSMSSTLTLTKDEYERHNS
YTCEATHKTSTSPIVKSENRNEC (Human full length IgG1 heavy chain variant 2)
SEQ ID NO: 16
QVQLVQSGAEVKKPGATVKISCKVSGYTFTDYYMHWVQQAPGKGLEWMG
LVDPEDGETIYAEKFQGRVTITADTSTDTAYMELSSLRSEDTAVYYCAT
DARGSGSYYPNHFDYWGQGTLVTVSSASTKGPSVFPLAPSSKSTSGGTA
ALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHN
HYTQKSLSLSPGK (Human full length IgG1 light chain variant 2)
SEQ ID NO: 17
DIVMTQTPDSLAVSLGERATINCKSSQSVLYSSNNKNYLAWYQQKPGQP
PKLLIYWASTRESGVPDRFSGSGSGTDFTLTINSLQAEDVAVYFCQQYY
DTPTFGQGTRLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSENRGEC (Fab heavy chain variant 1)
SEQ ID NO: 18
QVQLVESGAEVKKPGATVKISCKVSGYTFTDYYMHWVQQAPGKGLEWMG
LVDPEDGETIYAEKFQGRVTITADTSTDTAYMELSSLRSEDTAVYYCAT
DARGSGSYYPNHFDYWGQGTLVTVSSASTKGPSVFPLAPSSKSTSGGTA

ALGCLVKDYFPEPVTVSWNSGALTSGVHTFPAVLQSSGLYSLSSVVTVP

SSSLGTQTYICNVNHKPSNTKVDKKVEPKSC (Fab light chain variant 1)
SEQ ID NO: 19
DIVMTQSPDSLAVSLGERATINCKSSQSVLYSSNNKNYLAWYQQKPGQP

PKLLIYWASTRESGVPDRFSGSGSGTDFTLTINSLQAEDVAVYFCQQYY

DTPTFGQGTRLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSENRGEC (Human truncated Gremlin-1 used in crystallography without N-terminal tag)
SEQ ID NO: 20
AMPGEEVLESSQEALHVTERKYLKRDWCKTQPLKQTIHEEGCNSRTIIN

RFCYGQCNSFYIPRHIRKEEGSFQSCSFCKPKKFTTMMVTLNCPELQPP

TKKKRVTRVKQCRCISIDLD (Mature Gremlin-1 sequence of SEQ ID NO: 1 lacking the signal peptide of amino acids 1-21)
SEQ ID NO: 21
KKKGSQGAIPPPDKAQHNDSEQTQSPQQPGSRNRGRGQGRGTAMPGEEV

LESSQEALHVTERKYLKRDWCKTQPLKQTIHEEGCNSRTIINRFCYGQC

NSFYIPRHIRKEEGSFQSCSFCKPKKFTTMMVTLNCPELQPPTKKKRVT

RVKQCRCISIDLD (Human IgG4P heavy chain variant 1)
SEQ ID NO: 22
QVQLVESGAEVKKPGATVKISCKVSGYTFTDYYMHWVQQAPGKGLEWMG

LVDPEDGETIYAEKFQGRVTITADTSTDTAYMELSSLRSEDTAVYYCAT

DARGSGSYYPNHFDYWGQGTLVTVSSASTKGPSVFPLAPCSRSTSESTA

ALGCLVKDYFPEPVTVSWNSGALTSGVHTFPAVLQSSGLYSLSSVVTVP

SSSLGTKTYTCNVDHKPSNTKVDKRVESKYGPPCPPCPAPEFLGGPSVF

LFPPKPKDTLMISRTPEVTCVVVDVSQEDPEVQFNWYVDGVEVHNAKTK

PREEQFNSTYRVVSVLTVLHQDWLNGKEYKCKVSNKGLPSSIEKTISKA

KGQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHYT

QKSLSLSLGK (Human IgG4P light chain variant 1)
SEQ ID NO: 23
DIVMTQSPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSENRGEC (Human IgG1 heavy chain DNA variant 1)
SEQ ID NO: 24
caagtgcaactggtggaatccggggccgaagtgaaaaagcccggagccactgtgaagatct cttgcaaagtgtccggctacaccttcaccgactattacatgcactgggtccagcaggcacc tgggaagggccttgagtggatgggtctggtcgatcccgaggacggcgaaactatctacgcc gagaagttccagggtcgcgtcaccatcaccgccgacacttccaccgacaccgcgtacatgg agctgtccagcttgaggtccgaggacacagccgtgtactactgcgccacggatgctcgggg aagcggcagctactacccgaaccacttcgactactggggacagggcactctcgtgactgtc tcgagcgcttctacaaagggcccctccgtgttcccgctcgctccatcatcgaagtctacca gcggaggcactgcggctctcggttgcctcgtgaaggactacttcccggagccggtgaccgt gtcgtggaacagcggagccctgaccagcggggtgcacacctttccggccgtcttgcagtca agcggcctttactccctgtcatcagtggtgactgtcccgtccagctcattgggaacccaaa cctacatctgcaatgtgaatcacaaacctagcaacaccaaggttgacaagaaagtcgagcc caaatcgtgtgacaagactcacacttgtccgccgtgcccggcacccgaactgctgggaggt cccagcgtctttctgttccctccaaagccgaaagacacgctgatgatctcccgcaccccgg aggtcacttgcgtggtcgtggacgtgtcacatgaggacccagaggtgaagttcaattggta -continued cgtggatggcgtcgaagtccacaatgccaaaactaagcccagagaagaacagtacaattcg acctaccgcgtcgtgtccgtgctcacggtgttgcatcaggattggctgaacgggaaggaat acaagtgcaaagtgtccaacaaggcgctgccggcaccgatcgagaaaactatctccaaagc gaagggacagcctagggaacctcaagtctacacgctgccaccatcacgggatgaactgact aagaatcaagtctcactgacttgtctggtgaaggggttttaccctagcgacattgccgtgg agtgggaatccaacggccagccagagaacaactacaagactacccctccagtgctcgactc ggatggatcgttcttcctttactcgaagctcaccgtggataagtcccggtggcagcaggga aacgtgttctcctgctcggtgatgcatgaagccctccataaccactatacccaaaagtcgc tgtccctgtcgccgggaaag (Human IgG1 light chain DNA variant 1)
SEQ ID NO: 25
gacattgtgatgacccagtcccccgattcgcttgcggtgtccctgggagaacgggccacca ttaactgcaagagctcacagtccgtcctgtattcatcgaacaacaagaattacctcgcatg gtatcagcagaagcctggacagcctcccaagctgctcatctactgggctagcacccgcgaa tccggggtgccggatagattctccggatcgggttcgggcactgacttcactctgactatca actcactgcaagccgaggatgtcgcggtgtacttctgtcagcagtactacgacacccccgac ctttggacaaggcaccagactggagattaagcgtacggtggccgctcccctccgtgttcatc ttcccacccctccgacgagcagctgaagtccggcaccgcctccgtcgtgtgcctgctgaaca acttctaccccgcgaggccaaggtgcagtggaaggtggacaacgccctgcagtccggcaa ctcccaggaatccgtcaccgagcaggactccaaggacagcacctactccctgtcctccacc ctgacccctgtccaaggccgactacgagaagcacaaggtgtacgcctgcgaagtgacccacc agggcctgtccagccccgtgaccaagtccttcaaccggggcgagtgc (Human IgG4P heavy chain DNA variant 1)
SEQ ID NO: 26
caagtgcaactggtggaatccggggccgaagtgaaaaagcccggagccactgtgaagatct cttgcaaagtgtccggctacaccttcaccgactattacatgcactgggtccagcaggcacc tgggaagggccttgagtggatgggtctggtcgatcccgaggacggcgaaactatctacgcc gagaagttccagggtcgcgtcaccatcaccgccgacacttccaccgacaccgcgtacatgg agctgtccagcttgaggtccgaggacacagccgtgtactactgcgccacggatgctcgggg aagcggcagctactacccgaaccacttcgactactggggacagggcactctcgtgactgtc tcgagcgcttctacaaaggccccctccgtgttccctctggcccccttgctcccggtccacct ccgagtctaccgccgctctgggctgcctggtcaaggactacttccccgagcccgtgacagt gtcctggaactctggcgccctgacctccggcgtgcacaccttccctgccgtgctgcagtcc tccggcctgtactccctgtcctccgtcgtgaccgtgccctcctccagcctgggcaccaaga cctacacctgtaacgtggaccacaagccctccaacaccaaggtggacaagcgggtggaatc taagtacggccctccctgccccccctgccctgccctgaatttctgggcggaccttccgtg ttcctgttcccccccaaagcccaaggacaccctgatgatctcccggaccccgaagtgacct gcgtggtggtggacgtgtcccaggaagatcccgaggtccagttcaattggtacgtggacgg -continued

```
cgtggaagtgcacaatgccaagaccaagcccagagaggaacagttcaactccacctaccgg gtggtgtccgtgctgaccgtgctgcaccaggactggctgaacggcaaagagtacaagtgca aggtgtccaacaagggcctgccctccagcatcgaaaagaccatctccaaggccaagggcca gccccgcgagcccaggtgtacaccctgcccccctagccaggaagagatgaccaagaaccag gtgtccctgacctgtctggtcaagggcttctaccccctccgacattgccgtggaatgggagt ccaacggccagcccgagaacaactacaagaccaccccccctgtgctggacagcgacggctc cttcttcctgtactctcggctgaccgtggacaagtcccggtggcaggaaggcaacgtcttc tcctgctccgtgatgcacgaggccctgcacaaccactacacccagaagtccctgtccctga gcctgggcaag
```

(Human IgG4P light chain DNA variant 1)
SEQ ID NO: 27

```
gacattgtgatgacccagtcccccgattcgcttgcggtgtccctgggagaacgggccacca ttaactgcaagagctcacagtccgtcctgtattcatcgaacaacaagaattacctcgcatg gtatcagcagaagcctggacagcctcccaagctgctcatctactgggctagcacccgcgaa tccggggtgccggatagattctccggatcgggttcgggcactgacttcactctgactatca actcactgcaagccgaggatgtcgcggtgtacttctgtcagcagtactacgacaccccgac ctttggacaaggcaccagactggagattaagcgtacggtggccgctcccctccgtgttcatc ttcccaccctccgacgagcagctgaagtccggcaccgcctccgtcgtgtgcctgctgaaca acttctaccccgcgaggccaaggtgcagtggaaggtggacaacgccctgcagtccggcaa ctcccaggaatccgtcaccgagcaggactccaaggacagcacctactccctgtcctccacc ctgaccctgtccaaggccgactacgagaagcacaaggtgtacgcctgcgaagtgacccacc agggcctgtccagccccgtgaccaagtccttcaaccggggcgagtgc
```

(Mouse full length IgG1 heavy chain variant 2)
SEQ ID NO: 28

QVQLVQSGAEVKKPGATVKISCKVSGYTFTDYYMHWVQQAPGKGLEWMGLVDPEDGETIYA

EKFQGRVTITADTSTDTAYMELSSLRSEDTAVYYCATDARGSGSYYPNHFDYWGQGTLVTV

SSAKTTPPSVYPLAPGSAAQTNSMVTLGCLVKGYFPEPVTVTWNSGSLSSGVHTFPAVLQS

DLYTLSSSVTVPSSTWPSETVTCNVAHPASSTKVDKKIVPRDCGCKPCICTVPEVSSVFIF

PPKPKDVLTITLTPKVTCVVVDISKDDPEVQFSWFVDDVEVHTAQTQPREEQFNSTERSVS

ELPIMHQDWLNGKEFKCRVNSAAFPAPIEKTISKTKGRPKAPQVYTIPPPKEQMAKDKVSL

TCMITDFFPEDITVEWQWNGQPAENYKNTQPIMDTDGSYFVYSKLNVQKSNWEAGNTFTCS

VLHEGLHNHHTEKSLSHSPGK (Mouse full length IgG1 light chain variant 2)

SEQ ID NO: 29

DIVMTQTPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTDAAPTVSI

FPPSSEQLTSGGASVVCFLNNFYPKDINVKWKIDGSERQNGVLNSWTDQDSKDSTYSMSST

LTLTKDEYERHNSYTCEATHKTSTSPIVKSENRNEC (Human full length IgG1 heavy chain variant 1)

SEQ ID NO: 30

QVQLVESGAEVKKPGATVKISCKVSGYTFTDYYMHWVQQAPGKGLEWMGLVDPEDGETIYA

EKFQGRVTITADTSTDTAYMELSSLRSEDTAVYYCATDARGSGSYYPNHFDYWGQGTLVTV

SSASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQG

NVFSCSVMHEALHNHYTQKSLSLSPGK (Human full length IgG1 light chain variant 1)

SEQ ID NO: 31

DIVMTQSPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSENRGEC (Fab heavy chain variant 2)

SEQ ID NO: 32

QVQLVQSGAEVKKPGATVKISCKVSGYTFTDYYMHWVQQAPGKGLEWMGLVDPEDGETIYA

EKFQGRVTITADTSTDTAYMELSSLRSEDTAVYYCATDARGSGSYYPNHFDYWGQGTLVTV

SSASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSC (Fab light chain variant 2)

SEQ ID NO: 33

DIVMTQTPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSENRGEC (Human IgG4P heavy chain variant 2)
SEQ ID NO: 34

QVQLVQSGAEVKKPGATVKISCKVSGYTFTDYYMHWVQQAPGKGLEWMGLVDPEDGETIYA

EKFQGRVTITADTSTDTAYMELSSLRSEDTAVYYCATDARGSGSYYPNHFDYWGQGTLVTV

SSASTKGPSVFPLAPCSRSTSESTAALGCLVKDYFPEPVTVSWNSGALTSGVHTFPAVLQS

SGLYSLSSVVTVPSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRLTVDKSRWQEGNVE

SCSVMHEALHNHYTQKSLSLSLGK (Human IgG4P light chain variant 2)
SEQ ID NO: 35

DIVMTQTPDSLAVSLGERATINCKSSQSVLYSSNNKNYLAWYQQKPGQPPKLLIYWASTRE

SGVPDRESGSGSGTDFTLTINSLQAEDVAVYFCQQYYDTPTFGQGTRLEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSENRGEC (Human Gremlin-1; full sequence)
SEQ ID NO: 36 actcggtgcgccttccgcggaccgggcgacccagtgcacggccgccgcgtcactctcggtc ccgctgaccccgcgccgagcccggcggctctggccgcggccgcactcagcgccacgcgtc gaaagcgcaggccccgaggacccgccgcactgacaggtgagcgcggacgcacccggcaggg atgtgagtgggcggagggaagagggccgcaaaccaacccaggacccgctcagttccacgcg cggcagccctccgtgcgcgcaggctcgggtgcgttgttcgcgggggtgaattgtgaagaac catcgcggggtccttcctgctgaggccgcggacaccgtgacctcgctgctctgggtctgca gggaaacgtaggaaaaaaagttgtcaggagcgggcaggatgaccccacatcccgtttcca cctcccggaggcccccgaacacgctcctggtgctggtggcagcagcgcctggcagacgcgc ccgcttagcgagggcgcgaagtccaggccgccagagcgcaggagcatccggacctgctagt cggccgctgactgcgcggcgagttgccttgagagggtcccatgtgcttggggcgccgcgct gggtctgggggcgtcttggggcgcccattggagtccgcgggttggagcatccggagaatcc atgatgtgtgcatttgccgatccccgaggtgagatggagactggcaagggcagagccgctg tgttcagccacagcggaaaaccgaacgggggtaatccgacagctgcggtgcggggcgcgg ccctggccgcggggtccagcgaacccgcagtgctcacaaggcagacaccacacgcgctcgc ggaccggccacgcactcgcgggcgctcgcttctctactccagcctcttccccgccccgcgc acgcccgagctgaatggtagacgttctggcgccgggcagcggccaccggctggttcccact tccgcgcgcaccccttaaactgtgttctagaggccccagcctcgccttgcagcgcctcact agctcctgaggactagggactggcggctgaggcgggttggcggctgcaacgagctgggcgt ctttcgttctctctcgctgcctggctggctccgctggcccctccacagcttgcggagcaag gccatagcaggggagtgggaggtatattgggctgtcacctccttgctggccggagttatt tgtagactacagactccggaagaacagacgcgccaccgctctcgcttggcattgccttcgg -continued

```
atcgcagctcctccttgggggtgcccagcttggcgtttatttgcctgcgccaggctctgg cgacggtcaccgggccaggcggggagggacggacggcaggtgaccagcctctgctgtgaag aaattcctgcgcgcccggagctgtccctaatgcattcccgggtcgaatccgtctactgcct tccccctcctcgaccgactccgaatctcggctcttatagacagaaatacagcctcagcgtta ggggttaaaatcccctcttaaacggtccgagggcagagaggtgaccaccgataggtaatt ggatctcctgctggaaagagcaaatctgagcggtgtgcgcgtctgtttatgttcccttcg agatggtgccaggacacgaactgattaaaacaatctattgtgttaagtgggtcactagggt tttaagctgtcccagggaccccagagtagtggcttccttctggctgtacacacaagttaaa taaatagcgtagaagaggttaagataaccccattctagggtgaggagtcctctttcatccc tagggcttccccctccccttttctctttttttggaaggaggggggagcatgagagtcttgag gggggatgtacttttcaaagcaaggagggaaagatcttaagaaaactatatattctcact gcccccaagccaagtctataacagtaggtgatttgattactatctctggataaatggcac tgtcaaattgttaatattaactatttcagggattttttagcagggtagtggcagtatgtgtg cgtgtgtgtgtgtgtctgtgtgtgtgtttaacctccaggtcattgtaggaattagag tcttttgtaaacttttgtaatttcacaggtttcctattttcttaaaagttcattttttagtga aatgttttggtaacccacgctctgtaggaaatccaggttggctaatgcggtctttatgtga gtagttacacagggaaggataaaaacctttttatgtcctacatctctgaatgagggctgcct accctgtctttgaaactaagccgaagatgccttcagtctgaatggtcaagtattaaaagtg ataaaatgcaaagaaatttcatgccgcagacacctcccccaagaactgcttgttgacagca aagctgtggaacatgttccacaacagagagtaaaggacagccaggaaatataaaccttta tgtaaaggaaaggcaggtgggggacagtggttagggggaggtgactgcagcctctaaccaaa aggcaaccatcaggcaagtgctaccagcccgtgtcttcgatctgcaaggaattttttttag ttttaacatatgctcttagaaattcaaagtacaacaggaattcctgggacaagagaaatct ttttattcacatgtgaacatgaagatacaaaatagataattattttatttatagcactctt caaattgtattgcattagaaaacatatccattgacccactgttaaggacagcactgggtgt caataggacagtggttaaggacctgtgtttgggctagatagaattgggttaaactgctg gctgggctgggcacagtggctcacaccggtaatcccagcactttgggaggccaaggaggac ggatcacctgaggtcgggagttcgacaccagcctgaccaacatggaaaaatcccgtctcta ctaaaaacacaaaattagccaggcatggtggtgcatgcctgcaatcccagctacttgggag gctgaggcaggagaattgcttgaaaccgggaggcggaggttgtggtgagcccagatagcgc cattgcattccagcctgggcaacacgagtgaaaactccgtcaaaaaaacaaaacaaaacaa acaaacaaaaaaatgctggctttcccacttatgagctgtgtgaccttggacaaatttccaa cttttctgagtgtagattccctgattggtaaaaggaagatgatattatctacctcatatttt tgttatgaaaatagatgataaaattgggtcagaaatcagcataatgcctggcacagtaag ggcttcaaaataaaaggtagctcttattattagtaatggtgttaggaaaagtagcaatgtt atacagaaccaggatatatcacagggcagttctgaaattaaatcctgaatcctggccgggt gaggtggctcacgcttgtaatcctaagcactttcggagactgaggcaggcggatcacgagg tcaggagtttgagaccagcctggccaacacactgaaatcccgtctctactaaaaatacaaa aattagctgggtgtggtggcaggcgcctataatctcagctacttgggaggctgaggcagga gaatcacttgagcccaggaggcggaggttgcagtgagctgatatcgtgccagtgcactcca gcctgggtgacatctcttaaaaaaaaaaatcctgaataccacactacgcagtgactaacac
```

-continued

```
atctttcactacagaacagaacctgtaacttggccgtctctcagcagtgctgctcagtgaa catttaataatttattactttctaactcgtttcttgttgacctcaagaattgtacatagtc attaactttcctaagaaaatctttgacaaacatagagctcctgagatatttcacaaccagg tggtctcctccctgtcctatgcaatgttgggccccagcctgatttagccgacctggtcttc agacttgagaggctgtttagggttcttacaacacaaaggggatgagactttatcctctacc tgtgtgccaacaagggattcttcttatctccttggtgcaacttgtctgaaaaagaaagtca acacaattatottcttaaaagttaaagatcaaattaaaaataagctatagttttcccaaag atttagacctgagaaaaaggaatagatcttcctaaaacctggcctgcacttagagcatttg tagtcacttccactatttcttatgctgagagaataatttgatgtcatgcctattgaatgtc tttctaaagcttgattcatcaggaggaactgaccagaagtccatgcacagacatttggctt tcactgtaattcctactcaaaactccctttcactgattatgagcaggttgcttagctaaaa tgagaaatacagcaagaagagggatggaaagagctggcttaaactttcccaaagacatcat gaacactgggaacaggtcatacatataccattttttatttctcagtcctcagtattagaata ttgtgttcctagaggctttgtgaaaattggaatacattgccatgacctgcacaggatagag gtggttaatatggcttaccttgcttgtagatgtttactcttgatccctaagggaaactgga aggaaagcatgctgtagagaggacctgctttgagagtatgtgtcctctgggacaagtggaa tgaaagagaggatagaggcaaagagaaaaaaggtggagatggggtgagacttgctggtgg acagttgcaaagaaaactcatgatgagaataacatcacatttcttgaagaagctgaactgc attgatgggaagttgaggcagagtttgaaaagaagatatactgtctgcaaaaagaatcaa cggagatgtcaggtatcttgatgcaccctgagtctatgagatgcagcttaatttaatttaa tgatatgagtaggccatttcataagtggtggaaattaccataaagtgtttgcagctaatga cggcgcatgaatgatgtcataggaacctaagtctggatgagctatggattgaattttttact atgggacacccttctacatgttgctgtggaaaagaattgtcctcaagaaatgtacatcttc tgcatttcctctacatctctgatatttacaaagtgcacattatttggtgatactacaactg ggatttcaagtgcacatcactactatttccttcactgaagaatcaagagcagtctgggggt ggggagagcttgagtgattgacaaggatgtggcagagccctggttccactatgaattatag ttcttaccctgcttactgtcactcatgtagagcagctagtgtgcctcagagcactgctgtt ctctgagaagctgaggtctcgattgacattcttgaagttggtgtttacttctctctgaata aacaaaggttggcaactcagacatcttacaataagtactaaagattttgaagaataggtt tttaaaaaatgaaaaacattcactttccatagctaataaatcttattttgaggaaaatg tacttttctttaaaaaaaaaaaagcctgtctgtcactctagacccttggcttagaaggt aggcacactcacatagaaacagaaagtctgtccaaattaaaactgaaaaccacagttgact aattttgaattatagctctgctgttggcttctgcgatagtattaatttcaatggcttcaa ttagaaaatgaaacccatagcattccatatgagaacaggtaaaaagtcagggacatttgga gttttccaagaaaagaaagacaagtcttaggaagctctctaggatggaaggaatttgcca cactgagagttagacatccaaaggatagcaattggctcttctgctcatgggcactggtgaa ggcattttaaaatgcgaagaatggtacctctgtaaatcaatgaggttcataataatcatgc atttaccaaattttttataagcacctgccttgtgccaggcactgagggtaaggtgatgaata agccctcatcaactgtcagactagatatttactcaataacagatgtgaaaatgccaagaag gaaaagttgagtataaagaaagcccttaagttggttcagagaaataaaattgcattttcgg
```

-continued

```
atagatgtttatggaatcggccttatgaggtaaacttgtcctatgcagtgaacatacattc ccagttagtctcagattggcctctgtgatgacaaactcagagggtcctggtctaggagggg tgaatttgtctggaggccatttttcaggaggtatggaggaagactggggcataggcctgggg ccatcccatgtactcctcctctgaaatggggagcaactgaattgtgttttattttagatct tcgtccaacttgaataccagaaattcgtgaaaccttctcaaattcacactatattttgaga ccaggagaaggctccttgagaaattgccacactgtcttatcctagtctctggaaaaattca gtcctgtattataactgggcgtttctcataagtgctttttttttttcttttttcttttttata atactttaagttctgggatacatgtgcagaatgtgcaggtttgttacataggtatacacgt gccatggtggtttgctgcacccatcaacccatcatctacattaggtatttctcctaatgct accccttccctagcccccacccctcgacaggccccagtgtttgatgttcccctccctgtg tccatgtgttctcattgttcaactcccacttatgagtgagagcatgcggtgtttggttttc tgttcctgtgttagtttgctgagaatgatggttttttggcttcatccacgtccctgcaaagg acatgaactcatccttttatggctgcatagtattccatggtgtatatgtgccacatttgc tttatccagtctatcattgatgagcacttgggttggctccaagtctttgctattatgacta gtactgcgataaacatgtgtatatgtgtctttatattagaatgatttataatcctttaggt ctatacccagtaataggattcctgggtcaaatggtatttctggttctagatccttgaggaa ttgccacactgtcttccacaacggttgaactaatttacactcccaccaacagtgtaaaagc attcctatttctccacatcctctccaacatctgttgtttcctgactcttaatgacggcca ttctaactggcgtgaaatggtatctcattgtggttttgatttgcatttctctaatgaccac cgatgatgagcttttctcatatgtttgctggccccataaatgtcttcttttgagaaatgt ctgttcatatcctttgcccacttttgatgggttgtttgctttttcttgtaaatttgtt tgagttcctggtagattctggatattagccctttgtcagatggatagactgcaaaaatttt ctcccattctgtaggttgcctgttcactctgatggtagtttcttttgccatgcagaagctg tttagtttaattagatccaatttgtcagttttggcttttgttgccattgcttttggtgttt tagtcatgaagtctttgcccatgcctatgtcctgaattgtattgccctggttttcttctag gattttatggttttaggtcttacatttaagtctttaatccatcttgaattaattttttgta taaggtgtaaggaaagggtccagtttcagttttctgcgtatggctagccagttttcccaac gttatttattaaatagggaatccttcccattgcttgttttgtcaggtttgtcaaagat cagacggttgtagatgtgtggtgttatttctgaggcctctgttctgttccattggtctgta tatctgctttgataccagtaccgtgctgttttggttactgtagccttgtagtacagtttga agtcaggtagcgtgatgctttgttcttttgcttaggattgtcttggctatatgggctctt ttttggttctatatgaaatttaaagtagtttttcatagacatctatagaactctccaccc caaatcaacagaatatacattcttctcagtatcgcatcacacttattctaaaatgaccaca taattagaagtaaaacactcctcagcaaatgcaaaaaacagaaatcctaacagtctgtcag accccagtgcaatcaaattagaactcaggattaagaaacttactgaaaaccacacaactgc atggaaactgaacaacctgctcctgaatgactactgggtaaataacaaaattaaggcagaa ataaataggttctttgaaagaaatgagaacaaagacacaatataccagaatctctgggaca cagctaaagcagtgtttagagggaaattgatagcactaaatgcccacaggagaaagcggga cagatctaaaatcgacaccctaatatcacaattaaaagaactagagaaacaagagcaaaca aattcaaaagctagcagaagacaagaaataactaagatcagagcagaactgaaggagatag agacacaaaaaaccccttcaaaaaatcaatgaatccaggagctgttttttttttttttgaaaa
```

-continued

```
gattaatgaaatagactgctagccaaactaataaaggagaaaagagagaagaatcaaatag acaatagacacaataaaaagtgataaaggggatatcaccactgatcccacagaaatacaaa ctaccatcagagaatactataaacacctctacgcaaataaactagaaaattgggaagaaat ggatacattcctgaacgcatacaccctcccaagactaaaccaggaagaagttgaatccctg aatagaccaatagcaagttctgaaattgaggcagtaattagtagcctaccaaccaaaaaaa gcccaggaccagacagattcacagccgaagtctaccagaggtacaaagaggagctagtacc attccttctgaaactattccaaacaatagaaaagaaggactcctccctaactcattttat gaggccagcatcatcctgataccaaaacctggcagagacacaacataaaggaaattcaggc caatatccctgatgaacattgatgtgaaaatcctcaataaaatactggcagcacatcaaaa agcttacctgccatgatcaagttggcttcatccctgggatgcaaggctggttcaacatacg caaatcaataaacgtaatcaatcacatacacagaaccaatgacaaaaccacatgattatc tcaatagatgcagaaaaggccttcgataaaattcaacacccttcaatgctaagaactctc aataaactaggtattgatgaaacatatctcaaaataataagagttatttatgacaaaccca cagccagtatcatactgaatgggcaaaagctggaagcattccctttgaaaaccgccacaag gatgacttctctcaccactcctattcaacatactattggaagttctggccagggcaagcag gcaagacaaataaatagggtattcaaataggaagagaggaagtcaaattgtctctgttt gcagatgacatgattgtatatttagaaaaccccatcatctcagcccaaaatctccttaagc tgataagcaacttcagcaaagtctcaggatacaaaatcaatgtgcaaaaatcacaagcatt cctatacaccaataatagacaaacagccaaatcatgagtgaactcccattcacaagtgcta caaagaataaaatacctaggaatccaacttacaagggatgtgaaggacctcttcaaggaga actacagaccactgctcaaggtaataagagaggacacaaacaaatggaaaaacattccatg ctcatggataggaagaatcaatattatgaaaatggccatactgcccaaaacaatttataga ttcaatgccatccccatcaagctaccactgacttccttcacagaattagaaaaaaactact ttaaatttcatatggaactgaaaaaagagccggtatagccaagacgatcctaagcaaaaag aaaaaagctggaagcatcatgctacctgacttcaaactatactacaaggctacagtaacaa aaacagcatggtatagtataagtgcttttttttaaaagacaaagtaaagtaattttttttgt tgttggggtaaaacaaaagctctgcataaagagcagggatgttgtaacatacactgaccaa aggtgggaaacctacagttggagcagaagctgaatgtcacattatcagctccgaacttata atggtctaaaagtactaggttaatgttggaaagatggtgccatttaaagatatcttaaatt caatatttaattattttaatttgacattatcctagagttgaatggtgtttacttaccatgt gctgttcattagaaaatctagatcctacactgcctttgcgcaaggtagttgctctaataat accaacctgtccagttttggtgggagaaataatgttactgttaagttgcacttagtggtta ttatgtgtaatactggtattccaaagagagaaggaaaatgtttgctacacagctgtgttct taggttcagaaaaccacaggagtgggacaggagaaccttcaggattcaggtccgattgttg tgatggccgcaggagggagactgtgaatttgaaactgcatccattgaaaagaaaatccctc cacactttaataattctctccgtgcccatggcagcaagtgcttataggccttgctactca aagcttaataaaaaggcagacctgctgaatcataatctgcatcttaacaatatccccagat attgtctgcactttctttttttttttctttctttcttcttttttttgagacagagtc tcgctcagtcacccaggctggagtgcagtggcgcgatctcggctcactgcaagctctgact cccgggttcacgccattctcctgccttagactcccgagtagctggcactacaggcgcccgc
```

-continued

```
cactacgcccggctaatttttttgtattttagtagagatggggtttcaccgtgttagcca ggatggtctcgatctcctgacctcgtgatccgccgcccatctgggcctcccaaagtgctgg gattacaggcgtgagccactgcgcccggccaattgtctgcactttcaagtctaagaagcac tgtcccaggaggaaaatctttttagtctgaggcttctctcttgcactctccttttaaaaa tatgctgctccttctccacctttccctcttcttccgccttttctgtctgcctttactacct cccctgaacattcaacttgtagaagagttcccctttctctgaattgcattcttcacttcat tcattcttttctctctgtctatggtttcctattttttgtcggttttccctcacctcacc tccttgttattttttgccattgttcacatatcactgccctttcagacccatatctagcttc tgacccatccactaatccattgccactaatttattcagcatgcccatgccatttattaatg taaatatttgcacatacttgttctatcatgcccatttttctaccttttaaattgtatatac acagacacatgtgaatgacatatttcactatttaaaaggtagaaaaatgtatatcgtggta caaagtgatacattgagtatctgtgcccagtttcaagatgagaataagtgagaggtgaagc ctcatgagtcacgtcacctacacgctactgtctttcattccatctgcagtactgccacaca tttggttagttctccaattgctgtcacattgacatcgagttggatctgaacagcgtacctg gggagacgaagtattggtatctttgcttaaatggagtgatttactgagagacaaagtgaca tctttaagatcagatagcaagttactgcaccaggagcgcgacctttcctgttttgttgttt tccctctgtcaaatgccttctggtctccatgaatctctccttccacatatgataaaaatgc aaagtctcataagcattcacagctcaggaagcctcaggctagttggggagaaaagactggg aggtttccggaggaatgaagtcctctgagcagagaggttaattcatcttgctgtaaaacaa aatagaaaataagttcccctcaataagtgaacgtaatacaaagacaaatgtggttggtgcc agaggccaggaagaagttcttgtgagaataggtgcagagaagagctaggccctggctgagt ttaaaccttgacttagtcactgtgggactctgggtgagttactccatggattgatggctgg gtcatggagataatagtacctaattcatacaggtactgtgagaagtaaatggaatatttca cgttaagtgtttaacggtgcgtttaaatgctaggtgctattattattaattttaaattaa ctttgccatgttttgtgtcttccctctctgtgcttccttttctttagtatgagccgcacag cctacacggtgggagccctgcttctcctcttggggaccctgctgccggctgctgaagggaa aaagaaagggtcccaaggtgccatcccccgccagacaaggcccagcacaatgactcagag cagactcagtcgccccagcagcctggctccaggaaccggggcggggccaagggcgggca ctgccatgcccggggaggaggtgctggagtccagccaagaggccctgcatgtgacggagcg caaatacctgaagcgagactggtgcaaaacccagccgcttaagcagaccatccacgaggaa ggctgcaacagtcgcaccatcatcaaccgcttctgttacggccagtgcaactctttctaca tccccaggcacatccggaaggaggaaggttcctttcagtcctgctccttctgcaagcccaa gaaattcactaccatgatggtcacactcaactgccctgaactacagccacctaccaagaag aagagagtcacacgtgtgaagcagtgtcgttgcatatccatcgatttggattaagccaaat ccaggtgcacccagcatgtcctaggaatgcagccccaggaagtcccagacctaaaacaacc agattcttacttggcttaaacctagaggccagaagaaccccagctgcctcctggcaggag cctgcttgtgcgtagttcgtgtgcatgagtgtggatgggtgcctgtgggtgttttagaca ccagagaaaacacagtctctgctagagagcactccctattttgtaaacatatctgctttaa tggggatgtaccagaaaccccacctcaccccggctcacatctaaaggggggggccgtggtc tggttctgactttgtgttttttgtgccctcctggggaccagaatctcctttcggaatgaatg ttcatggaagaggctcctctgagggcaagagacctgttttagtgctgcattcgacatggaa
```

-continued aagtccttttaacctgtgcttgcatcctcctttcctcctcctcctcacaatccatctcttc ttaagttgatagtgactatgtcagtctaatctcttgtttgccaaggttcctaaattaattc acttaaccatgatgcaaatgttttcattttgtgaagaccctccagactctgggagaggct ggtgtgggcaaggacaagcaggatagtggagtgagaaagggagggtggagggtgaggccaa atcaggtccagcaaaagtcagtagggacattgcagaagcttgaaaggccaataccagaaca caggctgatgcttctgagaaagtcttttcctagtatttaacagaacccaagtgaacagagg agaaatgagattgccagaaagtgattaactttggccgttgcaatctgctcaaacctaacac caaactgaaaacataaatactgaccactcctatgttcggacccaagcaagttagctaaacc aaaccaactcctctgctttgtccctcaggtggaaaagagaggtagtttagaactctctgca tagggtgggaattaatcaaaaaccgcagaggctgaaattcctaatacctttcctttatcg tggttatagtcagctcatttccattccactatttcccataatgcttctgagagccactaac ttgattgataaagatcctgcctctgctgagtgtacctgacagtagtctaagatgagagagt ttagggactactctgttttagcaagagatattttgggggtcttttgttttaactattgtc aggagattgggctaaagagaagacgacgagagtaaggaaataaagggaattgcctctggct agagagtagttaggtgttaatacctggtagagatgtaagggatatgacctccctttcttta tgtgctcactgaggatctgagggaccctgttaggagagcatagcatcatgatgtattagc tgttcatctgctactggttggatggacataactattgtaactattcagtatttactggtag gcactgtcctctgattaaacttggcctactggcaatggctacttaggattgatctaagggc caaagtgcaggggggtgaactttattgtactttggatttggttaacctgttttcttcaag cctgaggttttatatacaaactccctgaatactcttttgccttgtatcttctcagcctcc tagccaagtcctatgtaatatggaaaacaaacactgcagacttgagattcagttgccgatc aaggctctggcattcagagaacccttgcaactcgagaagctgttttatttcgtttttgtt ttgatccagtgctctcccatctaacaactaaacaggagccatttcaaggcgggagatattt taaacacccaaaatgttgggtctgattttcaaacttttaaactcactactgatgattctca cgctaggcgaatttgtccaaacacatagtgtgtgtttgtatacactgtatgaccccac cccaaatctttgtattgtccacattctccaacaataaagcacagagtggatttaattaagc acacaaatgctaaggcagaattttgagggtgggagagaagaaaagggaagaagctgaaaa tgtaaaaccacaccagggaggaaaaatgacattcagaaccagcaaacactgaatttctctt gttgttttaactctgccacaagaatgcaatttcgttaacggagatgacttaagttggcagc agtaatcttcttttaggagcttgtaccacagtcttgcacataagtgcagatttggctcaag taaagagaatttcctcaacactaacttcactgggataatcagcagcgtaactaccctaaaa gcatatcactagccaaagagggaaatatctgttcttcttactgtgcctatattaagactag tacaaatgtggtgtgtcttccaactttcattgaaaatgccatatctataccatattttatt cgagtcactgatgatgtaatgatatatttttcattattatagtagaatattttatggca agatatttgtggtcttgatcatacctattaaaataatgccaaacaccaaatatgaatttta tgatgtacactttgtgcttggcattaaaagaaaaaaacacacatcctggaagtctgtaagt tgtttttgttactgtaggtcttcaaagttaagagtgtaagtgaaaaatctggaggagagg ataatttccactgtgtggaatgtgaatagttaaatgaaaagttatggttatttaatgtaat tattacttcaaatcctttggtcactgtgatttcaagcatgttttcttttttctcctttatat gactttctctgagttgggcaaagaagaagctgacacaccgtatgttgttagagtcttttat

```
                                           -continued
ctggtcaggggaaacaaaatcttgacccagctgaacatgtcttcctgagtcagtgcctgaa tctttatttttaaattgaatgttccttaaaggttaacatttctaaagcaatattaagaaa gactttaaatgttattttggaagacttacgatgcatgtatacaaacgaatagcagataatg atgactagttcacacataaagtcctttaaggagaaaatctaaaatgaaaagtggataaac agaacatttataagtgatcagttaatgcctaagagtgaaagtagttctattgacattcctc aagatatttaatatcaactgcattatgtattatgtctgcttaaatcatttaaaaacggcaa agaattatatagactatgaggtaccttgctgtgtaggaggatgaaaggggagttgatagtc tcataaaactaatttggcttcaagtttcatgaatctgtaactagaatttaattttcacccc aataatgttctatatagcctttgctaaagagcaactaataaattaaacctattctttctgt g (Human Gremlin-1; coding sequence)
                                                              SEQ ID NO: 37
atgagccgcacagcctacacggtgggagccctgcttctcctcttggggaccctgctgccgg ctgctgaagggaaaagaaagggtcccaaggtgccatcccccgccagacaaggcccagca caatgactcagagcagactcagtcgcccagcagcctggctccaggaaccggggcggggc caagggcggggcactgccatgcccggggaggaggtgctggagtccagccaagaggccctgc atgtgacggagcgcaaatacctgaagcgagactggtgcaaaacccagccgcttaagcagac catccacgaggaaggctgcaacagtcgcaccatcatcaaccgcttctgttacggccagtgc aactctttctacatccccaggcacatccggaaggaggaaggttcctttcagtcctgctcct tctgcaagcccaagaaattcactaccatgatggtcacactcaactgccctgaactacagcc acctaccaagaagaagagagtcacacgtgtgaagcagtgtcgttgcatatccatcgatttg gattaa
```

REFERENCES

Attar-Schneider, O., et al., Multiple myeloma and bone marrow mesenchymal stem cells' crosstalk: Effect on translation initiation. Mol Carcinog, 2015.

Azab, A. K., et al., Hypoxia promotes dissemination of multiple myeloma through acquisition of epithelial to mesenchymal transition-like features. Blood, 2012. 119 (24): p. 5782-94.

Bostrom, M. P. & Seigerman, D. A. (2005), HSS journal: The Musculoskeletal Journal of Hospital for Special Surgery 1, 9-18. The clinical use of allografts, demineralized bone matrices, synthetic bone graft substitutes and osteoinductive growth factors: a survey study.

Buza, J. A., 3rd & Einhorn, T. (2016), Clinical cases in mineral and bone metabolism: The Official Journal of the Italian Society of Osteoporosis, Mineral Metabolism, and Skeletal Diseases 13, 101-105. Bone healing in 2016.

Calon A, Lonardo E, Berenguer-Llergo A, Espinet E, Hernando-Momblona X, Iglesias M, et al. Stromal gene expression defines poor-prognosis subtypes in colorectal cancer. Nat Genet. 2015; 47(4):320-9.

Canalis, E., Parker, K. & Zanotti, S. (2012), J. Cell Physiol 227, 269-277. Gremlin1 is required for skeletal development and postnatal skeletal homeostasis.

Chen, J., et al., BAFF is involved in macrophage-induced bortezomib resistance in myeloma. Cell Death Dis, 2017. 8(11): p. e3161.

Chen, M. H., et al., Expression of gremlin 1 correlates with increased angiogenesis and progression-free survival in patients with pancreatic neuroendocrine tumors. J Gastroenterol, 2013. 48(1): p. 101-8.

Cheong, C. M., et al., Tetraspanin 7 (TSPAN7) expression is upregulated in multiple myeloma patients and inhibits myeloma tumour development in vivo. Exp Cell Res, 2015. 332(1): p. 24-38.

Chesi, M., et al., Drug response in a genetically engineered mouse model of multiple myeloma is predictive of clinical efficacy. Blood, 2012. 120(2): p. 376-85.

Cho, T. J., Gerstenfeld, L. C. & Einhorn, T. A. (2002), Journal of Bone and Mineral Research: The Official Journal of the American Society for Bone and Mineral Research 17, 513-520. Differential temporal expression of members of the transforming growth factor beta superfamily during murine fracture healing.

Ciuclan, L., et al., Treatment with anti-gremlin 1 antibody ameliorates chronic hypoxia/SU5416-induced pulmonary arterial hypertension in mice. Am J Pathol, 2013. 183(5): p. 1461-73.

Curran, S. P., et al., Deletion of Gremlin1 increases cell proliferation and migration responses in mouse embryonic fibroblasts. Cellular Signalling, 2012. 24(4): p. 889-98.

Dallas, S. L., et al., Ibandronate reduces osteolytic lesions but not tumour burden in a murine model of myeloma bone disease. Blood, 1999. 93(5): p. 1697-706.

Das, D. S., et al., A novel hypoxia-selective epigenetic agent RRx-001 triggers apoptosis and overcomes drug resistance in multiple myeloma cells. Leukemia, 2016. 30(11): p. 2187-2197.

Davis H, Irshad S, Bansal M, Rafferty H, Boitsova T, Bardella C, et al. Aberrant epithelial GREM1 expression initiates colonic tumorigenesis from cells outside the stem cell niche. Nat Med. 2015; 21(1):62-70.

Diamond, P., et al., Targeted disruption of the CXCL12/CXCR4 axis inhibits osteolysis in a murine model of myeloma-associated bone loss. J Bone Miner Res, 2009. 24(7): p. 1150-61.

Einhorn, T. A. & Gerstenfeld, L. C. (2015), Nat. Rev. Rheumatol. 11, 45-54. Fracture healing: mechanisms and interventions.

Ferguson, C., Alpern, E., Miclau, T. & Helms, J. A. (1999), Mechanisms of development 87, 57-66. Does adult fracture repair recapitulate embryonic skeletal formation?

Fowler, J. A., et al., Bone marrow stromal cells create a permissive microenvironment for myeloma development: a new stromal role for Wnt inhibitor Dkk1. Cancer Research, 2012. 72(9): p. 2183-9.

Gazzerro, E. et al. (2005), Endocrinology 146, 655-665. Skeletal overexpression of gremlin impairs bone formation and causes osteopenia.

Gazzerro, E. et al. (2007), J. Biol. Chem. 282, 31549-31557. Conditional deletion of gremlin causes a transient increase in bone formation and bone mass.

Ghobrial, I. M., Myeloma as a model for the process of metastasis: implications for therapy. Blood, 2012. 120(1): p. 20-30.

Goulet, J. A., Senunas, L. E., DeSilva, G. L. & Greenfield, M. L. (1997), Clinical Orthopaedics and Related Research, 76-81. Autogenous iliac crest bone graft. Complications and functional assessment.

Guan et al. (2017). Gremlin1 promotes carcinogensis of glimona in vitro. Exp Pharmacol Physiol, 44 (2): 244-256.

Hewett, D. R., et al., DNA Barcoding Reveals Habitual Clonal Dominance of Myeloma Plasma Cells in the Bone Marrow Microenvironment. Neoplasia (New York, N.Y.), 2017. 19(12): p. 972-981.

Hideshima, T., et al., Understanding multiple myeloma pathogenesis in the bone marrow to identify new therapeutic targets. Nature Reviews Cancer, 2007. 7(8): p. 585-98.

Hjertner, O., et al., Bone morphogenetic protein-4 inhibits proliferation and induces apoptosis of multiple myeloma cells. Blood, 2001. 97(2): p. 516-22.

Holien, T., et al., Bone morphogenetic proteins induce apoptosis in multiple myeloma cells by Smad-dependent repression of MYC. Leukemia, 2012. 26(5): p. 1073-80.

Howe J R, Bair J L, Sayed M G, Anderson M E, Mitros F A, Petersen G M, et al. Germline mutations of the gene encoding bone morphogenetic protein receptor 1A in juvenile polyposis. Nat Genet. 2001; 28(2):184-7.

Howe J, Roth S, Ringold J, Summers R, Jarvinen H, Sistonen P, et al. Mutations in the SMAD4/DPC4 gene in juvenile polyposis. Science. 1998; 280(5366):1086-8.

Hsu, D. R., Economides, A. N., Wang, X., Eimon, P. M. & Harland, R. M. (1998), Mol. Cell 1, 673-683. The Xenopus dorsalizing factor Gremlin identifies a novel family of secreted proteins that antagonize BMP activities.

Isella C, Terrasi A, Bellomo S E; Petti C, Galatola G, Muratore A, et al. Stromal contribution to the colorectal cancer transcriptome. Nat Genet. 2015; 47(4):312-9.

Irshad S, Bansal M, Guarnieri P, Davis H, Al Haj Zen A, Baran B, et al. Bone morphogenetic protein and Notch signalling crosstalk in poor-prognosis, mesenchymal-subtype colorectal cancer. J Pathol. 2017.

Jaeger E, Leedham S, Lewis A, Segditsas S, Becker M, Cuadrado P R, et al. Hereditary mixed polyposis syndrome is caused by a 40-kb upstream duplication that leads to increased and ectopic expression of the BMP antagonist GREM1. Nat Genet. 2012; January; 45(1):2-3.

Karagiannis, G. S., et al., Bone morphogenetic protein antagonist gremlin-1 regulates colon cancer progression. Biol Chem, 2015. 396(2): p. 163-83.

Karagiannis, G. S., et al., Enrichment map profiling of the cancer invasion front suggests regulation of colorectal cancer progression by the bone morphogenetic protein antagonist, gremlin-1. Mol Oncol, 2013. 7(4): p. 826-39.

Kim, M., et al., Gremlin-1 induces BMP-independent tumor cell proliferation, migration, and invasion. Plos One, 2012. 7(4): p. e35100.

Kim, H. S., et al., GREM1 is expressed in the cancer-associated myofibroblasts of basal cell carcinomas. Plos One, 2017. 12(3): p. e0174565.

Koketsu, K., et al., Gremlin, a bone morphogenetic protein antagonist, is a crucial angiogenic factor in pituitary adenoma. Int J Endocrinol, 2015. 2015: p. 834137.

Kyle, R. A. and S. V. Rajkumar, Multiple myeloma. N Engl J Med, 2004. 351(18): p. 1860-73.

Laurila, R., et al., The expression patterns of gremlin 1 and noggin in normal adult and tumor tissues. Int J Clin Exp Pathol, 2013. 6(7): p. 1400-8.

Lavoz, C., et al., Gremlin regulates renal inflammation via vascular endothelial growth factor receptor 2 pathway. J Pathol, 2015.

Lawson, M. A., et al., Osteoclasts control reactivation of dormant myeloma cells by remodelling the endosteal niche. Nat Commun, 2015. 6: p. 8983.

Lewis A, Freeman-Mills L, de la Calle-Mustienes E, Giraldez-Perez R M, Davis H, Jaeger E, et al. A polymorphic enhancer near GREM1 influences bowel cancer risk through differential CDX2 and TCF7L2 binding. Cell Rep. 2014; 8(4):983-90.

Mitola S, Ravelli C, Moroni E, Salvi V, Leali D, Ballmer-Hofer K, et al. Gremlin is a novel agonist of the major proangiogenic receptor VEGFR2. Blood. 2010; 116(18): 3677-80.

Mulvihill, M. S., et al., Gremlin is overexpressed in lung adenocarcinoma and increases cell growth and proliferation in normal lung cells. Plos One, 2012. 7(8): p. e42264.

Namkoong, H., et al., The bone morphogenetic protein antagonist gremlin 1 is overexpressed in human cancers and interacts with YWHAH protein. BMC Cancer, 2006. 6: p. 74.

Neufert, C., Becker, C. & Neurath, M. F. An inducible mouse model of colon carcinogenesis for the analysis of sporadic and inflammation-driven tumor progression. Nat Protoc 2, 1998-2004, (2007).

Noll, J., et al., Myeloma plasma cells alter the bone marrow microenvironment by stimulating the proliferation of mesenchymal stromal cells. Haematologica, 2014. 99(1).

Noll, J. E., et al., PTTG1 expression is associated with hyperproliferative disease and poor prognosis in multiple myeloma. J Hematol Oncol, 2015. 8: p. 106.

Noll, J. E., et al., SAMSN1 Is a Tumor Suppressor Gene in Multiple Myeloma. Neoplasia, 2014. 16(7): p. 572-85.

Plaks V, Kong N, Werb Z. The cancer stem cell niche: how essential is the niche in regulating sternness of tumor cells? Cell Stem Cell. 2015; 16(3):225-38.

Ponomarev, V., et al., A novel triple-modality reporter gene for whole-body fluorescent, bioluminescent, and nuclear noninvasive imaging. Eur J Nucl Med Mol Imaging, 2004. 31(5): p. 740-51.

Sato T, Vries R G, Snippert H J, van de Wetering M, Barker N, Stange D E, et al. Single Lgr5 stem cells build crypt-villus structures in vitro without a mesenchymal niche. Nature. 2009; 459(7244):262-5.

Schmid, G. J., Kobayashi, C., Sandell, L. J. & Ornitz, D. M. (2009), Developmental Dynamics: An Official Publication of the American Association of Anatomists 238, 766-774. Fibroblast growth factor expression during skeletal fracture healing in mice.

Scoville D, Sato T, He X, Li L. Current view: intestinal stem cells and signaling Gastroenterology. 2008; 134(3):849-64.

Sethi A, Wordinger R J, Clark A F. Gremlin utilizes canonical and non-canonical TGFbeta signaling to induce lysyl oxidase (LOX) genes in human trabecular meshwork cells. Exp Eye Res. 2013; 113:117-27.

Shoshkes-Carmel, M. et al. Subepithelial telocytes are an important source of Wnts that supports intestinal crypts. Nature 557, 242-246, (2018).

Sneddon, J. B., et al., Bone morphogenetic protein antagonist gremlin 1 is widely expressed by cancer-associated stromal cells and can promote tumor cell proliferation. Proc Natl Acad Sci USA, 2006. 103(40): p. 14842-7.

Tamminen, J. A., et al., Gremlin-1 associates with fibrillin microfibrils in vivo and regulates mesothelioma cell survival through transcription factor slug. Oncogenesis, 2013. 2: p. e66.

Tomlinson I P, Carvajal-Carmona L G, Dobbins S E, Tenesa A, Jones A M, Howarth K, et al. Multiple Common Susceptibility Variants near BMP Pathway Loci GREM1, BMP4, and BMP2 Explain Part of the Missing Heritability of Colorectal Cancer. PLoS Genet. 2011; 7(6): e1002105.

Topol, L. Z., et al., Identification of drm, a novel gene whose expression is suppressed in transformed cells and which can inhibit growth of normal but not transformed cells in culture. Mol Cell Biol, 1997. 17(8): p. 4801-10.

Vande Broek, I., et al., Extravasation and homing mechanisms in multiple myeloma. Clin Exp Metastasis, 2008. 25(4): p. 325-34.

Verheyden, J. M. and X. Sun, An Fgf/Gremlin inhibitory feedback loop triggers termination of limb bud outgrowth. Nature, 2008. 454(7204): p. 638-41.

Wang, D. J., et al., The bone morphogenetic protein antagonist Gremlin is overexpressed in human malignant mesothelioma. Oncology Reports, 2012. 27(1): p. 58-64.

Worthley, D. L., et al., Gremlin 1 identifies a skeletal stem cell with bone, cartilage, and reticular stromal potential. Cell, 2015. 160(1-2): p. 269-84.

Yin, Y., et al., Overexpression of Gremlin promotes non-small cell lung cancer progression. Tumour Biol, 2015.

Yu, Y. Y. et al. (2010), Bone 46, 841-851. Immunolocalization of BMPs, BMP antagonists, receptors, and effectors during fracture repair.

WO-2014159010 (Priority: 14 Mar. 2013) Regeneron Pharmaceuticals Inc. "Human antibodies to GREM 1".

WO-2013137686 (Priority: 15 Mar. 2012) Seoul National University and Db foundation, Korea "Gremlin1 antibody".

US 2009041757A1 (Priority: 16 Mar. 2007) Stanford University, "Bone morphogenetic protein antagonist and uses thereof".

WO2007124486 (Priority: 21 Apr. 2007) Children's Hospital Los Angeles, "BMP4 inhibitors".

WO2002054940 (Priority: 12 Jan. 2001) University of Medicine and Dentistry of New Jersey, "Bone morphogenetic protein-2 in the treatment and diagnosis of cancer".

---

The invention claimed is:

1. A method of treating a cancer having a stromal Gremlin-1 (GREM1) overexpression, wherein the method comprises administering a therapeutically effective amount of an anti-Gremlin-1 antagonist to a subject in need thereof, wherein the antagonist is an anti-Gremlin-1 antibody comprising a HCDR1/HCDR2/HCDR3/LCDR1/LCDR2/LCDR3 sequence combination of SEQ ID NOs: 4/5/6/7/8/9 or SEQ ID NOs: 3/5/6/7/8/9.

2. The method according to claim 1, wherein the cancer is a solid cancer.

3. The method according to claim 1, wherein the cancer is colorectal cancer.

4. The method according to claim 3, wherein the colorectal cancer is a mesenchymal subtype colorectal cancer.

5. The method according to claim 2, wherein the cancer is multiple myeloma.

6. The method according to claim 2, wherein the cancer is breast cancer.

7. The method according to claim 1, wherein:
(a) the cancer is a disseminated cancer; or
(b) the cancer is an established cancer.

8. The method according to claim 7, wherein the established cancer is an established colorectal cancer.

9. The method according to claim 1, wherein the anti-Gremlin-1 antibody comprises a heavy chain variable region (HCVR) sequence of SEQ ID NO: 10 or 12 and/or a light chain variable region (LCVR) sequence of SEQ ID NO: 11 or 13; optionally wherein the anti-Gremlin-1 antibody comprises a HCVR and LCVR sequence pair of SEQ ID NOs: 10/11 or 12/13.

10. The method according to claim 9, wherein the anti-Gremlin-1 antibody comprises a heavy chain of SEQ ID NO: 14, 16, 18, 22, 28, 30, 32 or 34 and/or a light chain of SEQ ID NO: 15, 17, 19, 23, 29, 31, 33 or 35; optionally wherein the anti-Gremlin-1 antibody comprises a heavy and light chain pair of SEQ ID NOs: 14/15, 16/17, 18/19, 22/23, 28/29, 30/31, 32/33 or 34/35.

11. The method according to claim 1, wherein:
(a) the antagonist antibody is a chimeric, human or humanised antibody; or
(b) the antagonist antibody is a Fab, Fab', F(ab')$_2$, Fv or an scFv.

12. The method according to claim 1, wherein the antagonist antibody is comprised in a pharmaceutical composition further comprising a pharmaceutically acceptable adjuvant and/or carrier.

13. The method according to claim 1, wherein:
(a) the method comprises separate, sequential or simultaneous administration of an additional anti-cancer agent; and/or
(b) the method comprises separate, sequential or simultaneous radiotherapy.

14. The method according to claim 13, wherein said additional anti-cancer agent is a chemotherapeutic agent.

15. The method according to claim 1, wherein the cancer is a familial cancer.

16. The method according to claim 1, wherein polyposis is associated with the cancer.

17. The method according to claim 16, wherein the cancer or polyposis associated with the cancer is familial adenomatous polyposis (FAP) or Hereditary Mixed Polyposis Syndrome (HMPS).

18. The method according to claim 1, wherein the anti-Gremlin-1 antibody comprises a HCDR1/HCDR2/HCDR3/LCDR1/LCDR2/LCDR3 sequence combination of SEQ ID NOs: 4/5/6/7/8/9.

19. The method according to claim 1, wherein the anti-Gremlin-1 antibody comprises a HCDR1/HCDR2/HCDR3/LCDR1/LCDR2/LCDR3 sequence combination of SEQ ID NOs: 3/5/6/7/8/9.

20. The method according to claim 1, wherein the cancer is selected from the group consisting of colorectal cancer, multiple myeloma, pancreatic cancer, bladder cancer, breast cancer, lung cancer, stomach cancer, duodenal cancer, oesophageal cancer, head and neck cancer, prostate cancer, glioma, endometrial cancer, liver cancer, spleen cancer, bone-resident cancer, and osteosarcoma.

21. A method of treating a cancer having epithelial GREM1 overexpression, wherein the method comprises administering a therapeutically effective amount of an anti-Gremlin-1 antagonist to a subject in need thereof, wherein the antagonist is an anti-Gremlin-1 antibody comprising a HCDR1/HCDR2/HCDR3/LCDR1/LCDR2/LCDR3 sequence combination of SEQ ID NOs: 4/5/6/7/8/9 or SEQ ID NOs: 3/5/6/7/8/9, optionally wherein the cancer is a GREM1-initiated cancer.

22. A method of treating a cancer having stromal GREM1 overexpression, wherein the method comprises administering a therapeutically effective amount of an anti-Gremlin-1 antagonist to a subject in need thereof, wherein the antagonist is an anti-Gremlin-1 antibody comprising a HCDR1/HCDR2/HCDR3/LCDR1/LCDR2/LCDR3 sequence combination of SEQ ID NOs: 4/5/6/7/8/9 or SEQ ID NOs: 3/5/6/7/8/9, wherein the method comprises separate, sequential or simultaneous administration of an additional anti-cancer agent.

23. The method according to claim 22, wherein the additional anti-cancer agent is a chemotherapeutic agent.

24. The method according to claim 22, wherein said anti-cancer or chemotherapeutic agent is suitable for treatment of colorectal cancer.

25. The method according to claim 24, wherein said anti-cancer or chemotherapeutic agent is selected from 5-fluoruracil, oxaliplatin, irinotecan, folinic acid, cetuximab, nivolumab or bevacizumab.

26. A method of treating a cancer having stromal GREM1 overexpression, wherein the method comprises administering a therapeutically effective amount of an anti-Gremlin-1 antagonist to a subject in need thereof, wherein the antagonist is an anti-Gremlin-1 antibody comprising a HCDR1/HCDR2/HCDR3/LCDR1/LCDR2/LCDR3 sequence combination of SEQ ID NOs: 4/5/6/7/8/9 or SEQ ID NOs: 3/5/6/7/8/9, wherein the method comprises separate, sequential or simultaneous administration of an additional anti-cancer agent or chemotherapeutic agent suitable for treatment of multiple myeloma.

27. The method according to claim 26, wherein the additional anti-cancer agent or chemotherapeutic agent is selected from an anti-CD38 antibody, an anti-SLAMF7 antibody, an anti-IL-6 antibody, bortezumib or an iMID.

28. The method according to claim 27, wherein:
(a) the anti-CD38 antibody is daratumumab;
(b) the anti-SLAMF7 antibody is elotuzumab; and
(c) the anti-IL-6 antibody is siltuximab.

29. The method according to claim 26, wherein the chemotherapeutic agent is an iMID, and wherein the iMID is lenalidomide/pomalenomide or an analogue of either thereof.

* * * * *

SEQUENCE LISTING

```
<160> NUMBER OF SEQ ID NOS: 43

<210> SEQ ID NO 1
<211> LENGTH: 184
<212> TYPE: PRT
<213> ORGANISM: Homo sapiens

<400> SEQUENCE: 1

Met Ser Arg Thr Ala Tyr Thr Val Gly Ala Leu Leu Leu Leu Leu Gly
1               5                   10                  15

Thr Leu Leu Pro Ala Ala Glu Gly Lys Lys Lys Gly Ser Gln Gly Ala
            20                  25                  30

Ile Pro Pro Pro Asp Lys Ala Gln His Asn Asp Ser Glu Gln Thr Gln
        35                  40                  45

Ser Pro Gln Gln Pro Gly Ser Arg Asn Arg Gly Arg Gly Gln Gly Arg
    50                  55                  60

Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
            100                 105                 110

Ile Ile Asn Arg Phe Cys Tyr Gly Gln Cys Asn Ser Phe Tyr Ile Pro
        115                 120                 125
```

```
Arg His Ile Arg Lys Glu Glu Gly Ser Phe Gln Ser Cys Ser Phe Cys
    130                 135                 140

Lys Pro Lys Lys Phe Thr Thr Met Met Val Thr Leu Asn Cys Pro Glu
145                 150                 155                 160

Leu Gln Pro Pro Thr Lys Lys Lys Arg Val Thr Arg Val Lys Gln Cys
            165                 170                 175

Arg Cys Ile Ser Ile Asp Leu Asp
            180

<210> SEQ ID NO 2
<211> LENGTH: 139
<212> TYPE: PRT
<213> ORGANISM: Artificial Sequence
<220> FEATURE:
<223> OTHER INFORMATION: Human truncated Gremlin-1 used in
      crystallography with N-terminal tag

<400> SEQUENCE: 2

Met Gly Ser Ser His His His His His Ser Gly Glu Asn Leu
1               5                   10                  15

Tyr Phe Gln Gly Ser Ala Met Pro Gly Glu Glu Val Leu Glu Ser Ser
                20                  25                  30

Gln Glu Ala Leu His Val Thr Glu Arg Lys Tyr Leu Lys Arg Asp Trp
        35                  40                  45

Cys Lys Thr Gln Pro Leu Lys Gln Thr Ile His Glu Glu Gly Cys Asn
    50                  55                  60

Ser Arg Thr Ile Ile Asn Arg Phe Cys Tyr Gly Gln Cys Asn Ser Phe
65                  70                  75                  80

Tyr Ile Pro Arg His Ile Arg Lys Glu Glu Gly Ser Phe Gln Ser Cys
                85                  90                  95

Ser Phe Cys Lys Pro Lys Lys Phe Thr Thr Met Met Val Thr Leu Asn
                100                 105                 110

Cys Pro Glu Leu Gln Pro Pro Thr Lys Lys Lys Arg Val Thr Arg Val
                115                 120                 125

Lys Gln Cys Arg Cys Ile Ser Ile Asp Leu Asp
        130                 135

<210> SEQ ID NO 3
<211> LENGTH: 10
<212> TYPE: PRT
<213> ORGANISM: Artificial Sequence
<220> FEATURE:
<223> OTHER INFORMATION: Ab7326 HCDR1 combined Kabat & Chothia

<400> SEQUENCE: 3

Gly Tyr Thr Phe Thr Asp Tyr Tyr Met His
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Ab7326 HCDR1 Kabat

<400> SEQUENCE: 4

Asp Tyr Tyr Met His
1               5

<210> SEQ ID NO 5
```

```
<211> LENGTH: 17
<212> TYPE: PRT
<213> ORGANISM: Artificial Sequence
<220> FEATURE:
<223> OTHER INFORMATION: Ab7326 HCDR2 Kabat

<400> SEQUENCE: 5

Leu Val Asp Pro Glu Asp Gly Glu Thr Ile Tyr Ala Glu Lys Phe Gln
1               5                   10                  15

Gly

<210> SEQ ID NO 6
<211> LENGTH: 15
<212> TYPE: PRT
<213> ORGANISM: Artificial Sequence
<220> FEATURE:
<223> OTHER INFORMATION: Ab7326 HCDR3 Kabat

<400> SEQUENCE: 6

Asp Ala Arg Gly Ser Gly Ser Tyr Tyr Pro Asn His Phe Asp Tyr
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Ab7326 LCDR1 Kabat

<400> SEQUENCE: 7

Lys Ser Ser Gln Ser Val Leu Tyr Ser Ser Asn Asn Lys Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Ab7326 LCDR2 Kabat

<400> SEQUENCE: 8

Trp Ala Ser Thr Arg Glu Ser
1               5

<210> SEQ ID NO 9
<211> LENGTH: 8
<212> TYPE: PRT
<213> ORGANISM: Artificial Sequence
<220> FEATURE:
<223> OTHER INFORMATION: Ab7326 LCDR3 Kabat

<400> SEQUENCE: 9

Gln Gln Tyr Tyr Asp Thr Pro Thr
1               5

<210> SEQ ID NO 10
<211> LENGTH: 124
<212> TYPE: PRT
<213> ORGANISM: Artificial Sequence
<220> FEATURE:
<223> OTHER INFORMATION: Ab7326 Heavy chain variable region variant 1

<400> SEQUENCE: 10

Gln Val Gln Leu Val Glu Ser Gly Ala Glu Val Lys Lys Pro Gly Ala
1               5                   10                  15
```

```
Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Ala Arg Gly Ser Gly Ser Tyr Tyr Pro Asn His Phe Asp
            100                 105                 110

Tyr Trp Gly Gln Gly Thr Leu Val Thr Val Ser Ser
        115                 120
```

```
<210> SEQ ID NO 11
<211> LENGTH: 112
<212> TYPE: PRT
<213> ORGANISM: Artificial Sequence
<220> FEATURE:
<223> OTHER INFORMATION: Ab7326 Light chain variable region variant 1

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Phe Cys Gln Gln
                85                  90                  95

Tyr Tyr Asp Thr Pro Thr Phe Gly Gln Gly Thr Arg Leu Glu Ile Lys
            100                 105                 110
```

```
<210> SEQ ID NO 12
<211> LENGTH: 124
<212> TYPE: PRT
<213> ORGANISM: Artificial Sequence
<220> FEATURE:
<223> OTHER INFORMATION: Ab7326 Heavy chain variable region variant 2

<400> SEQUENCE: 12

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
```

-continued

```
                85                  90                  95

Ala Thr Asp Ala Arg Gly Ser Gly Ser Tyr Tyr Pro Asn His Phe Asp
            100                 105                 110

Tyr Trp Gly Gln Gly Thr Leu Val Thr Val Ser Ser
        115                 120

<210> SEQ ID NO 13
<211> LENGTH: 112
<212> TYPE: PRT
<213> ORGANISM: Artificial Sequence
<220> FEATURE:
<223> OTHER INFORMATION: Ab7326 Light chain variable region variant 2

<400> SEQUENCE: 13

Asp Ile Val Met Thr Gln Thr Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Phe Cys Gln Gln
                85                  90                  95

Tyr Tyr Asp Thr Pro Thr Phe Gly Gln Gly Thr Arg Leu Glu Ile Lys
            100                 105                 110

<210> SEQ ID NO 14
<211> LENGTH: 448
<212> TYPE: PRT
<213> ORGANISM: Artificial Sequence
<220> FEATURE:
<223> OTHER INFORMATION: Mouse full length IgG1 heavy chain variant 1

<400> SEQUENCE: 14

Gln Val Gln Leu Val Glu Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Ala Arg Gly Ser Gly Ser Tyr Tyr Pro Asn His Phe Asp
            100                 105                 110

Tyr Trp Gly Gln Gly Thr Leu Val Thr Val Ser Ser Ala Lys Thr Thr
        115                 120                 125

Pro Pro Ser Val Tyr Pro Leu Ala Pro Gly Ser Ala Ala Gln Thr Asn
    130                 135                 140

Ser Met Val Thr Leu Gly Cys Leu Val Lys Gly Tyr Phe Pro Glu Pro
145                 150                 155                 160
```

```
Val Thr Val Thr Trp Asn Ser Gly Ser Leu Ser Ser Gly Val His Thr
            165                 170                 175

Phe Pro Ala Val Leu Gln Ser Asp Leu Tyr Thr Leu Ser Ser Ser Val
            180                 185                 190

Thr Val Pro Ser Ser Thr Trp Pro Ser Glu Thr Val Thr Cys Asn Val
            195                 200                 205

Ala His Pro Ala Ser Ser Thr Lys Val Asp Lys Lys Ile Val Pro Arg
210                 215                 220

Asp Cys Gly Cys Lys Pro Cys Ile Cys Thr Val Pro Glu Val Ser Ser
225                 230                 235                 240

Val Phe Ile Phe Pro Pro Lys Pro Lys Asp Val Leu Thr Ile Thr Leu
            245                 250                 255

Thr Pro Lys Val Thr Cys Val Val Val Asp Ile Ser Lys Asp Asp Pro
            260                 265                 270

Glu Val Gln Phe Ser Trp Phe Val Asp Asp Val Glu Val His Thr Ala
            275                 280                 285

Gln Thr Gln Pro Arg Glu Glu Gln Phe Asn Ser Thr Phe Arg Ser Val
            290                 295                 300

Ser Glu Leu Pro Ile Met His Gln Asp Trp Leu Asn Gly Lys Glu Phe
305                 310                 315                 320

Lys Cys Arg Val Asn Ser Ala Ala Phe Pro Ala Pro Ile Glu Lys Thr
                325                 330                 335

Ile Ser Lys Thr Lys Gly Arg Pro Lys Ala Pro Gln Val Tyr Thr Ile
            340                 345                 350

Pro Pro Pro Lys Glu Gln Met Ala Lys Asp Lys Val Ser Leu Thr Cys
            355                 360                 365

Met Ile Thr Asp Phe Phe Pro Glu Asp Ile Thr Val Glu Trp Gln Trp
370                 375                 380

Asn Gly Gln Pro Ala Glu Asn Tyr Lys Asn Thr Gln Pro Ile Met Asp
385                 390                 395                 400

Thr Asp Gly Ser Tyr Phe Val Tyr Ser Lys Leu Asn Val Gln Lys Ser
                405                 410                 415

Asn Trp Glu Ala Gly Asn Thr Phe Thr Cys Ser Val Leu His Glu Gly
            420                 425                 430

Leu His Asn His His Thr Glu Lys Ser Leu Ser His Ser Pro Gly Lys
            435                 440                 445

<210> SEQ ID NO 15
<211> LENGTH: 219
<212> TYPE: PRT
<213> ORGANISM: Artificial Sequence
<220> FEATURE:
<223> OTHER INFORMATION: Mouse full length IgG1 light chain variant 1

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Asn Ser Leu Gln Ala Glu Asp Val Ala Val Tyr Phe Cys Gln Gln
                85                  90                  95

Tyr Tyr Asp Thr Pro Thr Phe Gly Gln Gly Thr Arg Leu Glu Ile Lys
            100                 105                 110

Arg Thr Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 16
<211> LENGTH: 454
<212> TYPE: PRT
<213> ORGANISM: Artificial Sequence
<220> FEATURE:
<223> OTHER INFORMATION: Human full length IgG1 heavy chain variant 2

<400> SEQUENCE: 16

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Ala Arg Gly Ser Gly Ser Tyr Tyr Pro Asn His Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220
```

```
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 17
<211> LENGTH: 219
<212> TYPE: PRT
<213> ORGANISM: Artificial Sequence
<220> FEATURE:
<223> OTHER INFORMATION: Human full length IgG1 light chain variant 2

<400> SEQUENCE: 17

Asp Ile Val Met Thr Gln Thr Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Phe Cys Gln Gln
            85                  90                  95

Tyr Tyr Asp Thr Pro Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 18
<211> LENGTH: 227
<212> TYPE: PRT
<213> ORGANISM: Artificial Sequence
<220> FEATURE:
<223> OTHER INFORMATION: Fab heavy chain variant 1

<400> SEQUENCE: 18

```
Gln Val Gln Leu Val Glu Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Ala Arg Gly Ser Gly Ser Tyr Tyr Pro Asn His Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225
```

<210> SEQ ID NO 19
<211> LENGTH: 219
<212> TYPE: PRT
<213> ORGANISM: Artificial Sequence
<220> FEATURE:

<223> OTHER INFORMATION: Fab light chain variant 1

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Phe Cys Gln Gln
                85                  90                  95

Tyr Tyr Asp Thr Pro Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215

<210> SEQ ID NO 20
<211> LENGTH: 118
<212> TYPE: PRT
<213> ORGANISM: Artificial Sequence
<220> FEATURE:
<223> OTHER INFORMATION: Human truncated Gremlin-1 used in
      crystallography without N-terminal tag

<400> SEQUENCE: 20

Ala Met Pro Gly Glu Glu Val Leu Glu Ser Ser Gln Glu Ala Leu His
1               5                   10                  15

Val Thr Glu Arg Lys Tyr Leu Lys Arg Asp Trp Cys Lys Thr Gln Pro
            20                  25                  30

Leu Lys Gln Thr Ile His Glu Glu Gly Cys Asn Ser Arg Thr Ile Ile
        35                  40                  45

Asn Arg Phe Cys Tyr Gly Gln Cys Asn Ser Phe Tyr Ile Pro Arg His
        50                  55                  60

Ile Arg Lys Glu Glu Gly Ser Phe Gln Ser Cys Ser Phe Cys Lys Pro
65                  70                  75                  80

Lys Lys Phe Thr Thr Met Met Val Thr Leu Asn Cys Pro Glu Leu Gln
                85                  90                  95

Pro Pro Thr Lys Lys Lys Arg Val Thr Arg Val Lys Gln Cys Arg Cys
            100                 105                 110

Ile Ser Ile Asp Leu Asp

-continued

```
                115

<210> SEQ ID NO 21
<211> LENGTH: 160
<212> TYPE: PRT
<213> ORGANISM: Artificial Sequence
<220> FEATURE:
<223> OTHER INFORMATION: Mature Gremlin-1 sequence of SEQ ID NO: 1
      lacking the signal peptide of amino acids 1-21

<400> SEQUENCE: 21

Lys Lys Lys Gly Ser Gln Gly Ala Ile Pro Pro Asp Lys Ala Gln
1               5                   10                  15

His Asn Asp Ser Glu Gln Thr Gln Ser Pro Gln Gln Pro Gly Ser Arg
            20                  25                  30

Asn Arg Gly Arg Gly Gln Gly Arg Gly Thr Ala Met Pro Gly Glu Glu
        35                  40                  45

Val Leu Glu Ser Ser Gln Glu Ala Leu His Val Thr Glu Arg Lys Tyr
    50                  55                  60

Leu Lys Arg Asp Trp Cys Lys Thr Gln Pro Leu Lys Gln Thr Ile His
65                  70                  75                  80

Glu Glu Gly Cys Asn Ser Arg Thr Ile Ile Asn Arg Phe Cys Tyr Gly
                85                  90                  95

Gln Cys Asn Ser Phe Tyr Ile Pro Arg His Ile Arg Lys Glu Glu Gly
            100                 105                 110

Ser Phe Gln Ser Cys Ser Phe Cys Lys Pro Lys Lys Phe Thr Thr Met
        115                 120                 125

Met Val Thr Leu Asn Cys Pro Glu Leu Gln Pro Pro Thr Lys Lys Lys
    130                 135                 140

Arg Val Thr Arg Val Lys Gln Cys Arg Cys Ile Ser Ile Asp Leu Asp
145                 150                 155                 160

<210> SEQ ID NO 22
<211> LENGTH: 451
<212> TYPE: PRT
<213> ORGANISM: Artificial Sequence
<220> FEATURE:
<223> OTHER INFORMATION: Human IgG4P heavy chain variant 1

<400> SEQUENCE: 22

Gln Val Gln Leu Val Glu Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Ala Arg Gly Ser Gly Ser Tyr Tyr Pro Asn His Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140
```

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 23
<211> LENGTH: 219
<212> TYPE: PRT
<213> ORGANISM: Artificial Sequence
<220> FEATURE:
<223> OTHER INFORMATION: Human IgG4P light chain variant 1

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Asn Ser Leu Gln Ala Glu Asp Val Ala Val Tyr Phe Cys Gln Gln
                 85                  90                  95

Tyr Tyr Asp Thr Pro Thr Phe Gly Gln Gly Thr Arg Leu Glu Ile Lys
             100                 105                 110

Arg Thr Val Ala Ala Pro Ser Val Phe Ile Phe Pro Pro Ser Asp Glu
         115                 120                 125

Gln Leu Lys Ser Gly Thr Ala Ser Val Val Cys Leu Leu Asn Asn Phe
     130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 24
<211> LENGTH: 1362
<212> TYPE: DNA
<213> ORGANISM: Artificial Sequence
<220> FEATURE:
<223> OTHER INFORMATION: Human IgG1 heavy chain DNA variant 1

<400> SEQUENCE: 24
caagtgcaac tggtggaatc cggggccgaa gtgaaaaagc ccggagccac tgtgaagatc     60
tcttgcaaag tgtccggcta caccttcacc gactattaca tgcactgggt ccagcaggca    120
cctgggaagg ccttgagtg gatgggtctg gtcgatcccg aggacggcga aactatctac    180
gccgagaagt tccagggtcg cgtcaccatc accgccgaca cttccaccga caccgcgtac    240
atggagctgt ccagcttgag gtccgaggac acagccgtgt actactgcgc cacgatgct    300 cggggaagcg gcagctacta cccgaaccac ttcgactact ggggacaggg cactctcgtg    360
actgtctcga gcgcttctac aaagggcccc tccgtgttcc cgctcgctcc atcatcgaag    420
tctaccagcg gaggcactgc ggctctcggt tgcctcgtga aggactactt cccggagccg    480
gtgaccgtgt cgtggaacag cggagccctg accagcgggg tgcacacctt ccggccgtc    540 ttgcagtcaa gcggccttta ctccctgtca tcagtggtga ctgtcccgtc cagctcattg    600
ggaacccaaa cctacatctg caatgtgaat cacaaaccta gcaacaccaa ggttgacaag    660
aaagtcgagc ccaaatcgtg tgacaagact cacacttgtc cgccgtgccc ggcacccgaa    720
ctgctgggag tcccagcgt ctttctgttc cctccaaagc cgaaagacac gctgatgatc    780
tcccgcaccc cggaggtcac ttgcgtggtc gtggacgtgt cacatgagga cccagaggtg    840
aagttcaatt ggtacgtgga tggcgtcgaa gtccacaatg ccaaaactaa gcccagagaa    900
gaacagtaca attcgaccta ccgcgtcgtg tccgtgctca cggtgttgca tcaggattgg    960
ctgaacggga aggaatacaa gtgcaaagtg tccaacaagg cgctgccggc accgatcgag   1020
aaaactatct ccaaagcgaa gggacagcct agggaacctc aagtctacac gctgccacca   1080

```
tcacgggatg aactgactaa gaatcaagtc tcactgactt gtctggtgaa ggggttttac    1140
cctagcgaca ttgccgtgga gtgggaatcc aacggccagc cagagaacaa ctacaagact    1200 accccctccag tgctcgactc ggatggatcg ttcttccttt actcgaagct caccgtggat   1260
aagtcccggt ggcagcaggg aaacgtgttc tcctgctcgg tgatgcatga agccctccat    1320
aaccactata cccaaaagtc gctgtccctg tcgccgggaa ag                       1362
```

<210> SEQ ID NO 25
<211> LENGTH: 657
<212> TYPE: DNA
<213> ORGANISM: Artificial Sequence
<220> FEATURE:
<223> OTHER INFORMATION: Human IgG1 light chain DNA variant 1

<400> SEQUENCE: 25

```
gacattgtga tgacccagtc ccccgattcg cttgcggtgt ccctgggaga acgggccacc     60
attaactgca agagctcaca gtccgtcctg tattcatcga acaacaagaa ttacctcgca    120
tggtatcagc agaagcctgg acagcctccc aagctgctca tctactgggc tagcacccgc    180
gaatccgggg tgccggatag attctccgga tcgggttcgg gcactgactt cactctgact    240
atcaactcac tgcaagccga ggatgtcgcg gtgtacttct gtcagcagta ctacgacacc    300
ccgacctttg gacaaggcac cagactggag attaagcgta cggtggccgc tcccctccgtg   360 ttcatcttcc caccctccga cgagcagctg aagtccggca ccgcctccgt cgtgtgcctg    420
ctgaacaact ctacccccg cgaggccaag gtgcagtgga aggtggacaa cgccctgcag     480
tccggcaact cccaggaatc cgtcaccgag caggactcca aggacagcac ctactccctg    540
tcctccaccc tgaccctgtc caaggccgac tacgagaagc acaaggtgta cgcctgcgaa    600
gtgacccacc agggcctgtc cagccccgtg accaagtcct caaccgggg cgagtgc       657
```

<210> SEQ ID NO 26
<211> LENGTH: 1353
<212> TYPE: DNA
<213> ORGANISM: Artificial Sequence
<220> FEATURE:
<223> OTHER INFORMATION: Human IgG4P heavy chain DNA variant 1

<400> SEQUENCE: 26

```
caagtgcaac tggtggaatc cggggccgaa gtgaaaaagc ccggagccac tgtgaagatc     60
tcttgcaaag tgtccggcta caccttcacc gactattaca tgcactgggt ccagcaggca    120
cctgggaagg gccttgagtg gatgggtctg gtcgatcccg aggacggcga aactatctac    180
gccgagaagt tccagggtcg cgtcaccatc accgccgaca cttccaccga caccgcgtac    240
atggagctgt ccagcttgag gtccgaggac acagccgtgt actactgcgc cacggatgct    300
cggggaagcg gcagctacta cccgaaccac ttcgactact ggggacaggg cactctcgtg    360
actgtctcga gcgcttctac aaagggcccc tccgtgttcc ctctggcccc ttgctcccgg    420
tccacctccg agtctaccgc cgctctgggc tgcctggtca aggactactt ccccgagccc    480
gtgacagtgt cctggaactc tggcgccctg acctccggcg tgcacacctt ccctgccgtg    540
ctgcagtcct ccggcctgta ctccctgtcc tccgtcgtga ccgtgccctc ctccagcctg    600
ggcaccaaga cctacacctg taacgtggac cacaagccct caacaccaa ggtggacaag    660 cgggtggaat ctaagtacgg ccctccctgc cccccctgcc ctgcccctga atttctgggc    720
ggaccttccg tgttcctgtt ccccccaaag cccaaggaca cctgatgat ctcccggacc    780
```

```
cccgaagtga cctgcgtggt ggtggacgtg tcccaggaag atcccgaggt ccagttcaat    840
tggtacgtgg acggcgtgga agtgcacaat gccaagacca gcccagaga ggaacagttc     900 aactccacct accgggtggt gtccgtgctg accgtgctgc accaggactg gctgaacggc    960
aaagagtaca agtgcaaggt gtccaacaag ggcctgccct ccagcatcga aaagaccatc    1020
tccaaggcca agggccagcc ccgcgagccc caggtgtaca ccctgccccc tagccaggaa    1080
gagatgacca agaaccaggt gtccctgacc tgtctggtca agggcttcta ccccTccgac    1140
attgccgtgg aatgggagtc caacggccag cccgagaaca actacaagac cacccccct     1200 gtgctggaca cgacggctc cttcttcctg tactctcggc tgaccgtgga caagtcccgg    1260
tggcaggaag gcaacgtctt ctcctgctcc gtgatgcacg aggccctgca caaccactac    1320
acccagaagt ccctgtccct gagcctgggc aag                                1353

<210> SEQ ID NO 27
<211> LENGTH: 657
<212> TYPE: DNA
<213> ORGANISM: Artificial Sequence
<220> FEATURE:
<223> OTHER INFORMATION: Human IgG4P light chain DNA variant 1

<400> SEQUENCE: 27
gacattgtga tgacccagtc ccccgattcg cttgcggtgt ccctgggaga acgggccacc    60
attaactgca agagctcaca gtccgtcctg tattcatcga caacaagaa ttacctcgca    120 tggtatcagc agaagcctgg acagcctccc aagctgctca tctactgggc tagcacccgc    180
gaatccgggg tgccggatag attctccgga tcgggttcgg gcactgactt cactctgact    240
atcaactcac tgcaagccga ggatgtcgcg gtgtacttct gtcagcagta ctacgacacc    300
ccgacctttg gacaaggcac cagactggag attaagcgta cggtggccgc tcccctcgtg    360
ttcatcttcc caccctccga cgagcagctg aagtccggca ccgcctccgt cgtgtgcctg    420
ctgaacaact ctaccccccg cgaggccaag gtgcagtgga aggtggacaa cgccctgcag    480
tccggcaact cccaggaatc cgtcaccgag caggactcca aggacagcac ctactccctg    540
tcctccaccc tgaccctgtc caaggccgac tacgagaagc acaaggtgta cgcctgcgaa    600
gtgacccacc agggcctgtc cagccccgtg accaagtcct tcaaccgggg cgagtgc      657

<210> SEQ ID NO 28
<211> LENGTH: 448
<212> TYPE: PRT
<213> ORGANISM: Artificial Sequence
<220> FEATURE:
<223> OTHER INFORMATION: Mouse full length IgG1 heavy chain variant 2

<400> SEQUENCE: 28

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95
```

Ala Thr Asp Ala Arg Gly Ser Gly Ser Tyr Tyr Pro Asn His Phe Asp
            100                 105                 110

Tyr Trp Gly Gln Gly Thr Leu Val Thr Val Ser Ser Ala Lys Thr Thr
        115                 120                 125

Pro Pro Ser Val Tyr Pro Leu Ala Pro Gly Ser Ala Ala Gln Thr Asn
    130                 135                 140

Ser Met Val Thr Leu Gly Cys Leu Val Lys Gly Tyr Phe Pro Glu Pro
145                 150                 155                 160

Val Thr Val Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Pro Ser Ser Thr Trp Pro Ser Glu Thr Val Thr Cys Asn Val
        195                 200                 205

Ala His Pro Ala Ser Ser Thr Lys Val Asp Lys Lys Ile Val Pro Arg
    210                 215                 220

Asp Cys Gly Cys Lys Pro Cys Ile Cys Thr Val Pro Glu Val Ser Ser
225                 230                 235                 240

Val Phe Ile Phe Pro Pro Lys Pro Lys Asp Val Leu Thr Ile Thr Leu
                245                 250                 255

Thr Pro Lys Val Thr Cys Val Val Val Asp Ile Ser Lys Asp Asp Pro
            260                 265                 270

Glu Val Gln Phe Ser Trp Phe Val Asp Asp Val Glu Val His Thr Ala
        275                 280                 285

Gln Thr Gln Pro Arg Glu Glu Gln Phe Asn Ser Thr Phe Arg Ser Val
    290                 295                 300

Ser Glu Leu Pro Ile Met His Gln Asp Trp Leu Asn Gly Lys Glu Phe
305                 310                 315                 320

Lys Cys Arg Val Asn Ser Ala Ala Phe Pro Ala Pro Ile Glu Lys Thr
                325                 330                 335

Ile Ser Lys Thr Lys Gly Arg Pro Lys Ala Pro Gln Val Tyr Thr Ile
            340                 345                 350

Pro Pro Pro Lys Glu Gln Met Ala Lys Asp Lys Val Ser Leu Thr Cys
        355                 360                 365

Met Ile Thr Asp Phe Phe Pro Glu Asp Ile Thr Val Glu Trp Gln Trp
    370                 375                 380

Asn Gly Gln Pro Ala Glu Asn Tyr Lys Asn Thr Gln Pro Ile Met Asp
385                 390                 395                 400

Thr Asp Gly Ser Tyr Phe Val Tyr Ser Lys Leu Asn Val Gln Lys Ser
                405                 410                 415

Asn Trp Glu Ala Gly Asn Thr Phe Thr Cys Ser Val Leu His Glu Gly
            420                 425                 430

Leu His Asn His His Thr Glu Lys Ser Leu Ser His Ser Pro Gly Lys
        435                 440                 445

<210> SEQ ID NO 29
<211> LENGTH: 219
<212> TYPE: PRT
<213> ORGANISM: Artificial Sequence
<220> FEATURE:
<223> OTHER INFORMATION: Mouse full length IgG1 light chain variant 2

<400> SEQUENCE: 29

Asp Ile Val Met Thr Gln Thr Pro Asp Ser Leu Ala Val Ser Leu Gly
1               5                   10                  15

```
Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Asn Ser Leu Gln Ala Glu Asp Val Ala Val Tyr Phe Cys Gln Gln
                85                  90                  95

Tyr Tyr Asp Thr Pro Thr Phe Gly Gln Gly Thr Arg Leu Glu Ile Lys
                100                 105                 110

Arg Thr Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
    210                 215

<210> SEQ ID NO 30
<211> LENGTH: 454
<212> TYPE: PRT
<213> ORGANISM: Artificial Sequence
<220> FEATURE:
<223> OTHER INFORMATION: Human full length IgG1 heavy chain variant 1

<400> SEQUENCE: 30

Gln Val Gln Leu Val Glu Ser Gly Ala Glu Val Lys Lys Pro Gly Ala
1               5                   10                  15

Thr Val Lys Ile Ser Cys Lys Val Ser Gly Tyr Thr Phe Thr Asp Tyr
                20                  25                  30

Tyr Met His Trp Val Gln Gln Ala Pro Gly Lys Gly Leu Glu Trp Met
            35                  40                  45

Gly Leu Val Asp Pro Glu Asp Gly Glu Thr Ile Tyr Ala Glu Lys Phe
 50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Ala Thr Asp Ala Arg Gly Ser Gly Ser Tyr Tyr Pro Asn His Phe Asp
                100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160
```

```
Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 31
<211> LENGTH: 219
<212> TYPE: PRT
<213> ORGANISM: Artificial Sequence
<220> FEATURE:
<223> OTHER INFORMATION: Human full length IgG1 light chain variant 1

<400> SEQUENCE: 31

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60
```

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Phe Cys Gln Gln
                85                  90                  95

Tyr Tyr Asp Thr Pro Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
210                 215

<210> SEQ ID NO 32
<211> LENGTH: 227
<212> TYPE: PRT
<213> ORGANISM: Artificial Sequence
<220> FEATURE:
<223> OTHER INFORMATION: Fab heavy chain variant 2

<400> SEQUENCE: 32

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Ala Arg Gly Ser Gly Ser Tyr Tyr Pro Asn His Phe Asp
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Val Glu Pro
    210                 215                 220

Lys Ser Cys
225

<210> SEQ ID NO 33
<211> LENGTH: 219
<212> TYPE: PRT
<213> ORGANISM: Artificial Sequence
<220> FEATURE:
<223> OTHER INFORMATION: Fab light chain variant 2

<400> SEQUENCE: 33

Asp Ile Val Met Thr Gln Thr Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Phe Cys Gln Gln
                85                  90                  95

Tyr Tyr Asp Thr Pro Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 34
<211> LENGTH: 451
<212> TYPE: PRT
<213> ORGANISM: Artificial Sequence
<220> FEATURE:
<223> OTHER INFORMATION: Human IgG4P heavy chain variant 2

<400> SEQUENCE: 34

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe

```
            50                  55                  60
Gln Gly Arg Val Thr Ile Thr Ala Asp Thr Ser Thr Asp Thr Ala Tyr
 65                      70                  75                  80

Met Glu Leu Ser Ser Leu Arg Ser Glu Asp Thr Ala Val Tyr Tyr Cys
                     85                  90                  95

Ala Thr Asp Ala Arg Gly Ser Gly Ser Tyr Tyr Pro Asn His Phe Asp
                100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Cys Ser Arg Ser Thr Ser Glu
        130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 35
```

```
<211> LENGTH: 219
<212> TYPE: PRT
<213> ORGANISM: Artificial Sequence
<220> FEATURE:
<223> OTHER INFORMATION: Human IgG4P light chain variant 2

<400> SEQUENCE: 35
```

Asp Ile Val Met Thr Gln Thr Pro Asp Ser Leu Ala Val Ser Leu Gly
1               5                   10                  15

Glu Arg Ala Thr Ile Asn Cys Lys Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Phe Cys Gln Gln
                85                  90                  95

Tyr Tyr Asp Thr Pro Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 36
<211> LENGTH: 16654
<212> TYPE: DNA
<213> ORGANISM: Homo sapiens

<400> SEQUENCE: 36
```

| | | | | |
|---|---|---|---|---|
| actcggtgcg | ccttccgcgg | accgggcgac | ccagtgcacg | gccgccgcgt cactctcggt | 60 |
| cccgctgacc | ccgcgccgag | ccccggcggc | tctggccgcg | gccgcactca gcgccacgcg | 120 |
| tcgaaagcgc | aggccccgag | gacccgccgc | actgacaggt | gagcgcggac gcacccggca | 180 |
| gggatgtgag | tgggcggagg | gaagagggcc | gcaaaccaac | ccaggacccg ctcagttcca | 240 |
| cgcgcggcag | ccctccgtgc | gcgcaggctc | gggtgcgttg | ttcgcggggg tgaattgtga | 300 |
| agaaccatcg | cggggtcctt | cctgctgagg | ccgcggacac | cgtgacctcg ctgctctggg | 360 |
| tctgcaggga | aacgtaggaa | aaaagttgt | caggagcggg | caggatgacc cccacatccc | 420 |
| gtttccacct | cccggaggcc | cccgaacacg | ctcctggtgc | tggtggcagc agcgcctggc | 480 |
| agacgcgccc | gcttagcgag | ggcgcgaagt | ccaggccgcc | agagcgcagg agcatccgga | 540 |
| cctgctagtc | ggccgctgac | tgcgcggcga | gttgccttga | gagggtccca tgtgcttggg | 600 |
| gcgccgcgct | gggtctgggg | gcgtcttggg | gcgcccattg | gagtccgcgg gttggagcat | 660 |

```
ccggagaatc catgatgtgt gcatttgccg atccccgagg tgagatggag actggcaagg    720
gcagagccgc tgtgttcagc cacagcggaa aaccgaacgg tgggtaatcc gacagctgcg    780
gtgcggggcg cggccctggc cgcggggtcc agcgaacccg cagtgctcac aaggcagaca    840
ccacacgcgc tcgcggaccg gccacgcact cgcgggcgct cgcttctcta ctccagcctc    900
ttccccgccc cgcgcacgcc cgagctgaat ggtagacgtt ctggcgccgg gcagcggcca    960
ccggctggtt cccacttccg cgcgcacccc ttaaactgtg ttctagaggc cccagcctcg   1020
ccttgcagcg cctcactagc tcctgaggac tagggactgg cggctgaggc gggttggcgg   1080
ctgcaacgag ctgggcgtct ttcgttctct ctcgctgcct ggctggctcc gctggccct    1140
ccacagcttg cggagcaagg ccatagcagg ggagtgggag gtatattggg gctgtcacct   1200
ccttgctggc cggagttatt tgtagactac agactccgga agaacagacg cgccaccgct   1260
ctcgcttggc attgccttcg gatcgcagct cctccttggg ggtgccccag cttggcgttt   1320
atttgcctgc gccaggctct ggcgacggtc accgggccag gcggggaggg acggacggca   1380
ggtgaccagc ctctgctgtg aagaaattcc tgcgcgcccg gagctgtccc taatgcattc   1440
ccgggtcgaa tccgtctact gccttcccct cctcgaccga ctccgaatct cggctcttat   1500
agacagaaat acagcctcag cgttaggggt taaaatcccc ctcttaaacg gtccgagggc   1560
agagaggtga ccaccgatag gtaattggat ctcctgctgg aaagagcaaa tctgagcggt   1620
gtgcgcgtct gtttatgttc cccttcgaga tggtgccagg acacgaactg attaaaacaa   1680
tctattgtgt taagtgggtc actagggttt taagctgtcc cagggacccc agagtagtgg   1740
cttccttctg gctgtacaca caagttaaat aaatagcgta gaagaggtta agataacccc   1800
attctagggt gaggagtcct cttttcatcc ctagggcttcc ccctcccctt ttctcttttt   1860
ttggaaggag ggggagcatg agagtcttga gggggggatg tacttttcaa agcaaggagg   1920
gaaagatctt aagaaaacta tatattctca ctgcccccca agccaagtct ataacagtag   1980
gtgatttgat tactatctct ggataaatgg cactgtcaaa ttgttaatat taactatttc   2040
agggattttt agcagggtag tggcagtatg tgtgcgtgtg tgtgtgtgtg tctgtgtgtg   2100
tgtgtttaac ctccaggtca ttgtaggaat tagagtctt tgtaaacttt gtaatttcac    2160
aggtttccta ttttcttaaa agttcatttt tagtgaaatg ttttggtaac ccacgctctg   2220
taggaaatcc aggttggcta atgcggtctt tatgtgagta gttacacagg gaaggataaa   2280
aaccttttat gtcctacatc tctgaatgag ggctgcctac cctgtctttg aaactaagcc   2340
gaagatgcct tcagtctgaa tggtcaagta ttaaaagtga taaaatgcaa agaaatttca   2400
tgccgcagac acctccccca agaactgctt gttgacagca agctgtgga acatgttcca    2460
caacagagag taaaggacag ccaggaaata taaacctttt atgtaaagga aaggcaggtg   2520
ggggacagtg gttaggggag gtgactgcag cctctaacca aaaggcaacc atcaggcaag   2580
tgctaccagc ccgtgtcttc gatctgcaag gaatttttctt tagttttaac atatgctctt   2640
agaaattcaa agtacaacag gaattcctgg gacaagagaa atctttttat tcacatgtga   2700
acatgaagat acaaaataga taattatttt atttatagca ctcttcaaat tgtattgcat   2760
tagaaaacat atccattgac ccactgttaa ggacagcact gggtgtcaat aggacagtgg   2820
ttaaggacct gtgtttgggg ctagatagaa ttgggtttaa actgctggct gggctgggca   2880
cagtggctca caccggtaat cccagcactt tgggaggcca aggaggacgg atcacctgag   2940
gtcgggagtt cgacaccagc ctgaccaaca tggaaaaatc ccgtctctac taaaaacaca   3000
```

```
aaattagcca ggcatggtgg tgcatgcctg caatcccagc tacttgggag gctgaggcag    3060
gagaattgct tgaaaccggg aggcggaggt tgtggtgagc ccagatagcg ccattgcatt    3120
ccagcctggg caacacgagt gaaaactccg tcaaaaaaac aaaacaaaac aaacaaacaa    3180
aaaaatgctg gctttcccac ttatgagctg tgtgaccttg acaaatttc  caacttttct    3240 gagtgtagat tccctgattg gtaaaaggaa gatgatatta tctacctcat attttgttat    3300
gaaaaataaa tgataaaatt gggtcagaaa tcagcataat gcctggcaca gtaagggctt    3360
caaaataaaa ggtagctctt attattagta atggtgttag gaaaagtagc aatgttatac    3420
agaaccagga tatatcacag gcagttctg  aaattaaatc ctgaatcctg gccgggtgag    3480
gtggctcacg cttgtaatcc taagcacttt cggagactga ggcaggcgga tcacgaggtc    3540
aggagtttga gaccagcctg gccaacacac tgaaatcccg tctctactaa aaatacaaaa    3600
attagctggg tgtggtggca ggcgcctata atctcagcta cttgggaggc tgaggcagga    3660
gaatcacttg agcccaggag gcggaggttg cagtgagctg atatcgtgcc agtgcactcc    3720
agcctgggtg acatctctta aaaaaaaaaa tcctgaatac cacactacgc agtgactaac    3780
acatctttca ctacagaaca gaacctgtaa cttggccgtc tctcagcagt gctgctcagt    3840
gaacatttaa taatttatta ctttctaact cgtttcttgt tgacctcaag aattgtacat    3900
agtcattaac tttcctaaga aaatctttga caaacataga gctcctgaga tatttcacaa    3960
ccaggtggtc tcctccctgt cctatgcaat gttgggcccc agcctgattt agccgacctg    4020
gtcttcagac ttgagaggct gtttagggtt cttacaacac aaaggggatg agactttatc    4080
ctctacctgt gtgccaacaa gggattcttc ttatctcctt ggtgcaactt gtctgaaaaa    4140
gaaagtcaac acaattatct tcttaaaagt taaagatcaa attaaaaata agctatagtt    4200
ttcccaaaga tttagacctg agaaaaagga atagatcttt ctaaacctg  gcctgcactt    4260 agagcatttg tagtcacttc cactatttct tatgctgaga gaataatttg atgtcatgcc    4320
tattgaatgt ctttctaaag cttgattcat caggaggaac tgaccagaag tccatgcaca    4380
gacatttggc tttcactgta attcctactc aaaactccct ttcactgatt atgagcaggt    4440
tgcttagcta aaatgagaaa tacagcaaga agagggatgg aaagagctgg cttaaacttt    4500
cccaaagaca tcatgaacac tgggaacagg tcatacatat accattttta tttctcagtc    4560
ctcagtatta gaatattgtg ttcctagagg cttttgtgaaa attggaatac attgccatga    4620
cctgcacagg atagaggtgg ttaatatggc ttaccttgct tgtagatgtt tactcttgat    4680
ccctaaggga aactggaagg aaagcatgct gtagagagga cctgctttga gagtatgtgt    4740
cctctgggac aagtggaatg aaagagagga tagaggcaaa gagaaaaaaa ggtggagatg    4800
gggtgagact tgctggtgga cagttgcaaa gaaaactcat gatgagaata acatcacatt    4860
tcttgaagaa gctgaactgc attgatggga agttgaggca gagtttgaaa agaagatata    4920
ctgtctgcaa aaaagaatca acggagatgt caggtatctt gatgcaccct gagtctatga    4980
gatgcagctt aatttaattt aatgatatga gtaggccatt tcataagtgg tggaaattac    5040
cataaagtgt ttgcagctaa tgacggcgca tgaatgatgt cataggaacc taagtctgga    5100
tgagctatgg attgaatttt tactatggga caccttcta  catgttgctg tggaaaagaa    5160
ttgtcctcaa gaaatgtaca tcttctgcat ttcctctaca tctctgatat ttacaaagtg    5220
cacattattt ggtgatacta caactgggat ttcaagtgca catcactact atttccttca    5280
ctgaagaatc aagagcagtc tgggggtggg gagagcttga gtgattgaca aggatgtggc    5340
agagccctgg ttccactatg aattatagtt cttaccctgc ttactgtcac tcatgtagag    5400
```

```
cagctagtgt gcctcagagc actgctgttc tctgagaagc tgaggtctcg attgacattc    5460
ttgaagttgg tgtttacttc tctctgaata acaaaggtt ggcaactcag acatcttaca    5520
ataagtacta aagattttg aagaataggt ttttaaaaaa tgaaaaaaca tttcactttc    5580
catagctaat aaatcttatt ttgaggaaaa tgtactttc tttaaaaaaa aaaaaagcct    5640
gtctgtcact ctagacccctt tggcttagaa ggtaggcaca ctcacataga aacagaaagt    5700
ctgtccaaat taaaactgaa aaccacagtt gactaatttt gaatttatag ctctgctgtt    5760
ggcttctgcg atagtattaa tttcaatggc ttcaattaga aaatgaaacc catagcattc    5820
catatgagaa caggtaaaaa gtcagggaca tttggagttt tccaagaaaa agaaagacaa    5880
gtcttaggaa gctctctagg atggaaggaa tttgccacac tgagagttag acatccaaag    5940
gatagcaatt ggctcttctg ctcatgggca ctggtgaagg cattttaaaa tgcgaagaat    6000
ggtacctctg taaatcaatg aggttcataa taatcatgca tttaccaaat ttttataagc    6060
acctgccttg tgccaggcac tgagggtaag gtgatgaata agccctcatc aactgtcaga    6120
ctagatattt actcaataac agatgtgaaa atgccaagaa ggaaaagttg agtataaaga    6180
aagccttaag ttggttcaga gaaataaaat tgcattttc ggatagatgt ttatggaatc    6240
ggccttatga ggtaaacttg tcctatgcag tgaacataca ttcccagtta gtctcagatt    6300
ggcctctgtg atgacaaact cagagggtcc tggtctagga ggggtgaatt tgtctggagg    6360
ccattttcag gaggtatgga ggaagactgg ggcataggcc tggggccatc ccatgtactc    6420
ctcctctgaa atggggagca actgaattgt gtttatttt agatcttcgt ccaacttgaa    6480
taccagaaat tcgtgaaacc ttctcaaatt cacactatat tttgagacca ggagaaggct    6540
ccttgagaaa ttgccacact gtcttatcct agtctctgga aaaattcagt cctgtattat    6600
aactgggcgt ttctcataag tgcttttttt ttttcttttt ctttttataa tactttaagt    6660
tctgggatac atgtgcagaa tgtgcaggtt tgttacatag gtatacacgt gccatggtgg    6720
tttgctgcac ccatcaaccc atcatctaca ttaggtattt ctcctaatgc tacccctttcc    6780 ctagccccccc acccctcgac aggccccagt gtttgatgtt ccctccctg tgtccatgtg    6840 ttctcattgt tcaactccca cttatgagtg agagcatgcg gtgtttggtt ttctgttcct    6900
gtgttagttt gctgagaatg atggttttg gcttcatcca cgtccctgca aaggacatga    6960
actcatcctt tttatggctg catagtattc catggtgtat atgtgccaca tttgctttat    7020
ccagtctatc attgatgagc acttgggttg gctccaagtc tttgctatta tgactagtac    7080
tgcgataaac atgtgtatat gtgtcttat attagaatga tttataatcc tttaggtcta    7140
tacccagtaa taggattcct gggtcaaatg gtatttctgg ttctagatcc ttgaggaatt    7200
gccacactgt cttccacaac ggttgaacta atttacactc ccaccaacag tgtaaaagca    7260
ttcctatttc tccacatcct ctccaacatc tgttgtttcc tgactcttta atgacggcca    7320
ttctaactgg cgtgaaatgg tatctcattg tggttttgat ttgcatttct ctaatgacca    7380
ccgatgatga gcttttctc atatgtttgc tggccccata aatgtcttct tttgagaaat    7440
gtctgttcat atcctttgcc cacttttga tggggttgtt tgctttttc ttgtaaattt    7500 gtttgagttc ctggtagatt ctggatatta gcccttgtc agatggatag actgcaaaaa    7560
ttttctccca ttctgtaggt tgcctgttca ctctgatggt agtttctttt gccatgcaga    7620
agctgtttag tttaattaga tccaatttgt cagtttggc ttttgttgcc attgcttttg    7680
gtgttttagt catgaagtct ttgcccatgc ctatgtcctg aattgtattg ccctggtttt    7740
```

```
cttctaggat ttttatggtt ttaggtctta catttaagtc tttaatccat cttgaattaa   7800
tttttgtata aggtgtaagg aaagggtcca gtttcagttt tctgcgtatg gctagccagt   7860
tttcccaacg ttatttatta aatagggaat cctttcccca ttgcttgttt ttgtcaggtt   7920
tgtcaaagat cagacggttg tagatgtgtg gtgttatttc tgaggcctct gttctgttcc   7980
attggtctgt atatctgctt tgataccagt accgtgctgt tttggttact gtagccttgt   8040
agtacagttt gaagtcaggt agcgtgatgc tttgttcttt ttgcttagga ttgtcttggc   8100
tatatgggct ctttttttggt tctatatgaa atttaaagta gttttttcat agacatctat   8160
agaactctcc accccaaatc aacagaatat acattcttct cagtatcgca tcacacttat   8220
tctaaaatga ccacataatt agaagtaaaa cactcctcag caaatgcaaa aaacagaaat   8280
cctaacagtc tgtcagaccc cagtgcaatc aaattagaac tcaggattaa gaaacttact   8340
gaaaaccaca caactgcatg gaaactgaac aacctgctcc tgaatgacta ctgggtaaat   8400
aacaaaatta aggcagaaat aaataggttc tttgaaagaa atgagaacaa agacacaata   8460
taccagaatc tctgggacac agctaaagca gtgtttagag ggaaattgat agcactaaat   8520
gcccacagga gaaagcggga cagatctaaa atcgacaccc taatatcaca attaaaagaa   8580
ctagagaaac aagagcaaac aaattcaaaa gctagcagaa gacaagaaat aactaagatc   8640
agagcagaac tgaaggagat agagacacaa aaacccttc aaaaaatcaa tgaatccagg   8700
agctgttttt ttttttttga aaagattaat gaaatagact gctagccaaa ctaataaagg   8760
agaaaagaga gaagaatcaa atagacaata gacacaataa aaagtgataa aggggatatc   8820
accactgatc ccacagaaat acaaactacc atcagagaat actataaaca cctctacgca   8880
aataaactag aaaattggga agaaatggat acattcctga acgcatacac cctcccaaga   8940
ctaaaccagg aagaagttga atccctgaat agaccaatag caagttctga aattgaggca   9000
gtaattagta gcctaccaac caaaaaaagc ccaggaccag acagattcac agccgaagtc   9060
taccagaggt acaagagga gctagtacca ttccttctga aactattcca aacaatagaa   9120
aaagaaggac tcctccctaa ctcattttat gaggccagca tcatcctgat accaaaacct   9180
ggcagagaca caacataaag gaaattcagg ccaatatccc tgatgaacat tgatgtgaaa   9240
atcctcaata aaatactggc agcacatcaa aaagcttacc tgccatgatc aagttggctt   9300
catccctggg atgcaaggct ggttcaacat acgcaaatca ataaacgtaa tcaatcacat   9360
acacagaacc aatgacaaaa accacatgat tatctcaata gatgcagaaa aggccttcga   9420
taaaattcaa caccccttca atgctaagaa ctctcaataa actaggtatt gatgaaacat   9480
atctcaaaat aataagagtt atttatgaca aacccacagc cagtatcata ctgaatgggc   9540
aaaagctgga agcattccct ttgaaaaccg ccacaaggat gacttctctc accactccta   9600
ttcaacatac tattggaagt tctggccagg gcaagcaggc aagacaaata aataaagggt   9660
attcaaatag gaagagagga agtcaaattg tctctgtttg cagatgacat gattgtatat   9720
ttagaaaacc ccatcatctc agcccaaaat ctccttaagc tgataagcaa cttcagcaaa   9780
gtctcaggat acaaaatcaa tgtgcaaaaa tcacaagcat tcctatacac caataataga   9840
caaacagcca atcatgagt gaactcccat tcacaagtgc tacaaagaat aaaataccta   9900
ggaatccaac ttacaaggga tgtgaaggac ctcttcaagg agaactacag accactgctc   9960
aaggtaataa gagaggacac aaacaaatgg aaaaacattc catgctcatg gataggaaga  10020
atcaatatta tgaaaatggc catactgccc aaaacaattt atagattcaa tgccatcccc  10080
atcaagctac cactgacttc cttcacagaa ttagaaaaaa actactttaa atttcatatg  10140
```

```
gaactgaaaa aagagccggt atagccaaga cgatcctaag caaaaagaaa aaagctggaa    10200
gcatcatgct acctgacttc aaactatact acaaggctac agtaacaaaa acagcatggt    10260
atagtataag tgctttttt taaaagacaa agtaaagtaa ttttttttgtt gttggggtaa    10320 aacaaaagct ctgcataaag agcagggatg ttgtaacata cactgaccaa aggtgggaaa    10380
cctacagttg gagcagaagc tgaatgtcac attatcagct ccgaacttat aatggtctaa    10440
aagtactagg ttaatgttgg aaagatggtg ccatttaaag atatcttaaa ttcaatattt    10500
aattatttta atttgacatt atcctagagt tgaatggtgt ttacttacca tgtgctgttc    10560
attagaaaat ctagatccta cactgccttt gcgcaaggta gttgctctaa taataccaac    10620
ctgtccagtt ttggtgggag aaataatgtt actgttaagt tgcacttagt ggttattatg    10680
tgtaatactg gtattccaaa gagagaagga aaatgtttgc tacacagctg tgttcttagg    10740
ttcagaaaac cacaggagtg ggacaggaga accttcagga ttcaggtccg attgttgtga    10800
tggccgcagg agggagactg tgaatttgaa actgcatcca ttgaaaagaa aatccctcca    10860
cactttaata attctctccg tgccccatgg cagcaagtgc ttataggcct tgctactcaa    10920
agcttaataa aaaggcagac ctgctgaatc ataatctgca tcttaacaat atccccagat    10980
attgtctgca cttctttt ttttttcttt ctttctttct tcttttttt gagacagagt    11040 ctcgctcagt cacccaggct ggagtgcagt ggcgcgatct cggctcactg caagctctga    11100
ctcccgggtt cacgccattc tcctgcctta gactcccgag tagctggcac tacaggcgcc    11160
cgccactacg cccggctaat tttttgtat ttttagtaga gatggggttt caccgtgtta    11220
gccaggatgg tctcgatctc ctgacctcgt gatccgccgc ccatctgggc ctcccaaagt    11280
gctgggatta caggcgtgag ccactgcgcc cggccaattg tctgcacttt caagtctaag    11340
aagcactgtc ccaggaggaa aatcttttta gtctgaggct tctctcttgc actctccttt    11400
ttaaaaatat gctgctcctt ctccacctt ccctcttctt ccgccttttc tgtctgcctt    11460
tactacctcc cctgaacatt caacttgtag aagagttccc ctttctctga attgcattct    11520
tcacttcatt cattctttc tctctctgtc tatggtttcc tattttttgt cggttttccc    11580
tcacctcacc tccttgttat tttttgccat tgttcacata tcactgccct ttcagaccca    11640
tatctagctt ctgacccatc cactaatcca ttgccactaa tttattcagc atgcccatgc    11700
catttattaa tgtaaatatt tgcacatact tgttctatca tgcccatttt tctacctttt    11760
aaattgtata tacacagaca catgtgaatg acatatttca ctatttaaaa ggtagaaaaa    11820
tgtatatcgt ggtacaaagt gatacattga gtatctgtgc ccagtttcaa gatgagaata    11880
agtgagaggt gaagcctcat gagtcacgtc acctacacgc tactgtcttt cattccatct    11940
gcagtactgc cacacatttg gttagttctc caattgctgt cacattgaca tcgagttgga    12000
tctgaacagc gtacctgggg agacgaagta ttggtatctt tgcttaaatg gagtgattta    12060
ctgagagaca aagtgacatc tttaagatca gatagcaagt tactgcacca ggagcgcgac    12120
ctttcctgtt ttgttgtttt ccctctgtca aatgccttct ggtctccatg aatctctcct    12180
tccacatatg ataaaaatgc aaagtctcat aagcattcac agctcaggaa gcctcaggct    12240
agttggggag aaaagactgg gaggtttccg gaggaatgaa gtcctctgag cagagaggtt    12300
aattcatctt gctgtaaaac aaaatagaaa ataagttccc ctcaataagt gaacgtaata    12360
caaagacaaa tgtggttggt gccagaggcc aggaagaagt tcttgtgaga ataggtgcag    12420
agaagagcta ggccctggct gagtttaaac cttgacttag tcactgtggg actctgggtg    12480
```

| | |
|---|---|
| agttactcca tggattgatg gctgggtcat ggagataata gtacctaatt catacaggta | 12540 |
| ctgtgagaag taaatggaat atttcacgtt aagtgtttaa cggtgcgttt aaatgctagg | 12600 |
| tgctattatt attaattttt aaattaactt tgccatgttt tgtgtcttcc cctctctgtg | 12660 |
| cttcctttct ttagtatgag ccgcacagcc tacacggtgg gagccctgct tctcctcttg | 12720 |
| gggaccctgc tgccggctgc tgaagggaaa aagaaagggt cccaaggtgc catcccccg | 12780 |
| ccagacaagg cccagcacaa tgactcgag cagactcagt cgcccagca gcctggctcc | 12840 |
| aggaaccggg ggcggggcca agggcgggc actgccatgc ccggggagga ggtgctggag | 12900 |
| tccagccaag aggccctgca tgtgacggag cgcaaatacc tgaagcgaga ctggtgcaaa | 12960 |
| acccagccgc ttaagcagac catccacgag gaaggctgca acagtcgcac catcatcaac | 13020 |
| cgcttctgtt acggccagtg caactctttc tacatcccca ggcacatccg gaaggaggaa | 13080 |
| ggttcctttc agtcctgctc cttctgcaag cccaagaaat tcactaccat gatggtcaca | 13140 |
| ctcaactgcc ctgaactaca gccacctacc aagaagaaga gagtcacacg tgtgaagcag | 13200 |
| tgtcgttgca tatccatcga tttggattaa gccaaatcca ggtgcaccca gcatgtccta | 13260 |
| ggaatgcagc cccaggaagt cccagaccta aacaaccag attcttactt ggcttaaacc | 13320 |
| tagaggccag aagaaccccc agctgcctcc tggcaggagc ctgcttgtgc gtagttcgtg | 13380 |
| tgcatgagtg tggatgggtg cctgtgggtg tttttagaca ccagagaaaa cacagtctct | 13440 |
| gctagagagc actccctatt ttgtaaacat atctgcttta atgggatgt accagaaacc | 13500 |
| cacctcaccc cggctcacat ctaaagggc ggggccgtgg tctggttctg actttgtgtt | 13560 |
| tttgtgccct cctgggggacc agaatctcct ttcggaatga atgttcatgg aagaggctcc | 13620 |
| tctgagggca agagacctgt tttagtgctg cattcgacat ggaaaagtcc ttttaacctg | 13680 |
| tgcttgcatc ctcctttcct cctcctcctc acaatccatc tcttcttaag ttgatagtga | 13740 |
| ctatgtcagt ctaatctctt gtttgccaag gttcctaaat taattcactt aaccatgatg | 13800 |
| caaatgtttt tcattttgtg aagaccctcc agactctggg agaggctggt gtgggcaagg | 13860 |
| acaagcagga tagtggagtg agaaagggag ggtggagggt gaggccaaat caggtccagc | 13920 |
| aaaagtcagt agggacattg cagaagcttg aaaggccaat accagaacac aggctgatgc | 13980 |
| ttctgagaaa gtcttttcct agtatttaac agaacccaag tgaacagagg agaaatgaga | 14040 |
| ttgccagaaa gtgattaact ttggccgttg caatctgctc aaacctaaca ccaaactgaa | 14100 |
| aacataaata ctgaccactc ctatgttcgg acccaagcaa gttagctaaa ccaaaccaac | 14160 |
| tcctctgctt tgtccctcag gtggaaaaga gaggtagttt agaactctct gcataggggt | 14220 |
| gggaattaat caaaaaccgc agaggctgaa attcctaata cctttccttt atcgtggtta | 14280 |
| tagtcagctc atttccattc cactatttcc cataatgctt ctgagagcca ctaacttgat | 14340 |
| tgataaagat cctgcctctg ctgagtgtac ctgacagtag tctaagatga gagagtttag | 14400 |
| ggactactct gttttagcaa gagatatttt gggggtcttt tgttttaac tattgtcagg | 14460 |
| agattgggct aaagagaaga cgacgagagt aaggaaataa agggaattgc ctctggctag | 14520 |
| agagtagtta ggtgttaata cctggtagag atgtaaggga tatgacctcc ctttctttat | 14580 |
| gtgctcactg aggatctgag gggaccctgt taggagagca tagcatcatg atgtattagc | 14640 |
| tgttcatctg ctactggttg gatggacata actattgtaa ctattcagta tttactggta | 14700 |
| ggcactgtcc tctgattaaa cttggcctac tggcaatggc tacttaggat tgatctaagg | 14760 |
| gccaaagtgc agggtgggtg aactttattg tactttggat ttggttaacc tgttttcttc | 14820 |
| aagcctgagg ttttatatac aaactccctg aatactcttt ttgccttgta tcttctcagc | 14880 |

```
ctcctagcca agtcctatgt aatatggaaa acaaacactg cagacttgag attcagttgc    14940
cgatcaaggc tctggcattc agagaaccct tgcaactcga gaagctgttt ttatttcgtt    15000
tttgttttga tccagtgctc tcccatctaa caactaaaca ggagccattt caaggcggga    15060
gatatttttaa acaccaaaaa tgttgggtct gattttcaaa cttttaaact cactactgat    15120
gattctcacg ctaggcgaat tgtccaaac acatagtgtg tgtgttttgt atacactgta    15180
tgaccccacc ccaaatcttt gtattgtcca cattctccaa caataaagca cagagtggat    15240
ttaattaagc acacaaatgc taaggcagaa ttttgagggt gggagagaag aaaagggaaa    15300
gaagctgaaa atgtaaaacc acaccaggga ggaaaaatga cattcagaac cagcaaacac    15360
tgaatttctc ttgttgtttt aactctgcca caagaatgca atttcgttaa cggagatgac    15420
ttaagttggc agcagtaatc ttcttttagg agcttgtacc acagtcttgc ataagtgc     15480
agatttggct caagtaaaga gaatttcctc aacactaact tcactgggat aatcagcagc    15540
gtaactaccc taaaagcata tcactagcca aagagggaaa tatctgttct tcttactgtg    15600
cctatattaa gactagtaca aatgtggtgt gtcttccaac tttcattgaa aatgccatat    15660
ctataccata ttttattcga gtcactgatg atgtaatgat atatttttc attattatag    15720
tagaatattt ttatggcaag atatttgtgg tcttgatcat acctattaaa ataatgccaa    15780
acaccaaata tgaattttat gatgtacact ttgtgcttgg cattaaaaga aaaaaacaca    15840
catcctggaa gtctgtaagt tgtttttttgt tactgtaggt cttcaaagtt aagagtgtaa    15900
gtgaaaaatc tggaggagag gataatttcc actgtgtgga atgtgaatag ttaaatgaaa    15960
agttatggtt atttaatgta attattactt caaatccttt ggtcactgtg atttcaagca    16020
tgttttcttt ttctccttta tatgactttc tctgagttgg gcaaagaaga agctgacaca    16080
ccgtatgttg ttagagtctt ttatctggtc aggggaaaca aaatcttgac ccagctgaac    16140
atgtcttcct gagtcagtgc ctgaatcttt atttttttaaa ttgaatgttc cttaaaggtt    16200
aacatttcta aagcaatatt aagaaagact ttaaatgtta ttttggaaga cttacgatgc    16260
atgtatacaa acgaatagca gataatgatg actagttcac acataaagtc cttttaagga    16320
gaaaatctaa aatgaaaagt ggataaacag aacatttata agtgatcagt taatgcctaa    16380
gagtgaaagt agttctattg acattcctca agatatttaa tatcaactgc attatgtatt    16440
atgtctgctt aaatcattta aaaacggcaa agaattatat agactatgag gtaccttgct    16500
gtgtaggagg atgaaagggg agttgatagt ctcataaaac taatttggct tcaagtttca    16560
tgaatctgta actagaattt aattttcacc ccaataatgt tctatatagc ctttgctaaa    16620
gagcaactaa taaattaaac ctattctttc tgtg                                16654
```

<210> SEQ ID NO 37
<211> LENGTH: 555
<212> TYPE: DNA
<213> ORGANISM: Homo sapiens

<400> SEQUENCE: 37

```
atgagccgca cagcctacac ggtgggagcc ctgcttctcc tcttggggac cctgctgccg      60
gctgctgaag ggaaaaagaa agggtcccaa ggtgccatcc ccccgccaga caaggcccag    120
cacaatgact cagagcagac tcagtcgccc cagcagcctg gctccaggaa ccggggggcgg    180
ggccaagggc ggggcactgc catgcccggg gaggaggtgc tggagtccag ccaagaggcc    240
ctgcatgtga cggagcgcaa atacctgaag cgagactggt gcaaaaccca gccgcttaag    300
```

```
cagaccatcc acgaggaagg ctgcaacagt cgcaccatca tcaaccgctt ctgttacggc    360
cagtgcaact ctttctacat ccccaggcac atccggaagg aggaaggttc ctttcagtcc    420
tgctccttct gcaagcccaa gaaattcact accatgatgg tcacactcaa ctgccctgaa    480
ctacagccac ctaccaagaa gaagagagtc acacgtgtga agcagtgtcg ttgcatatcc    540
atcgatttgg attaa                                                     555

<210> SEQ ID NO 38
<211> LENGTH: 20
<212> TYPE: DNA
<213> ORGANISM: Artificial Sequence
<220> FEATURE:
<223> OTHER INFORMATION: Mouse Grem1 forward primer

<400> SEQUENCE: 38
gcgcaagtat ctgaagcgag                                                 20

<210> SEQ ID NO 39
<211> LENGTH: 20
<212> TYPE: DNA
<213> ORGANISM: Artificial Sequence
<220> FEATURE:
<223> OTHER INFORMATION: Mouse Grem1 reverse primer

<400> SEQUENCE: 39
cggttgatga tagtgcggct                                                 20

<210> SEQ ID NO 40
<211> LENGTH: 21
<212> TYPE: DNA
<213> ORGANISM: Artificial Sequence
<220> FEATURE:
<223> OTHER INFORMATION: Human Grem1 forward primer

<400> SEQUENCE: 40
aggcccagca caatgactca g                                               21

<210> SEQ ID NO 41
<211> LENGTH: 21
<212> TYPE: DNA
<213> ORGANISM: Artificial Sequence
<220> FEATURE:
<223> OTHER INFORMATION: Human Grem1 reverse primer

<400> SEQUENCE: 41
gtctcgcttc aggtatttgc g                                               21

<210> SEQ ID NO 42
<211> LENGTH: 20
<212> TYPE: DNA
<213> ORGANISM: Artificial Sequence
<220> FEATURE:
<223> OTHER INFORMATION: Beta-actin forward primer

<400> SEQUENCE: 42
gatcattgct cctcctgagc                                                 20

<210> SEQ ID NO 43
<211> LENGTH: 22
<212> TYPE: DNA
```

```
<213> ORGANISM: Artificial Sequence
<220> FEATURE:
<223> OTHER INFORMATION: Beta-actin reverse primer

<400> SEQUENCE: 43
gtcatagtcc gcctagaagc at                                                22
```